(12) United States Patent
Jebrail et al.

(10) Patent No.: US 11,857,961 B2
(45) Date of Patent: Jan. 2, 2024

(54) SEQUENCING BY SYNTHESIS USING MECHANICAL COMPRESSION

(71) Applicant: mirOculus Inc., San Francisco, CA (US)

(72) Inventors: Mais Jehan Jebrail, Toronto (CA); Foteini Christodoulou, San Francisco, CA (US); Ana Eugenia Carvajal, San Francisco, CA (US); Eduardo Cervantes, San Francisco, CA (US); Rohit Lal, San Francisco, CA (US); Mark Lewis, San Francisco, CA (US)

(73) Assignee: mirOculus Inc., San Francisco, CA (US)

(*) Notice: Subject to any disclaimer, the term of this patent is extended or adjusted under 35 U.S.C. 154(b) by 0 days.

(21) Appl. No.: 18/062,007

(22) Filed: Dec. 5, 2022

(65) Prior Publication Data

US 2023/0219083 A1 Jul. 13, 2023

Related U.S. Application Data

(60) Provisional application No. 63/418,028, filed on Oct. 20, 2022, provisional application No. 63/417,302, filed on Oct. 18, 2022, provisional application No. 63/393,815, filed on Jul. 29, 2022, provisional application No. 63/298,973, filed on Jan. 12, 2022.

(51) Int. Cl.
*C12Q 1/68* (2018.01)
*B01L 3/00* (2006.01)
*C12Q 1/6874* (2018.01)

(52) U.S. Cl.
CPC ... *B01L 3/502715* (2013.01); *B01L 3/502784* (2013.01); *C12Q 1/6874* (2013.01); *B01L 2200/027* (2013.01); *B01L 2200/0642* (2013.01); *B01L 2300/0816* (2013.01); *B01L 2300/165* (2013.01); *B01L 2300/18* (2013.01); *B01L 2400/022* (2013.01); *B01L 2400/0403* (2013.01); *B01L 2400/0475* (2013.01)

(58) Field of Classification Search
None
See application file for complete search history.

(56) References Cited

U.S. PATENT DOCUMENTS

| 4,469,863 A | 9/1984 | Ts'o et al. |
| 4,492,322 A | 1/1985 | Hieftje et al. |
| 4,569,575 A | 2/1986 | Le Pesant et al. |

(Continued)

FOREIGN PATENT DOCUMENTS

| CA | 2470847 A1 | 7/2003 |
| CA | 2740113 A1 | 4/2010 |

(Continued)

OTHER PUBLICATIONS

Cooney et al. (Microfluid Nanofluid, 2006, 2:435-446, IDS reference) (Year: 2006).*

(Continued)

*Primary Examiner* — Stephanie K Mummert
(74) *Attorney, Agent, or Firm* — Shay Glenn LLP

(57) ABSTRACT

Methods and apparatuses for sequencing by synthesis using mechanical compression. These methods and apparatuses may mechanically control microfluidic movement using a force applicator and an elastically deformable sheet.

23 Claims, 64 Drawing Sheets

(56) References Cited

U.S. PATENT DOCUMENTS

| | | |
|---|---|---|
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 3/2002 | Krulevitch et al. |
| 6,401,552 B1 | 6/2002 | Elkins |
| 6,495,369 B1 | 12/2002 | Kercso et al. |
| 6,565,727 B1 | 5/2003 | Shenderov |
| 6,596,988 B2 | 7/2003 | Corso et al. |
| 6,723,985 B2 | 4/2004 | Schultz et al. |
| 6,773,566 B2 | 8/2004 | Shenderov |
| 6,787,111 B2 | 9/2004 | Roach et al. |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,057,031 B2 | 6/2006 | Olejnik et al. |
| 7,147,763 B2 | 12/2006 | Elrod et al. |
| 7,163,612 B2 | 1/2007 | Sterling et al. |
| 7,214,302 B1 | 5/2007 | Reihs et al. |
| 7,323,345 B1 | 1/2008 | Stjernstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Bousse et al. |
| 7,439,014 B1 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,897,737 B2 | 3/2011 | Wu et al. |
| 7,901,947 B2 | 3/2011 | Pollack et al. |
| 7,919,330 B2 | 4/2011 | de Guzman et al. |
| 7,939,021 B2 | 5/2011 | Smith et al. |
| 7,998,436 B2 | 8/2011 | Pollack et al. |
| 8,007,739 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,187,864 B2 | 5/2012 | Wheeler et al. |
| 8,190,371 B2 | 5/2012 | Allawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,367,370 B2 | 2/2013 | Wheeler et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,153 B2 | 6/2013 | Feiglin et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,653,832 B2 | 2/2014 | Hadwen et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,821,705 B2 | 9/2014 | Bjornson et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,901,043 B2 | 12/2014 | Eckhardt et al. |
| 8,926,065 B2 | 1/2015 | Winger |
| 8,927,296 B2 | 1/2015 | Sista et al. |
| 8,936,708 B2 | 1/2015 | Feiglin et al. |
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,039,973 B2 | 5/2015 | Watson et al. |
| 9,046,514 B2 | 6/2015 | Sista et al. |
| 9,091,649 B2 | 7/2015 | Pollack et al. |
| 9,140,635 B2 | 9/2015 | Graham et al. |
| 9,188,615 B2 | 11/2015 | Sturmer et al. |
| 9,223,317 B2 | 12/2015 | Winger |
| 9,238,222 B2 | 1/2016 | Delattre et al. |
| 9,248,450 B2 | 2/2016 | Bauer |
| 9,377,439 B2 | 6/2016 | Lee et al. |
| 9,435,765 B2 | 9/2016 | Reimitz et al. |
| 9,446,404 B2 | 9/2016 | Bauer et al. |
| 9,476,811 B2 | 10/2016 | Mudrik et al. |
| 9,476,856 B2 | 10/2016 | Pamula et al. |
| 9,513,253 B2 | 12/2016 | Winger |
| 9,517,469 B2 | 12/2016 | Shenderov et al. |
| 9,594,056 B2 | 3/2017 | Fobel et al. |
| 9,851,365 B2 | 12/2017 | Mousa et al. |
| 9,975,117 B2 | 5/2018 | Lee et al. |
| 10,232,374 B2 | 3/2019 | Jebrail et al. |
| 10,464,067 B2 | 11/2019 | Jebrail et al. |
| 10,596,572 B2 | 3/2020 | Hong et al. |
| 10,695,762 B2 | 6/2020 | Jebrail et al. |
| 11,097,276 B2 | 8/2021 | Jebrail et al. |
| 11,253,860 B2 | 2/2022 | Jebrail et al. |
| 11,298,700 B2 | 4/2022 | Hong et al. |
| 11,311,882 B2 | 4/2022 | Soto-Moreno et al. |
| 11,413,617 B2 | 8/2022 | Jebrail et al. |
| 11,471,888 B2 | 10/2022 | Jebrail et al. |
| 11,524,298 B2 | 12/2022 | Soto-Moreno et al. |
| 2002/0150683 A1 | 10/2002 | Troian et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |

(56) References Cited

U.S. PATENT DOCUMENTS

| | | |
|---|---|---|
| 2005/0148091 A1 | 7/2005 | Kitaguchi et al. |
| 2005/0191759 A1 | 9/2005 | Pedersen Bjergaard et al. |
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0148763 A1 | 6/2007 | Huh et al. |
| 2007/0258864 A1 | 11/2007 | Braymer et al. |
| 2007/0269825 A1 | 11/2007 | Wang et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0241831 A1 | 10/2008 | Fan et al. |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0207206 A1 | 8/2009 | Harada |
| 2009/0286297 A1 | 11/2009 | Pihl et al. |
| 2010/0015614 A1 | 1/2010 | Beer et al. |
| 2010/0022414 A1 | 1/2010 | Link et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0087012 A1 | 4/2010 | Shenderov |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0288368 A1 | 11/2010 | Beebe et al. |
| 2010/0311599 A1 | 12/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0220501 A1 | 9/2011 | Witkowski et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0000777 A1 | 1/2012 | Garrell et al. |
| 2012/0045748 A1 | 2/2012 | Willson et al. |
| 2012/0045768 A1 | 2/2012 | Arunachalam et al. |
| 2012/0149018 A1 | 6/2012 | Dahlberg et al. |
| 2012/0190027 A1 | 7/2012 | Loeffert et al. |
| 2012/0208705 A1 | 8/2012 | Steemers et al. |
| 2012/0208724 A1 | 8/2012 | Steemers et al. |
| 2012/0259233 A1 | 10/2012 | Chan et al. |
| 2012/0261264 A1 | 10/2012 | Srinivasan et al. |
| 2012/0289581 A1 | 11/2012 | Chang et al. |
| 2012/0325665 A1 | 12/2012 | Chiou et al. |
| 2013/0017544 A1 | 1/2013 | Eckhardt et al. |
| 2013/0018611 A1 | 1/2013 | Sturmer |
| 2013/0062205 A1 | 3/2013 | Hadwen et al. |
| 2013/0068622 A1 | 3/2013 | Schertzer et al. |
| 2013/0105318 A1 | 5/2013 | Bhattacharya et al. |
| 2013/0123979 A1 | 5/2013 | Elliot et al. |
| 2013/0157259 A1 | 6/2013 | Choi et al. |
| 2013/0168250 A1 | 7/2013 | Fogleman et al. |
| 2013/0171546 A1 | 7/2013 | White et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0236377 A1 | 9/2013 | Kim et al. |
| 2013/0270114 A1 | 10/2013 | Feiglin |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0005066 A1 | 1/2014 | Boles et al. |
| 2014/0054174 A1 | 2/2014 | Wang |
| 2014/0124037 A1 | 5/2014 | Foley |
| 2014/0141409 A1 | 5/2014 | Foley et al. |
| 2014/0161686 A1 | 6/2014 | Bort et al. |
| 2014/0174926 A1 | 6/2014 | Bort et al. |
| 2014/0179539 A1 | 6/2014 | Lohman et al. |
| 2014/0194305 A1 | 7/2014 | Kayyem et al. |
| 2014/0216559 A1 | 8/2014 | Foley |
| 2014/0273100 A1 | 9/2014 | Saito et al. |
| 2014/0335069 A1 | 11/2014 | Graham et al. |
| 2014/0353157 A1 | 12/2014 | Hoffmeyer et al. |
| 2015/0001078 A1 | 1/2015 | Feiglin |
| 2015/0008123 A1 | 1/2015 | Cheng et al. |
| 2015/0021182 A1 | 1/2015 | Rival et al. |
| 2015/0075986 A1 | 3/2015 | Cyril et al. |
| 2015/0111237 A1 | 4/2015 | Graham et al. |
| 2015/0144489 A1 | 5/2015 | Hoffmeyer et al. |
| 2015/0148549 A1 | 5/2015 | Van dam et al. |
| 2015/0198604 A1 | 6/2015 | Ermantraut et al. |
| 2015/0205272 A1 | 7/2015 | Yi et al. |
| 2015/0212043 A1 | 7/2015 | Pollack |
| 2015/0238959 A1 | 8/2015 | Prakash et al. |
| 2015/0258520 A1 | 9/2015 | Griffiths et al. |
| 2015/0267242 A1 | 9/2015 | Foegeding et al. |
| 2015/0322272 A1 | 11/2015 | Pokroy et al. |
| 2016/0068901 A1 | 3/2016 | Eckhardt et al. |
| 2016/0108432 A1 | 4/2016 | Punnamaraju et al. |
| 2016/0108433 A1 | 4/2016 | Fair et al. |
| 2016/0116438 A1 | 4/2016 | Pamula et al. |
| 2016/0129437 A1 | 5/2016 | Kayyem et al. |
| 2016/0161343 A1 | 6/2016 | Smith et al. |
| 2016/0175859 A1 | 6/2016 | Yi et al. |
| 2016/0199832 A1 | 7/2016 | Jamshidi et al. |
| 2016/0298173 A1 | 10/2016 | Wang et al. |
| 2016/0319354 A1 | 11/2016 | Tocigi et al. |
| 2016/0370317 A9 | 12/2016 | Sudarsan et al. |
| 2017/0184546 A1 | 6/2017 | Fobel et al. |
| 2017/0315090 A1 | 11/2017 | Wheeler et al. |
| 2017/0354973 A1 | 12/2017 | Sustarich et al. |
| 2018/0001286 A1 | 1/2018 | Wu |
| 2018/0015469 A1 | 1/2018 | Reiter et al. |
| 2018/0059056 A1 | 3/2018 | Taylor et al. |
| 2018/0095067 A1 | 4/2018 | Huff et al. |
| 2018/0099275 A1 | 4/2018 | Wu et al. |
| 2018/0120335 A1 | 5/2018 | Mousa et al. |
| 2018/0221882 A1 | 8/2018 | Roberts et al. |
| 2018/0250672 A1 | 9/2018 | Jamshidi et al. |
| 2019/0060900 A1 | 2/2019 | Breinlinger et al. |
| 2019/0210026 A1 | 7/2019 | Jebrail et al. |
| 2020/0114359 A1 | 4/2020 | Jebrail et al. |
| 2020/0164367 A1 | 5/2020 | Wunsch et al. |
| 2020/0316606 A1 | 10/2020 | Soto-Moreno et al. |
| 2021/0069714 A1 | 3/2021 | Jebrail et al. |
| 2021/0291175 A1 | 9/2021 | Gartner et al. |
| 2021/0370304 A1 | 12/2021 | Jebrail et al. |
| 2022/0118455 A1 | 4/2022 | Jebrail et al. |
| 2022/0161216 A1 | 5/2022 | Cervantes et al. |
| 2022/0219172 A1 | 7/2022 | Soto-Moreno et al. |
| 2022/0250078 A1 | 8/2022 | Soto-Moreno et al. |

FOREIGN PATENT DOCUMENTS

| | | |
|---|---|---|
| CA | 2881783 A1 | 2/2014 |
| CN | 1668527 A | 9/2005 |
| CN | 101609063 A | 12/2009 |
| CN | 102549804 A | 7/2012 |
| CN | 102719526 A | 10/2012 |
| CN | 102740976 A | 10/2012 |
| CN | 102836653 A | 12/2012 |

(56) References Cited

FOREIGN PATENT DOCUMENTS

| | | |
|---|---|---|
| CN | 103014148 A | 4/2013 |
| CN | 103170383 A | 6/2013 |
| CN | 103502386 A | 1/2014 |
| CN | 103946712 A | 7/2014 |
| CN | 104144748 A | 11/2014 |
| CN | 104321141 A | 1/2015 |
| CN | 104995261 A | 10/2015 |
| CN | 105764490 A | 7/2016 |
| CN | 105849032 A | 8/2016 |
| CN | 106092865 A | 11/2016 |
| DE | 19949735 A1 | 5/2001 |
| EP | 2111554 B1 | 5/2013 |
| GB | 2533952 | 7/2016 |
| JP | 2002321449 A | 11/2002 |
| JP | 2006220606 A | 8/2006 |
| JP | 2010500596 A | 1/2010 |
| JP | 2010098133 A | 4/2010 |
| JP | 2010515877 A | 5/2010 |
| JP | 2010180222 A | 8/2010 |
| JP | 2012525687 A | 10/2012 |
| JP | 2015529815 A | 10/2015 |
| WO | WO2000/067907 A2 | 11/2000 |
| WO | WO2001/025137 A1 | 4/2001 |
| WO | WO2003/045556 A2 | 6/2003 |
| WO | WO2004/074169 A1 | 9/2004 |
| WO | WO2005/068993 A1 | 7/2005 |
| WO | WO2005/118129 A1 | 12/2005 |
| WO | WO2006/000828 A2 | 1/2006 |
| WO | WO2006/102309 A2 | 9/2006 |
| WO | WO2007/120240 A2 | 10/2007 |
| WO | WO2007/123908 A2 | 11/2007 |
| WO | WO2007/130294 A2 | 11/2007 |
| WO | WO2007/136386 A2 | 11/2007 |
| WO | WO2008/066828 A2 | 6/2008 |
| WO | WO2009/026339 A2 | 2/2009 |
| WO | WO2009/052348 A2 | 4/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | WO2010/042637 A2 | 4/2010 |
| WO | WO2010/069977 A1 | 6/2010 |
| WO | WO2010/091334 A2 | 8/2010 |
| WO | WO2010/111265 A1 | 9/2010 |
| WO | WO2011/002957 A2 | 1/2011 |
| WO | WO2011/062557 A1 | 5/2011 |
| WO | WO2012/061832 A1 | 5/2012 |
| WO | WO2012/172172 A1 | 12/2012 |
| WO | WO2013/006312 A2 | 1/2013 |
| WO | WO2013/040562 A2 | 3/2013 |
| WO | WO2013/090889 A1 | 6/2013 |
| WO | WO2013/096839 A1 | 6/2013 |
| WO | WO2013/116039 A1 | 8/2013 |
| WO | WO2013/176767 A1 | 11/2013 |
| WO | WO2014/078100 A1 | 5/2014 |
| WO | WO2014/083622 A1 | 6/2014 |
| WO | WO2014/100473 A1 | 6/2014 |
| WO | WO2014/106167 A1 | 7/2014 |
| WO | WO2014/108185 A1 | 7/2014 |
| WO | WO2014/183118 A1 | 11/2014 |
| WO | WO2015/023745 A1 | 2/2015 |
| WO | WO2015/077737 A1 | 5/2015 |
| WO | WO2015/172255 A1 | 11/2015 |
| WO | WO2015/172256 A1 | 11/2015 |
| WO | WO2016/094589 A1 | 6/2016 |
| WO | WO2016/128544 A1 | 8/2016 |
| WO | WO2016/182814 A2 | 11/2016 |
| WO | WO2016/197013 A1 | 12/2016 |
| WO | WO2017/094021 A1 | 6/2017 |
| WO | WO2017/223026 A1 | 12/2017 |
| WO | WO2018/119253 A1 | 6/2018 |
| WO | WO2018/126082 A1 | 7/2018 |
| WO | WO2019/023133 A1 | 1/2019 |
| WO | WO2019/046860 A1 | 3/2019 |
| WO | WO2019/075211 A1 | 4/2019 |
| WO | WO2019/226919 A1 | 11/2019 |
| WO | WO2020/160520 A1 | 8/2020 |
| WO | WO2020/176816 A8 | 9/2020 |
| WO | WO2021/016614 A1 | 1/2021 |
| WO | WO2021/092325 A1 | 5/2021 |
| WO | WO2021/173621 | 9/2021 |

OTHER PUBLICATIONS

Chen et al. (Proceedings of the Fifth International Conference on Nanochannels, Microchannels and Minichannels, Jun. 18-20, 2007, p. 1-7, IDS reference) (Year: 2007).*
Nge et al. (Chem Rev, 2013, 113:2550-2583) (Year: 2013).*
Abdelgawad et al., All-terrain droplet actuation, Lab on a Chip, 8(5), pp. 672-677, May 2008.
Abdelgawad et al.; Low-cost, rapid-prototyping of digital microfluidics devices, Microfluidics and Nanofluidics, 4, pp. 349-355, Apr. 2008.
Abdelgawad et al.; Rapid prototyping in copper substrates for digital microfluidics, Adv. Mater., 19(1), pp. 133-137; Jan. 2007.
Abdelgawad et al; Hybrid microfluidics: a digital-to-channel interface for in-line sample processing and chemical separations, Lab on a Chip, 9(8), pp. 1046-1051, Apr. 2009.
Abdelgawad; Digital Microfluidics for Integration of Lab-on-a-Chip Devices (Doctoral dissertation); University of Toronto; © 2009.
Albrecht et al.; Laboratory testing of gonadal steroids in children; Pediatric Endocrinology Reviews; 5(suppl 1); pp. 599-607; Oct. 2007.
Analog Devices; 24-bit Capicitance-to-Digital converter with temperature sensor, AD7745/AD7746; Analog Devices; Norwood, MA; 28 pages; (the year of publication is sufficiently earlier than the effective U.S. filing date and any foreign priority date so that the particular month of publication is not in issue) 2005.
Analog Devices: Extending the capacitive input range of AD7745/AD7746 Capicitance-to-Digital converter; Analog Devices; Norwood, MA; 5 pages; (the year of publication is sufficiently earlier than the effective U.S. filing date and any foreign priority date so that the particular month of publication is not in issue) 2009.
Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.
Armstrong et al.; A study of plasma free amino acid levels. II. Normal values for children and adults, Metabolism, 22(4), pp. 561-569, Apr. 1973.
Asiello et al.; Miniaturized isothermal nucleic acid amplification, a review; Lab Chip; 11(8); pp. 1420-1430; Apr. 2011.
Au et al., Integrated microbioreactor for culture and analysis of bacteria, algae and yeast, Biomedical Microdevices, 13(1), pp. 41-50, Feb. 2011.
Au et al.; A new angle on pluronic additives: Advancing droplets and understanding in digital microfluidics; Langmuir; 27; pp. 8586-8594; Jun. 2011.
Banatvala et al., Rubella, The Lancet, 363(9415), pp. 1127-1137, Apr. 2004.
Banér et al.; Signal amplification of padlock probes by rolling circle replication; Nuc. Acids Res.; 26(22); pp. 5073-5078; Nov. 1998.
Barany; Genetic disease detection and DNA amplification using cloned thermostable ligase; PNAS; 88(1); pp. 189-193; Jan. 1991.
Barbulovic-Nad et al., A microfluidic platform for complete mammalian cell culture, Lab on a Chip, 10(12), pp. 1536-1542; Jun. 2010.
Barbulovic-Nad et al.; Digital microfluidics for cell-based assays, Lab Chip, 8(4), pp. 519-526; Apr. 2008.
Baxendale et al.; Multistep synthesis using modular flow reactors: bestmann-ohira reagent for the formation of alkynes and triazoles; Angewandte Chemie International Edition; 48(22); pp. 4017-4021; May 2009.

(56) References Cited

OTHER PUBLICATIONS

Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.
Beaucage et al., The Functionalization of Oligonucleotides via Phosphoramidite Derivatives, Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Bergkvist et al., Improved chip design for integrated solid-phase microextraction in on-line proteomic sample preparation, Proteomics, 2(4), pp. 422-429, Apr. 2002.
Bi et al.; Dumbbell probe-mediated cascade isothermal amplification: A novel strategy for label-free detection of microRNAs and its application to real sample assay; Analytica Chimica Acta; 760; pp. 69-74; Jan. 2013.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Boles et al.; Droplet-Based Pyrosequencing Using Digital Microfluidics, Analytical Chemistry; 83(22); pp. 8439-8447; Oct. 14, 2011.
Bollström et al.; A Multilayer Coated Fiber-Based Substrate Suitable for Printed Functionality; Organic Electronics; 10(5); pp. 1020-1023; Aug. 2009.
Bonneil et al., Integration of solid-phase extraction membranes for sample multiplexing: Application to rapid protein identification from gel-isolated protein extracts, Electrophoresis, 23(20), pp. 3589-3598, Oct. 2002.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chem. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Chatterjee et al.; Droplet-based microfluidics with nonaqueous solvents and solutions, Lab Chip, 6(2), pp. 199-206, Feb. 2006.
Chen et al.; Selective Wettability Assisted Nanoliter Sample Generation via Electrowetting-Based Transportation; Proceedings of the 5th International Conference on Nanochannels, Microchannels and Minichannels (ICNMM); Puebla, Mexico; Paper No. ICNMM2007-30184; pp. 147-153; Jun. 18-20, 2007.
Chen et al.; The chemistrode: a droplet-based microfluidic device for stimulation and recording with high temporal, spatial, and chemical resolution; Proceedings of the National Academy of Sciences; 105(44); pp. 16843-16848; Nov. 2004.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Choi et al., Automated digital microfluidic platform for magnetic-particle-based immunoassays with optimization by design of experiments, Anal. Chem., 85(20), pp. 9638-9646; Oct. 2013.
Choi et al., Digital Microfluidics, Annu. Rev. Anal. Chem., 5, pp. 413-440, (Epub) Apr. 2012.
Christiansen; Hormone Replacement Therapy and Osteoporosis; Maturitas, 23, Suppl. pp. S71-S76, May 1996.
Chuang et al.; Direct Handwriting Manipulation of Droplets by Self-Aligned Mirror-EWOO Across a Dielectric Sheet; 19th IEEE International Conf. on Micro Electro Mechanical Systems (MEMS); Instanbul, Turkey; pp. 538-541; Jan. 22-26, 2006.
Cipriano et al.; The cost-effectiveness of expanding newborn screening for up to 21 inherited metabolic disorders using tandem mass spectrometry: results from a decision-analytic model. Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.
Coregenomics; How do SPRI beads work; 31 pages; retrieved from the internet (http://core-genomics.blogspot.com/2012/04/how-do-spri-beads-work.html); Apr. 28, 2012.
Cottam et al.; Accelerated synthesis of titanium oxide nanostructures using microfluidic chips; Lab on a Chip; 7(2); pp. 167-169; Feb. 2007.
Crabtree et al.; Microchip injection and separation anomalies due to pressure effects, Anal. Chem., 73(17), pp. 4079-4086, Sep. 2001.
Cunningham; Testosterone replacement therapy for late-onset hypogonadism. Nature Clinical Practice Urology, 3(5), pp. 260-267, May 2006.
Cuzick; Chemoprevention of breast cancer. Women's Health, 2(6), pp. 853-861, Nov. 2006.
Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.
Dambrot; Of microchemistry and molecules: Electronic microfluidic device synthesizes biocompatible probes; 4 pages, retrieved from the internet (https://phys.org/news/2012-01-microchemistry-molecules-electronic-microfluidic-device.html); Jan. 26, 2012.
Danton et al.; Porphyrin profiles in blood, urine and faeces by HPLC/electrospray ionization tandem mass spectrometry. Biomedical Chromatography, 20(6-7), pp. 612-621, Jun.-Jul. 2006.
Davoust et al.; Evaporation rate of drop arrays within a digital microfluidic system; Sensors and Actuators B Chemical; 189; pp. 157-164; Dec. 2013.
De Mesmaeker et al.; Comparison of rigid and flexible backbones in antisense oligonucleotides; Bioorganic & Medicinal Chem. Lett; 4(3); pp. 395-398; Feb. 1994.
Deligeorgiev et al.; Intercalating Cyanine Dyes for Nucleic Acid Detection; Recent Pat Mat Sci; 2(1); pp. 1-26; Jan. 2006.
Dempcy et al., Synthesis of a thymidyl pentamer of deoxyribonucleic guanidine and binding studies with DNA homopolynucleotides, Proc. Natl. Acad. Sci., 92(13), pp. 6097-6101, Jun. 1995.
Deng et al.; Rapid determination of amino acids in neonatal blood samples based on derivatization with isobutyl chloroformate fol-

(56) References Cited

OTHER PUBLICATIONS lowed by solid-phase microextraction and gas chromatography/mass spectrometry. Rapid Communications in Mass Spectrometry, 18(1), pp. 2558-2564, Nov. 2004.

Denneulin et al.; Infra-red assisted sintering of inkjet printed silver tracks on paper substrates; J Nanopart Res; 13(9); pp. 3815-3823; Sep. 2011.

Dibbelt et al.; Determination of natural and synthetic estrogens by radioimmunoassay: Comparison of direct and extraction methods for quantification of estrone in human serum. Clinical Laboratory, 44(3), 137-143, Mar. 1998.

Dietzen et al.; National academy of clinical biochemistry laboratory medicine practice guidelines: follow-up testing for metabolic disease identified by expanded newborn screening using tandem mass spectrometry; executive summary, Clinical Chemistry, 55(9), pp. 1615-1626, Sep. 2009.

Diver et al.; Warning on plasma oestradiol measurement. Lancet, 330(8567), p. 1097, Nov. 1987.

Divino Filho et al.; Simultaneous measurements of free amino acid patterns of plasma, muscle and erythrocytes in healthy human subjects, Clinical Nutrition, 16(6), pp. 299-305, Dec. 1997.

Dixon et al.; An inkjet printed, roll-coated digital microfluidic device for inexpensive, miniaturized diagnostic assays; Lab on a Chip; 16(23); pp. 4560-4568; Nov. 2016.

Djerassi; Chemical birth of the pill. American Journal of Obstetrics and Gynecology, 194(1), pp. 290-298, Jan. 2006.

Dobrowolski et al.; DNA microarray technology for neonatal screening, Acta Paediatrica Suppl, 88(432), pp. 61-64, Dec. 1999.

Doebler et al.; Continuous-flow, rapid lysis devices for biodefense nucleic acid diagnostic systems; Journal of the Association for Laboratory Automation; 14(3); pp. 119-125; Jun. 2009.

Dong et al.; Highly sensitive multiple microRNA detection based on flourescence quenching of graphene oxide and isothermal strand-displacement polymerase reaction; Anal Chem; 84; pp. 4587-4593; Apr. 2012.

Dryden et al.; Integrated digital microfluidic platform for voltammetric analysis; Analytical Chemistry; 85(18); pp. 8809-8816; Sep. 2013.

Duffy et al.; Rapid prototyping of microfluidic systems in Poly (dimethylsiloxane), Anal. Chem., 70(23), pp. 4974-4984, Dec. 1998.

Edgar et al.; Capillary electrophoresis separation in the presence of an immiscible boundary for droplet analysis, Anal. Chem., 78(19), pp. 6948-6954 (author manuscript, 15 pgs.), Oct. 2006.

Egholm et al., PNA hybridizes to complementary oligonucleotides obeying the Watson-Crick hydrogen-bonding rules, Nature, 365(6446), pp. 566-568, Oct. 1993.

Egholm et al., Recognition of guanine and adenine in DNA by cytosine and thymine containing peptide nucleic acids (PNA), J. Am. Chem. Soc., 114(24), pp. 9677-9678; Nov. 1992.

Ehrmann; Polycystic ovary syndrome. New England Journal of Medicine; 352(12); pp. 1223-1236; Mar. 2005.

Ekstrom et al., Miniaturized solid-phase extraction and sample preparation for MALDI MS using a microfabricated integrated selective enrichment target, Journal of Proteome Research, 5(5), pp. 1071-1081, May 2006.

Ekstrom et al., Polymeric integrated selective enrichment target (ISET) for solid-phase-based sample preparation in MALDI-TOF MS, Journal of Mass Spectrometry, 42(11), pp. 1445-1452, Nov. 2007.

Ekstrom et al.,On-chip microextraction for proteomic sample preparation of in-gel digests, Proteomics, 2(4), pp. 413-421, Apr. 2002.

El-Ali et al.; Cells on chips; Nature (2006) insight Review; 442(7101); pp. 403-411; Jul. 2006.

Fair; Digital microfluidics: Is a true lab-on-a-chip possible?; Microfuid. Nanofluid.; 3(3); pp. 245-281; Jun. 2007.

Falk et al.; Measurement of Sex Steroid Hormones in Breast Adipocytes: Methods and Implications; Cancer Epidemiol Biomarkers Prev; 17(8); pp. 1891-1895; Aug. 2008.

Fan et al.; Cross-scale electric manipulations of cells and droplets by frequency-modulated dielectrophoresis and electrowetting; Lab Chip; 8(8); pp. 1325-1331; Aug. 2008.

Fan et al.; Electrically Programmable Surfaces for Configurable Patterning of Cells; Advanced Materials; 20(8); pp. 1418-1423; Apr. 2008.

Fan et al.; Integrated barcode chips for rapid, multiplexed analysis of proteins in microliter quanties of blood; Nature Biotechnology; 26(12); pp. 1373-1378; 15 pages (Author Manuscript); Dec. 2008.

Faure et al.; Improved electrochemical detection of a transthyretin synthetic peptide in the nanomolar range with a two-electrode system integrated in a glass/PDMS microchip; Lab on a Chip; 14(15); pp. 2800-2805, Aug. 2014.

Fobel et al.; DropBot: An open-source digital microfluidic control system with precise control of electrostatic driving force and instantaneous drop velocity measurement; Applied Physics Letters: 102(19); 193513 (5 pgs.); May 2013.

Foote et al., Preconcentration of proteins on microfluidic devices using porous silica membranes, Analytical Chemistry, 77(1), pp. 57-63, Jan. 2005.

Freire et al.; A practical interface for microfluidics and nanoelectrospray mass spectrometry, Electrophoresis, 29(9), pp. 1836-1843, May 2008.

Fridley et al., Controlled release of dry reagents in porous media for tunable temporal and spatial distribution upon rehydration, Lab Chip, 12(21), pp. 4321-4327 (author manuscript, 14 pgs.), Nov. 2012.

Fu et al., Controlled Reagent Transport in Disposable 2D Paper Networks, Lab. Chip, 10(7), pp. 918-920 (author manuscript, 9 pgs.), Apr. 2010.

Gao et al.; Unusual conformation of a 3'-thioformacetal linkage in a DNA duplex; J. Biomol. NMR; 4(1); pp. 17-34; Jan. 1994.

Gentili et al.; Analysis of free estrogens and their conjugates in sewage and river waters by solid-phase extraction then liquid chromatography-electrospray-tandem mass spectrometry. Chromatographia 56(1), pp. 25-32, Jul. 2002.

Gerasimova et al.; Fluorometric method for phenylalanine microplate assay adapted for phenylketonuria screening, Clinical Chemistry, 35(10), pp. 2112-2115, Oct. 1989.

Gong et al., All-Electronic Droplet Generation On-Chip With Real-Time Feedback Control for EWOD Digital Microfluidics, Lab Chip, 8(6), pp. 898-906 (author manuscript, 20 pgs.), Jun. 2008.

Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.

Gong et al.; Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.

Goto et al.; Colorimetric detection of loop-mediated isothermal amplification reaction by using hydroxy naphthol blue; Biotechniques; 46(3); pp. 167-172; Mar. 2009.

Gottschlich et al.; Integrated microchip-device for the digestion, separation and postcolumn labeling of proteins and peptides, J. Chromatogr. B, 745(1), pp. 243-249, Aug. 2000.

Govindarajan et al., A low cost point-of-care viscous sample preparation device for molecular diagnosis in the developing world; an example of microfluidic origami, Lab Chip. 12(1), pp. 174-181, Jan. 2012.

Green et al.; Neonatal screening by DNA microarray: spots and chips, Nature Reviews Genetics, 6(2), pp. 147-151, Feb. 2005.

Hatch et al., Integrated preconcentration SDS-PAGE of proteins in microchips using photopatterned cross-linked polyacrylamide gels, Analytical Chemistry, 78(14), pp. 4976-4984, Jul. 2006.

He et al. (ed); Food microbiological inspection technology; Chapter 5: Modern food microbiological inspection technology; China Quality Inspection press; pp. 111-113; (English Translation included) Nov. 2013.

Henderson et al.; Estrogens as a cause of human cancer: The Richard and Hinda Rosenthal Foundation award lecture. Cancer Res, 48(2), pp. 246-253, Jan. 1988.

(56) References Cited

OTHER PUBLICATIONS

Hennequin et al.; Synthesizing microcapsules with controlled geometrical and mechanical properties with microfluidic double emulsion technology; Langmuir; 25(14); pp. 7857-7861; Jul. 2009.

Herdewijn et al.; 2'-5'-Oligoadenylates (2-5A) as Mediators of Interferon Action. Synthesis and Biological Activity of New 2-5A Analogues. E. De Clerq (ed.) Frontiers in Microbiology, 231-232, Springer, Dordrecht Jan. 1987.

Hertz et al.; Estrogen-progestogen combinations for contraception. Journal of the American Medical Association, 198(9), pp. 1000-1006, Nov. 1966.

Hong et al.; Three-dimensional digital microfluidic manipulation of droplets in oil medium; Scientific Reports; 5 (Article No. 10685); 5 pgs.; Jun. 2015.

Horn et al.; Oligonucleotides with alternating anionic and cationic phosphoramidate linkages: Synthesis and hybridization of stereo-uniform isomers; Tetrahedron Lett.; 37(6); pp. 743-746; Feb. 1996.

Hou et al.; Microfluidic devices for blood fractionation; Micromachines; 2(3); pp. 319-343; Jul. 20, 2011.

Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.

Ihalainen et al; Application of paper-supported printed gold electrodes for impedimetric immunosensor development; Biosensors; 3(1); pp. 1-17; Mar. 2013.

Jacobson et al.; High-Speed Separations on a Microchip, Anal. Chem., 66(7), pp. 1114-1118, Apr. 1994.

Jacobson et al.; Precolumn Reactions with Electrophoretic Analysis Integrated on a Microchip, Anal. Chem., 66(23), pp. 4127-4132, Dec. 1994.

Jebrail et al., Combinatorial Synthesis of Peptidomimetics Using Digital Microfluidics, J. Flow Chem., 2(3), pp. 103-107; (online) Aug. 2012.

Jebrail et al., Let's get digital: digitizing chemical biology with microfluidics, Curr. Opin. Chem. Biol., 14(5), 574-581, Oct. 2010.

Jebrail et al., Synchronized synthesis of peptide-based macrocycles by digital microfluidics, Angew. Chem. Int. Ed. Eng., 49(46), pp. 8625-8629, Nov. 2010.

Jebrail et al., World-to-digital-microfluidic interface enabling extraction and purification of RNA from human whole blood, Analytical Chemistry, 86(8), pp. 3856-3862, Apr. 2014.

Jebrail et al.; A Solvent Replenishment Solution for Managing Evaporation of Biochemical Reactions in Air-Matrix Digital Microfluidics Devices, Lab on a Chip, 15(1), pp. 151-158; Jan. 2015.

Jebrail et al.; Digital Microfluidic Method for Protein Extraction by Precipitation; Analytical Chemistry; 81(1); pp. 330-335; Jan. 2009.

Jebrail et al.; Digital Microfluidics for Automated Proteomic Processing, Journal of Visualized Experiments, 33 (e1603), 5 pgs., Nov. 2009.

Jebrail et al.; Digital microfluidics: a versatile tool for applications in chemistry, biology and medicine; Lab Chip; 12 (14); pp. 2452-2463; Jul. 2012.

Jemere et al., An integrated solid-phase extraction system for sub-picomolar detection, Electrophoresis, 23(20), pp. 3537-3544, Oct. 2002.

Jenkins et al., The biosynthesis of carbocyclic nucleosides; Chem. Soc. Rev.; 24(3); pp. 169-176; Jan. 1995.

Jensen et al.; Free-running enzymatic oligonucleotide synthesis for data storage applications; bioRxiv; 1:355719; 7 pages; Jan. 2018.

Jessome et al.; Ion Suppression: A Major Concern in Mass Spectrometry. LC-GC North America, 24(5), pp. 498-510, May 2006.

Jia et al.; Ultrasensitive detection of microRNAs by exponential isothermal amplification; Angew. Chem. Int. Ed. Engl.; 49(32); pp. 5498-5501; Jul. 2010.

Jung et al.; Hybridization of Alternating Cationic/Anionic Oligonucleotides to RNA Segments; Nucleosides & Nucleotides; 13(6-7); pp. 1597-1605; Jul. 1994.

Kaaks et al.; Postmenopausal serum androgens, oestrogens and breast cancer risk: The European prospective investigation into cancer and nutrition. Endocrine-Related Cancer, 12(4), pp. 1071-1082, Dec. 2005.

Keng et al., Micro-chemical synthesis of molecular probes on an electronic microfluidic device,PNAS, 109(3), pp. 690-695; Jan. 2012.

Kiedrowski et al., Parabolic Growth of a Self-Replicating Hexadeoxynucleotide Bearing a 3'-5'-Phosphoamidate Linkage; Angew. Chemie Intl. Ed.; 30(4); pp. 423-426; Apr. 1991.

Kim et al.; Automated digital microfluidic sample preparation for next-generation DNA sequencing; JALA; Journal of the Association for Laboratory Automation; 16(6); pp. 405-414; Dec. 2011.

Kim et al., A Microfluidic DNA Library Preparation Platform for Next-Generation Sequencing, PLOS ONE, 8(7), Article ID: e68988; 9 pgs., Jul. 2013.

Kim et al.; Microfabricated Monolithic Multinozzle Emitters for Nanoelectrospray Mass Spectrometry; Anal Chem; 79(10); pp. 3703-3707; May 2007.

Koster et al.; Drop-based microfluidic devices for encapsulation of single cells; Lab on a Chip; 8(7); pp. 1110-1115; Jul. 2008.

Kralj et al.; Integrated continuous microfluidic liquid-liquid extraction. Lab on a Chip, 7(2), pp. 256-263, Feb. 2007.

Kutter et al., Solid phase extraction on microfluidic devices, Journal of Microcolumn Separations, 12(2), pp. 93-97, Jan. 2000.

Kutter et al., Solvent-Programmed Microchip Open-Channel Electrochromatography, Analytical Chemistry, 70(15), pp. 3291-3297, Aug. 1998.

Labrie et al.; Androgen glucuronides, instead of testosterone, as the new markers of androgenic activity in women. The Journal of Steroid Biochemistry and Molecular Biology, 99(4-5), pp. 182-188, Jun. 2006.

Labrie; Intracrinology. Molecular and Cellular Endocrinology, 78(3), pp. C113-C118, Jul. 1991.

Lamar et al.; Serum sex hormones and breast cancer risk factors in postmenopausal women. Cancer Epidemiol Biomarkers Prev, 12(4), pp. 380-383, Apr. 2003.

Langevin et al., A rapid and unbiased method to produce strand-specific RNA-Seq libraries from small quantities of starting materiaRNA Biol., 10(4), pp. 502-515, (online) Apr. 2013.

Lawyer et al.; High-level expression, purification, and enzymatic characterization of full-length Thermus aquaticus DNA polymerase and a truncated form deficient in 5' to 3' exonuclease activity; Genome Res; 2(4); pp. 275-287; May 1993.

Lawyer et al.; Isolation, characterization, and expression in *Escherichia coli* of the DNA polymerase gene from Thermus aquaticus; J. Biol. Chem.; 264; pp. 6427-6437; Apr. 1989.

Lebrasseur et al.; Two-dimensional electrostatic actuation of droplets using a single electrode panel and development of disposable plastic film card; Sensors and Actuators A; 136(1); pp. 368-386; May 2007.

Lee et al.; Electrowetting and electrowetting-on-dielectric for microscale liquid handling, Sens. Actuators A, 95(2), pp. 259-268, Jan. 2002.

Lee et al.; Removal of bovine serum albumin using solid-phase extraction with in-situ polymerized stationary phase in a microfluidic device; Journal of Chromatography A; 1187(1-2); pp. 11-17; Apr. 2008.

Lee et al.; Surface-Tension-Driven Microactuation Based on Continuous Electrowetting; J. Microelectromechanical Systems; 9(2); pp. 171-180; Jun. 2000.

Leriche et al.; Cleavable linkers in chemical biology; Bioorganic & Medicinal Chemistry; 20(2); pp. 571-582; Jan. 15, 2012.

Letsinger et al., Cationic oligonucleotides, J. Am. Chem. Soc., 110(13), pp. 4470-4471, Jun. 1988.

Letsinger et al.; Effects of pendant groups at phosphorus on binding properties of d-ApA analogues, Nucl. Acids Res., 14(8), pp. 3487-3499, Apr. 1986.

Letsinger et al., Phosphoramidate analogs of oligonucleotides, J. Org. Chem., 35(11), pp. 3800-3803, Nov. 1970.

Lettieri et al., A novel microfluidic concept for bioanalysis using freely moving beads trapped in recirculating flows, Lab on a Chip, 3(1), pp. 34-39, Feb. 2003.

(56) References Cited

OTHER PUBLICATIONS

Levy et al.; Genetic screening of newborns, Annual Review of Genomics and Human Genetics, 1, pp. 139-177, Sep. 2000.

Li et al., A perspective on paper-based microfluidics: Current status and future trends, Biomicrofluidics, 6(1), pp. 011301 (13 pgs), Mar. 2012.

Li et al., Application of microfluidic devices to proteomics research: identification of trace-level protein digests and affinity capture of target peptides, Molecular & cellular Proteomics, 16(2), pp. 157-168, Feb. 2002.

Li et al., Paper-based microfluidic devices by plasma treatment, Anal. Chem., 80(23), pp. 9131-9134, Nov. 2008.

Li et al.; A Low-Cost and High resolution droplet position detector for an intelligent electrowetting on dielectric device; Journal of Lab. Automation 2015; 20(6); pp. 663-669; Dec. 2015.

Li et al.; One-step ultrasensitive detection of microRNAs with loop-mediated isothermal amplification (LAMP); Chem Commun; 47(9); pp. 2595-2597; Mar. 2011.

Li et al.; Test structure for characterizing low voltage coplanar EWOD system; IEEE Transaction on Semiconductor Manufacturing; IEEE Service Center; Piscataway, NJ.; 22(1); pp. 88-95; Feb. 4, 2009.

Liana et al.; Recent Advances in Paper-Based Sensors; Sensors; 12(9); pp. 11505-11526; Aug. 2012.

Link et al.; Electric Control of Droplets in Microfluidic Devices; Angew Chem Int Ed Engl; 45(16); pp. 2556-2560; Apr. 2006.

Liu et al., Three-dimensional paper microfluidic devices assembled using the principles of origami, JACS, 133(44), pp. 17564-17566, Nov. 2011.

Liu et al.; Attomolar ultrasensitive microRNA detection by DNA-scaffolded silver-nanocluster probe based on isothermal amplification; Anal Chem; 84(12); pp. 5165-5169; Jun. 2012.

Lizardi et al.; Mutation detection and single-molecule counting using isothermal rolling-circle amplification; Nat. Genet.; 19(3); pp. 225-232; Jul. 1998.

Locascio et al.; Surface chemistry in polymer microfluidic systems; in Lab-on-a-Chip; Elsevier Science; 1st Ed.; pp. 65-82; Oct. 2003.

Loeber; Neonatal screening in Europe; the situation in 2004, Journal of Inherited Metabolic Disease, 30(4), pp. 430-438, Aug. 2007.

Lohman et al.; Efficient DNA ligation in DNA-RNA hybrid helices by Chlorella virus DNA ligase; Nucleic Acids Research; 42(3); pp. 1831-1844; Nov. 2013.

Luk et al.; Pluronic Additives: A Solution to Sticky Problems in Digital Microfluidics, Langmuir, 24(12), pp. 6382-6389, Jun. 2008.

Luk et al.; A digital microfluidic approach to proteomic sample processing; Analytical Chemistry; 81(11); pp. 4524-4530; Jun. 2009.

Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.

Mais et al.; A solvent replenishment solution for managing evaporation of biochemical reactions in air-matrix digital microfluidics devices; Lab on a Chip; 15(1); pp. 151-158; Jan. 2015.

Makamba et al.; Surface modification of poly(dimethylsiloxane) microchannels; Electrophoresis; 24(21); pp. 3607-3619; Nov. 2003.

Malloggi et al.; Electrowetting—A versatile tool for controlling microdrop generation, Eur. Phys. J. E, 26(1), pp. 91-96, May 2008.

Mandl et al.; Newborn screening program practices in the United States: notification, research, and consent, Pediatrics, 109(2), pp. 269-273, Feb. 2002.

Maroney et al.; A Rapid, quantitative assay for direct detection of microRNAs and other small RNAs using splinted ligation; RNA; 13(6); pp. 930R936; Jun. 2007.

Maroney et al.; Direct detection of small RNAs using splinted ligation; Nat. Protocols3(2); pp. 279-287; Jan. 2008.

Marre et al.; Synthesis of micro and nanostructures in microfluidic systems; Chemical Society Reviews; 39(3); pp. 1183-1202; Mar. 2010.

Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.

Martinez et al., Three-dimensional microfluidic devices fabricated in layered paper and tape, PNAS, 105(50), pp. 19606-19611, Dec. 2008.

Martinez et al.; Patterned paper as a platform for inexpensive low-volume, portable bioassays, Angewandte Chemie, 46(8), pp. 1318-1320, Feb. 2007.

Martinez-Sanchez et al.; MicroRNA Target Identification—Experimental Approaches; Biology; 2; pp. 189-205; Jan. 2013.

Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.

Mauney, Thermal Considerations for Surface Mount Layouts, in Texas Instruments Portable Power Supply Design Seminar, 16 pgs., 2006.

Mega; Heterogenous ion-exchange membranes RALEX; 3 pgs.; retrieved Mar. 1, 2016 from the internet: http://www.mega.cz/heterogenous-ion-exchange-membranes-ralex.html.

Meier et al., The photochemistry of stilbenoid compounds and their role in materials technology, Chem. Int. Ed. Engl., 31(11), pp. 1399-1420, Nov. 1992.

Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.

Michigan Dept. of Community Health; Specimen collection procedure from Michigan Newborn Screening Program, 37 pgs., (retrieved Feb. 9, 2017 online: http://web.archive.org/web/20100715000000*/http://www.michigan.gov/documents/Bloodco2_60773_7.pdf) Jul. 2009.

Miller et al.; A digital microfluidic approach to homogeneous enzyme assays, Anal. Chem., 80(5), pp. 1614-1619, Mar. 2008.

Millington et al.; Digital Microfluidics: A Future Technology in the Newborn Screening Laboratory?, Seminars in Perinatology, 34(2), pp. 163-169 (Author Manuscript, 14 pgs.), Apr. 2010.

Millington et al.; Digital Microfluidics: A novel platform for multiplexed detection of LSDs with potential for newborn screening (conference presentation); Oak Ridge Conference; 15 pgs.; 2009.

Millington et al.; Tandem mass spectrometry: a new method for acylcarnitine profiling with potential for neonatal screening for inborn errors of metabolism, Journal of Inherited Metabolic Disease, 13(3), pp. 321ý324, May 1990.

Millington et al.; The Analysis of Diagnostic Markers of Genetic Disorders in Human Blood and Urine Using Tandem Mass Spectrometry With Liquid Secondary Ion Mass Spectrometry, International Journal of Mass Spectrometry, 111, pp. 211-228, Dec. 1991.

Miralles et al.; A Review of Heating and Temperature Control in Microfluidic Systems: Techniques and Applications; Diagnostics; 3; pp. 33-67; Jan. 2013.

Mitchell et al.; Circulating microRNAs as stable blood-based markers for cancer detection; Proc Nat Acad Sci; 105(30); pp. 10513-10518; Jul. 2008.

Moon et al.; An integrated digital microfluidic chip for multiplexed proteomic sample preparation and analysis by MALDI-MS. Lab Chip, 6(9), pp. 1213-1219, Sep. 2006.

Moqadam et al.; The Hunting of Targets: Challenge in miRNA Research; Leukemia; 27(1); pp. 16-23; Jan. 2013.

Mousa et al.; Droplet-scale estrogen assays in breast tissue, blood, and serum, Science Translational Medicine, 1(1), 6 pgs., Oct. 2009.

Murran et al.; Capacitance-based droplet position estimator for digital microfluidic devices; Lab Chip;12(11); pp. 2053-2059; May 2012.

Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.

Nelson et al., Incubated protein reduction and digestion on an EWOD digital microfluidic chip for MALDI-MS, Analytical Chemistry, 82(23), pp. 9932-9937, Dec. 2010.

(56) References Cited

OTHER PUBLICATIONS

Newborn Screening Ontario, The newborn screening ontario unsatisfactory sample indicator (educational resource), 3 pgs., retrieved online: https://www.newbornscreening.on.ca/en/health-care-providers/submitters/report-cards/nso_unsatisfatory_sample_indicator_jan_2017. (web address was available to applicant(s) at least as of Jan. 2010).

Ng et al., Digital microfluidic magnetic separation for particle-based immunoassays, Anal. Chem., 84(20), 8805-8812, Oct. 2012.

Nilsson et al.; RNA-templated DNA ligation for transcript analysis; Nucl. Acid Res.; 29(2); pp. 578-581; Jan. 2001.

Njiru; Loop-Mediated Isothermal Amplification Technology: Towards Point of Care Diagnostics; PLOS; 6(6); pp. e1572 (4 pgs.); Jun. 2012.

Notomi et al.; Loop-mediated isothermal amplification of DNA; Nucleic Acid Research; 28(12); p. e63 (7 pgs.); Jun. 2000.

Okubo et al. .; Liquid-liquid extraction for efficient synthesis and separation by utilizing micro spaces. Chemical Engineering Science, 63(16), pp. 4070-4077, Aug. 2008.

Oleschuk et al., Trapping of bead-based reagents within microfluidic systems: On-chip solid-phase extraction and electrochromatography, Analytical Chemistry, 72(3), pp. 585-590, Feb. 2000.

Padilla et al.; Newborn screening in the Asia Pacific region, Journal of Inherited Metabolic Disease, 30(4), pp. 490-506, Aug. 2007.

Palluk et al.; De novo DNA synthesis using polymerase-nucleotide conjugates; Nature biotechnology; 36(7); pp. 645-650; Jun. 18, 2018.

Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.

Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.

Parida et al.; Rapid detection and differentiation of Dengue virus serotypes by a real-time reverse transcription-loop-mediated isothermal amplification assay; J Clinical Microbiology; 43(6); pp. 2895-2903; Jun. 2005.

Pauwels et al., Biological-Activity of New 2-5a Analogs, Chemica Scripta, 26(1), pp. 141-145, Mar. 1986.

Peltonen et al.; Printed electrodes on tailored paper enable electrochemical functionalization of paper; TAPPI Nanotechnology Conference; Espoo, Finland; 20 pgs.; Sep. 2010.

Peterschmitt et al.; Reduction of false negative results in screening of newborns for homocystinuria, New England Journal of Medicine, 341(21), 1572-1576, Nov. 1999.

Petersen et al., On-chip electro membrane extraction, Microfluidics and Nanofluidics, 9(4), pp. 881-888, Oct. 2010.

Pitt et al.; Hormone replacement therapy for osteoporosis. Lancet, 335(8695), p. 978, Apr. 1990.

Pollack et al.; Electrowetting-based actuation of droplets for integrated microfluidics; Lab on a Chip; 2(2); pp. 96-101; May 2002.

Pollack et al.; Electrowetting-based actuation of liquid droplets for microfluidic applications, Appl. Phys. Lett., 77(11), pp. 1725-1726, Sep. 2000.

Provincial Health Services Authority (British Columbia Perinatal Health Program), Perinatal Services BC Neonatal Guideline 9: Newborn Screening, 29 pgs., (retrieved Feb. 9, 2017 online: http://www.perinatalservicesbc.ca/health-professionals/guidelines-standards/newborn) guideline revised: Dec. 2010.

Rahhal et al.; The impact of assay sensitivity in the assessment of diseases and disorders in children. Steroids, 73(13), pp. 1322-1327, Dec. 2008.

Rashad; Clinical applications of tandem mass spectrometry: ten years of diagnosis and screening for inherited metabolic diseases, Journal of Chromatography B: Biomedical Sciences and Applications, 758(1), pp. 27-48, Jul. 2001.

Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.

Rawls, Optimistic About Antisense: Promising clinical results and chemical strategies for further improvements delight antisense drug researchers; Chemical & Engineering News; 75(22); pp. 35-39; Jun. 2, 1997.

Ren et al., Automated on-chip droplet dispensing with volume control by electro-wetting actuation and capacitance metering, Sens. Actuator B Chem., 98(2-3), pp. 319-327, Mar. 2004.

Ren et al.; Design and testing of an interpolating mixing architecture for electrowetting-based droplet-on-chip chemical dilution; 12th International Conference on Transducers, Solid-State Sensors, Actuators and Microsystems; vol. 2; Boston, MA, USA; pp. 619-622; Jun. 8-12, 2003.

Ro et al.; Poly (dimethylsiloxane) microchip for precolumn reaction and micellar electrokinetic chromatography of biogenic amines, Electrophoresis, 23(7-8), pp. 1129-1137, Apr. 2002.

Roman et al.; Fully integrated microfluidic separations systems for biochemical analysis, J. Chromatogr. A, 1168(1-2), pp. 170-188, Oct. 2007.

Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.

Sabourin et al.; Interconnection blocks: a method for providing reusable, rapid, multiple, aligned and planar microfluidic interconnections; Journal of Micromechanics and Microengineering; 19(3); 10 pages; doi: 10.1088/0960-1317/19/3/035021; Feb. 18, 2009.

Sadeghi et al.; On Chip Droplet Characterization: A Practical, High-Sensitivity Measurement of Droplet Impedance in Digital Microfluidics; Anal. Chem.; 84(4); pp. 1915-1923; Feb. 2012.

Sahai et al.; Newborn screening, Critical Reviews in Clinical Laboratory Sciences, 46(2), pp. 55-82, (online) Mar. 2009.

Samsi et al.; A Digital Microfluidic Electrochemical Immunoassay; Lab on a Chip; 14(3); pp. 547-554; Feb. 2014.

Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.

Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.

Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.

Sasano et al.; From Endocrinology to Intracrinology. Endocr Pathol, 9(1), pp. 9-20, Spring 1998.

Satoh et al.; Electrowetting-based valve for the control of the capillary flow, J. Appl. Phys., 103(3), 034903, Feb. 2008.

Satoh et al.; On-chip microfluidic transport and mixing using electrowetting and incorporation of sensing functions, Anal. Chem., 77(21), pp. 6857-6863, Nov. 2005.

Sawai et al., Synthesis and properties of oligoadenylic acids containing 2?-5? phosphoramide linkage, Chem. Lett., 13(5), pp. 805-808, May 1984.

Schertzer et al.; Using capacitance measurements in EWOD devices to identify fluid composition and control droplet mixing; Sens. Actuators B; 145(1); pp. 340-347; Mar. 2010.

Scriver_Commentary; A Simple Phenylalanine Method for Detecting Phenylketonuria in Large Populations of Newborn Infants by Guthrie et al., Pediatrics, 32(3), 338-343, Sep. 1963.

Shah et al., On-demand droplet loading for automated organic chemistry on digital microfluidics, Lab Chip, 13(14), pp. 2785-2795, Jul. 2013.

Shamsi et al; A digital microfluidic electrochemical immunoassay; Lab on a Chip; 14(3); pp. 547-554; (the year of publication is sufficiently earlier than the effective U.S. filing date and any foreign priority date so that the particular month of publication is not in issue) 2014.

Shih et al., A feedback control system for high-fidelity digital microfluidics, Lab Chip, 11(3), pp. 535-540, Feb. 2011.

(56) References Cited

OTHER PUBLICATIONS

Simpson et al.; Estrogen—the Good, the Bad, and the Unexpected. Endocr Rev, 26(3), pp. 322-330; May 2005.
Sinha et al., A Versatile Automated Platform for Micro-scale Cell Stimulation Experiments, J. Vis. Exp., e50597, 8 pgs., Aug. 2013.
Sinton et al.; Electroosmotic velocity profiles in microchannels, Colloids Surf. A, 222(1-3), pp. 273-283, Jul. 2003.
Skendzel, Rubella immunity: Defining the level of protective antibody, Am. J. Clin. Pathol., 106(2), 170-174, Aug. 1996.
Smith et al; Diagnosis and Management of Female Infertility. Journal of the American Medical Association 290(13), pp. 1767-1770, Oct. 2003.
Sooknanan et al., Nucleic Acid Sequence-Based Amplification, Ch. 12; Molecular Methods for Virus Detection (1st Ed.), Academic Press, Inc., pp. 261-285; Jan. 1995.
Sprinzl et al., Enzymatic incorporation of ATP and CTP analogues into the 3' end of tRNA, Eur. J. Biochem., 81(3), pp. 579-589, Dec. 1977.
Srinivasan et al.; An integrated digital microfluidic lab-on-a-chip for clinical diagnostics on human physiological fluids, Lab Chip, 4(4), pp. 310-315, Aug. 2004.
Stanczyk et al.; Standardization of Steroid Hormone Assays Why, How, and When?, Cancer Epidemiol Biomarkers Prev, 16(9), pp. 1713-1719, Sep. 2007.
Steckl et al.; Flexible Electrowetting and Electrowetting on Flexible Substrates; Proc. SPIE 7956; Advances in Display Technologies; and E-papers and Flexible Displays; 795607 (6 pgs.); Feb. 2011.
Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.
Sun et al.; Rapid and direct microRNA quantification by an enzymatic luminescence assay; (author manuscript; 17 pgs.) Analytical Biochemistry; 429(1); pp. 11-17; Oct. 2012.
Svoboda et al.; Cation exchange membrane integrated into a microfluidic device; Microelectronic Engineering; 86; pp. 1371-1374; Apr.-Jun. 2009.
Szarewski et al.; Contraception. Current state of the art. British Medical Journal, 302(6787), pp. 1224-1226, May 1991.
Szymczak et al.; Concentration of Sex Steroids in Adipose Tissue after Menopause. Steroids, 63(5-6), pp. 319-321, May/Jun. 1998.
Tachibana et al.; Application of an enzyme chip to the microquantification of L-phenylalanine, Analytical Biochemistry, 359(1), pp. 72-78, Dec. 2006.
Tan et al.; A lab-on-a-chip for detection of nerve agent sarin in blood; Lab Chip; 8(6); pp. 885-891; Jun. 2008.
Tang et al.; Mechano-regulated surface for manipulating liquid droplets; Nature Communications; 10 pages; DOI: 10.1038/ncomms14831; ; Apr. 4, 2017.
Teh et al.; Droplet microfluidics, Lab Chip, 8(2), pp. 198-220, Feb. 2008.
Theberge et al.; Microdroplets in microfluidics: an evolving plarform for discoveries in chemistry and biology; Angewandte Chemie International Edition; 49(34); pp. 5846-5868; Aug. 2010.
Therrell et al.; Newborn screening in North America, Journal of Inherited Metabolic Disease, 30(4), pp. 447-465, Aug. 2007.
Tian et al., Printed two-dimensional micro-zone plates for chemical analysis and ELISA, Lab on a Chip, 11(17), pp. 2869-2875, Sep. 2011.
Tobjörk et al., IR-sintering of ink-jet printed metal-nanoparticles on paper, Thin Solid Films, 520(7), pp. 2949-2955, Jan. 2012.
Tomita et al.; Loop-mediated isothermal amplification (LAMP) of gene sequences and simple visual detection of products; Nature Protocols; 3(5); pp. 877-882; (online) Apr. 2008.
Torkkeli; Droplet microfluidics on a planar surface; VTT Technical Research Centre of Finland; Publications 504; 214 pages (Dissertation); Oct. 2003.
Turgeon et al.; Combined Newborn Screening for Succinylacetone, Amino Acids, and Acylcarnitines in Dried Blood Spots, Clinical Chemistry, 54(4), pp. 657-664, Apr. 2008.

Udenfriend et al.; Fluorescamine: a reagent for assay of amino acids, peptides, proteins, and primary amines in the picomole range, Science, 178(4063), pp. 871-872, Nov. 1972.
Unger et al.; Monolithic microfabricated valves and pumps by multilayer soft lithography, Science, 288(5463), pp. 113-116, Apr. 2000.
Univ. of Maryland—Baltimore Washington Medical Center; Plasma amino acids, 6 pgs., retrieved Feb. 10, 2017 from: http://www.mybwmc.org/library/1/003361, Web address available to applicant(s) at least as of Jan. 2010.
Verkman; Drug Discovery in Academia; Am J Physiol Cell Physiol; 286(3); pp. C465-C474; Feb. 2004.
Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.
Walker et al.; A passive pumping method for microfluidic devices, Lab Chip, 2(3), pp. 131-134, Aug. 2002.
Wang et al., Paper-based chemiluminescence ELISA: lab-on-paper based on chitosan modified paper device and, Biosens. Bioelectron., 31(1), pp. 212-218, Jan. 2012.
Wang et al., Simple and covalent fabrication of a paper device and its application in sensitive chemiluminescence immunoassay, Analyst, 137(16), pp. 3821-3827, Aug. 2012.
Wang et al.; An integrated microfluidic device for large-scale in situ click chemistry screening; Lab on a Chip; 9(16); 9(16); pp. 2281-2285; 9 pages (Author Manuscript); Aug. 2009.
Wang et al.; Highly sensitive detection of microRNAs based on isothermal exponential amplification-assisted generation of catalytic G-quadruplexDNAzyme; Biosensors and Bioelectronics, 42; pp. 131-135; Apr. 2013.
Washburn et al.; Large-scale analysis of the yeast proteome by multidimensional protein identification technology, Nat. Biotechnol., 19(3), pp. 242-247, Mar. 2001.
Watson et al.; Multilayer hybrid microfluidics: a digital-to-channel interface for sample processing and separations; Anal. Chem.; 82(15); pp. 6680-6686; Aug. 2010.
Wheeler et al.; Electrowetting-Based Microfluidics for Analysis of Peptides and Proteins by Matrix-Assisted Laser Desorption/Ionization Mass Spectrometry; Anal Chem; 76(16): pp. 4833-4838; Aug. 2004.
Wheeler; Chemistry. Putting electrowetting to work; Science; 322(5901); pp. 539-540; Oct. 2008.
Wlodkowic et al.; Tumors on chips: oncology meets microfluidics; Current opinion in Chemical Biology; 14(5); pp. 556-567; Oct. 2010.
Wu et al.; Design, Simulation and Fabrication of Electrowetting-Based Actuators for Integrated Digital Microfluidics; Proceedings of the 1st IEEE International Conference on Nano/Micro Engineered and Molecular Systems; Zhuhai, China; pp. 1097-1100; Jan. 18-21, 2006.
Wu et al.; Electrophoretic separations on microfluidic chips, J. Chromatogr. A, 1184(1-2), pp. 542-559, Mar. 2008.
Yan et al., A microfluidic origami electrochemiluminescence aptamer-device based on a porous Au-paper electrode and a phenyleneethynylene derivative, Chem. Commun. (Camb), 49(14), pp. 1383-1385, Feb. 2013.
Yan et al., Paper-based electrochemiluminescent 3D immunodevice for lab-on-paper, specific, and sensitive point-of-care testing, Chem.— Eur. J., 18(16), pp. 4938-4945, Apr. 2012.
Yi et al.; Spangler et al., Eds; Channel-to-droplet extractions for on-chip sample preparation, in Proceedings of Solid-State Sensor, Actuator and Microsystems Workshop, pp. 128-131, Jun. 2006.
Yin et al.; One-step, multiplexed fluorescence detection of microRNAs based on duplex-specific nuclease signal amplification; J. American Chem. Soc.; 134(11); pp. 5064-5067; Mar. 2012.
Yoon et al.; Preventing Biomolecular Adsorption in Electrowetting-Based Biofluidic Chips; Anal Chem; 75; pp. 5097-5102; Aug. 2003.
Yoon; Open-Surface Digital Microfluidics; The Open Biotechnology Journal; 2(1); pp. 94-100; Apr. 2008.
Young et al.; Calculation of DEP and EWOD Forces for Application in Digital Microfluidics, J. Fluids Eng., 130(8), pp. 081603-1-081603-9, Jul. 2008.

(56) References Cited

OTHER PUBLICATIONS

Yu et al., Monolithic porous polymer for on-chip solid-phase extraction and preconcentration prepared by photoinitiated in situ polymerization within a microfluidic device, Analytical Chemistry, 73(21), pp. 5088-5096, Nov. 2001.

Yu et al., Preparation of monolithic polymers with controlled porous properties for microfluidic chip applications using photoinitiated free-radical polymerization, Journal of Polymer Science, Part A: Polymer Chemistry, 40(6), pp. 755-769, Mar. 2002.

Yu et al.; A plate reader-compatible microchannel array for cell biology assays; Lab Chip; 7(3); pp. 388-391; Mar. 2007.

Yu et al.; Microfabrication of a digital microfluidic platform integrated with an on-chip electrochemical cell; Journal of Micromechanics and Micromgineering; 23(9): pp. 10 pages; doi: 10.1088/0960-1317/23/9/095025; Aug. 2013.

Yu et al.; Microfabrication of a digital microfluidic platform integrated with an on-chip electrochemical cell; Journal of Micromechanics and Microengineering; 23(9); doi:10.1088/0960-1317/23/9/095025, 10 pages; Aug. 28, 2013.

Yu et al.; Parallel-plate lab-on-chip electrochemical analysis; Journal of Micromechanics and Microengineering; 24(1); 7 pages; doi: 10.1088/0960-1317/24/1/015020; Dec. 16, 2013.

Yue; Undergraduate Chemistry experiment (11); Hunan Normal University Press; First Edition; p. 96; (Machine Translation included); Oct. 2008.

Yung et al.; Micromagnetic-microfluidic blood cleansing devices; Lab on a Chip; 9(9); pp. 1171-1177; May 2009.

Zaffanello et al.; Multiple positive results during a neonatal screening program: a retrospective analysis of incidence, clinical implications and outcomes, Journal of Perinatal Medicine, 33(3), pp. 246-251, May 2005.

Zhang et al.; Multiplexed detection of microRNAs by tuning DNA-scaffolded silver nanoclusters; Analyst; 138(17); pp. 4812-4817; Sep. 2013.

Zhang et al.; The permeability characteristics of silicone rubber; In Proceedings of 2006 SAMPE Fall Technical Conference; 10 pages; Nov. 6, 2006.

Zhao et al., Lab on Paper, Lab Chip, 8(12), pp. 1988-1991, Dec. 2008.

Znidarsic-Plazl et al.; Steroid extraction in a microchannel system—mathematical modelling and experiments. Lab Chip, 7(7), pp. 883-889, Jul. 2007.

Zuker; Mfold Web Server for Nucleic Acid Folding and Hybridization Prediction; Nucleic Acid Research ; 31(13); pp. 3406-3415; Jul. 2003.

Zytkovicz et al.; Tandem mass spectrometric analysis for amino, organic, and fatty acid disorders in newborn dried blood spots: a two-year summary from the New England Newborn Screening Program, Clinical Chemistry, 47(11), pp. 1945-1955, Nov. 2001.

Soto-Moreno et al.; U.S. Appl. No. 17/775,373 entitled "Digital microfluidics systems, apparatus and method of using them," filed May 9, 2022.

Jebrail et al.; U.S. Appl. No. 17/760,104 entitled "Information storage using enzymatic DNA synthesis and digital microfluidics," filed Aug. 4, 2022.

Jebrail et al.; U.S. Appl. No. 17/888,461 entitled "Digital microfluidics systems and methods with integrated plasma collection device," filed Aug. 15, 2022.

Jebrail et al.; U.S. Appl. No. 18/062,011 entitled "Methods of mechanical microfluidic manipulation ," filed Dec. 5, 2022.

Davoust et al.; Evaporation Rate of Drop Arrays within a Digital Microsystem; Procedia Engineering; vol. 47; pp. 1-4; Jan. 1, 2012.

Jebrail et al.; U.S. Appl. No. 17/967,671 entitled "Evaporation Management in Digital Mecrofluidic Devices," filed Oct. 17, 2022.

Soto-Moreno et al.; U.S. Appl. No. 18/064,893 entitled "Digital microfluidics devices and methods of use thereof," filed Dec. 12, 2022.

TECAN; Freedom EVO; 16 pages; retrieved from the internet: https (//instruments.cz/wp-content/uploads/2018/04/EVO.pdf) Oct. 4, 2023.

* cited by examiner

FIG. 40A  FIG. 40B

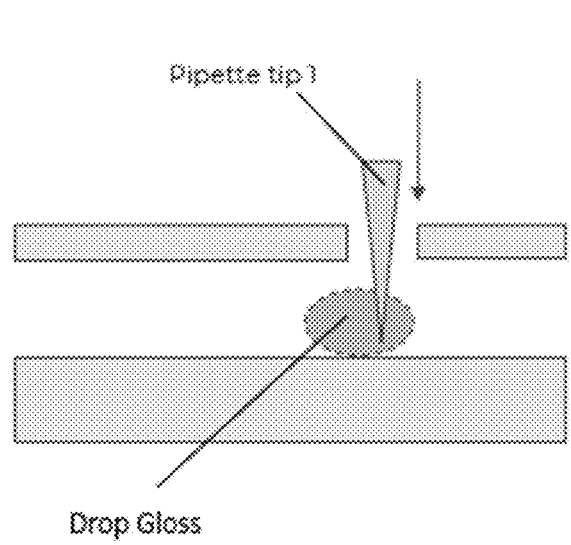
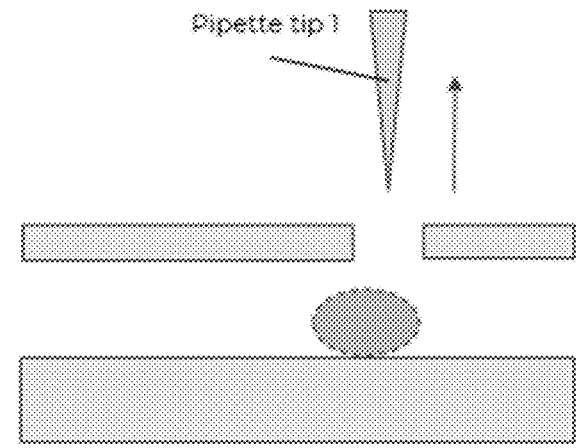
FIG. 62A  FIG. 62B
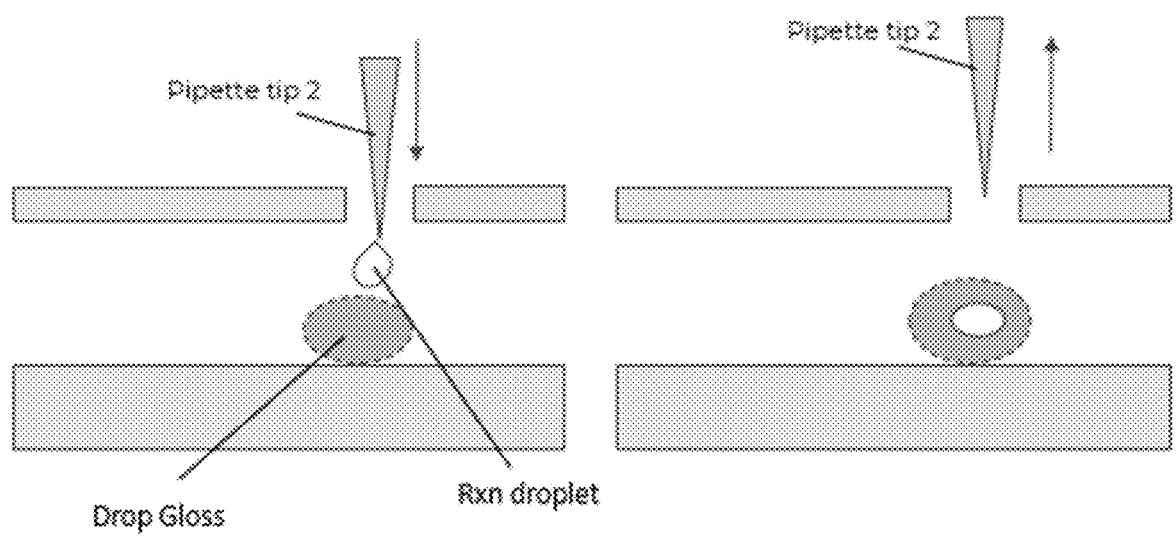
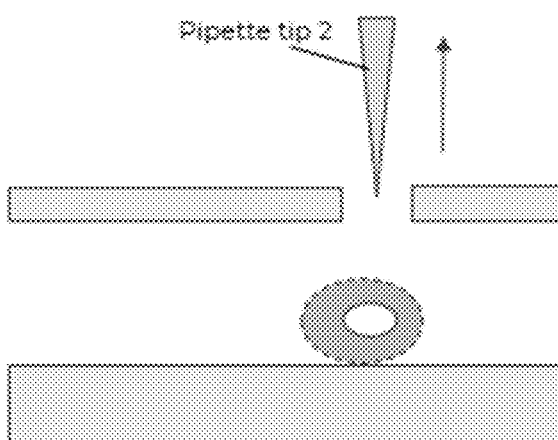
FIG. 62C  FIG. 62D

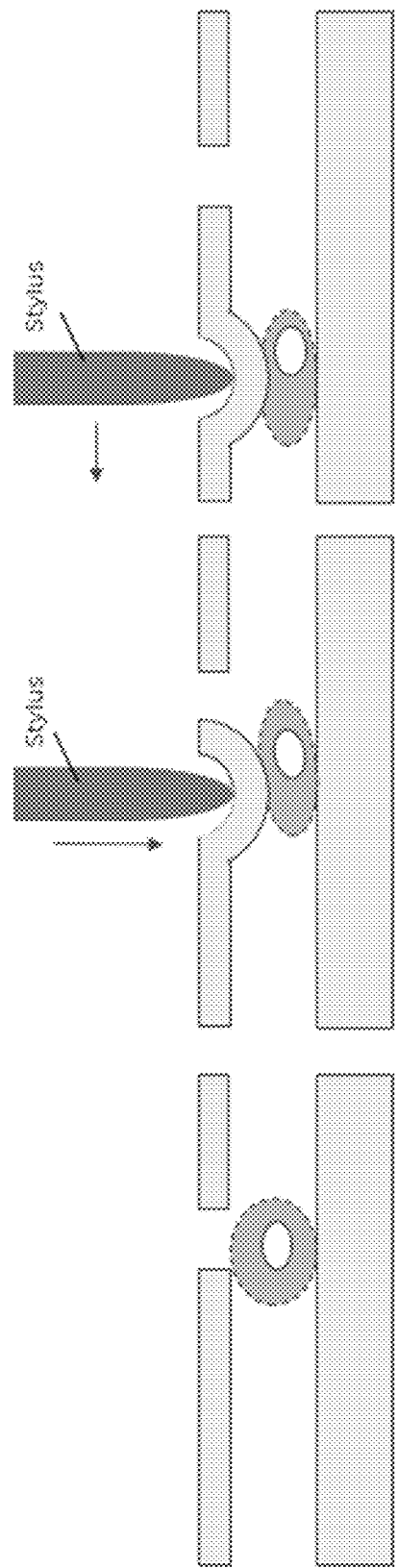
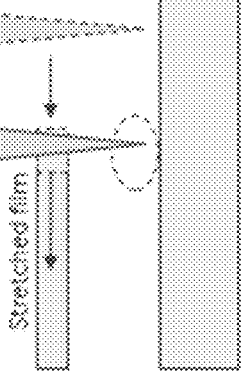
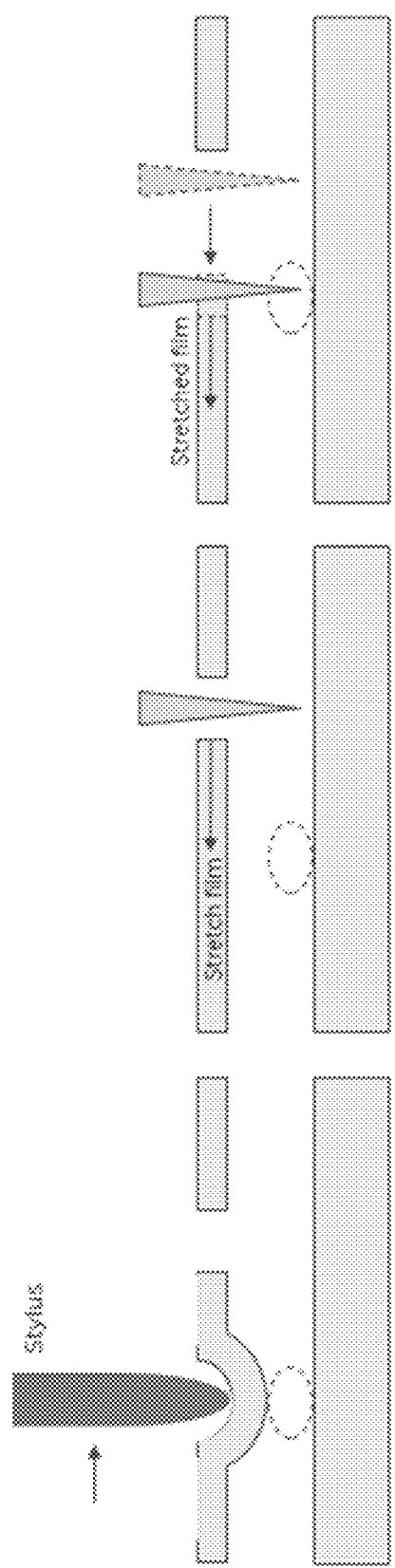
FIG. 62E
FIG. 62F
FIG. 62G
FIG. 62H
FIG. 62I
FIG. 62J

SEQUENCING BY SYNTHESIS USING MECHANICAL COMPRESSION

CLAIM OF PRIORITY

This patent application claims priority to U.S. Provisional Patent Application No. 63/298,973, titled "MICROFLUIDIC TWO-DIMENSIONAL CAPILLARY MANIPULATION DEVICES AND METHODS," filed on Jan. 12, 2022, U.S. Provisional Patent Application No. 63/393,815, titled "MECHANICAL MICROFLUIDIC MANIPULATION DEVICES AND METHODS," filed on Jul. 29, 2022, U.S. Provisional Patent Application No. 63/417,302, titled "MECHANICAL MICROFLUIDIC MANIPULATION DEVICES AND METHODS," filed on Oct. 18, 2022, and U.S. Provisional Patent Application No. 63/418,028, titled "MECHANICAL MICROFLUIDIC MANIPULATION DEVICES AND METHODS," filed on Oct. 20, 2022. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Microfluidics deal with very small volumes of fluids, down to femtoliters (fL) which is a quadrillionth of a liter. Fluids behave very differently on the micrometric scale than they do in everyday life: these unique features are the key for new scientific experiments and innovations. Microfluidic devices may include micro-channels and require microminiaturized devices containing chambers and tunnels through which fluids flow or are confined.

For example, digital microfluidics (DMF) is a powerful technique for simple and precise manipulation of microscale droplets of fluid. DMF has rapidly become popular for chemical, biological, and medical applications, as it allows straightforward control over multiple reagents (no pumps, valves, or tubing required), facile handling of both solids and liquids (no channels to clog), and compatibility with even troublesome reagents (e.g., organic solvents, corrosive chemicals) because hydrophobic surfaces (typically Teflon-coated) in contact with the droplets of fluid are chemically inert. However, conventional DMF devices use relatively large electric fields selectively applied to an array of electrodes to manipulate the droplets. The generation and control of these electric fields requires specialized and complex circuitry capable of withstanding the relative high voltages.

SUMMARY OF THE DISCLOSURE

Described herein are methods of performing sequencing by synthesis using mechanical compression to manipulate droplets within an air gap formed between a first elastically deformable sheet and a second sheet. The first sheet and the second sheet may each include hydrophobic and oleophobic surfaces facing the air gap. Either or both surfaces may be functionalized, e.g., to include hybridization regions, such as primer hybridization region). In general, these methods may include the use of a mechanical force actuator that can be driven to locally deform the first, elastically deformable sheet to form localized region of lower gap width adjacent to a droplet and can be moved along the surface of the first sheet to pull the droplet after it to translate the region of locally reduced gap width. The droplet will follow the region of lower gap width within the air gap by capillary action. Also described herein are apparatuses (e.g., devices and systems, including cartridges) for performing any of these methods for sequencing by synthesis.

In general, these methods and apparatuses may be used for preparing, manipulating and/or analyzing fluidic droplets, such as microfluidic droplets. For example, described herein are microfluidic apparatuses that may be especially helpful for handling and analyzing a clinical, laboratory, biological, or chemical samples. These apparatuses may generally operate by applying a mechanical force, such as a compression force, to an elastically deformable sheet that at least partially covers an air gap over a subregion of the air gap, to reduce the height of the air gap in a region that is adjacent to a droplet, causing the droplet to move towards this region of reduced height. By controlling the relative height of the air gap near the droplet (e.g., by controlling the application of force to deform the elastically deformable sheet), a droplet may be efficiently and quickly moved around the air gap, allowing processing of the droplet including combining the droplet, dividing the droplet, mixing the droplet, cooling/heating the droplet (e.g., thermocycling the droplet), using magnetic particles within the droplet (e.g., to bind/remove materials from the droplet) and the like.

Described herein are apparatuses (systems, devices, etc.) for controlling microfluidic movement, e.g., droplet movement) on a surface by mechanical means. These apparatuses may be referred to herein as mechanical microfluidics actuation devices ("mechanical microfluidics actuators") and may include a force applicator for applying force to an elastically deformable sheet that at least partially encloses an air gap within which one or more droplets resides. The elastically deformable sheet may be a part of the mechanical microfluidics actuator apparatus, or it may be part of a separate or integrated cartridge that is operated on by the mechanical microfluidics actuator apparatus. In some examples the cartridge may include a first (e.g., upper) elastically deformable sheet, a second (e.g., lower) sheet which are held apart from each other (e.g. by a frame) to form an air gap within which one or more droplets may manipulated by the force applicator (e.g., a stylus, etc.). The mechanical microfluidics actuator may include force applicator, a force applicator driver subassembly (e.g., a force applicator subassembly), and thermal sub-assembly for controlling the temperature of one or more regions of the air gap. Any of these mechanical microfluidics actuator apparatuses may also include a magnetic control sub-assembly for controllably applying a magnetic field within the air gap. In some examples, the apparatus may include a cartridge holder for securing the cartridge to a cartridge seat or seating region of the mechanical microfluidics actuator. Optionally the apparatuses may include a vacuum/suction sub-assembly for securing the cartridge to the seating region of the mechanical microfluidics actuator. In some examples the mechanical microfluidics actuator apparatus may include a fluid handling (e.g., pipetting) sub-assembly for adding and/or removing fluid from the air gap. Other sub-assemblies forming a part of the mechanical microfluidics actuator apparatus may include imaging sub-assemblies (e.g., for imaging droplets within the air gap) and/or for sensing sub-assemblies (e.g., for sensing droplets or other inputs from the air gap and mechanical microfluidics actuator). The mechanical microfluidics actuator apparatuses described herein may also include one or more control inputs (e.g., keyboards, touchscreens, buttons, switches, etc.) and/or one or more outputs (e.g., displays, LEDs, wireless communications outputs/inputs, etc.) and hardware, software and/or firmware for controlling these. In some cases the same features may be used for control inputs and outputs. In general, the mechanical microfluidics actuators described herein may include one or more controllers for controlling and coordinating operation of the various sub-assemblies.

For example, described herein are microfluidics apparatuses including: a cartridge comprising a first sheet and a second sheet, wherein the first and second sheets are secured opposite and approximately parallel at a predetermined distance relative to each other with an air gap therebetween; a controller configured to selectively reduce the predetermined distance in one or more regions within the air gap adjacent to a fluidic droplet positioned within the air gap to move the fluidic droplet within the air gap of the cartridge. The controller and/or cartridge may be part of a mechanical microfluidics actuator; in some examples the cartridge may be separate from the mechanical microfluidics actuator and may be removable from the mechanical microfluidics actuator. Cartridges may be single-use or reusable (e.g., washable, sterilizable, etc.). In some cases the cartridge may be integrated into the mechanical microfluidics actuator.

The second sheet may be elastically deformable or non-deformable. In some examples the second sheet is made of the same material as the first sheet (e.g., an elastic material). The second sheet may be configured to be secured (via suction) to the system holding the cartridge so that it makes consistent thermal contact with the second sheet, so that the temperature may be rapidly and efficiently changed by heating/cooling a localized region (thermally controlled region) of the second sheet to heat/cool a droplet within the air gap, in a region overlying the thermally controlled region. In some examples the droplet may be moved and/or pinned by deforming the lower sheet to change the height of the local region of the air gap; alternatively or additionally, the droplet may be moved and/or pinned by deforming the upper sheet to change the height of the local region of the air gap. When the force deforming the sheet (either or both first and second sheets) is removed, the sheets may return to the neutral, un-deformed state, so that the air gap returns to approximately the same predetermined distance.

In any of these examples, the controller may be configured to selectively reduce the predetermined distance in the one or more regions within the air gap without reducing the predetermined distance in one or more adjacent regions. The sheet may comprise a first surface facing the air gap. In general, either or both the surfaces of the air gap may be hydrophobic and oleophobic; for examples, the first surface may be hydrophobic and oleophobic, and/or the plate may include a surface facing the air gap that is hydrophobic and oleophobic. In general, the surfaces (or materials forming the sheet(s)) described herein may be oleophobic in addition to hydrophobic.

In any of these examples, the air gap may include at least one input/output port. For example, the sheet and/or the plate may be configured to introduce a first fluidic droplet into the air gap by including one or more input and/or output ports. In some examples the fluidic droplet may be inserted into (or removed out of) the air gap. The inlet/outlet port may be a region of the first sheet that is cut away. This cut-away (opening) may be between 1 mm and 10 cm long and between 1 mm and 10 cm wide (e.g., between 5 mm and 7 cm long and between 5 mm and 4 cm wide, etc.). The opening through the first sheet may be offset from the edge of the sheet, e.g., by 5 mm or more (e.g., by 6 mm or more, 7 mm or more, 8 mm or more, 9 mm or more, 1 cm or more, 1.5 cm or more, 2 cm or more, etc.). The inlet/outlet port may be configured so that tension is maintained on the sheet in the region surrounding the inlet/outlet. Thus, the edge of the inlet/outlet may be tensioned.

The air gap may generally be any appropriate height ("thickness") when force is not being applied to the sheet. For example, the air gap may have a height of between about 0.4 mm and about 7 mm (e.g., between about 0.5 mm and about 6 mm, between about 0.5 mm and about 5 mm, between about 0.5 mm and 4 mm, etc.). In general the apparatuses described herein (including, but not limited to cartridges) may include an air gap formed between the first (e.g., upper) and second (e.g., lower) sheets. The controller may be configured to apply a compression force to the sheet to selectively reduce the predetermined distance.

For example, described herein are microfluidics apparatuses comprising: a cartridge comprising a first sheet and a second sheet, wherein the first sheet and the second sheet are secured opposite and approximately parallel at a predetermined distance relative to each other with an air gap therebetween; a controller configured to selectively reduce the predetermined distance in one or more regions within the air gap adjacent to a fluidic droplet positioned within the air gap to move the fluidic droplet within the air gap of the cartridge.

The controller may generally be configured to selectively reduce the predetermined distance in the one or more regions within the air gap without reducing the predetermined distance in one or more adjacent regions by applying force (pressure) to elastically deform the first sheet (e.g., the upper sheet). The first sheet may comprise a first surface facing the air gap, wherein the first surface is hydrophobic; the second sheet may comprise a second surface facing the air gap, and the second surface facing the air gap may also be hydrophobic and oleophobic. The cartridge further may include at least one input port on the first sheet and/or the second configured to introduce a first fluidic droplet into the air gap.

The controller may generally be configured to apply (and move) a compression force across the sheet to selectively reduce the predetermined distance so that the width of the air gap changes dynamically in a manner that draws a droplet to follow the reduced height of the air gap as it moves across the sheet. The movement may be continuous or periodic.

In general, the first (and/or second) sheet is configured to elastically deform in response to compression forces. In any of these methods and apparatuses, the first sheet and/or the second sheet may be partially or completely clear (e.g., optically transparent) or opaque depending. In some cases both the first and second sheets are clear. In some examples just the second sheet is clear. In some examples, just the first sheet is clear.

As used here the sheet includes at least one surface that extends in a plane (e.g., in an x, y direction). In some examples the sheet may be relatively thin, as in the elastically deformable first sheet. In some examples the sheet may include regions of different thicknesses. The second sheet may not be elastically deformable. In some cases the second sheet is rigid. In some cases the second sheet may have regions of different thicknesses. In some examples, the second sheet may be elastically deformable. In some examples the second sheet may be referred to as a layer, plate, base, or the like.

Any of these apparatuses may include a force applicator (e.g., in some examples a stylus) positioned to apply a force to an outer surface of the first sheet to reduce the height of the air gap in a local region, wherein the controller may be configured to command movement of the force applicator relative to the outer surface (e.g., so that it moves across the outer surface). The force applicator may be a mechanical force applicator (e.g., stylus, roller, ball point, etc.) and/or a pressure applicator (e.g., jet applicator, etc.). The force applicator may be contact or non-contract. In some examples the force applicator may comprise a source of pressurized fluid.

As mentioned, as least one of the first or second sheets may be elastically deformable. In some examples the first sheet may be referred to as the top or upper sheet and the second sheet may be referred to as a bottom or lower sheet. The second sheet may also be referred to as a plate in some examples.

In apparatuses including a cartridge, the cartridge may include a frame to which the first sheet (and/or the second sheet) is tensioned to maintain the first sheet opposite and approximately parallel to the second sheet. The frame may include a tensioner. In some examples the tension may be applied at the time of fabrication and the sheet may be affixed (e.g., mechanically and/or chemically, e.g., by an adhesive) to the frame under tension. The frame may surround the periphery of the cartridge. In some examples the cartridge may be divided up into regions, including lanes, chambers, etc. that may be separated by one or more walls (e.g., dividers, etc.). The dividers may be fixed (e.g., adhesively attached, welded, etc.) to the upper and/or lower sheets. In some examples the frame and the spacers are combined into a single component, referred to herein as a spacer frame.

The second sheet may be the same material as the first sheet (e.g., an elastic material) or it may be a different material. In some examples the second sheet is formed of an inelastic material. In some examples the second sheet is formed of a material is more rigid or stiff than the first sheet. The second sheet may be referred to in some examples as a plate. In any of the apparatuses and methods described herein the second sheet maybe relatively thermally conductive to allow heating therethrough. In some examples the first sheet and the second sheet both comprise an elastic material held in tension to a frame of the cartridge. The first and second sheets may be any appropriate thickness, and may be the same thickness, or may be different thicknesses. For example, the first and/or second sheet may be between 0.05 mm and 5 mm thick (e.g., between about 0.075 mm and 2 mm, between about 0.1 mm and 5 mm, between about 0.1 mm and 4 mm, between about 0.2 mm and 4 mm, between about 0.1 mm and 3.5 mm, between about 0.2 mm and 3.5 mm, etc.).

The first and second sheets may be formed of any appropriate material. In any of these apparatuses and methods the first and second sheet are formed of an elastomeric material. In some examples, the first sheet is a polyester material (e.g., TPE, TPU, etc.).

Any of these apparatuses may include a controller that is configured to operate the force applicator to apply the force (e.g., a "compression force") against the first or second sheets to reduce the height of a portion of the air gap adjacent to a droplet in order to cause the droplet to move (e.g., by capillary action) to the region of reduced height. The controller may generally control the force applicator, including controlling the z-height, e.g., based on the height of the air gap, and/or the x and/or y movement of the force applicator along the outer surface of the first (or in some examples, the second) sheet. As the force applicator is moved along the upper sheet, it may drive movement of the droplet which may follow the lower-height region of the air gap formed by the moving force applicator.

The controller may receive input from one or more sensors (e.g., optical sensor, electrical sensors, force sensors, pressure sensors, etc.) including sensors identifying the position of the droplet. In some examples the force applicator includes one or more sensors. The controller may be configured to execute pre-programmed and/or dynamic steps, including moving the force applicator in a pattern in order to achieve one or more fluid handling maneuvers, such as splitting or dividing a droplet, combining a droplet, mixing a droplet, washing a droplet (or a material, such as a magnetic material, magnetic beads, etc. within the droplet), etc. For example the controller may be configured to apply a pinning compression force to divide the first fluidic droplet and to apply an actuation compression force proximate to the pinning compression force to elongate and form a second fluidic droplet from the first fluidic droplet and wherein the pinning compression force is greater than the actuation compression force. The controller may be configured to apply a pinning compression force to divide the first fluidic droplet and to apply an actuation compression force proximate to the pinning compression force to elongate and form a second fluidic droplet from the first fluidic droplet and wherein the pinning compression force is greater than the actuation compression force.

In some examples the controller is configured to: apply a compression force to the sheet between two or more separate fluidic droplets; and release the compression force to combine the two or more separate fluidic droplets into a single fluidic droplet. In some examples the controller is configured to alternately apply a first compression force and a second compression force different than the first compression force to the sheet to mix together two or more separate fluidic droplets. Thus, the controller may be configured to mix together two or more fluidic droplets by repeatedly applying and releasing a compression force to the sheet adjacent to the two or more fluidic droplets.

The controller may also be configured to coordinate one or more processes in addition to controlling movement of the force applicator. For example, the coordinator may control and/or coordinate the additional of fluid into the air gap (e.g., fluid dispensing, which may be manually, automatically or semi-automatically performed.). A controller may also control or coordinate the activity of one or more heaters, magnets, etc. For example, in some examples the controller is configured to control a magnet to attract ferrous particles suspended within the first fluidic droplet. The controller may be further configured to re-suspend one or more ferrous particles in the fluidic droplet by applying and releasing a compression force to the fluidic droplet and disabling a magnet. The first sheet may further comprise two or more pinning posts disposed on the surface and extending into the gap, the pinning posts being configured to restrict movement of the first fluidic droplet. Any of these apparatuses may include a heater disposed under the second surface opposite the two or more pinning posts. Alternatively, the apparatuses described herein may be used without posts.

Any of the apparatuses described herein may include a well into which the droplet may be moved. The well may be part of the cartridge and/or part of the mechanical microfluidics actuation device ("mechanical microfluidics actuator"). In some examples the well is formed on a base or seating region of the mechanical microfluidics actuator. For example, the cartridge may seat in the seating region of the mechanical microfluidics actuator and may conform to a shape of the seating region including one or more wells. In some examples the well is part of the cartridge, for example, the well is configured to restrict movement of the fluidic droplet.

Any of these apparatuses (e.g., mechanical microfluidics actuator apparatuses) may include base having a cartridge seat configured to secure the cartridge so that the second sheet is held against cartridge seat with at least a region of the cartridge in communication with a heating element disposed beneath the seat and configured to heat the fluidic droplet within the air gap. In some examples the mechanical microfluidics actuator apparatus may include a securement, such as a clamp, for securing the cartridge to and/or in the seat. In some examples the seat may include a plurality of suction ports to apply a negative pressure to hold the cartridge (e.g., the second or lower sheet of the cartridge) to the seat. The use of suction may be particularly beneficial to secure the cartridge in place snugly so that good thermal contact is maintained. This use of suction may also allow transfer of three-dimensional structures (e.g., wells, ridges, shelves, etc.) to the cartridge (e.g., the lower sheet of the cartridge may conform to the shape of the seat).

In examples having wells, the heaters, magnets, etc. may be configured to effect the well. In some examples the heater and/or magnet may be arranged to effect a droplet within the air gap in a region that is not part of a well, including in a rail region. In general, the heater and/or magnet may be part of the cartridge or may be part of the actuation device (e.g., drive unit).

Also described herein are methods of manipulating one or more microfluidic droplets using mechanical actuation of droplets. For example, described herein are methods including: introducing a first fluidic droplet into an air gap formed between: a first sheet having a first surface that is hydrophobic and oleophobic and a second sheet having a second surface that is hydrophobic and oleophobic, wherein the first sheet and the second sheet are secured opposite and approximately parallel at a predetermined distance relative to each other with an air gap therebetween; and applying a force (e.g., mechanical force) to elastically deform the first sheet to reduce the distance of the air gap between the first sheet and the second sheet in a region within the air gap that is adjacent to the fluidic droplet to move the fluidic droplet within the air gap. Applying force may comprise moving the force along the outer surface of the sheet to selectively reduce the distance between the first sheet and the second sheet so that the droplet follows the applied force. In any of these examples applying the force may comprise moving a stylus against the first sheet. Applying the force may comprise driving movement of a pressure applicator to apply a compression force to an outer surface of the first sheet, wherein the pressure applicator is controlled by a controller. Any of these methods may include forming a second fluidic droplet from the fluidic droplet by: applying a pinning compression force to the first sheet to divide the fluidic droplet; and applying an actuation compression force to the first sheet proximate to the pinning compression force to elongate and form the second fluidic droplet, wherein the pinning compression force is greater than the actuation compression force.

For example, a method of microfluidically manipulating a droplet may include: introducing the droplet into an air gap formed between a first sheet that is elastically deformable and a second sheet, wherein the first sheet is spaced opposite from the second sheet to form an air gap having a gap width of a predetermined distance in a neutral state; applying a compression force against the first sheet using a mechanical force applicator to form a region of locally reduced gap width within the air gap that is adjacent to droplet, thereby drawing the droplet towards the region of locally reduced air gap; and moving the droplet within the air gap by translating the mechanical force applicator along an outer surface of the first sheet to translate the region of locally reduced gap width within the air gap so that the droplet follows the mechanical force applicator.

In any of these methods moving the droplet may comprise moving the droplet along a rail region of the air gap, wherein the rail region has a gap width that is less than the gap width of a region of the air gap surrounding the rail region.

For example a method of microfluidically manipulating a droplet may include: introducing the droplet into an air gap formed between a first sheet that is elastically deformable and a second sheet, wherein the first sheet is spaced opposite from the second sheet to form an air gap having a gap width of a predetermined distance in a neutral state, wherein the air gap is open to atmospheric pressure and unpressurized, further wherein the droplet positioned in a rail region of the air gap having a gap width that is less than the gap width of a region surrounding the rail region; applying a compression force against the first sheet using a mechanical force applicator to form a region of locally reduced gap width within the air gap that is adjacent to droplet, thereby drawing the droplet towards the region of locally reduced air gap by capillary action; and moving the droplet along the rail region of the air gap by translating the mechanical force applicator along an outer surface of the first sheet to translate the region of locally reduced gap width within the air gap and thereby pull the droplet within the air gap.

Any of these methods may include moving the droplet into a well formed by the second sheet. The well may be used to modify the droplet. For example, the well may be used to heat/cool the droplet, and/or to react material within the droplet. The methods described herein may include controlling a temperature of the well. For example, a method of microfluidically manipulating a droplet may include: introducing the droplet into an air gap formed between a first sheet that is hydrophobic and oleophobic and is that is elastically deformable, and a second sheet that is hydrophobic and oleophobic, wherein the first sheet is spaced opposite from the second sheet to form an air gap having a gap width of a predetermined distance in a neutral state, wherein the air gap is open to atmospheric pressure and unpressurized; applying a compression force against the first sheet using a mechanical force applicator to form a region of locally reduced gap width within the air gap that is adjacent to droplet, thereby drawing the droplet towards the region of locally reduced air gap by capillary action; and moving the droplet into a well formed by the second sheet by translating the mechanical force applicator along an outer surface of the first sheet to translate the region of locally reduced gap width within the air gap and thereby pull the droplet within the air gap and into the well; modifying the droplet within the well; and moving the droplet out of the well by translating the mechanical force applicator along the outer surface of the first sheet to translate the region of locally reduced gap width within the air gap away from the well and thereby pull the droplet out of the well. Any of these methods may include moving the droplet out of the well by translating the mechanical force applicator along the outer surface of the first sheet to translate the region of locally reduced gap width within the air gap away from the well and thereby pull the droplet out of the well.

Thus, in general, any of these methods may include modifying the droplet within the air gap. Modifying may include one or more of: reacting one or more materials within the droplet, heating the droplet, adding material to the droplet, and applying energy to the droplet.

As mentioned, the first sheet may have a first hydrophobic and oleophobic surface that is positioned opposite from a second hydrophobic and oleophobic surface of the second sheet.

In general, the methods and apparatuses described herein may manipulate the droplet(s) within the air gap by reducing the gap width (e.g., the distance between the upper and lower sheets), which may pull the droplet into the reduced-height region by capillary action. It may be particularly beneficial to have the air gap may be open to atmospheric pressure, and unpressurized. This is in contrast to systems that drive the droplet by pressure (e.g., squeezing the fluid material between the sheets), in an attempt to push the droplet, or alternatively to suck the droplet by negative pressure.

Any of these methods may include applying the compression force against the first sheet using the mechanical force applicator draws the droplet towards the region of locally reduced air gap by capillary action.

In general, these methods may be part of a method of any one of nucleic acid extraction, library preparation, sequencing, and protein synthesis. For example, the step of introducing, applying and moving may be part of a method of one or more of: nucleic acid extraction, library preparation, sequencing, and protein synthesis.

In general, any appropriate mechanical force applicator may be used. For example, a tip of the mechanical force applicator may have a rounded profile, a circular profile, an oval profile, a rectangular profile, or a square profile. In some examples a tip of the mechanical force applicator comprises a roller.

Any of these methods and apparatuses may be configured to detect a light transmitted or reflected through the droplet. Any of these methods or apparatuses may be configured to apply a voltage to the droplet from the mechanical force applicator or from a region beneath the second sheet. Any of these methods may include attracting magnetic particles suspended within the droplet via a magnet within the mechanical force applicator or a region beneath the second sheet.

In general, these methods may include mixing the droplet within the air gap. Mixing may be chaotic or gentle. For example chaotic mixing may be performed on the droplet by a repeated application and removal of the compression force by the mechanical force applicator, e.g., moving the mechanical force applicator (or any force applicator) in the z axis, transverse to the first sheet. Alternatively or additionally, mixing the droplet may be performed by moving the mechanical force applicator against the first sheet in a plane of the first sheet, e.g., in an x and/or y axis direction.

The methods and apparatuses described herein may be configured to separate the droplet by: applying a pinning compression force to the first sheet; and applying an actuation compression force to the first sheet proximate to the pinning compression force to elongate and divide the droplet, wherein the pinning compression force is greater than the actuation compression force. Any of these methods may include removing all or a portion of the droplet from the air gap through an opening in the first sheet. Any of these methods may include introducing the droplet by passing the droplet through an opening in the first sheet from the mechanical force applicator.

As mentioned, also described herein are methods of combining droplets using mechanical actuation through the elastically deformable sheet. For example, any of these methods may include applying a compression force to the first sheet to deform the first sheet between two or more separate fluidic droplets; and releasing the compression force to combine the two or more separate fluidic droplets into a single fluidic droplet.

Also described herein are methods of separating droplets using mechanical actuation through the elastically deformable sheet. For example, a method may include alternately applying a first compression force and a second compression force different than the first compression force to the first sheet to mix together two or more separate fluidic droplets within the air gap.

Also described herein are methods of mixing droplets using mechanical actuation through the elastically deformable sheet. For example, any of these methods may include repeatedly applying and releasing a compression force to an outer surface of the first sheet in a region of the first sheet that is adjacent to two or more fluidic droplets within the air gap in order to mix together the two or more fluidic droplets. In addition or instead of mixing by moving the mechanical force applicator in the z-axis, any of these methods and apparatuses may mix by moving the mechanical force applicator against the first sheet in the y or x axis (e.g., in the plane of the sheet), which may result in more gentle mixing than the more chaotic mixing resulting from moving the mechanical force applicator in the z direction. Gentle mixing may be particularly preferred when mixing long polynucleotides in order to avoid shearing.

These methods may also be used with magnetic beads or particles that may be condensed (e.g., using a magnet, as described herein), washed, and resuspended. The methods may include any of the moving, mixing, dividing and combining of droplets. The controller may be configured to execute and control any of these steps. Also described herein are methods of attracting, with a magnet outside of the air gap, ferrous particles suspended within the fluidic droplet. Any of these methods may also include re-suspending one or more ferrous particles in the fluidic droplet by applying a compression force to an outer surface of the first sheet over or adjacent to the fluidic droplet within the air gap and disabling a controllable magnet.

In some examples the methods described herein may include restricting movement of the first fluidic droplet via two or more pinning posts disposed within the air gap. Alternatively or additionally these methods may include using a well to hold the droplet, particularly when adjusting the temperature (e.g., thermal cycling). Holding the droplet in a well (and/or 'pinning' the droplet with one or more pinning posts) may prevent unintentional movement of the droplet during operation, including in particular when heating the droplet. Any of the methods described herein may include heating, by a heating element, the droplet restricted by the well and/or pinning post(s). Any of these methods may include heating, e.g., by a heating element (of the mechanical microfluidics actuator), the fluidic droplet in the well.

In use, any of these methods and apparatuses may be used with a coating material, which may be referred to as a gloss coat (e.g., also referred to equivalently as drop gloss, gloss coating or gloss material). The gloss coat may be a low surface-tension material (e.g., oil), and may be immiscible with the droplet. The gloss coating material may be a hydrophobic material if the droplet is an aqueous material. The gloss coating may be applied to the droplet before it is applied into the air gap, or after it is applied to the air gap. The gloss coat may be removed, e.g., by wicking to a material that is absorbent for the gloss material. The gloss coat may be particularly helpful in preventing evaporation of the droplet within the air gap.

Also described herein are methods including electroporating of cells or particles within the droplet. For example, any of these methods may include applying energy to an electrode on the plate and/or the force applicator to create temporary pores in cell membranes of cells within the fluidic droplet.

In general, the methods and apparatuses described herein may be particularly useful for treating fluidic droplets having a variety of low- and medium-volumes. For example, the methods described herein may be useful for fluidic droplets having a volume of between about $10^{-15}$ and $10^{-6}$ liters.

Also described herein are mechanical microfluidics actuator apparatuses. These microfluidic apparatuses may include: a cartridge seating surface ("seat"); a force applicator configured to contact an elastically deformable outer surface of a cartridge when the cartridge is seated in the cartridge seating surface to apply a compression force to the elastically deformable surface of the cartridge; a force applicator drive configured to move the force applicator across the deformable outer surface; and a controller coupled to control the force applicator drive to move the force applicator relative to the deformable outer surface of the cartridge to dynamically reduce a height of an air gap within the cartridge to move a fluidic droplet within the air gap of the cartridge. The force applicator drive may include one or more motors for moving the force applicator in x, y and/or z. Although most of the examples shown herein are configured to move the force applicator while the cartridge remains fixed (e.g., the force applicator is moved relative to the elastically deformable sheet and air gap) in some examples the apparatus may be configured to move the cartridge (e.g., the elastically deformable sheet and air gap) while the force applicator remains fixed; alternatively both the force applicator and the cartridge (e.g., the elastically deformable sheet and air gap) may move relative to each other.

The mechanical microfluidics actuator may include one or more force applicators. In some example multiple force applicators may be controlled independently (in parallel or in series). In some examples, the mechanical microfluidics actuator may switch out one type of force applicator for another type. Ins some examples the mechanical microfluidics actuator may be configured to perform multiple concurrent actuations using multiple different force applicators.

The force applicator may have any appropriate shape, particularly shapes that apply sufficient compression to the elastically deformable sheet so as to reduce the height of the air gap, while preventing or limiting damage to the sheet. For example, a tip of the force applicator may be configured to have a profile comprising a circle, an oval, a rectangle, or a square. In some examples the force applicator comprises a wheel, ball point or roller.

In some examples the force applicator may be adapted to perform one or more additional functions, in addition to applying a force against the elastically deformable sheet of air gap in order to decrease the height of the air gap to drive movement (e.g., by 2D capillary action) of a droplet within the air gap. In some examples the tip of the force applicator includes a thermal output configured to control a temperature of the tip. In some examples the tip of the force applicator includes a light source. In some examples the tip of the force applicator includes a light source, and the cartridge seating source comprises a light sensor configured to detect light transmitted or reflected through a fluidic droplet.

In some examples the force applicator includes an electrode configured to apply a voltage (e.g., for applying electroporation). In some examples the force applicator includes a magnet. For example, the force applicator may be further configured to provide a variable magnetic field strength. In some examples the force applicator comprises a sonication probe configured to emit at least one of sonic and ultrasonic waves.

Also described herein are method of moving a droplet using mechanical actuation through the elastically deformable sheet. For example, these method may include: introducing a fluidic droplet into an air gap formed between a first elastically deformable sheet and a second sheet, wherein the first sheet is approximately parallel to and spaced opposite from the second sheet by a predetermined distance to form the air gap; and applying a compression force against the elastically deformable sheet using a force applicator, thereby reducing the predetermined distance in at least one region within the air gap adjacent to the fluidic droplet to move the droplet within the air gap.

Any of these methods may also include moving the force applicator across the elastically deformable sheet while applying the compression force so that the droplet follows a region of decreased distance (e.g., height) within the gap that is formed by the force applicator. A tip of the force applicator may be configured to have a rounded profile, a circular profile, an oval profile, a rectangular profile, or a square profile. In some examples the tip is a roller, ball point or wheel.

Any of the methods described herein may also include controlling a temperature of a region beneath the second sheet to control a temperature of the fluidic droplet within the air gap. In some examples, the method may include controlling a temperature of the force applicator to control a temperature of the fluidic droplet. In some examples the method may include detecting a light transmitted or reflected through the fluidic droplet. The light may be part of a sensor for detecting the presence of the droplet and/or one or more characteristics of the droplet. The light may be emitted by a light source on the force applicator.

Any of these methods may include applying a voltage from the force applicator or from a region beneath the second sheet. The first sheet and/or the second sheet may be a dielectric material. Any of these methods may include attracting, via a magnet within the force applicator or a region beneath the second sheet, ferrous particles (e.g., magnetic beads) suspended within the fluidic droplet. In some examples the method my include removing ferrous particles from the fluidic droplet. The methods may include mixing the fluidic droplet via a repeated application and removal of the compression force by the force applicator. Any of these methods may include aspirating the fluidic droplet through an opening in the sheet using the force applicator.

In some examples the methods may include delivering the fluidic droplet into the air gap from the force applicator. Introducing the fluidic droplet may comprise passing the droplet through an opening in the elastically deformable sheet from the force applicator. The method may include applying at least one of sonic and ultrasonic energy to the fluidic droplet from the force applicator.

Thus, described herein are methods and apparatuses (e.g., devices and systems, including cartridges) for preparing, manipulating and/or analyzing fluidic droplets, such as microfluidic droplets. For example, described herein are microfluidic apparatuses that may be especially helpful for handling and analyzing a clinical, laboratory, biological, or chemical samples. These apparatuses may generally operate by applying a force, such as a compression force, to an elastically deformable sheet that at least partially covers an air gap over a subregion of the air gap, to reduce the height of the air gap in a region that is adjacent to a droplet, causing the droplet to move towards this region of reduced height. By controlling the relative height of the air gap near the droplet (e.g., by controlling the application of force to deform the elastically deformable sheet), a droplet may be efficiently and quickly moved around the air gap, allowing processing of the droplet including combining the droplet, dividing the droplet, mixing the droplet, cooling/heating the droplet (e.g., thermocycling the droplet), using magnetic particles within the droplet (e.g., to bind/remove materials from the droplet) and the like.

The apparatuses described herein may include two parallel hydrophobic and oleophobic sheets spaced apart by a gap of a predetermined distance. The gap may be filled with air or an immiscible fluid, with respect to the microfluidic droplet. The microfluidic droplet may be manipulated (e.g., moved, controlled, separated, mixed, and the like) by selectively reducing the gap, particularly near the microfluidic droplet. In some examples, the gap may be reduced applying a force (e.g., a compressive force) to one or more of the parallel sheets.

Examples described in this disclosure may be implemented as a microfluidic device. The microfluidic device may include a cartridge that, in turn, includes a first sheet comprising a first surface and a second surface, wherein the first surface of the first sheet is hydrophobic and oleophobic, a second sheet comprising a first surface and a second surface, wherein the first surface of the second sheet is hydrophobic and oleophobic and the first surface of the first sheet is disposed toward and separated from the first surface of the second sheet by a predetermined distance to form a gap between the first sheet and the second sheet, and at least one input port on the first sheet configured to introduce a first microfluidic droplet into the gap. The microfluidic device may also include a controller configured selectively reduce the predetermined distance in one or more regions within the gap adjacent to the first microfluidic droplet, wherein the reduced predetermined distance moves the first microfluidic droplet within the cartridge.

In some examples, the controller of the microfluidic device may be configured to apply a compression force to the second surface of the first sheet to selectively reduce the predetermined distance.

In some examples, the first sheet may be configured to deflect in response to compression forces and the second sheet may be configured to resist deflection in response to compression forces.

In some examples, the controller may be configured to apply a pinning compression force to divide the first microfluidic droplet and apply an actuation compression force proximate to the pinning compression force to elongate and form a second microfluidic droplet from the first microfluidic droplet, where the pinning compression force is greater than the actuation compression force.

In some examples, the controller may be configured to apply a compression force to the first sheet between two or more separate microfluidic droplets and release the compression force to combine the two or more separate microfluidic droplets into a single microfluidic droplet.

In some examples, the controller may be configured to alternately apply a first compression force and a second compression force different than the first compression force to the first sheet to mix together two or more separate microfluidic droplets.

In some other examples, the controller may be configured to mix together two or more microfluidic droplets by repeatedly applying and releasing a compression force to the first sheet adjacent to the two or more microfluidic droplets.

In some examples, the controller may be configured to control a magnet to attract ferrous particles suspended within the first microfluidic droplet.

In some other examples, the controller may be further configured to re-suspend one or more ferrous particles in the first microfluidic droplet by applying and releasing a compression force to the first microfluidic droplet and disabling a magnet.

In some examples, the first sheet may further comprise two or more pinning posts disposed on the first surface and extending into the gap, the pinning posts being configured to restrict movement of the first microfluidic droplet. In such cases, the device may further include a heater disposed under the second surface opposite the two or more pinning posts.

In some examples, the cartridge may further comprise a well-disposed through an opening on the second sheet and configured to restrict movement of the first microfluidic droplet. In such cases, the cartridge may further include a heating element disposed beneath the well and configured to heat the first microfluidic droplet.

In some examples, the second sheet may further comprise an electrode configured to create temporary pores in cell membranes of cells within the first microfluidic droplet.

In some other examples, the first microfluidic droplet may have a volume between $10^{-6}$ and $10^{-15}$ liters.

Examples described in this disclosure may be implemented as a method of manipulating one or more microfluidic droplets. The method may include introducing a first microfluidic droplet into a gap formed between a first sheet comprising a first surface and a second surface, wherein the first surface of the first sheet is hydrophobic and oleophobic and a second sheet comprising a first surface and a second surface, wherein the first surface of the second sheet is hydrophobic and oleophobic and the first surface of the first sheet is disposed toward and separated from the first surface of the second sheet by a predetermined distance to form the gap. The method may further include selectively reducing, by a control unit, the predetermined distance in one or more regions within the gap adjacent to the first microfluidic droplet to move the first microfluidic droplet.

In some examples, the method may include applying a compression force to the second surface of the first sheet to selectively reduce the predetermined distance.

In some other examples, the first sheet may be configured to deflect in response to compression forces and the second sheet is configured to resist deflection in response to compression forces.

In some examples, the method may include forming a second microfluidic droplet from the first microfluidic droplet by applying a pinning compression force to the first sheet to divide the first microfluidic droplet and applying an actuation compression force proximate to the pinning compression force to elongate and form the second microfluidic droplet, where the pinning compression force is greater than the actuation compression force.

In some examples, the method may include applying a compression force to the first sheet between two or more separate microfluidic droplets and releasing the compression force to combine the two or more separate microfluidic droplets into a single microfluidic droplet.

In some examples, the method may include alternately applying a first compression force and a second compression force different than the first compression force to the first sheet to mix together two or more separate microfluidic droplets.

In some other examples, the method may include repeatedly applying and releasing a compression force to the second sheet adjacent to two or more microfluidic droplets to mix together the two or more microfluidic droplets.

In some examples, the method may include attracting, with a controllable magnet, ferrous particles suspended within the first microfluidic droplet. In another example, the method may include re-suspending one or more ferrous particles in the first microfluidic droplet by applying a compression force to the first microfluidic droplet and disabling a controllable magnet.

In some examples, the method may include restricting the movement of the first microfluidic droplet via two or more pinning posts disposed on the first surface of the first sheet extending into the gap. Furthermore, the method may include heating, by a heating element, the first microfluidic droplet restricted by the two or more pinning posts.

In some examples, the method may include restricting movement of the first microfluidic droplet via a well. Furthermore, the method may include heating, by a heating element, the first microfluidic droplet in the well.

In some examples, the method may include creating temporary pores, with an electrode on the second sheet, in cell membranes of cells within the first microfluidic droplet.

In some examples, the first microfluidic droplet may have a volume between $10^{-6}$ and $10^{-15}$ liters.

Other examples described in this disclosure may be implemented as a non-transitory computer-readable storage medium comprising instructions that, when executed by one or more processors of a device, cause the device to perform operations. The operations may include sensing a first microfluidic droplet disposed in a gap between first sheet comprising a first surface and a second surface, wherein the first surface of the first sheet is hydrophobic and oleophobic and a second sheet comprising a first surface and a second surface, wherein the first surface of the second sheet is hydrophobic and oleophobic and the first surface of the first sheet is disposed toward and separated from the first surface of the second sheet by a predetermined distance to form the gap. The operation may further include selectively reducing the predetermined distance in one or more regions within the gap adjacent to the first microfluidic droplet to move the first microfluidic droplet.

Other examples described in this disclosure may be implemented as a device that includes a first sheet comprising a first surface and a second surface, wherein the first surface of the first sheet is hydrophobic and oleophobic, a second sheet comprising a first surface and a second surface, wherein the first surface of the second sheet is hydrophobic and the first surface of the first sheet is disposed toward and separated from the first surface of the second sheet by a predetermined distance to form a gap between the first sheet and the second sheet, and a pressure actuator coupled to the first sheet and configured to apply pressure to the first sheet to selectively reduce the gap between the first sheet and the second sheet.

Other examples described herein may be implemented as a device that includes a cartridge including a first sheet comprising a first surface and a second surface, wherein the first surface of the first sheet is hydrophobic and oleophobic, a second sheet comprising a first surface and a second surface, wherein the first surface of the second sheet is hydrophobic and oleophobic and the first surface of the first sheet is disposed toward and separated from the first surface of the second sheet by a predetermined distance to form a gap between the first sheet and the second sheet, and a stylus configured to contact the first sheet and selectively reduce the predetermined distance in at least one region within the gap, In some examples, the predetermined distance may be reduced by a compression force provided by the stylus. Furthermore, in some examples the reduced predetermined distance may cause a microfluidic droplet to move within the gap. The tip of the stylus may have a profile of a circle, oval, rectangle, square, or a combination thereof.

In some examples, a tip of the stylus may include a temperature control device configured to control the temperature of a microfluidic droplet within the gap. In some other examples, a tip of the stylus may include a light source and the second sheet includes a light sensor configured to detect light transmitted or reflected through a microfluidic droplet. Furthermore, the tip of the stylus may include an electrode configured to receive a voltage sufficient to attract a microfluidic droplet through the first sheet. In some examples the first sheet may be a dielectric material.

In some examples, the stylus of the device may include a magnet configured to attract ferrous particles suspended within a microfluidic droplet disposed within the gap. The magnet may be further configured to provide a variable magnetic field strength.to filter ferrous particles from the microfluidic droplet.

Other examples described herein may be implemented as a method of manipulating one or more microfluidic droplets. The method may include introducing a microfluidic droplet into a gap formed between: a first sheet comprising a first surface and a second surface, wherein the first surface of the first sheet is hydrophobic and oleophobic and a second sheet comprising a first surface and a second surface, wherein the first surface of the second sheet is hydrophobic and oleophobic and the first surface of the first sheet is disposed toward and separated from the first surface of the second sheet by a predetermined distance to form the gap. The method may further include providing, by a stylus, a compression force thereby reducing the predetermined distance in at least one region within the gap adjacent to the microfluidic droplet.

In some examples, the reduced predetermined distance may cause the microfluidic droplet to move within the gap. The tip of the stylus may be configured to have a profile of a circle, oval, rectangle, square, or a combination thereof.

Some examples of the methods described herein may include controlling the temperature of the microfluidic droplet with a temperature control device disposed on a tip of the stylus. Some examples of the methods described herein may include detecting light transmitted or reflected through the microfluidic droplet via a light sensor. In some examples, the methods may include providing a voltage to an electrode disposed on the stylus, wherein the voltage attracts the microfluidic droplet through the first sheet toward the stylus. The first sheet may be a dielectric material.

In some examples, the methods may include attracting, via a magnet within the stylus, ferrous particles suspended within the microfluidic droplet. Furthermore, the method may include filtering ferrous particles from the microfluidic droplet. The methods may include dispersing particles within the microfluidic droplet via a repeated application and removal of a compression force by the stylus.

In some examples, the methods may further include aspirating, by the stylus, the microfluidic droplet through a first septa in the first sheet and receiving, by a lumen in the stylus coupled to the first septa, the microfluidic droplet. In some examples, methods may further include injecting, by the stylus, the microfluidic droplet into a second septa different than the first septa. In some further examples, the method may include controlling, by a temperature control element in the stylus, the temperature of the microfluidic droplet. In some examples, the method may include detecting, within the stylus, light transmitted or reflected by the microfluidic droplet. In some further examples, the method may include providing, within the stylus, at least one of sonic and ultrasonic waves to the microfluidic droplet.

Other examples described herein may be implemented as a non-transitory computer-readable storage medium comprising instructions that, when executed by one or more processors of a device, may cause the device to perform operations comprising: sensing a first microfluidic droplet disposed in a gap between first sheet comprising a first surface and a second surface, wherein the first surface of the first sheet is hydrophobic and oleophobic and a second sheet comprising a first surface and a second surface, wherein the first surface of the second sheet is hydrophobic and oleophobic and the first surface of the first sheet is disposed toward and separated from the first surface of the second sheet by a predetermined distance to form the gap and providing, by a stylus, a compression force thereby reducing the predetermined distance in at least one region within the gap adjacent to the microfluidic droplet.

Any of the methods and apparatuses described herein may be adapted to perform sequency by synthesis. For example, described herein are methods of sequencing by synthesis using mechanical compression, the method comprising: sequentially moving each droplet of a series of fluidic droplets within a cartridge, wherein the cartridge comprises an air gap formed between a first sheet having a first surface that is hydrophobic and oleophobic and a second sheet having a second surface that is hydrophobic and oleophobic, wherein the first sheet and the second sheet are secured opposite each other at a predetermined spacing relative to each other with the air gap therebetween, further comprising a plurality of clusters of polynucleotides on the first sheet or the second sheet, wherein moving each droplet comprises moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet; and imaging the plurality of clusters of polynucleotides to detect addition or hybridization of a nucleotide to clusters of the plurality of clusters of polynucleotides.

Any of these methods may include repeating the steps of sequentially moving each droplet and imaging the plurality of clusters to generate sequence data for the plurality of clusters of polynucleotides. These methods may also include introducing the series of fluidic droplets into the air gap. For example, sequentially moving each droplet may comprise moving each droplet as it is introduced into the air gap. In any of these methods, imaging may comprise imaging the plurality of clusters of polynucleotides after moving the first wash buffer droplet over the plurality of clusters of polynucleotides. The plurality of clusters of polynucleotides may be arranged in a patterned or, in some examples, an unpatterned arrangement.

In any of these examples, moving the one or more mechanical force applicators against the first sheet to elastically deform the first sheet comprises moving one or more styluses against the first sheet.

Any of these methods may include mixing. For example, the method may include chaotically mixing by repeatedly applying and releasing a compression force to the first sheet over the plurality of clusters of polynucleotides to mix one droplet of the series of fluidic droplets over the plurality of clusters of polynucleotides. Alternatively or additionally, the methods may include gently mixing by moving the mechanical force applicator against the first sheet in a plane of the first sheet, e.g., in an x and/or y axis direction.

Sequentially moving each droplet of the series of fluidic droplets may comprise removing each droplet of the series of fluidic droplets from the air gap after it been moved over the plurality of clusters of polynucleotides.

The method described herein may be used with very low volume droplets. For example, the droplets of the series of fluidic droplets has a volume between $10^{-6}$ and $10^{-15}$ liters (e.g., microliter or less).

In general, in an of these methods, the air gap may be open to atmospheric pressure and unpressurized. Thus, the droplet is not moved by pressure, but instead by the change in gap width (also referred to as gap height), resulting in a capillary force pulling the droplet.

Any of these methods may include hybridizing a library of polynucleotides to either the first sheet or the second sheet in the air gap to form the clusters of polynucleotides.

In some examples a method of sequencing by synthesis using mechanical compression may include: sequentially moving each droplet of a series of fluidic droplets within a cartridge, wherein the cartridge comprises an air gap formed between a first sheet having a first surface that is hydrophobic and oleophobic and a second sheet having a second surface that is hydrophobic and oleophobic, wherein the first sheet and the second sheet are secured opposite each other at a predetermined spacing relative to each other with the air gap therebetween, further comprising a plurality of clusters of polynucleotides on the second sheet, wherein moving each droplet comprises moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet; imaging the plurality of clusters of polynucleotides to detect addition or hybridization of a nucleotide to clusters of the plurality of clusters of polynucleotides; and repeating the steps of sequentially moving each droplet and imaging the plurality of clusters to generate sequence data for the plurality of clusters of polynucleotides.

A method of sequencing by synthesis using mechanical compression may include: sequentially introducing a series of fluidic droplets into an air gap formed between: a first sheet having a first surface that is hydrophobic and oleophobic; and a second sheet having a second surface that is hydrophobic and oleophobic, wherein the first sheet and the second sheet are secured opposite at a predetermined spacing relative to each other with the air gap therebetween, further comprising a plurality of clusters of polynucleotides on the second sheet; sequentially moving each droplet of the series of fluidic droplets over the plurality of clusters of polynucleotides by moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet; imaging the plurality of clusters of polynucleotides to detect addition or hybridization of a nucleotide to clusters of the plurality of clusters of polynucleotides; and repeating the steps of sequentially introducing the series of fluidic droplets, moving each droplet and imaging the plurality of clusters.

All of the methods and apparatuses described herein, in any combination, are herein contemplated and can be used to achieve the benefits as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the features and advantages of the methods and apparatuses described herein will be obtained by reference to the following detailed description that sets forth illustrative embodiments, and the accompanying drawings of which:

FIGS. 40A-40D illustrate one examples cartridges for use with a mechanical microfluidics actuator. FIG. 40A shows an example of a cartridge having three lanes. FIG. 40B shows an example of a cartridge having eight lanes. FIG. 40C shows an example of a portion of the cartridge of FIG. 40A; FIG. 40D shows an enlarged view of the sectional view of FIG. 40C.

FIG. 43C shows the cartridge of FIG. 43B with a droplet within the air gap of the cartridge.

FIG. 44A shows an example of a cartridge coupled to a mechanical microfluidics actuator having a seating region including a recessed seating surface. FIG. 44B shows a mechanical microfluidics actuator having a seating region with a raised section. FIG. 44C shows an example of a mechanical microfluidics actuator having a thermally-conductive cylindrical rail (forming a rail region) projecting from the seating region. FIG. 44D shows an example of a mechanical microfluidics actuator having a thermally-conductive flat platform rail (e.g., rail region) projecting from the seating region. FIG. 44E shows an example of a mechanical microfluidics actuator having a thermally-conductive domed platform rail (rail region) projecting from the seating region.

FIG. 45A shows the seating region; FIG. 45B shows the seating region made partially transparent; FIG. 45C shows the seating region with a cartridge coupled thereto.

FIGS. 62A-62J illustrate loading and unloading of droplets within a cartridge as described herein.

DETAILED DESCRIPTION

A microfluidic apparatus (e.g., device, system or the like) for controlled liquid manipulation may include a two-dimensional (planar) fluidic chamber. The chamber may include a first sheet and a second sheet separated by a gap therebetween. The gap may separate the first and second sheets by any feasible distance. The first and second sheets may be hydrophobic or may include hydrophobic coatings. In some examples the first and second sheet are hydrophobic and oleophobic and/or include a hydrophobic and oleophobic coating.

Microfluidic droplets may be manipulated through mechanical manipulation that applies forces directly or indirectly to the first sheet or second sheet selectively reducing the gap. This process may sometimes be referred to as mechanical actuation on the surface (MAOS), also described as the use of mechanical compression to change the capillary force. The applied forces, which may include compressive forces, may be applied near or adjacent to droplets within the gap. In some aspects, reducing the gap may cause the droplets to move, separate, combine, mix, incubate, or the like.

In some examples, the forces may be applied by a stylus. The stylus may include an electrode and/or a controllable magnet. The microfluidic droplets may be manipulated with a combination of pressure, exerted by the stylus, in conjunction with a voltage provided by the electrode and/or a magnetic field provided by the magnet.

Figure 1A:
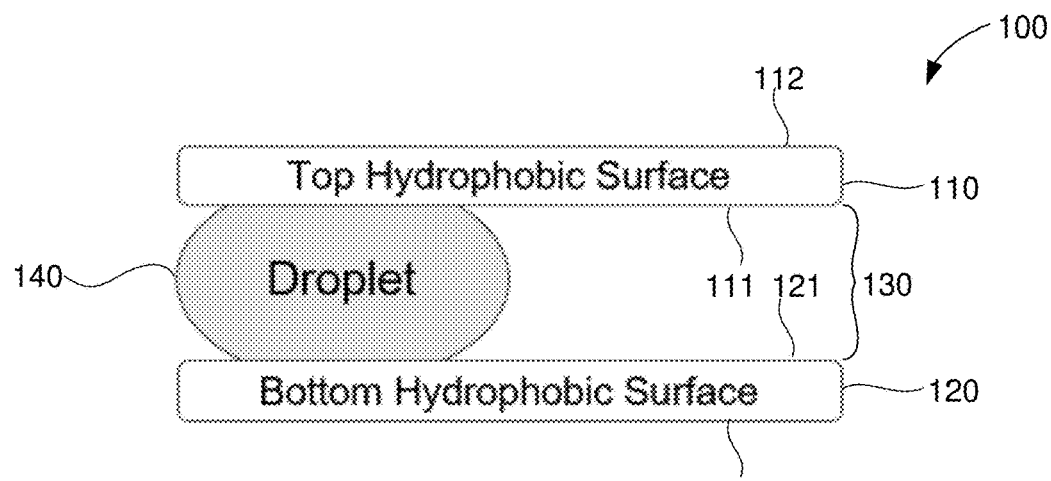
FIGS. 1A-1C show a portion of a microfluidic apparatus (e.g., a portion of a mechanical microfluidics actuator or cartridge for use in a mechanical microfluidics actuator).

FIG. 1A shows a portion of a microfluidic device 100. Any of the devices described herein may be implemented in part or in whole as a system or any other feasible apparatus. The microfluidic device 100 may include a first sheet 110 and a second sheet 120 separated by a gap 130. In some examples, the gap 130 may generally be filled with air. In some examples, the microfluidic device 100 may be a cartridge that may be selectively coupled to a control unit or base station. As shown, the first sheet 110 may be a "top" sheet and the second sheet 120 may be a "bottom" sheet. That is, the first sheet 110 may be higher or "above" the second sheet 120. The second sheet 120 may be closer to the ground than the first sheet 110. In other examples, the second sheet 120 may be above the first sheet 110.

The first sheet 110 and the second sheet 120 may form a planar structure that occupies any feasible area. The first sheet 110 and the second sheet 120 are shown in an initial position. In the initial position, the first sheet 110 and the second sheet 120 are relatively parallel to each other separated by a distance associated with and/or determined by the gap 130.

Each sheet may include two surfaces. For example, the first sheet 110 may include a first surface 111 and a second surface 112 and the second sheet 120 may include a first surface 121 and a second surface 122. For ease of description, the first surfaces 111 and 121 may be disposed toward the gap 130, while the second surfaces 112 and 122 may be disposed on opposite sides of the first sheet 110 and the second sheet 120, respectively. In other words, the second surfaces 121 and 122 may be disposed away from the gap 130.

The first surfaces 111 and 121 may be hydrophobic (water repelling). In some examples, the first and second sheets 110 and 120 (and thus the first surfaces 111 and 121) may be formed from a hydrophobic and oleophobic material. In some other examples, the first surfaces 111 and 121 may be a hydrophobic and oleophobic coating or layer applied upon the first and second sheets 110 and 120, respectively.

A droplet 140 may be introduced into the gap 130. In some cases, the droplet 140 may be introduced in the gap 130 through a port or opening (not shown) on the first sheet 110 and/or the second sheet 120. The droplet 140 may be mechanically manipulated by selectively reducing the gap near the droplet 140. In some examples, one or more of the sheets 110 and 120 may be flexible. Flexible sheets may deflect in response to one or more forces. For example, the first sheet 110 may be flexible and the second sheet 120 may be rigid or semi-rigid. Rigid or semi-rigid sheets may resist deflection in response to one or more forces. In other examples, the second sheet 120 may be flexible and the first sheet 110 may be rigid or semi-rigid. In still other examples, both the first sheet 110 and the second sheet 120 may be flexible. As used herein, the term flexible may describe any material that may flex, deform, bend, move, or the like.

The droplet 140 may have a predetermined volume. In some cases, the droplet 140 may be a microfluidic droplet having a volume of the droplet 140 may be between $10^{-6}$ and $10^{-15}$ liters, although in some examples the volume of the droplet 140 can have any other feasible volume. The gap 130 may be determined, at least in part, by the volume of the droplet 140. In other words, the gap 130 may be chosen or selected such that the droplet 140 (e.g., the volume of the droplet 140) can touch both the first and second sheets 110 and 120.

Figure 1B:
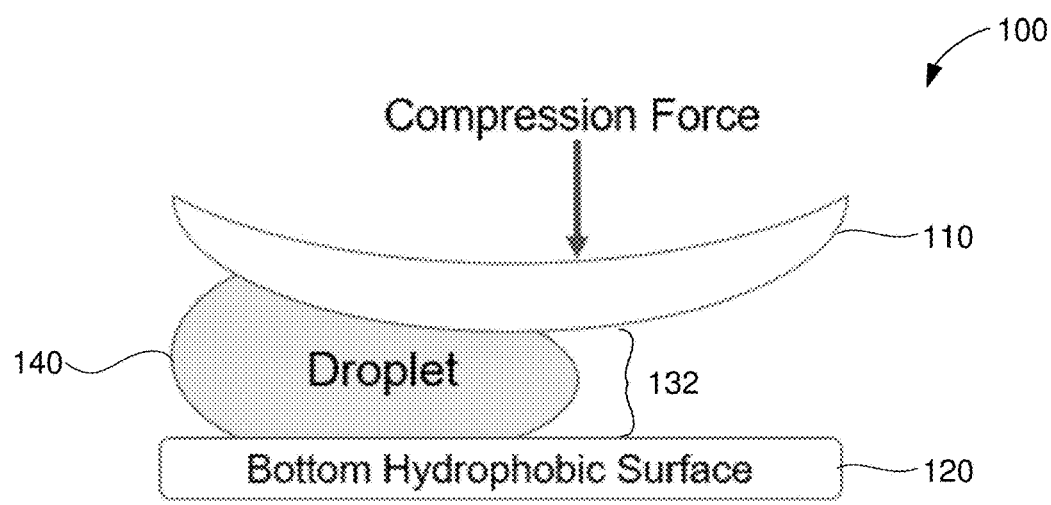

FIG. 1B shows another view of the microfluidic device 100. In this view, the first sheet 110 may be deflected by a compression force near or adjacent to one side or end of the droplet 140. The compression force creates a reduced gap 132 between the first sheet 110 and the second sheet 120 toward the end or side of the droplet 140. As the reduced gap 132 is formed, the droplet 140 may deform asymmetrically and be drawn toward the reduced gap 132. In some cases, the droplet movement may be caused by differential capillary action and/or a differential pressure gradient within the droplet 140. The compression force may be provided by any feasible means. For example, an array of electro-mechanical, mechanical, and/or pneumatic actuators may be disposed next to the first sheet 110 and/or the second sheet 120 to selectively provide a compression force to form the reduced gap 132. In another example, the compression force may be provided by a stylus that may contact the first sheet 110 and/or the second sheet 120.

In some examples, the microfluidic device 100 may include one or more optical sensors (not shown). The one or more optical sensors may detect the presence and/or position of the droplet 140. In this manner, data from the optical sensors may be used to assist the application of a compression force near or adjacent to the droplet 140.

Figure 1C:
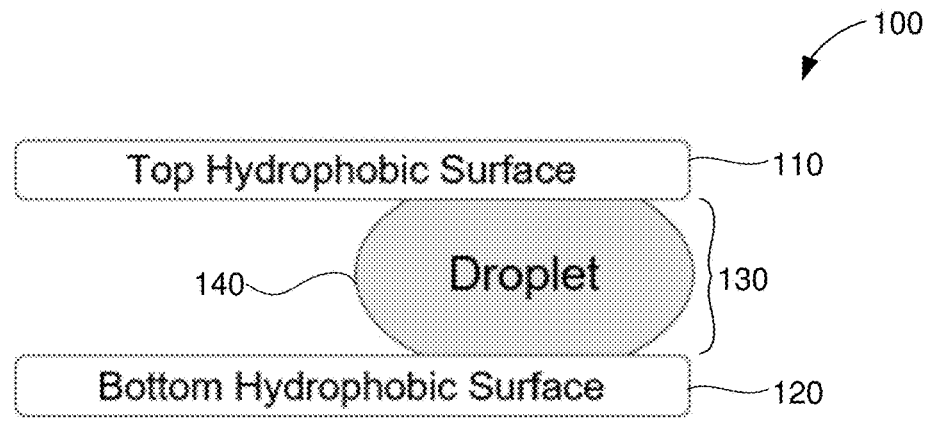

FIG. 1C shows another view of the microfluidic device 100. In this view, the compression force on the first sheet 110 has been removed or reduced and the first sheet 110 and the second sheet 120 has returned to an initial position (as shown in FIG. 1A). The gap 130 may be similar to the gap 130 of FIG. 1A. The droplet 140 is shown in a second position having moved in response to the compression force described with respect to FIG. 1B.

Thus, in the manner described within FIGS. 1A-1C, any droplet may be manipulated to any area within the microfluidic device 100 by reducing the gap near one end of the droplet. This method advantageously avoids the generation and control of high voltages as well as the need for a plurality of electrodes that are associated with conventional microfluidic devices. The compression force described herein may be provided by any feasible source. For example, mechanical levers, balls, rollers, or the like may apply the compression force to at least one of the first or second sheets 110 and 120, respectively. In some examples, the compression force may be computer or processor controlled. Thus the manipulation of the droplet 140 may be computer and/or processor controlled.

Figure 2:
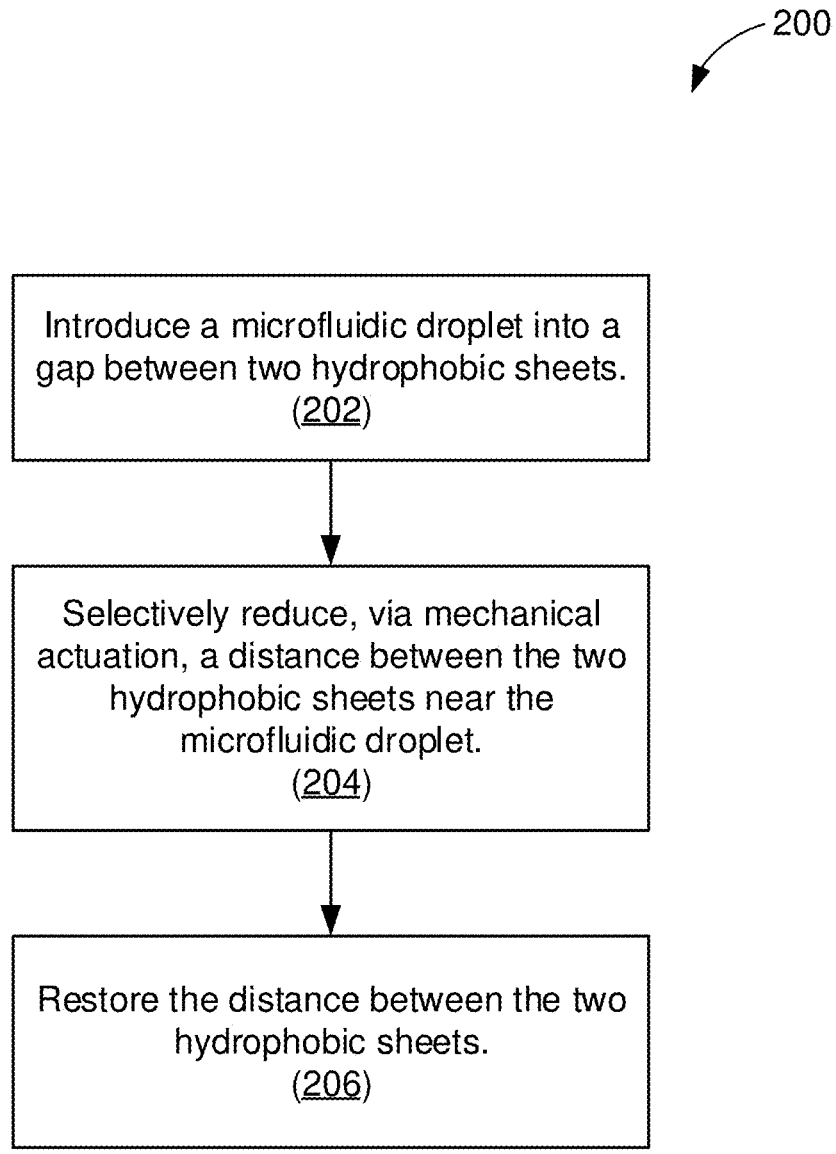
FIG. 2 is a flowchart showing an example operation for manipulating a microfluidic droplet.

FIG. 2 is a flowchart showing an example operation 200 for manipulating a microfluidic droplet. Some examples may perform the operations described herein with additional operations, fewer operations, operations in a different order, operations in parallel, and some operations differently. The operation 200 is described below with respect to the microfluidic device 100 of FIGS. 1A-1C, however, the operation 200 may be performed by any other suitable system or device.

The operation 200 begins in block 202 as a microfluidic droplet is introduced into a gap between two hydrophobic and oleophobic sheets. For example, the droplet 140 may be loaded into the gap 130 between the first sheet 110 and the second sheet 120 of the microfluidic device 100. The gap 130 may be an initial separation distance between the first sheet 110 and the second sheet 120. The first sheet 110 and the second sheet 120 may be hydrophobic and oleophobic or include surfaces covered with a hydrophobic and oleophobic layer. The droplet 140 may be placed in an initial position. The gap 130 may be filled with any feasible gas, such as air. In some examples, the gap 130 may be filled with an immiscible (with respect to the droplet 140) fluid. The presence and/or location of the droplet 140 may be determined with an optical sensor (not shown). Example optical sensors may include one or more digital cameras, an array of visible and/or invisible light detectors, or the like. Thus, an optical sensor may determine when the droplet 140 is introduced into the gap 130

Next, in block 204 the distance between the two hydrophobic and oleophobic sheets is selectively reduced, via mechanical actuation, near the microfluidic droplet. The reduced distance may result in a reduced gap 132 between the first sheet 110 and the second sheet 120. In some examples, a compression force may be provided to the sheet 110 adjacent to (e.g., next to) one side of the droplet 140. The compression force may reduce the gap 130 causing the droplet 140 to move toward the compression force. In some examples, the compression force may deform one end of the droplet 140.

Next, in block 206 the distance between the two hydrophobic and oleophobic sheets is restored. For example, the compression force applied in block 204 may be removed allowing the first sheet 110 and/or the second sheet 120 to return to its initial separation distance. In some examples, the distance between first sheet 110 and second sheet 120 is returned to a distance similar to the initial separation distance of block 202. The microfluidic droplet may come to rest at a different position having moved from the initial position of block 202.

The steps of blocks 202-206 may be repeated any number of times to manipulate one or more droplets to any arbitrary location in the gap 130 of the microfluidic device 100. In some examples, different compression forces (e.g., different force amplitudes) may be applied to the droplet to perform different manipulations.

Figure 3A:
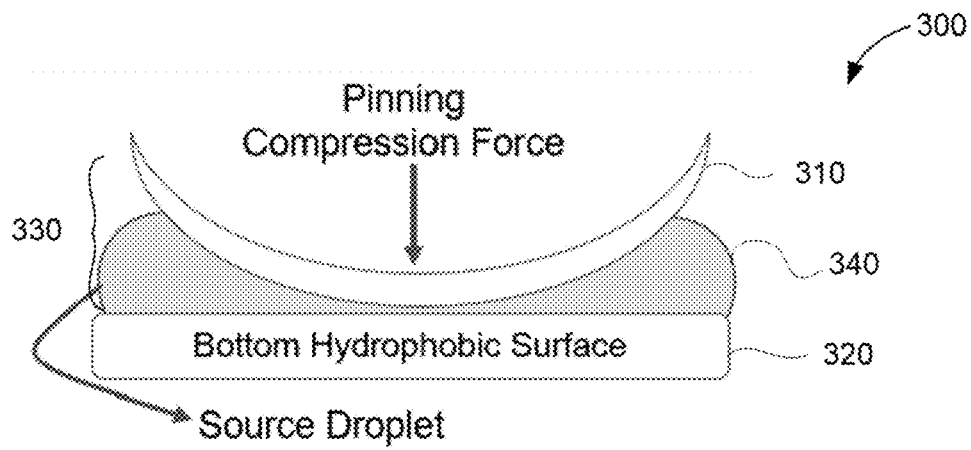
FIGS. 3A-3C show a portion of another microfluidic apparatus (e.g., mechanical microfluidics actuator).

FIG. 3A shows a portion of another microfluidic device 300. The microfluidic device 300 may include a first sheet 310, a second sheet 320, and a gap 330 that may be examples of the first sheet 110, the second sheet 120 and the gap 130 of FIG. 1. A source droplet 340 (which may be similar to the droplet 140) may be introduced into the gap 330 as described above with respect to FIGS. 1A and 2.

A pinning compression force may be applied to the source droplet 340. Although shown as being applied to the first sheet 310, in other examples the pinning compression force may be applied to the second sheet 320. As shown, the pinning compression force may be applied approximately toward the center or middle of the source droplet 340. The pinning compression force may be provided by any technical feasible device or operation. The pinning compression force may begin to divide or separate the source droplet 340 into two droplets.

Figure 3B:
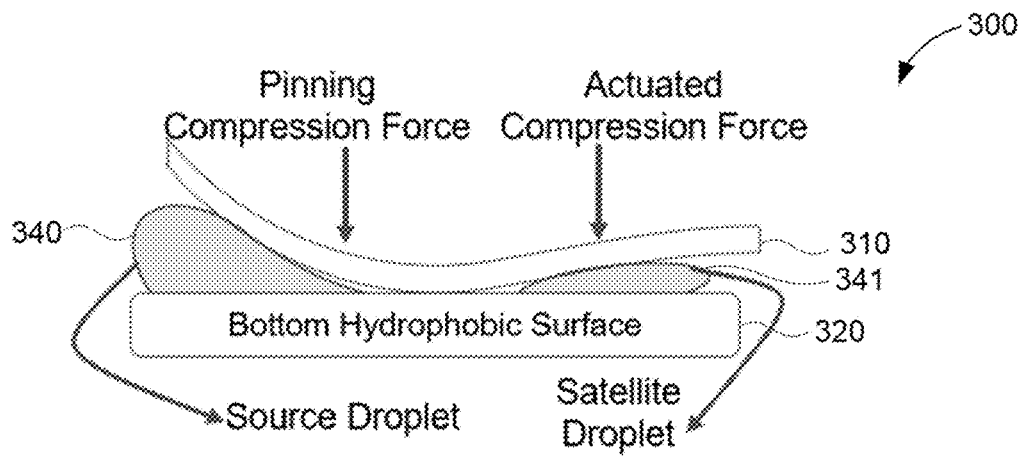

FIG. 3B shows another view of the microfluidic device 300. As shown, an actuation compression force may be applied to the source droplet 340. The actuation compression force may be less than the pinning compression force applied in FIG. 3A. The actuation compression force may be applied at the same time (coincident with) or after applying the pinning compression force. The actuation compression force may separate and guide a satellite droplet 341 away from the source droplet 340. In some examples, the pinning compression force may cause the first sheet 310 to contact the second sheet 320 helping separate the satellite droplet 341 from the source droplet 340.

Figure 3C:
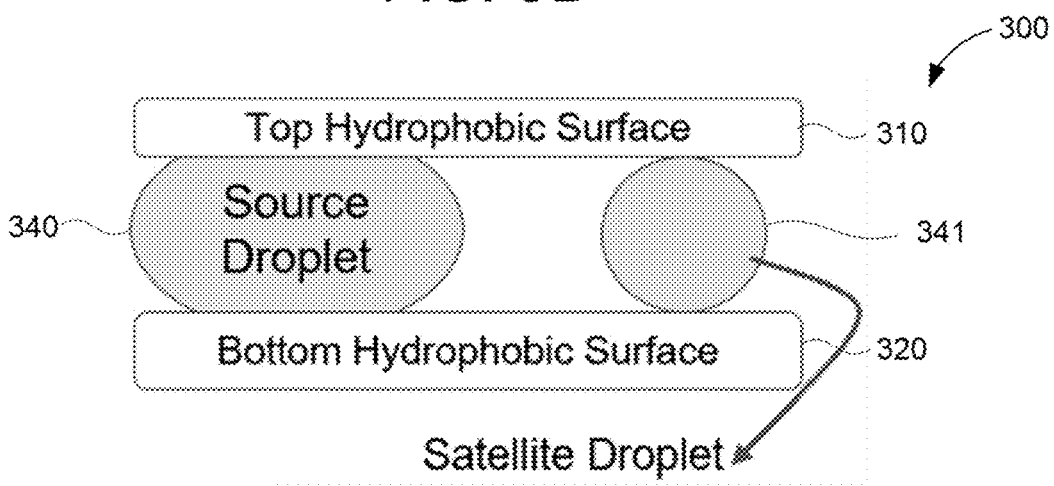

FIG. 3C shows another view of the microfluidic device 300. As shown, the pinning and actuation forces have been removed or reduced allowing the first sheet 310 and/or the second sheet 320 to return to their initial positions, such as the initial positions shown in FIG. 3A. The source droplet 340 is shown separated from the satellite droplet 341.

Figure 4:
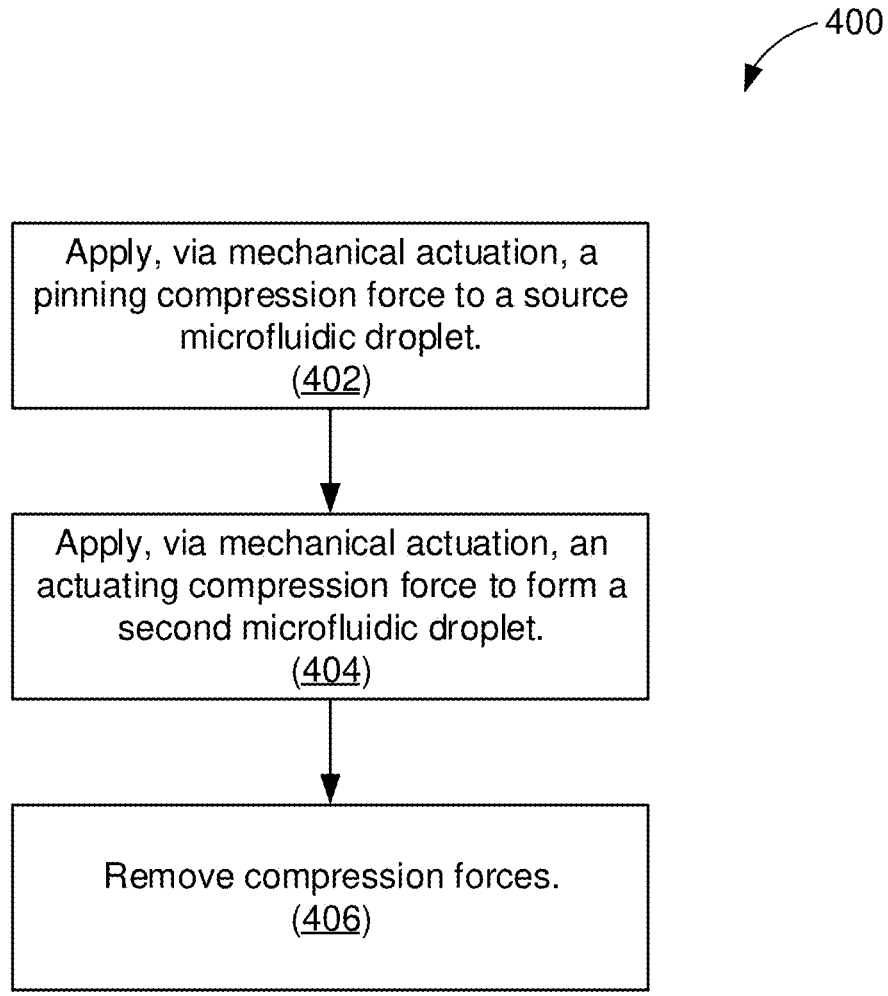
FIG. 4 is a flowchart showing an example operation for separating a microfluidic droplet into two or more microfluidic droplets.

FIG. 4 is a flowchart showing an example operation 400 for separating a microfluidic droplet into two or more microfluidic droplets. The operation 400 is described below with respect to microfluidic device 300 of FIGS. 3A-3C, however, the operation 400 may be performed by any other suitable system or device.

The operation 400 begins in block 402 as a pinning compression force is applied, via mechanical actuation, to a source microfluidic droplet. The source microfluidic droplet (which may be similar to the source microfluidic droplet 340) may have previously been introduced into a gap between the first sheet 310 and the second sheet 320, for example as described above with respect to FIGS. 1A and 2. In some examples, the pinning compression force may begin to divide or separate the source microfluidic droplet into two or more droplets. The pinning compression force may be a mechanical actuation force provided to the first sheet 310 and/or the second sheet 320 and may be provided by any feasible means. In some cases, the pinning compression force may be applied toward the middle or center of the source microfluidic droplet. In some examples, the pinning compression force may cause the first sheet 310 to contact the second sheet 320.

Next, in block 404, an actuation compression force is applied, via mechanical actuation, to the source microfluidic droplet. The actuation force may be applied to separate, direct, and/or steer a satellite microfluidic droplet away from the source microfluidic droplet. The actuation compression force may be another mechanical actuation force that, in this instance, is less in force than the pinning compression force. The actuation compression force may be applied coincident with, or after the pinning compression force is applied.

In block 406, the pinning compression force and the actuation compression force is removed or reduced. In the absence of the compression forces, the first sheet 310 and the second sheet 320 may return to associated initial positions, such as depicted in FIG. 3C. As the pinning and actuation compression forces are removed or reduced, the satellite droplet may remain separated from the source droplet.

In some examples, two or more separate droplets may be merged together using a compression force. One such example is described in conjunction with FIGS. 5A-5C and 6. Droplets of different sizes or the same size may be merged. For example, 250 nL-80 µL volumes may be robustly actuated and merged with an equal volume, larger or smaller volume that already exists in the air gap.

Figure 5A:
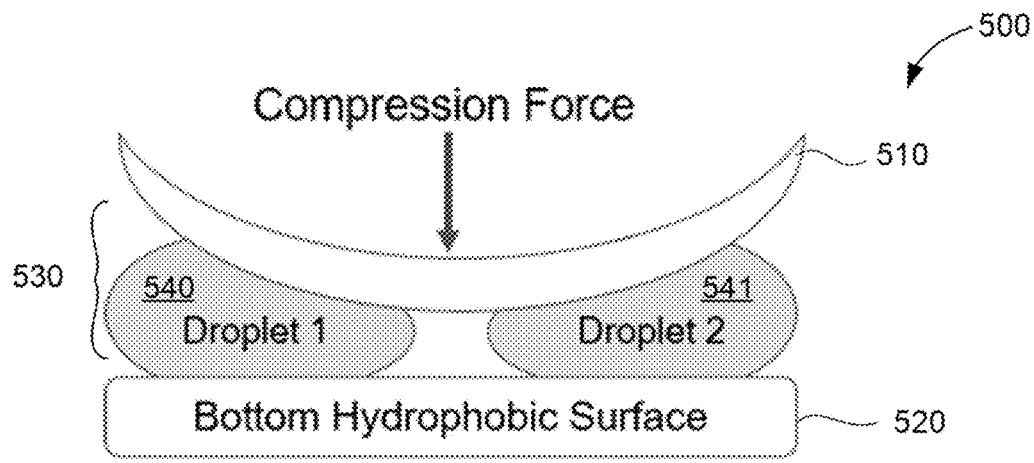
FIGS. 5A-5C show a portion of another microfluidic apparatus.

FIG. 5A shows a portion of another microfluidic device 500. As shown in FIG. 5A, the microfluidic device 500 may include a first sheet 510, a second sheet 520, and a gap 530 that may be other examples of the first sheet 110, the second sheet 120 and the gap 130 of FIG. 1A. A first droplet 540 and a second droplet 541 (which may be similar to the droplet 140 of FIG. 1A or the source droplet 340 and satellite droplet 341 of FIG. 3C) may be introduced into the gap 530 as described above with respect to FIGS. 1A-1C, 2, 3A-3C, and 4.

A compression force may be applied to the first sheet 510 and/or the second sheet 520. In some examples, the compression force may be applied between the first droplet 540 and the second droplet 541 causing the respective droplets to deform, move, and in some cases, combine. The compression force may be a mechanical actuation force as described herein.

Figure 5B:
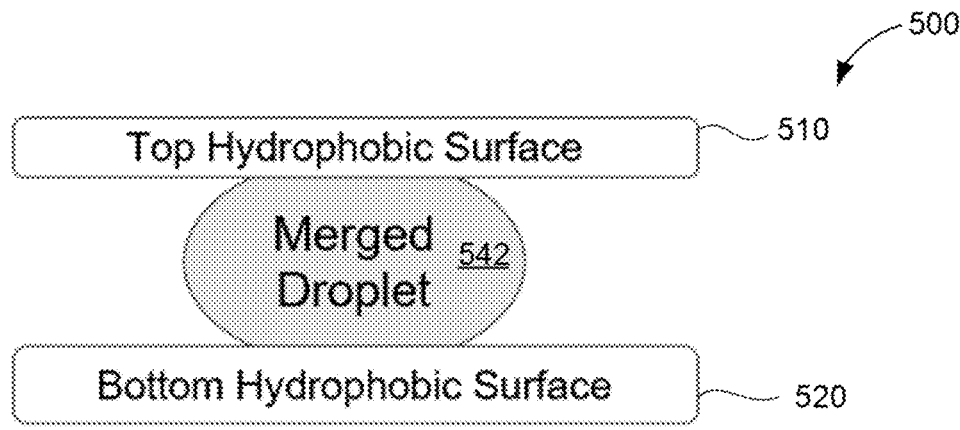

FIG. 5B, shows another view of the microfluidic device 500. The compression force is removed or reduced thereby allowing the first sheet 510 and/or the second sheet 520 to return to initial (uncompressed) positions. As shown, the first droplet 540 and the second droplet 541 may be combined into a merged droplet 542. Although combined into a single droplet, the individual droplets, or components within the first droplet 540 and the second droplet 541 may not be well-mixed within the merged droplet 542.

Figure 5C:
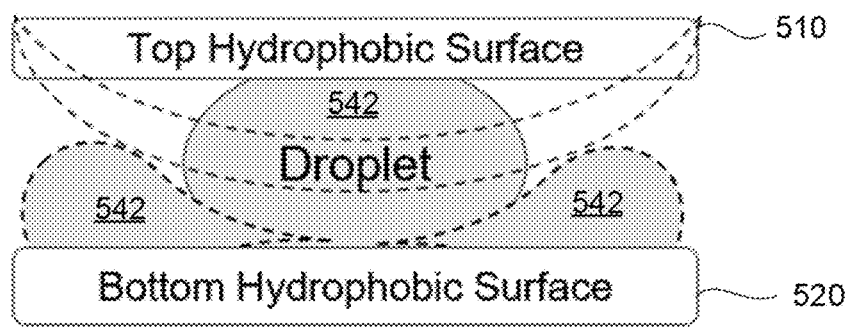

FIG. 5C shows another view of the microfluidic device 500. A compression force may be repeatedly applied and released to and from the first sheet 510 and/or the second sheet 520 to mix the contents of the merged droplet 542. The repeated application of the compression force may repeatedly cause the merged droplet 542 to deform and recover thereby causing the contents of the merged droplet 542 to mix. In some examples, the compression/relaxation cycle, caused by the application and release of the compression force, may be repeated for a predetermined number of times to mix the contents of the merged droplet 542.

Figure 6:
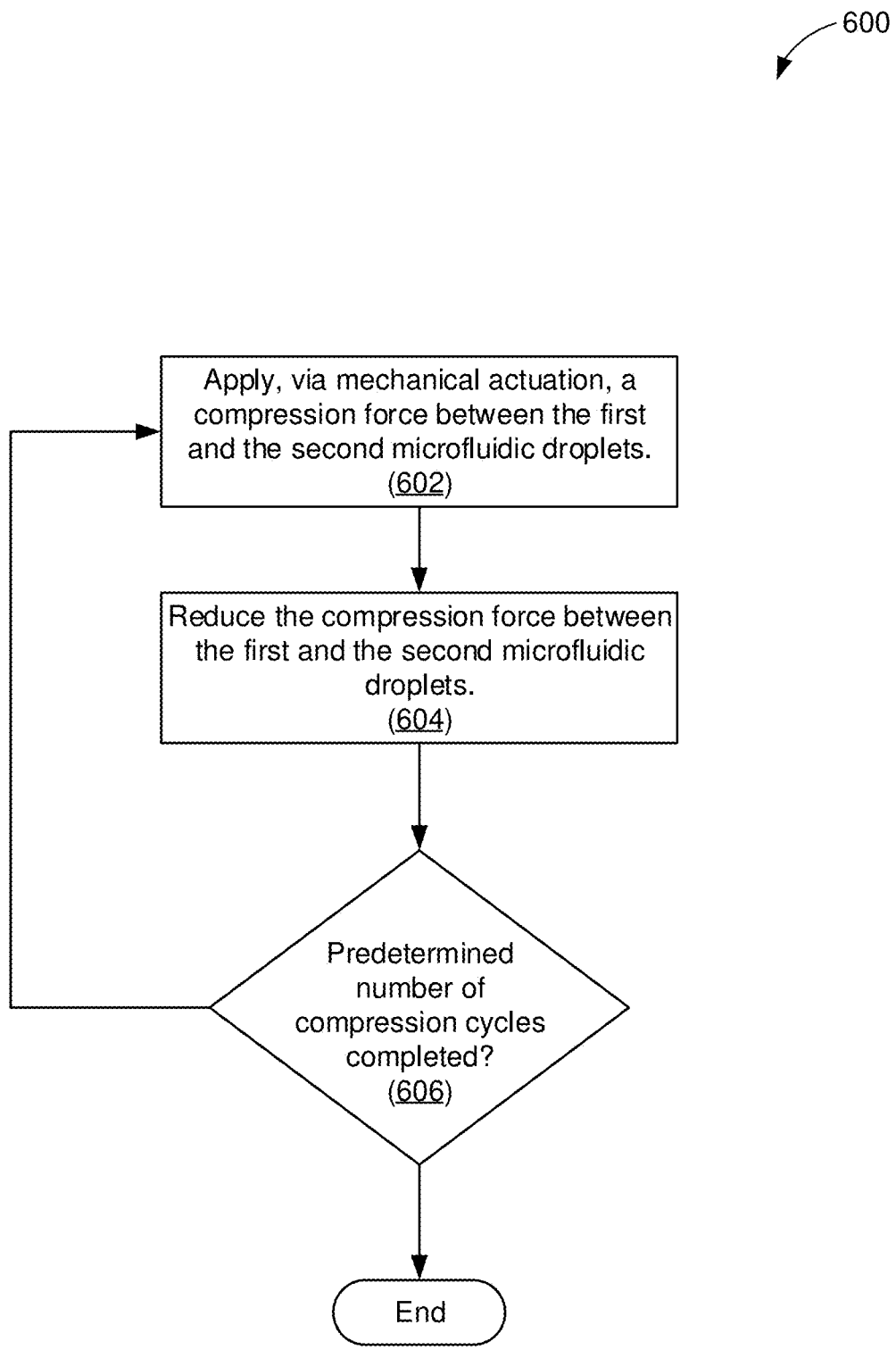
FIG. 6 is a flowchart showing an example operation for mixing a microfluidic droplet.

FIG. 6 is a flowchart showing an example operation 600 for mixing a microfluidic droplet. The operation 600 is described with respect to the microfluidic device 500 of FIG. 5A-5C, however the operation 600 may be performed by any other suitable system or device. The operation 600 begins in block 602 as a compression force is applied, via mechanical actuation, to the first sheet 510 and/or the second sheet 520 between first and second microfluidic droplets 540 and 541. The compression force may be a mechanical actuation force provided by any feasible means. The compression force may cause the first and second microfluidic droplets 540 and 541 to move toward each other and, in some cases, combine into a single (merged) microfluidic droplet 542.

In block 604, the compression force is reduced or removed from the first sheet 510 and/or the second sheet 520. In some examples, reducing or removing the compression force may allow the first sheet 510 and/or the second sheet 520 to return to an initial position.

In some cases, additional agitation of the merged microfluidic droplet 542 may be desired to provide additional mixing. To provide the additional agitation, a compression force may be repeatedly applied and removed (or reduced) for a predetermined number of cycles. Therefore, in block 606, the number of completed compression cycles is determined. A completed compression cycle may include the application and removal or reduction of a compression force. If the number of compression cycles is less than a predetermined number, then the operation may return to block 602. On the other hand, if the number of compression cycles is greater than or equal to the predetermined number, then the operation 600 may end.

In some examples, ferrous particles may be suspended within a microfluidic droplet to assist with processing or assaying. After one or more processing steps have been completed, the ferrous particles may be removed from the droplet for further processing.

Figure 7A:
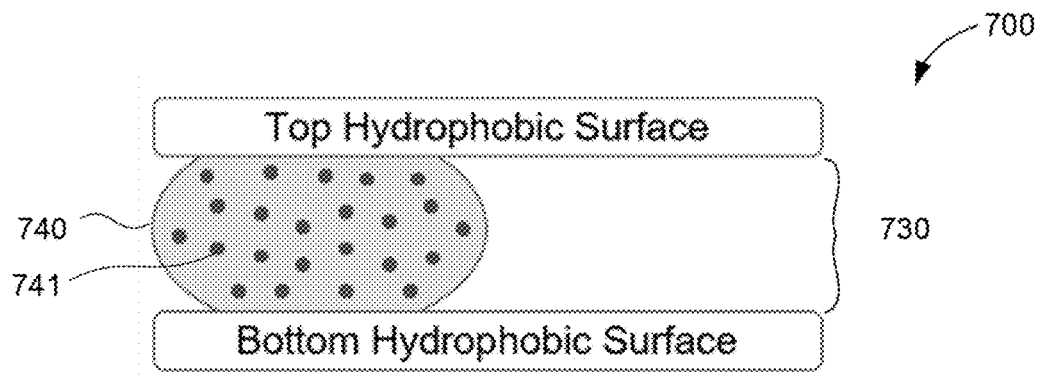
FIGS. 7A-7C show a portion of another microfluidic apparatus.

FIG. 7A shows a portion of another microfluidic device 700. The microfluidic device 700 may include a first sheet 710, a second sheet 720 and a gap 730 which may be examples of the first sheet 110, the second sheet 120, and the gap 130 of FIG. 1. A droplet 740 may include one or more ferrous particles that 741 that may be suspended within the droplet 740. The microfluidic device 700 may also include a magnet 750 (not shown).

Figure 7B:
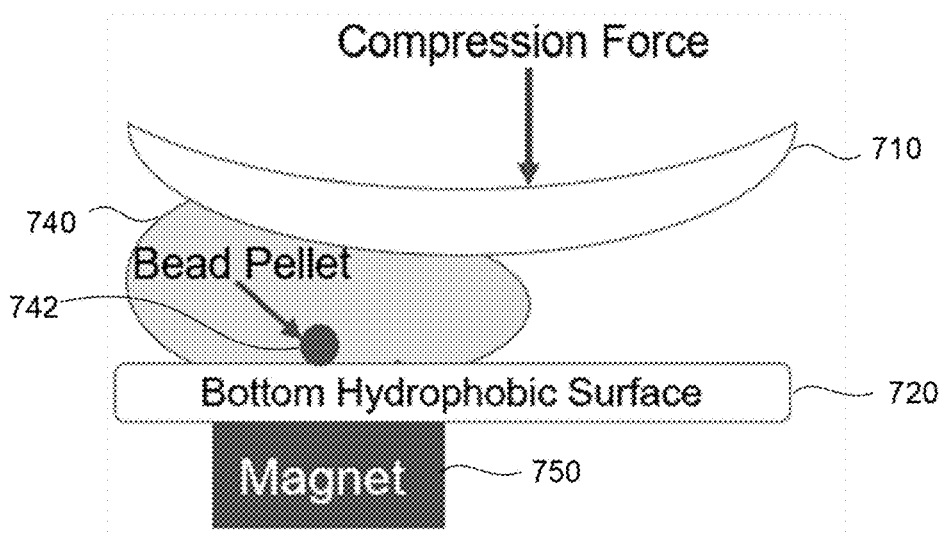

FIG. 7B shows another view of the microfluidic device 700. The magnet 750 is activated or enabled. For example, the magnet 750 may be an electromagnet that may be enabled through an application of power. In another example, the magnet 750 may be a permanent magnet that may be moved toward the droplet 740. In addition, a compression force may be applied to the first sheet 710 and/or the second sheet 720 toward one side of the droplet 740. The compression force may be applied at or near the same time as the magnet 750 is enabled or moved.

The magnet 750 may cause the ferrous particles 741 to collect into one or more ferrous beads 742. Thus, the ferrous particles 741 may come out of suspension from the droplet 740. In addition, the compression force may cause the droplet 740 to move away from the magnet 750. The droplet movement may, in some cases, filter or remove the ferrous particles from the droplet 740.

Figure 7C:
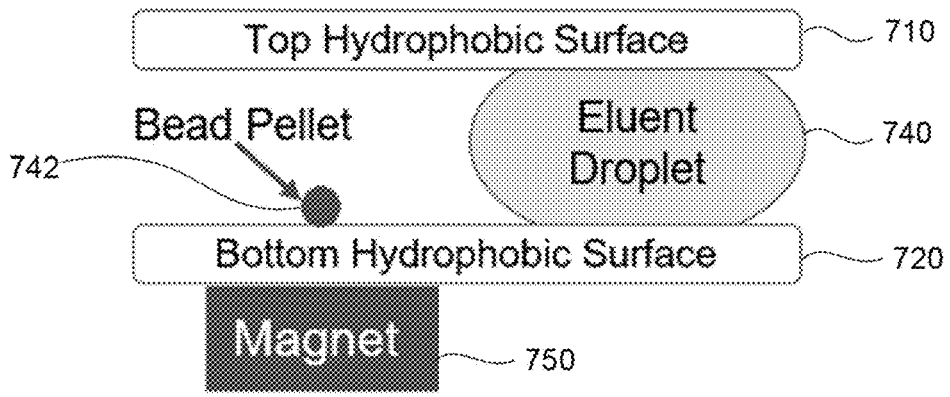

FIG. 7C shows another view of the microfluidic device 700. The compression force is removed or reduced and the first sheet 710 and the second sheet 720 return to initial positions. The compression force applied in FIG. 7B and removed or reduced in FIG. 7C may cause the droplet 740 to move away from the magnet 750. Since the magnet 750 may attract and/or limit the movement of the ferrous bead 742, droplet movement may filter the ferrous material from the droplet 740.

Figure 8:
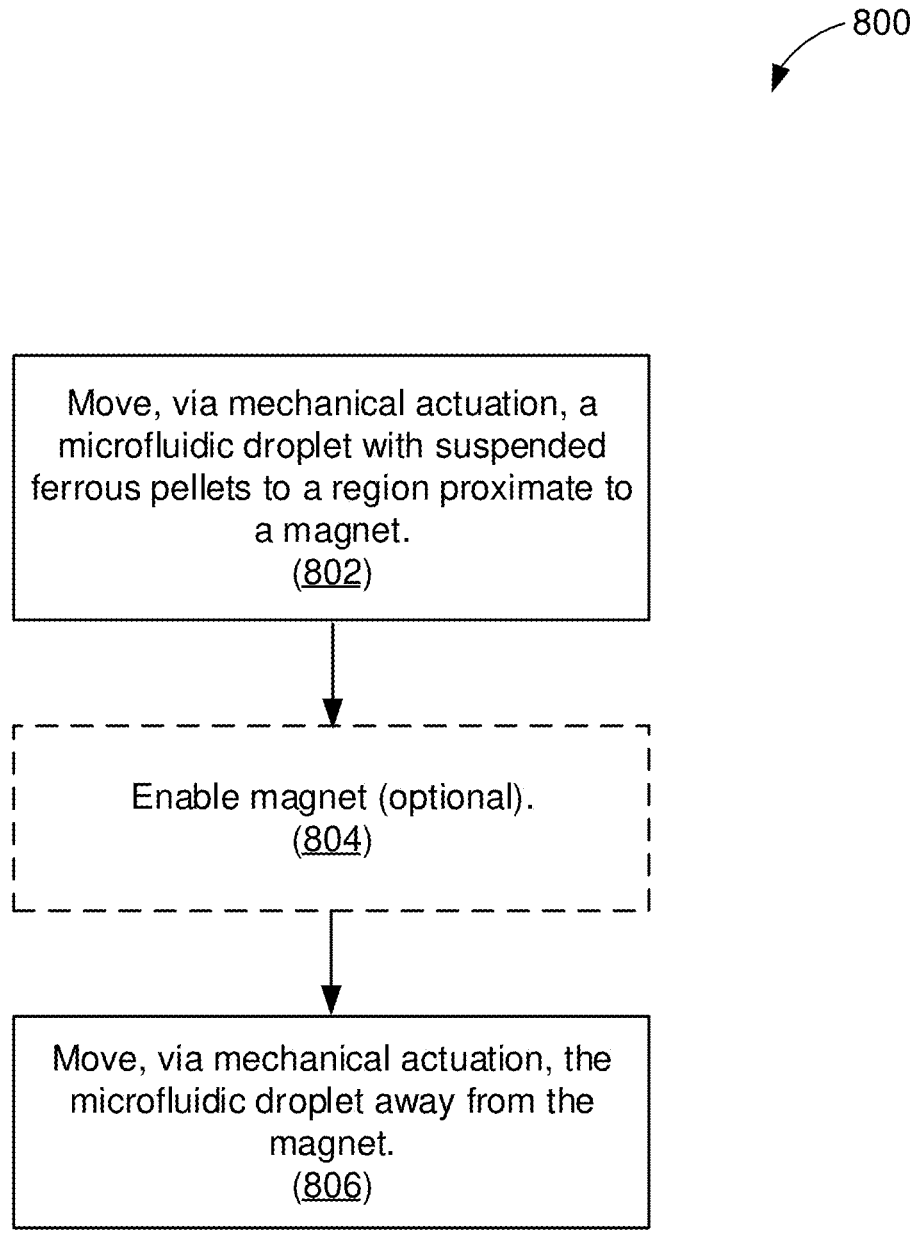
FIG. 8 is a flowchart showing an example operation for removing suspended ferrous particles from a microfluidic droplet.

FIG. 8 is a flowchart showing an example operation 800 for removing suspended ferrous particles from a microfluidic droplet. The operation 800 is described with respect to the microfluidic device 700 of FIGS. 7A-7C, however the operation 800 may be performed by any other suitable system or device.

The operation 800 begins in block 802 as a microfluidic droplet with suspended ferrous particles is moved via mechanical manipulation to a region proximate to a magnet. For example, a microfluidic droplet 740 may be moved near a magnet 750. In some examples, the droplet 740 may be moved through the application of forces to one or more sheets as described herein.

Next, in block 804 a magnet is enabled. In some cases this step may be optional as indicated with dashed lines in FIG. 8. In some examples, the magnet 750 may be a permanent and stationary magnet. In some other examples, the magnet 750 may be enabled by moving the magnet 750 toward the microfluidic droplet 740 or the magnet 750 may be an electromagnet and may receive power. The magnet 750 may cause ferrous particles to fall out of suspension and collect toward the magnet 750. In some examples, the ferrous particles 741 may be collected into one or more ferrous beads 742.

Next, in block 806, the microfluidic droplet 740 may be moved away from the magnet 750 through mechanical actuation. For example, a compressive force may be applied to first or second sheets 710 or 720 to move the microfluidic droplet 740 away from the magnet 750. Moving the microfluidic droplet 740 away from the magnet may filter the ferrous material from the microfluidic droplet 740.

In some examples, ferrous material may be placed back into suspension within a droplet through mechanical actuation. One such example is described below in conjunction with FIGS. 9-10.

Figure 9A:
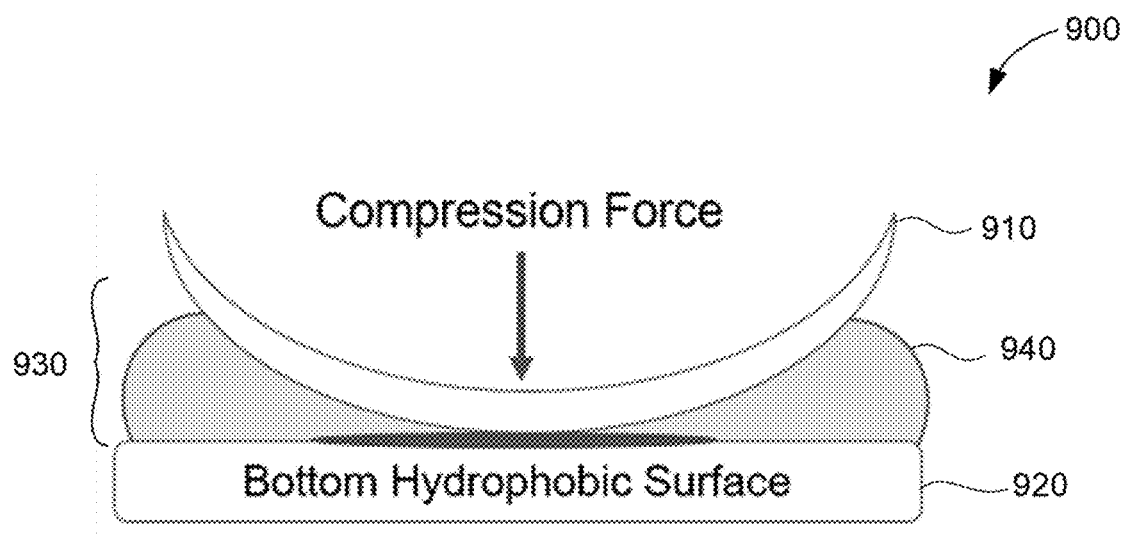
FIG. 9A-9B show a portion of another microfluidic apparatus.

FIG. 9A shows a portion of another microfluidic device 900. The microfluidic device 900 may include a first sheet 910, a second sheet 920, and a gap 930. The first sheet 910, the second sheet 920, and the gap 930 may be examples of the first sheet 110, the second sheet 120, and the gap 130 of FIG. 1A.

A droplet 940 may include non-dispersed ferrous or non-ferrous particles. A compression force may be applied to the first sheet 910 and/or the second sheet 920 (not shown) that can compress or deform the droplet 940. In some cases, a compression force may be applied to the center or middle of the droplet 940.

Figure 9B:
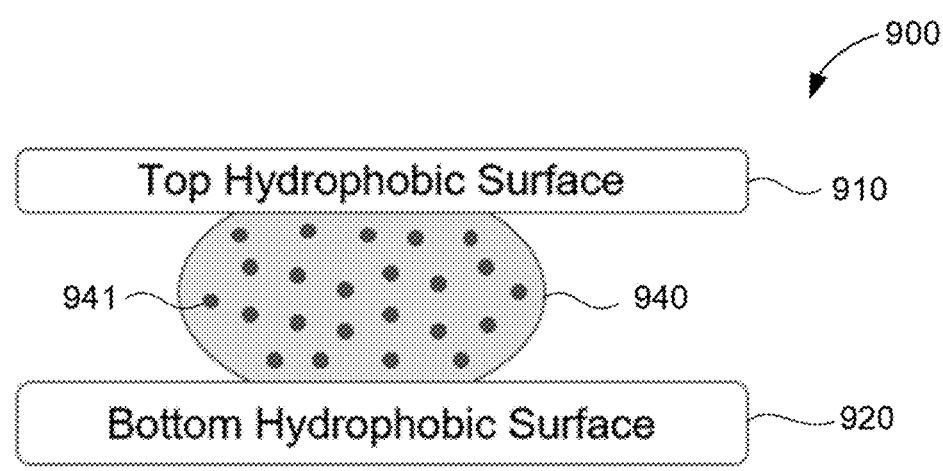

FIG. 9B shows another view of the microfluidic device 900. The compression force may be removed or reduced from the first sheet 910 and/or the second sheet 920. Removal or release of the compression force may allow the droplet 940 to return to a non-compressed or non-deformed state. Transitioning from a compressed to a non-compressed state (or vice-versa) may cause one or more ferrous or non-ferrous particles 941 within the droplet 940 to become suspended. In some cases, the compression force may be applied and/or removed quickly or abruptly. Sudden application and/or removal of compression forces may assist in dispersing ferrous and non-ferrous particles 941 throughout the droplet 940. In some cases, the compression force may be repeatedly applied and removed to disperse particles more evenly.

Figure 10:
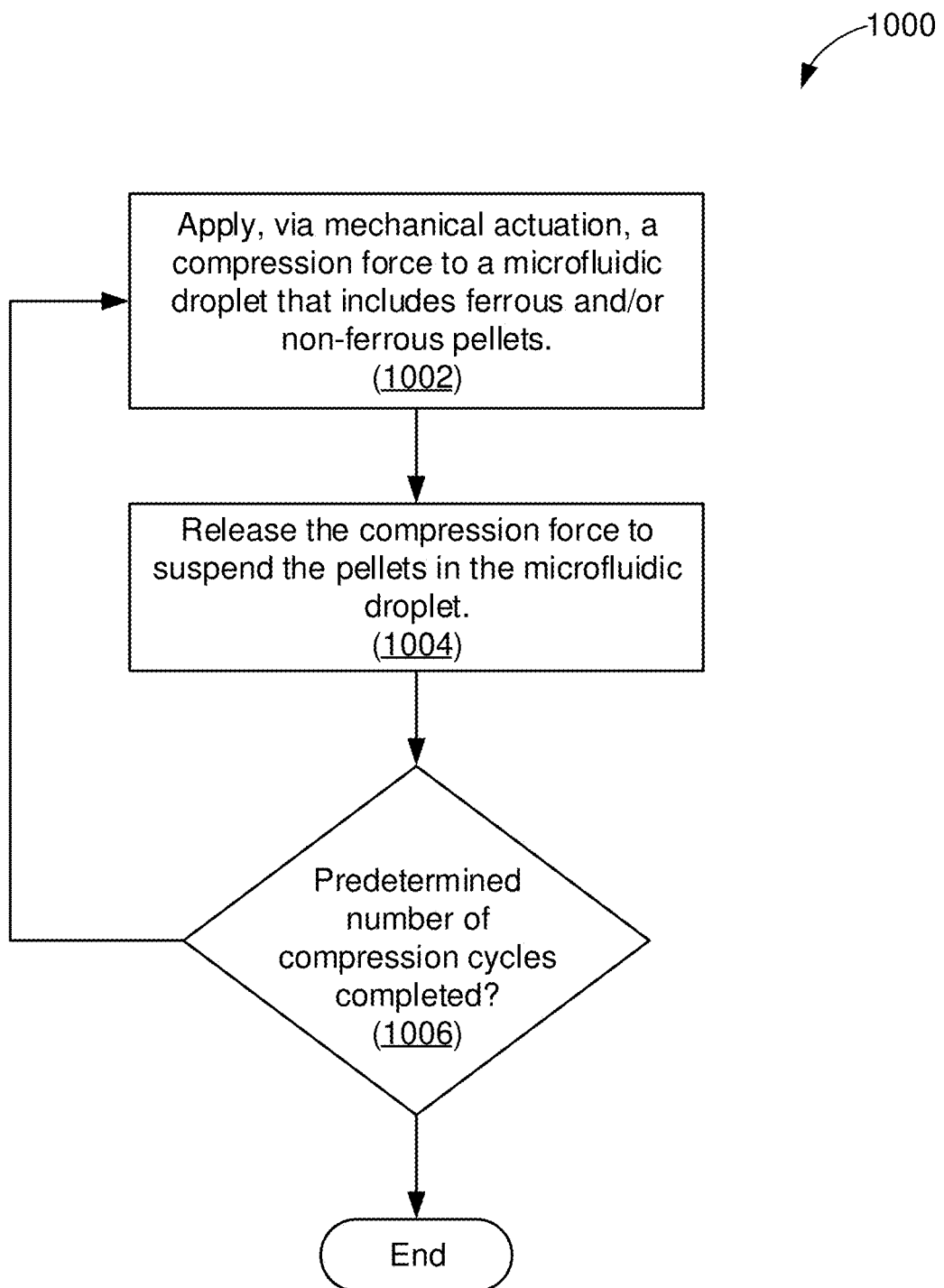
FIG. 10 is a flowchart showing an example operation for dispersing particles in a microfluidic droplet.

FIG. 10 is a flowchart showing an example operation 1000 for dispersing particles in a microfluidic droplet. The operation 1000 is described below with respect to the microfluidic device 900 of FIGS. 9A-9B, however the operation 1000 may be performed by any other suitable system or device.

The operation 1000 begins in block 1002 where a compression force is applied via mechanical actuation, to a microfluidic droplet that includes ferrous and/or non-ferrous particles 941 that are to be suspended. The compression force may be provided by a mechanical actuation force that may be applied to the first sheet 910 and/or the second sheet 920 and also to the droplet 940. The compression force may cause the droplet 940 to deform or spread.

Next, in block 1004 the compression force may be released or reduced to suspend the ferrous and/or non-ferrous particles 941 in the droplet 940. The removal or reduction of the compression force may cause the microfluidic droplet 940 to return to a spherical or quasi-spherical shape that causes ferrous or non-ferrous particles to become at least partially suspended within the droplet 940.

In some cases, additional agitation of the microfluidic droplet may be desired to enhance the distribution of the particles in the microfluidic droplet 940. To provide the additional agitation, a compression force may be repeatedly applied and removed (or reduced) for a predetermined number of cycles. Therefore, in block 1006, the number of completed compression cycles is determined. A completed compression cycle may include the application and removal or reduction of a compression force. If the number of compression cycles is less than a predetermined number, then the operation 1000 may return to block 1002. On the other hand, if the number of compression cycles is greater than or equal to the predetermined number, then the operation 1000 may end.

In some examples, heating of a droplet may be desired as part of droplet analysis or assay. However, a droplet may move during a heating operation and may not remain centered or positioned over a heating element. In some cases, pinning posts may be used to control the position of the droplet.

Figure 11A:
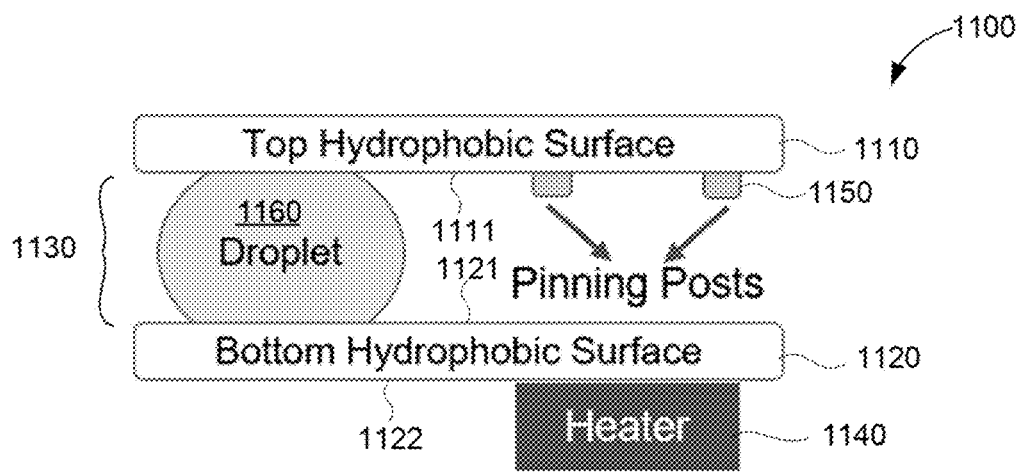
FIGS. 11A-11C show a portion of another microfluidic apparatus.

FIG. 11A shows a portion of another microfluidic device 1100. As shown in FIG. 11A, the microfluidic device 1100 may include a first sheet 1110, a second sheet 1120, a gap 1130, and a heater 1140. The first sheet 1110, the second sheet 1120, and the gap 1130 may be examples of the first sheet 110, the second sheet 120, and the gap 130 of FIG. 1A. The first sheet 1110 may include one or more pinning posts 1150 attached to a first surface 1111 of the first sheet 1110. In some examples, the pinning posts 1150 may be attached to the second sheet 1120.

The second sheet 1120 may include a first surface 1121 and a second surface 1122. The first surface 1121 may be disposed toward (e.g., adjacent to) the gap 1130. As shown, the heater 1140 may be disposed on the second surface 1122 of the second sheet 1120 opposite the pinning posts 1150. The pinning posts 1150 may provide features on the first surface 1111 with which a droplet 1160 may temporarily bind with and thereby limit the movement of the droplet 1160. The droplet 1160 may initially be disposed away from the heater 1140 and the pinning posts 1150.

Figure 11B:
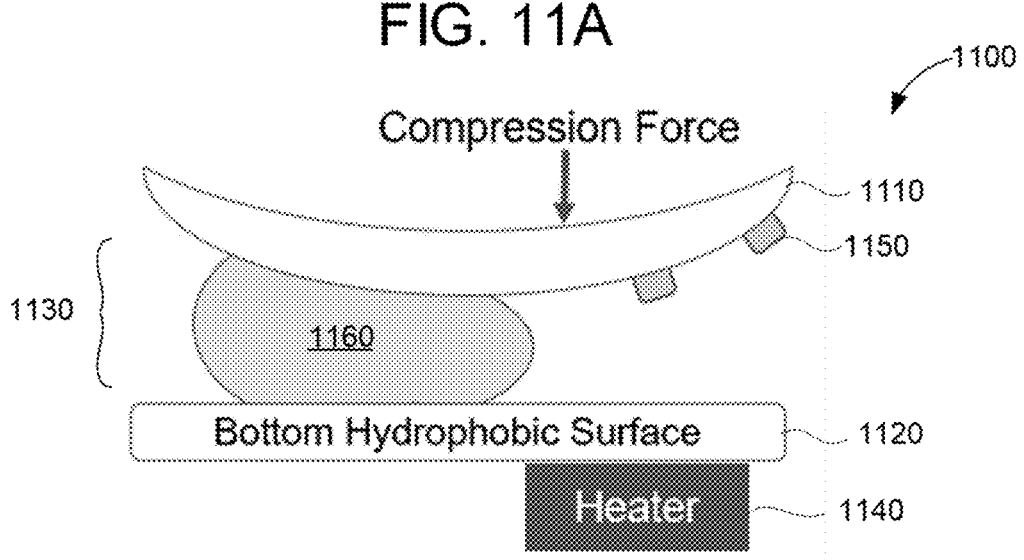

FIG. 11B, shows another view of the microfluidic device 1100. In FIG. 11B, a compression force may be provided to the first sheet 1110 and/or the second sheet 1120 to decrease the gap 1130 and move the droplet 1160 toward the heater 1140 and the pinning posts 1150.

Figure 11C:
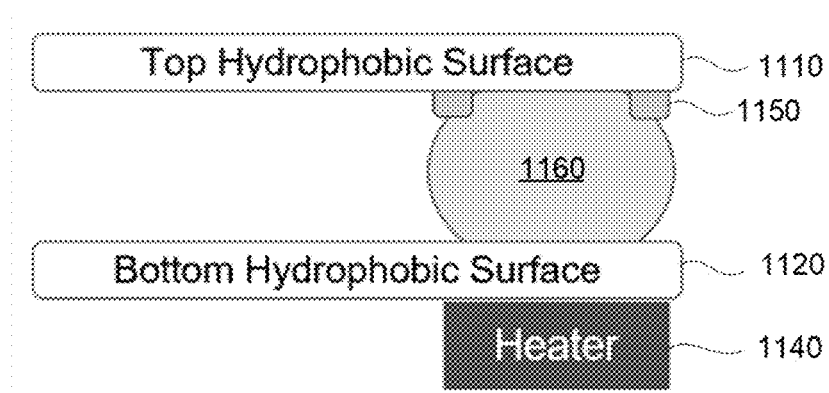

FIG. 11C shows another view of the microfluidic device 1100. In FIG. 11C, the droplet 1160 is positioned in contact with the pinning posts 1150 and the compression force removed. Thus, the first sheet 1110 and the second sheet 1120 may return to an initial position and the droplet 1160 is positioned over the heater 1140. As the pinning posts 1150 engage with the droplet 1160, movement of the droplet 1160 may be reduced. Reduced motion may be particularly advantageous when the droplet 1160 is undergoing a procedure, such as heating by the heater 1140.

Figure 12:
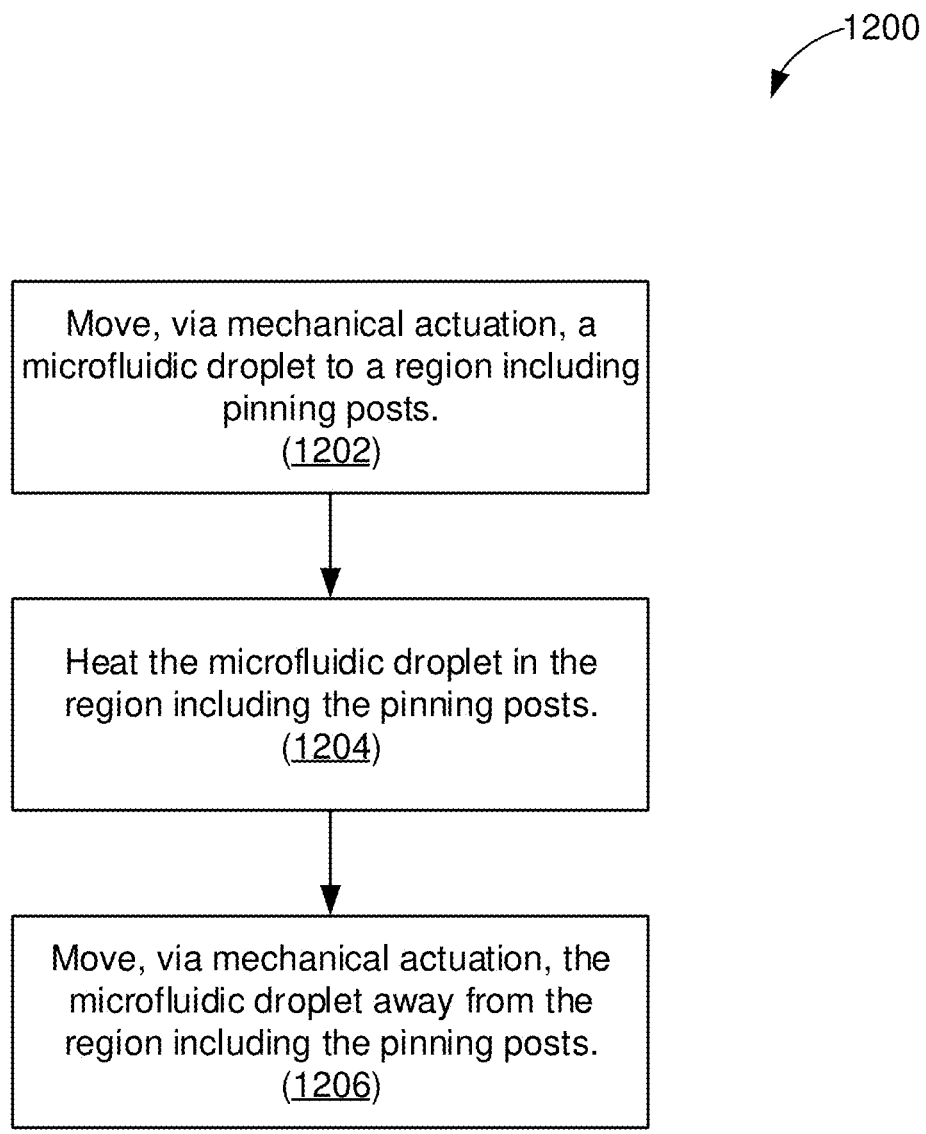
FIG. 12 is a flowchart showing an example operation for manipulating a microfluidic droplet in conjunction with pinning posts.

FIG. 12 is a flowchart showing an example operation 1200 for manipulating a microfluidic droplet in conjunction with pinning posts. The operation 1200 is described below with respect to microfluidic device 1100 of FIGS. 11A-11C, however, the operation 1200 may be performed by any other suitable system or device.

The operation 1200 begins in block 1202 as a microfluidic droplet 1160 is moved via mechanical manipulation to a region of the microfluidic device 1100 that includes pinning posts 1150. The mechanical manipulation may include the use of compression forces as described with respect to FIGS. 1A-1C and 2.

Next, in block 1204 the microfluidic droplet 1160 in the region of the pinning posts 1150 is heated. In some examples, the heat may be provided by the heater 1140. Next, in block 1206 the microfluidic droplet 1160 may be moved, via mechanical manipulation, away from the region of the microfluidic device that includes the pinning posts 1150.

In some examples, a well may be disposed within a microfluidic device to contain and process a microfluidic droplet. One example is described in conjunction with FIGS. 13A-13E and 14.

Figure 13A:
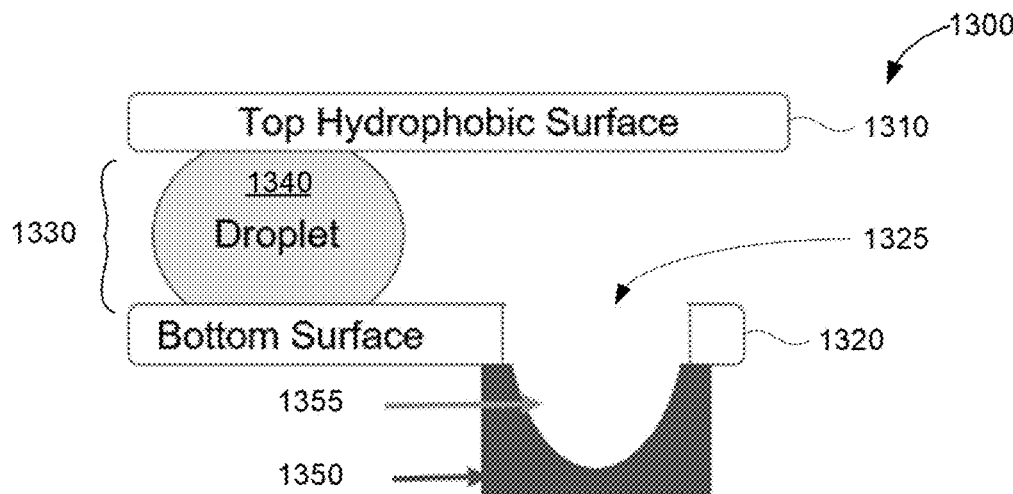
FIGS. 13A-13E show a portion of another microfluidic apparatus.

FIG. 13A shows a portion of a microfluidic device 1300. As shown in FIG. 13A, the microfluidic device 1300 may include a first sheet 1310, a second sheet 1320, and a gap 1330. The first sheet 1310, the second sheet 1320, and the gap 1330 may be examples of the first sheet 110, the second sheet 120, and the gap 130 of FIG. 1A. In addition, the second sheet 1320 may include an opening 1325 that couples the gap 1330 to a heater 1350. The heater 1350 may be formed in the shape of a well 1355. Thus, the well 1355 may be coupled to the gap 1330 through the opening 1325. As shown, a droplet 1340 may be positioned away from the opening 1325.

For ease of use, the second sheet 1320 may be disposed below (e.g., closer to the ground) than the first sheet 1310. Such a configuration may allow gravity to assist in receiving or moving the droplet 1340 in the well 1355. In some other examples, an opening and well may be disposed on the first sheet 1310. In such configurations, surface tension and/or capillary action may cause the droplet 1340 to remain in the well, despite the well 1355 being inverted.

Figure 13B:
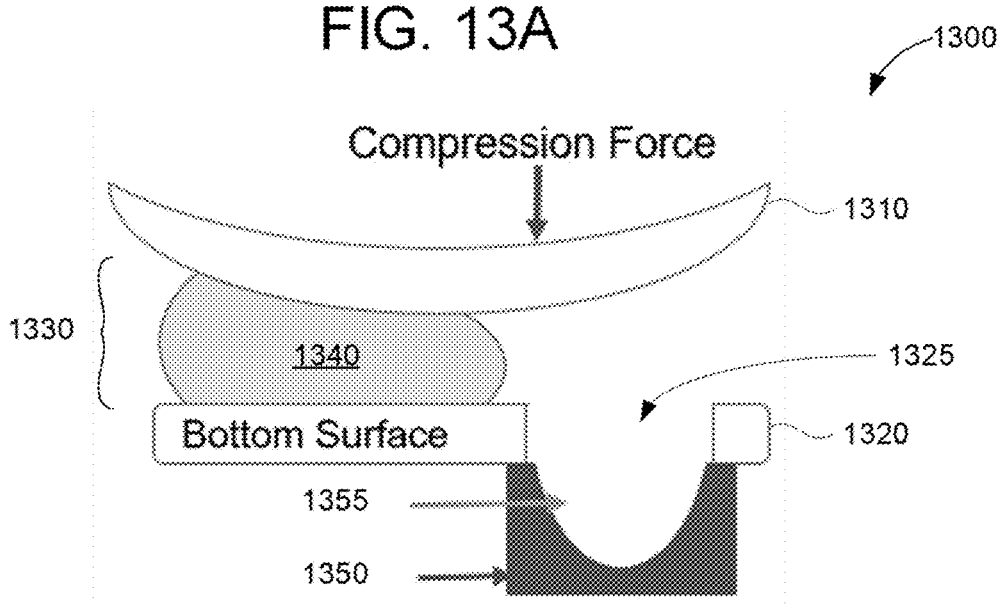

FIG. 13B shows another view of the microfluidic device 1300. In FIG. 13B, the droplet 1340 is moved, via mechanical manipulation, toward the opening 1325 in the second sheet 1320. For example, a compression force may be applied to the first sheet 1310 and/or the second sheet 1320 to reduce the gap 1330 and cause the droplet 1340 to move.

Figure 13C:
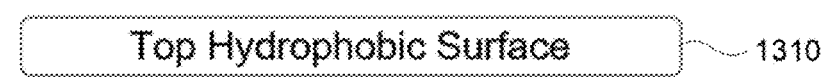

FIG. 13C shows another view of the microfluidic device 1300. In FIG. 13C, the droplet 1340 within the well 1355 of the heater 1350. The compression force may be removed or reduced allowing the first sheet 1310 and the second sheet 1320 to return to an initial position. The well 1355 may advantageously restrict movement of the droplet 1340, particularly while being heated by the heater 1350.

Figure 13D:
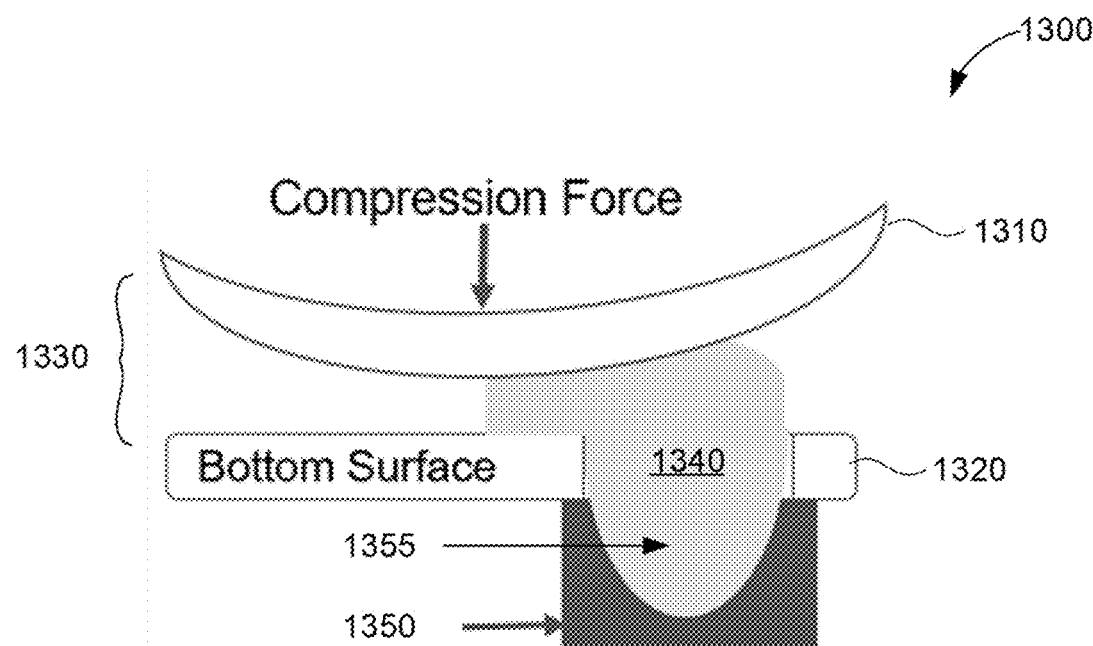

FIG. 13D shows another view of the microfluidic device 1300. In FIG. 13D, the droplet 1340 is being drawn out of well 1355 of the heater 1350 via mechanical manipulation. For example, a compression force may be applied to the first sheet 1310 and/or the second sheet 1320 to reduce the gap 1330 and contact the droplet 1340. In some examples, the compression force may be applied to a region of the microfluidic device 1300 associated with a direction to receive the droplet 1340.

Figure 13E:
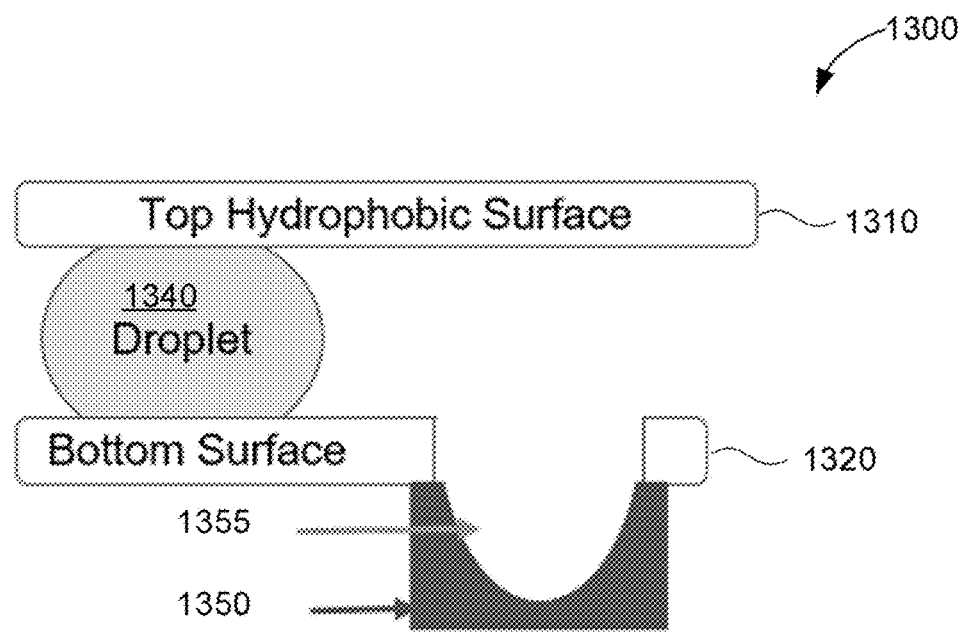

FIG. 13E shows the compression force removed or reduced from the microfluidic device 1300. The first sheet 1310 and the second sheet 1320 may return to an initial position and the droplet 1340 may be positioned away from the well 1355 and the heater 1350.

Figure 14:
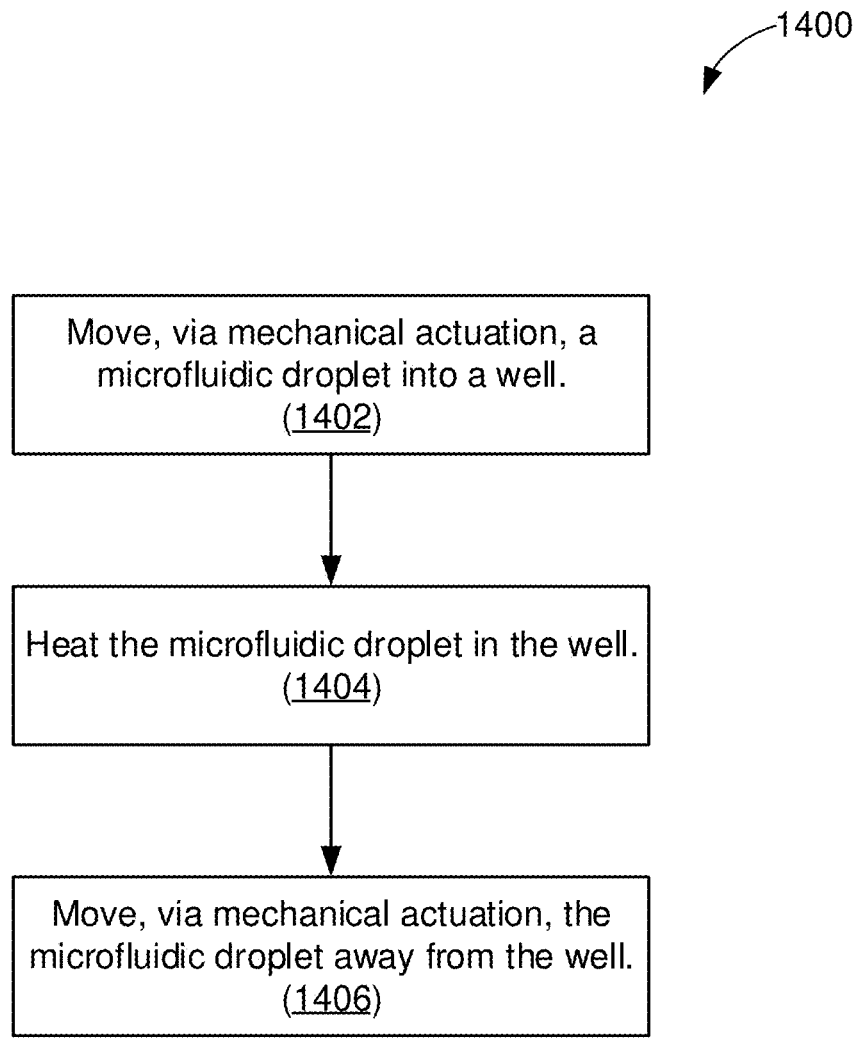
FIG. 14 is a flowchart showing an example operation for manipulating a microfluidic droplet in conjunction with a well.

FIG. 14 is a flowchart showing an example operation 1400 for manipulating a microfluidic droplet in conjunction with a well. The operation 1400 is described below with respect to the microfluidic device 1300 of FIGS. 13A-13E, however the operation 1400 may be performed by any other suitable system or device.

The operation begins in block 1402 as a microfluidic droplet is moved, via mechanical actuation, into a well. For example, a compression force may be applied to the first sheet 1310 or the second sheet 1320 to cause the microfluidic droplet 1340 into the well 1355.

Next, in block 1404 the microfluidic droplet 1340 may be heated in the well. For example, the heater 1350 may heat the microfluidic droplet 1340 within the well 1355. Next, in block 1406, the microfluidic droplet 1340 may be moved, via mechanical manipulation, away from the well. For example, a compression force may be applied to the first sheet 1310 and/or the second sheet 1320 to reduce the gap 1330 and cause the microfluidic droplet 1340 to come out of the well 1355.

Figure 15A:
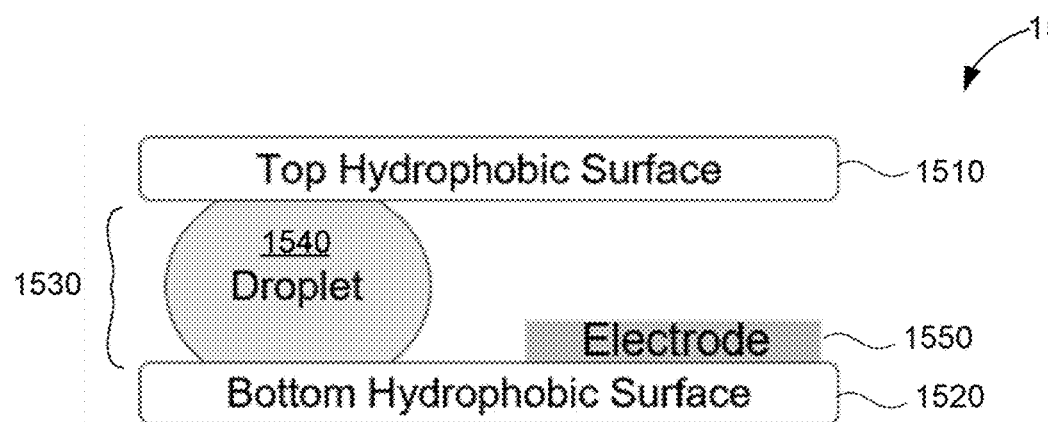
FIGS. 15A-15C show a portion of another microfluidic apparatus.

FIG. 15A shows a portion of a microfluidic device 1500. As shown in FIG. 15A, the microfluidic device 1500 may include a first sheet 1510, a second sheet 1520, a gap 1530, and an electrode 1550. The first sheet 1510, the second sheet 1520, and the gap 1530 may be examples of the first sheet 110, the second sheet 120, and the gap 130 of FIG. 1A. The electrode 1550 may be coupled to electrical circuits and the like (not shown) that provide high energy electric fields associated with causing electroporation (the creation of temporary pores or openings within cell membranes). As shown, a droplet 1540 may be positioned away from the electrode 1550.

Figure 15B:
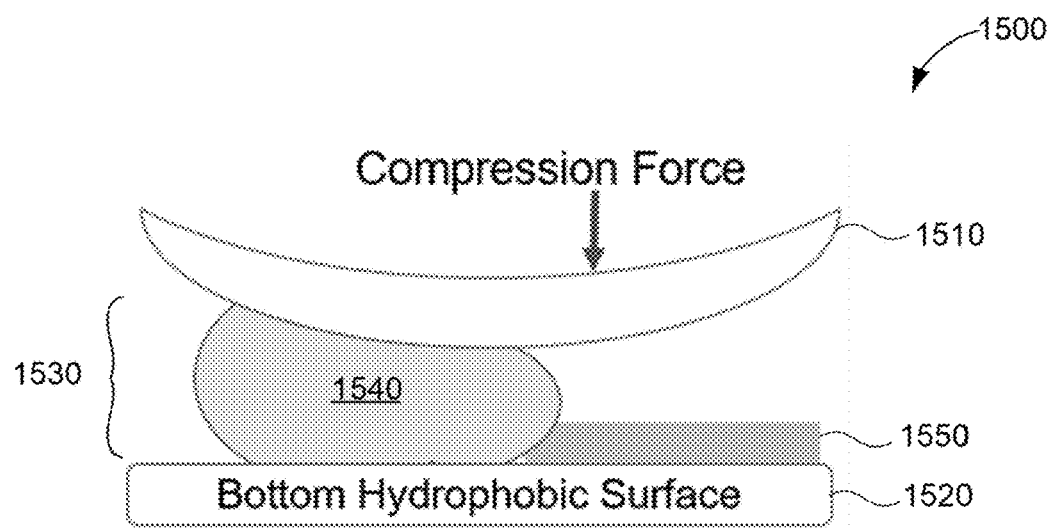

FIG. 15B shows another view of the microfluidic device 1500. In FIG. 15B, a compression force may be applied to the first sheet 1510 and/or the second sheet 1520. The compression force (e.g., mechanical actuation) may reduce the gap 1530 and cause the droplet 1540 to move toward the electrode 1550.

Figure 15C:
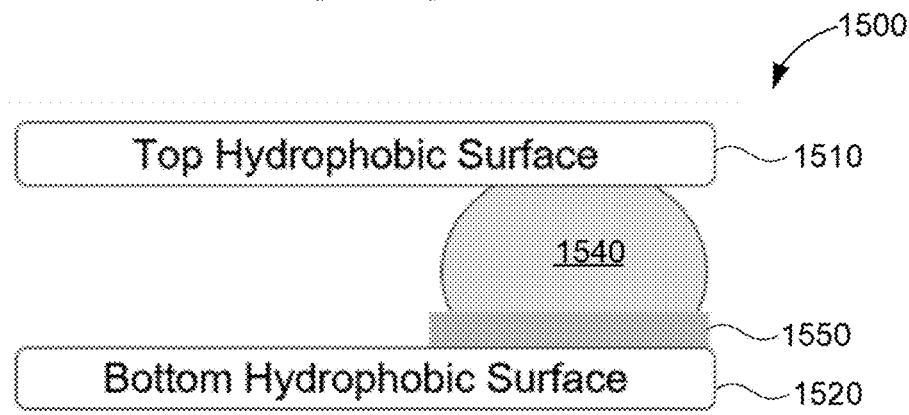

FIG. 15C shows another view of the microfluidic device 1500. In FIG. 15C, the compression force is removed or reduced thereby allowing the first sheet 1510 and/or the second sheet 1520 to return to an initial position. The mechanical actuation of FIG. 15B has positioned the droplet 1540 on the electrode 1550. The droplet 1540 may undergo electroporation using the electrode 1550.

Figure 16:
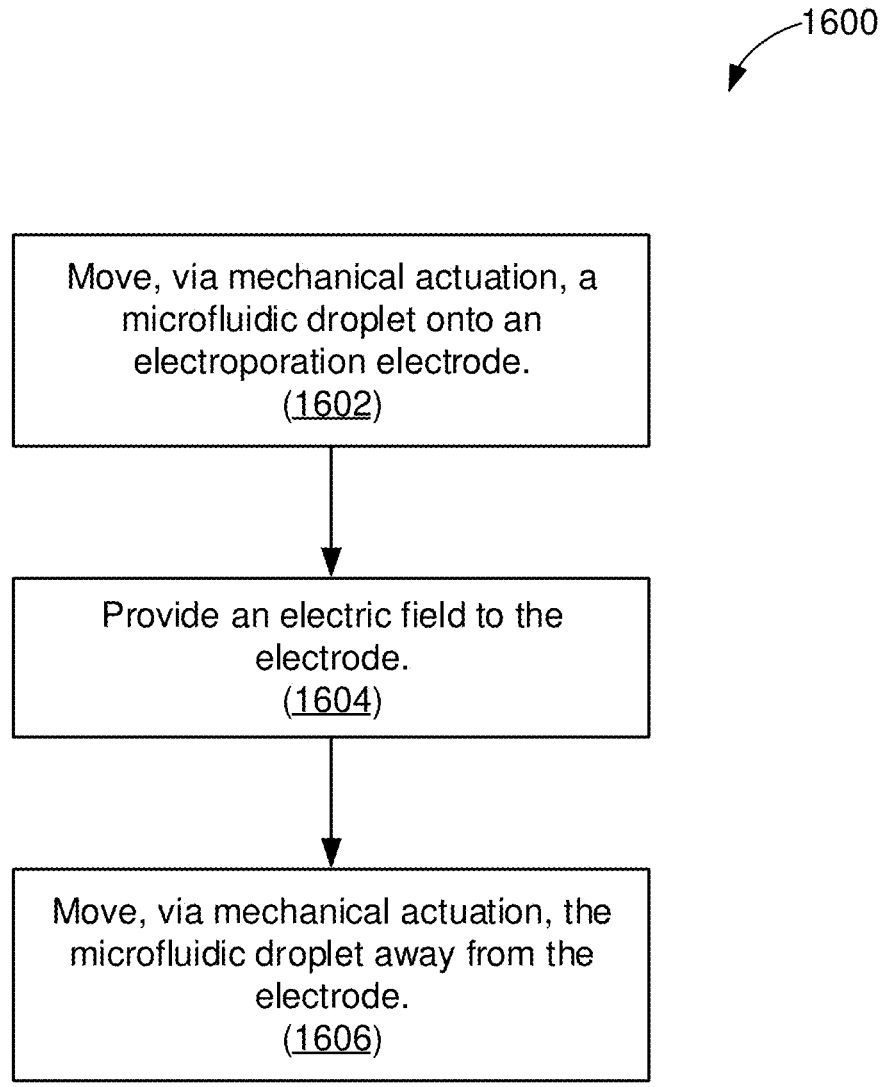
FIG. 16 is a flowchart showing an example operation for providing electroporation.

FIG. 16 is a flowchart showing an example operation 1600 for providing electroporation. The operation 1600 is described with respect to the microfluidic device 1500 of FIGS. 15A-15C, however the operation 1600 may be performed by any other suitable system or device.

The operation 1600 begins in block 1602 where a microfluidic droplet is moved, via mechanical actuation, onto an electroporation electrode. For example, a compression force may be applied to the first sheet 1510 and/or the second sheet 1520 to move the microfluidic droplet 1540 onto the electrode 1550.

Next, in block 1604, the electrode 1550 provides an electric field to the microfluidic droplet 1540. The electric field may be a high-power electric field provided by one or more circuits and devices. The electric field may temporarily provide openings or "pores" in the cell walls of cellular material within the microfluidic droplet 1540.

Next, in block 1606, the microfluidic droplet is moved, via mechanical manipulation, away from the electrode. For example, compressive forces may be used in conjunction with the first sheet 1510 and the second sheet 1520 to move the microfluidic droplet away from the electrode 1550.

Figure 17:
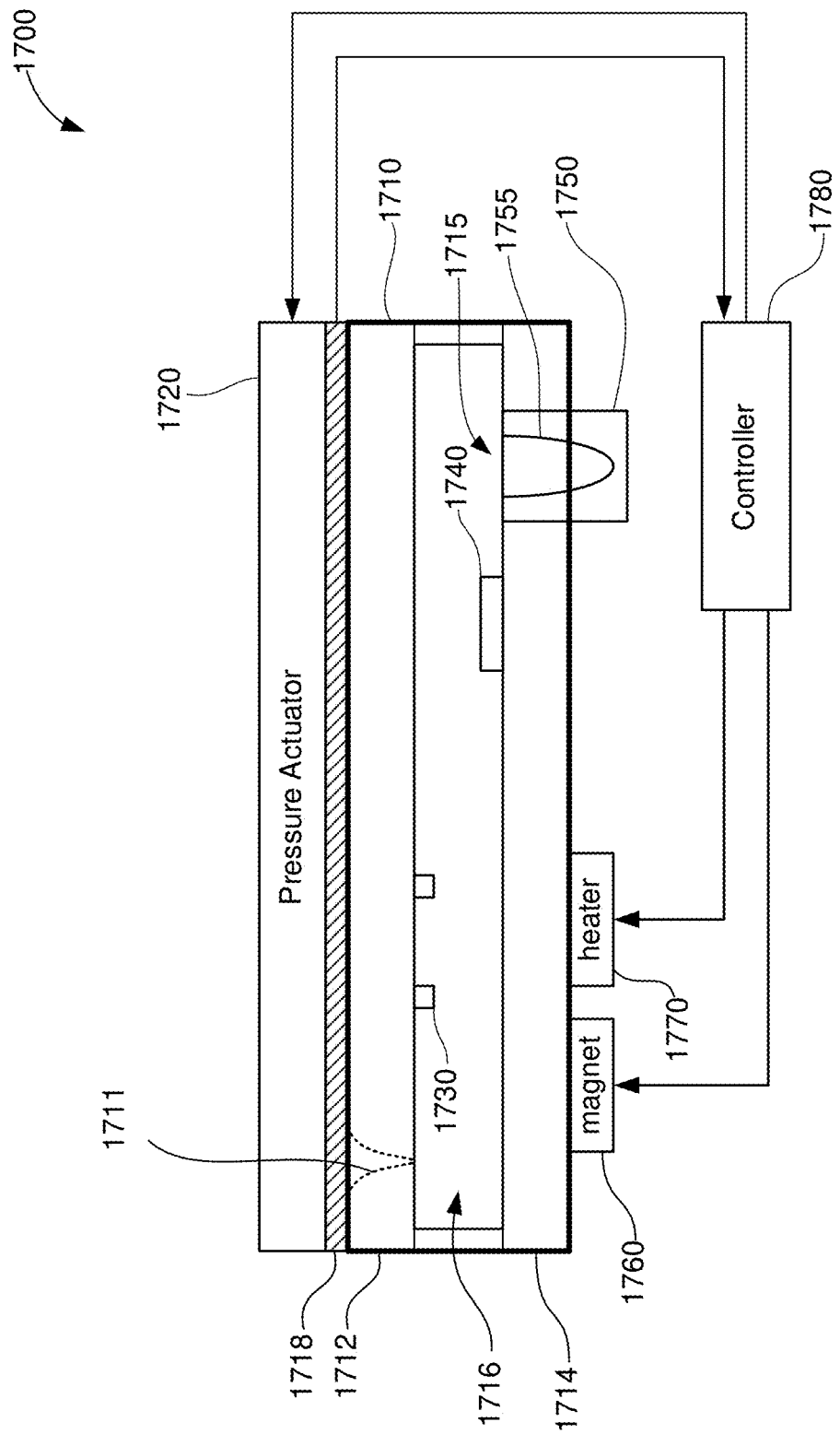
FIG. 17 shows an example microfluidic apparatus (e.g., a mechanical microfluidics actuator).

FIG. 17 shows an example microfluidic system 1700. The microfluidic system 1700 may include a cartridge 1710, a pressure actuator 1720, a magnet 1760, a heater 1770, and a controller 1780. In some examples, the pressure actuator 1720, the magnet 1760, the heater 1770, and the controller 1780 may be included with a housing or base station that may couple to the cartridge 1710.

The cartridge 1710 may be an example of the microfluidic devices 100, 300, 500, 700, 900, 1100, 1300, and 1500 of FIGS. 1, 3, 5, 7, 9, 11, 13, and 15, respectively. The cartridge 1710 may include an input port 1711, a first sheet 1712, a second sheet 1714, an optical sensor 1718, one or more pinning posts 1730, one or more electrodes 1740 and a first heater 1750. The first sheet 1712 and the second sheet 1714 may be hydrophobic and oleophobic sheets or may include a hydrophobic and oleophobic layer on one or more surfaces. The first heater 1750 may be coupled to a gap 1716 through an opening 1715 in and the second sheet 1714. The first heater 1750 may form a well 1755. One or more droplets may be inserted into the cartridge 1710 through the input port 1711. Although only one input port 1711 is shown, in other examples the cartridge 1710 may include any feasible number of input ports.

The pressure actuator 1720 may contact or otherwise be coupled to the cartridge 1710. As shown, the pressure actuator 1720 may be coupled to the first sheet 1712. In other examples, the pressure actuator 1720 may be coupled to the second sheet 1714. The pressure actuator 1720 may also be coupled to the controller 1780. The controller 1780 may cause the pressure actuator 1720 to selectively apply one or more compressive forces to the first sheet 1712 and/or the second sheet 1714. The compressive forces may manipulate the position of any droplets within the gap 1716. The optical sensor 1718 may detect the presence and/or location of a droplet (e.g., a microfluidic droplet) within the gap 1716. The optical sensor 1718 may be coupled to the controller 1780. In this manner, data from the optical sensor may be used to guide or direct the pressure actuator 1720.

The magnet 1760 may be disposed adjacent to or on the cartridge 1710. Operation of the magnet 1760 may be controlled by the controller 1780. Similarly, a second heater 1770 may be disposed adjacent to, or on the cartridge 1710 and may also be controlled by the controller 1780.

The controller 1780 may control operations of the microfluidic system 1700. Thus, the controller 1780 may control operations of the pressure actuator 1720, the magnet 1760, the first and second heaters 1750 and 1770 and the one or more electrodes 1740 to perform one or more operations described herein.

Figure 18A:
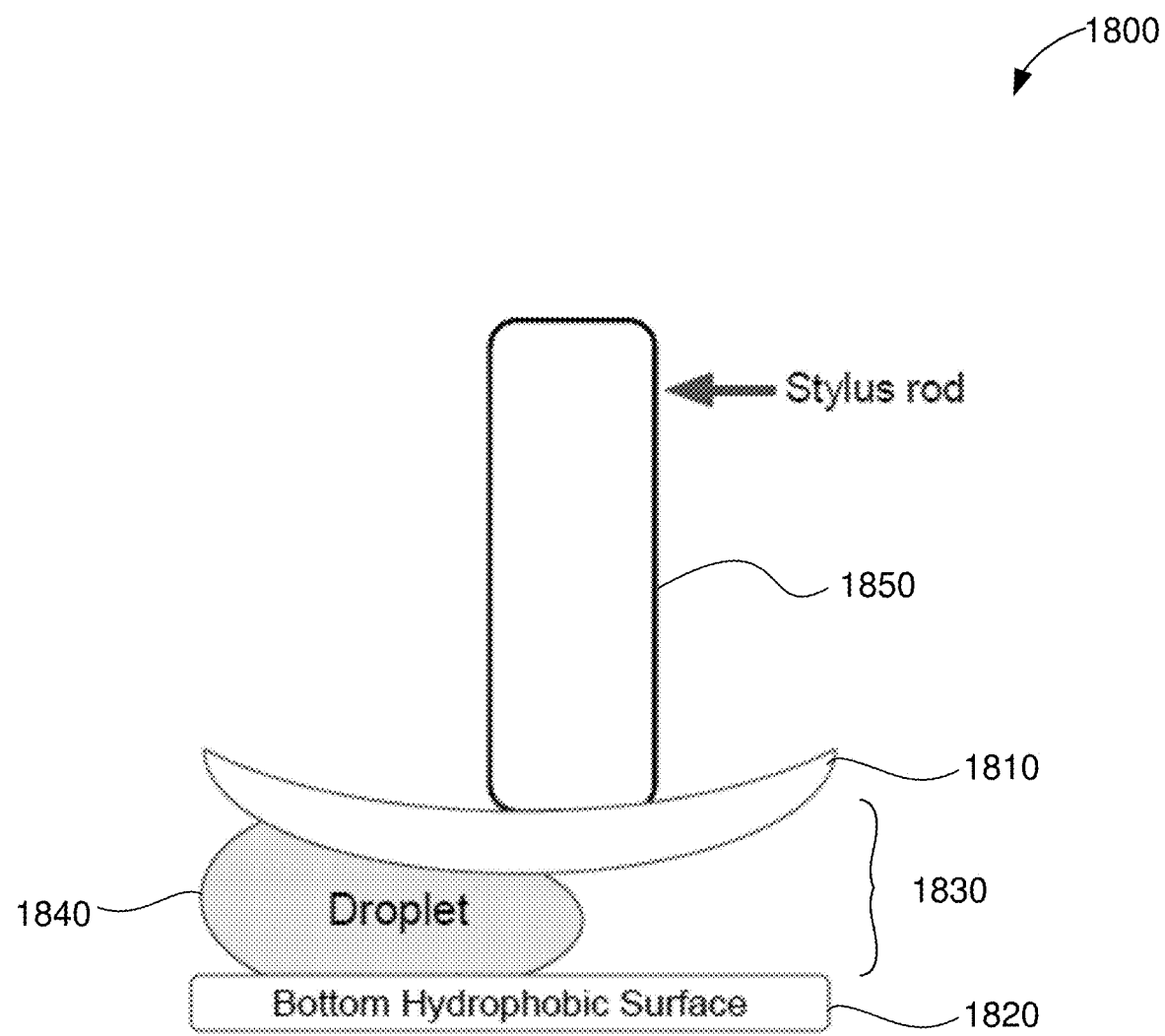
FIG. 18A shows an example of a portion of a microfluidic apparatus as described herein.

FIG. 18A shows a portion of another microfluidic device 1800. The microfluidic device 1800 may include a first sheet 1810, a second sheet 1820, and a stylus 1850. The first sheet 1810 may be separated from the second sheet 1820 by a gap 1830. The first sheet 1810, the second sheet 1820 and the gap 1830 may be other examples of the first sheet 110, the second sheet 120 and the gap 130 of FIG. 1A. The stylus 1850 may selectively provide a compression force to either the first sheet 1810 or the second sheet 1820 (as shown, the stylus 1850 is selectively providing a compression force to the first sheet 1810). The compression force from the stylus 1850 may selectively reduce the gap 1830 in some regions of the microfluidic device 1800 to move a droplet 1840 as described above in conjunction with FIGS. 1-17. For example, a position and compression force of the stylus 1850 may be controlled by the controller 1780 of FIG. 17.

In some examples, the stylus tip area may be selected to correspond to an anticipated size of a droplet 1840. The droplet 1840 may be any feasible droplet, including any feasible microfluidic droplet. Thus, the droplet 1840 may be between $10^{-6}$ and $10^{-15}$ liters. Furthermore, in some examples, the tip of the stylus may be shaped or treated to avoid scratching and/or abrading the surface of the first sheet 1810 or the second sheet 1820. For example, the tip of the stylus 1850 may include a roller to apply the compression force to the first sheet 1810. In some other examples, the tip of the stylus 1850 may be coated with a lubricant.

Figure 18B:
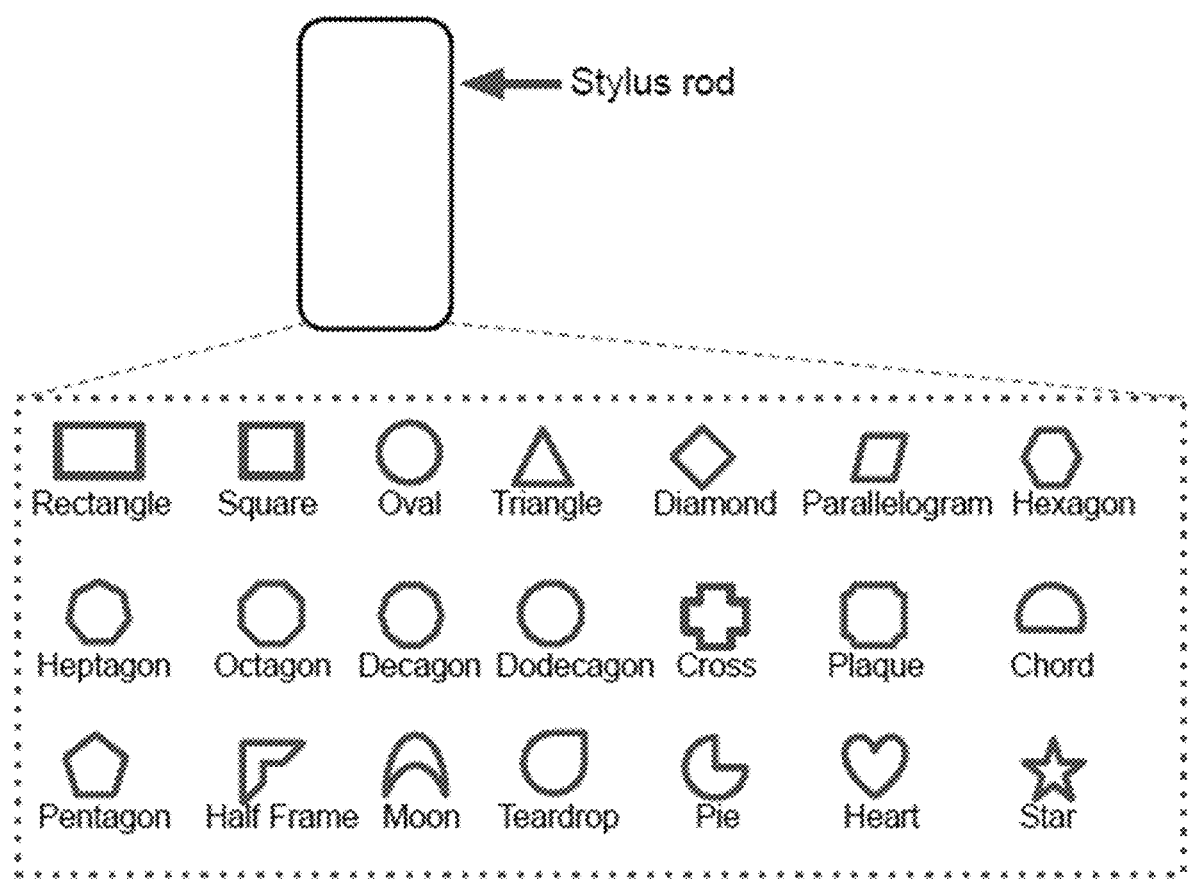
FIG. 18B shows possible associated end profiles of a stylus such as that shown in FIG. 18A.

FIG. 18B shows the stylus 1850 and possible associated end profiles 1860. The end profiles 1860 are not meant to be limiting (e.g., the end profiles 1860 are not an exhaustive listing of all possible end profiles) but are instead meant to be exemplary. Thus, other end profiles for the stylus 1850 are possible. Some end profiles 1860 may more effectively move or manipulate the droplet 1840. For example, circular, rectangular, or oval profiles may more effectively move the droplet 1840.

Figure 19A:
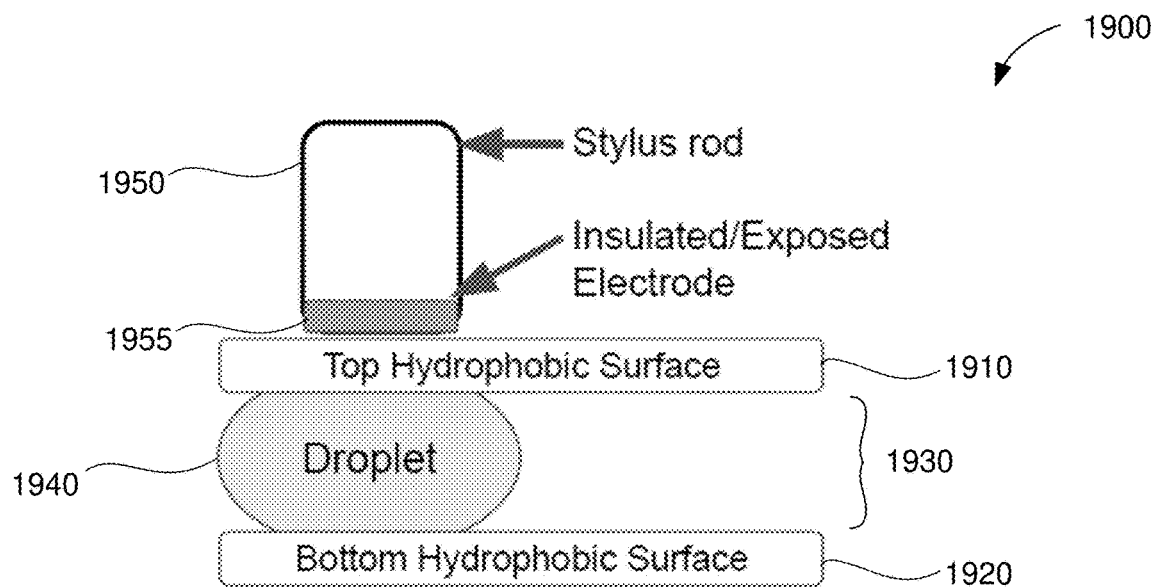
FIGS. 19A and 19B show a portion of another microfluidic apparatus.

FIG. 19A shows a portion of another microfluidic device 1900. The microfluidic device 1900 may include a first sheet 1910, a second sheet 1920, a gap 1930, and a stylus 1950 which may be examples of the first sheet 1810, the second sheet 1820, the gap 1830, and the stylus 1850 of FIG. 18A. The stylus 1950 may include an insulated and/or exposed electrode 1955. In some examples, the electrode 1955 may be disposed toward a tip of the stylus 1950 that may contact at least one of the first sheet 1910 or the second sheet 1920.

In some examples, the electrode 1955 may be provided a voltage (e.g., an electric potential) that attracts the droplet 1940. When the stylus 1950 is placed in contract with at least one of the sheets of the microfluidic device 1900 (shown here as the first sheet 1910), the associated sheet can perform as or be a hydrophobic and oleophobic dielectric separating the electrode 1955 from the droplet 1940.

The applied or provided voltage may be sufficient to affect or control surface tension of the droplet 1940. In this manner, the stylus 1950 may attract and/or move the droplet 1940 in the gap 1930 without applying a compression force, but instead by providing a voltage to the electrode 1955, and then moving the position of the stylus 1950 with respect to the first and second sheets 1910 and 1920, respectively.

Figure 19B:
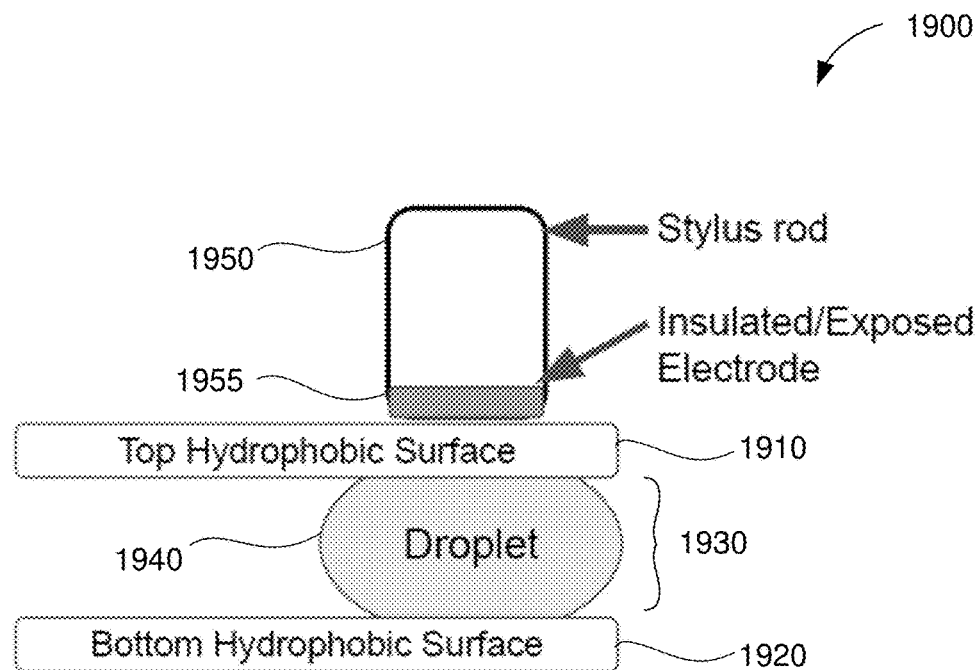

FIG. 19B shows another view of the microfluidic device 1900. As shown, the stylus 1950 may be moved planarly with respect to the first sheet 1910 and the second sheet 1920. When the stylus 1950 is moved planarly while the electrode 1955 is energized with a sufficient voltage, the droplet 1940 may move to follow the stylus 1950. Thus, any of the droplet manipulations described with respect to FIGS. 1-17 may be performed by energizing the electrode 1955 and moving the stylus 1950 instead of using a compressive force.

Figure 20:
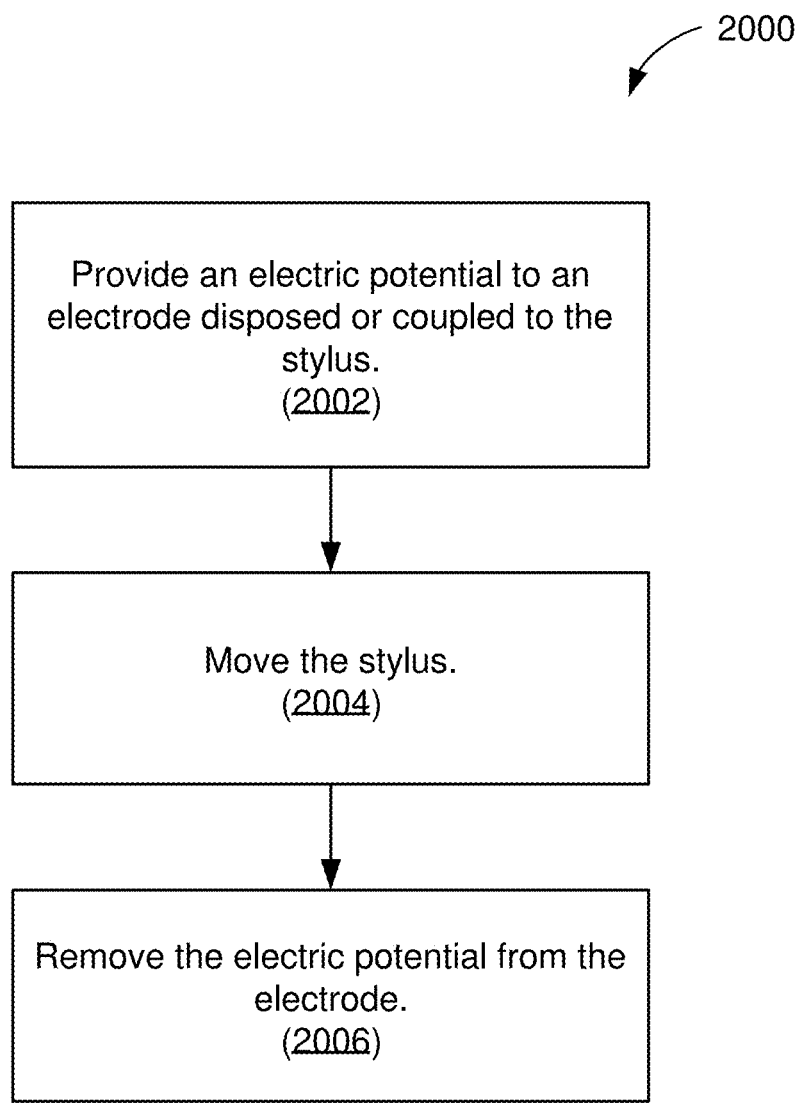
FIG. 20 is a flowchart showing an example operation for manipulating a microfluidic droplet.

FIG. 20 is a flowchart showing an example operation 2000 for manipulating a microfluidic droplet. The operation 2000 is described with respect to the microfluidic device 1900 of FIGS. 19A and 19B, however the operation 2000 may be performed by any other suitable system or device. The operation 2000 begins in block 2002 as an electric potential is provided to an electrode disposed or coupled to a stylus. For example, a voltage may be provided to the electrode 1955 that is disposed on or near a tip of the stylus 1950. In addition, the stylus 1950 may be in contact with at least one sheet (e.g., the first sheet 1910 or the second sheet 1920) of the microfluidic device 1900. The applied or provided voltage may be sufficient to affect or control surface tension of the droplet 1940.

Next, in block 2004, the stylus is moved. For example, the stylus 1950 may be moved relative to the first sheet 1910 and the second sheet 1920. Since a sufficient voltage is applied or provided to the electrode 1955 (in block 2002), the droplet 1940 may move in response to motion of the stylus 1950.

Next, in block 2006, the voltage or potential is removed from the electrode. For example, in block 2004 the stylus 1950 may be moved to position the droplet 1940 into a predetermined treatment zone. Since the movement is complete, the voltage or potential may be removed from the electrode 1955.

Figure 21A:
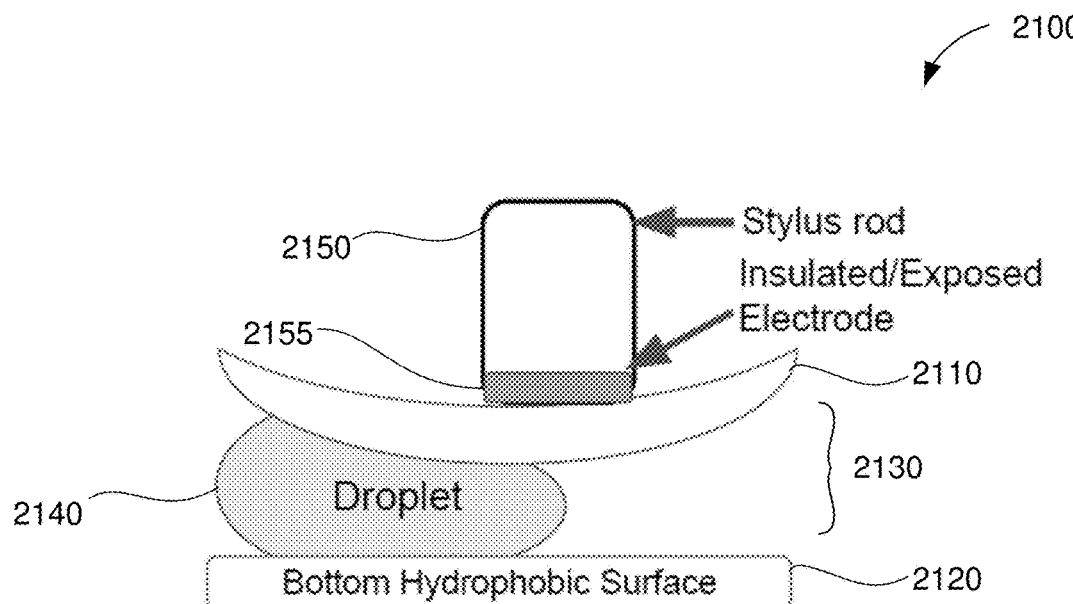
FIGS. 21A and 21B show a portion of another microfluidic apparatus.

FIG. 21A shows a portion of another microfluidic device 2100. The microfluidic device 2100 may include a first sheet 2110, a second sheet 2120, a gap 2130, a stylus 2150, and an electrode 2155 which may be examples of the first sheet 1910, the second sheet 1920, the gap 1930, the stylus 1950, and the electrode 1955 of FIG. 19A.

In contrast to the microfluidic device 1900, the microfluidic device 2100 may use a combination of a compression forces and applied voltages to manipulate a droplet 2140. As shown, the stylus 2150 may be positioned to one side of the droplet 2140. To move the droplet 2140, the stylus 2150 may provide a compression force to reduce the gap 2130 while a voltage is provided to the electrode 2155. In this manner, the droplet 2140 may be moved by a combination of compressive and electromotive (e.g., voltage) forces. For example, while the stylus 2150 is providing a compression force and a voltage is applied to the electrode 2155, the stylus 2150 may be moved to change the position or location of the droplet 2140 within the gap 2130. The compression force may be provided to either the first sheet 2110 or the second sheet 2120. FIG. 21A shows one example as the stylus 2150 provides a compression force to the first sheet 2110.

Figure 21B:
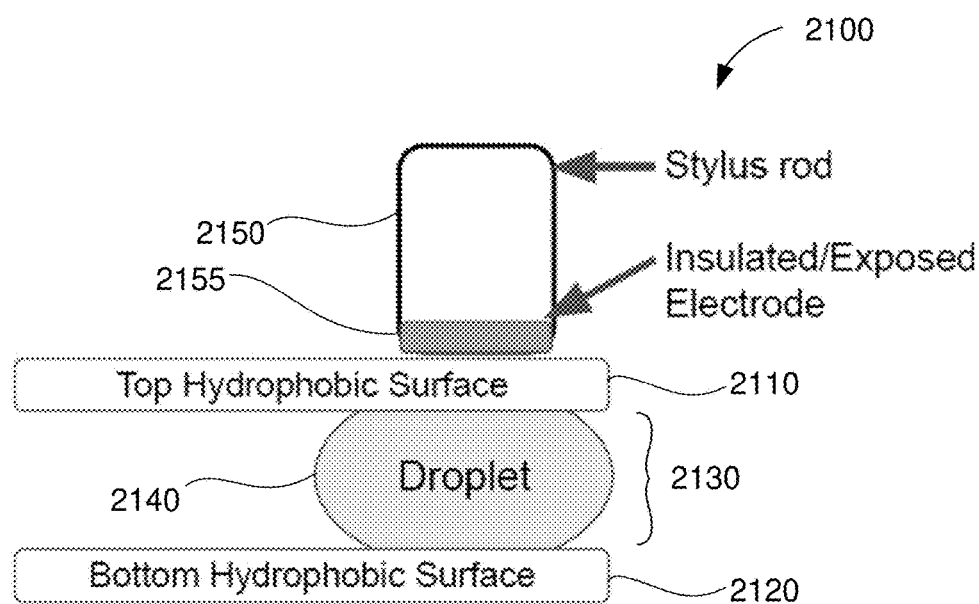

FIG. 21B shows another view of the microfluidic device 2100. In this view, the stylus 2150 has been moved to a new position with respect to the first sheet 2110 and the second sheet 2120. The droplet 2140 has been moved in response to previously provided compression and voltage provided by and to the stylus 2150. Thus, in FIG. 21B the compression force is removed from the first sheet 2110 and the voltage is removed from the electrode 2155.

Figure 22:
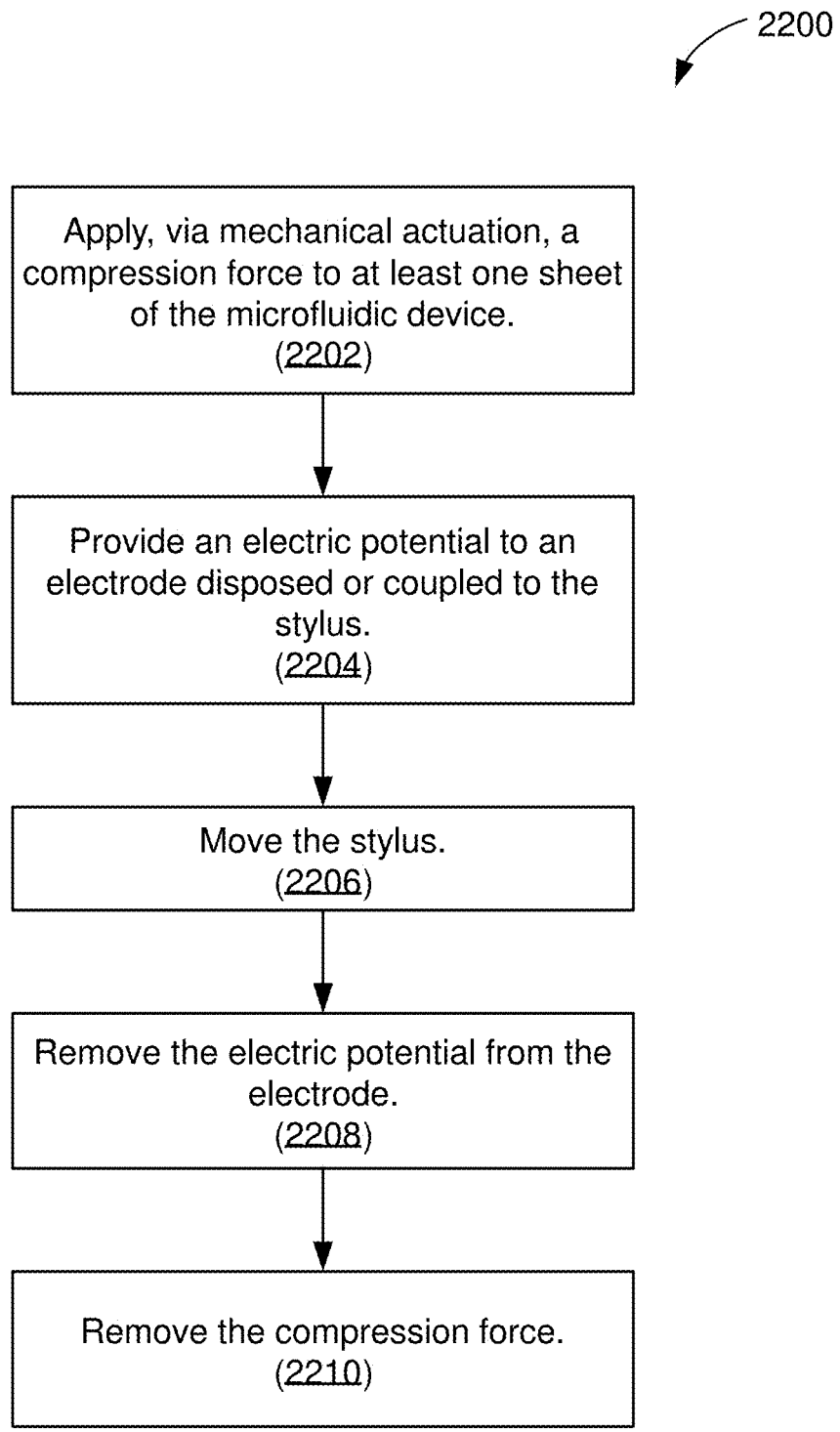
FIG. 22 is a flowchart showing an example operation for manipulating a microfluidic droplet.

FIG. 22 is a flowchart showing an example operation 2200 for manipulating a microfluidic droplet. The operation 2200 is described with respect to the microfluidic device 2100 of FIGS. 21A and 21B, however the operation 2200 may be performed by any other suitable system or device. The operation may begin in block 2202 as a compression force is applied, via mechanical actuation, to at least one of the sheets of a microfluidic device. For example, the stylus 2150 may provide a compression force to the first sheet 2110 and reduce the gap 2130 near a droplet 2140. The reduced gap may manipulate, at least in part, the droplet 2140 between the first sheet 2110 and the second sheet 2120.

Next, in block 2204 an electric potential is provided to an electrode disposed or coupled to the stylus. For example, a voltage may be provided to the electrode 2155 that is disposed on or near the tip of the stylus 2150. The stylus 2150 may be in contact with at least one sheet of the microfluidic device 2100. The applied or provided voltage may be sufficient to affect or control surface tension of the droplet 2140.

Next, in block 2206, the stylus is moved. For example, the stylus 2150 may be moved relative to the first sheet 2110 and the second sheet 2120. In this manner, the droplet 2140 may be manipulated or moved using a combination of compression forces provided by the stylus 2150 and a voltage applied to the electrode 2155.

Next, in block 2208 the electric potential is removed from the electrode. For example, a voltage may be removed from the electrode 2155. Then, in block 2210 the compression force is removed from at least one sheet of the microfluidic device. For example, the stylus 2150 may be moved away from the first sheet 2110 or the second sheet 2120. Because the droplet 2140 has been moved into a predetermined (e.g., desired) position in block 2206, the compression force and voltage may be removed from the stylus 2150.

In some examples, ferrous particles may be suspended within a microfluidic droplet to assist with processing or assaying. After one or more processing steps have been completed, the ferrous particles may be removed from the droplet for further processing.

Figure 23A:
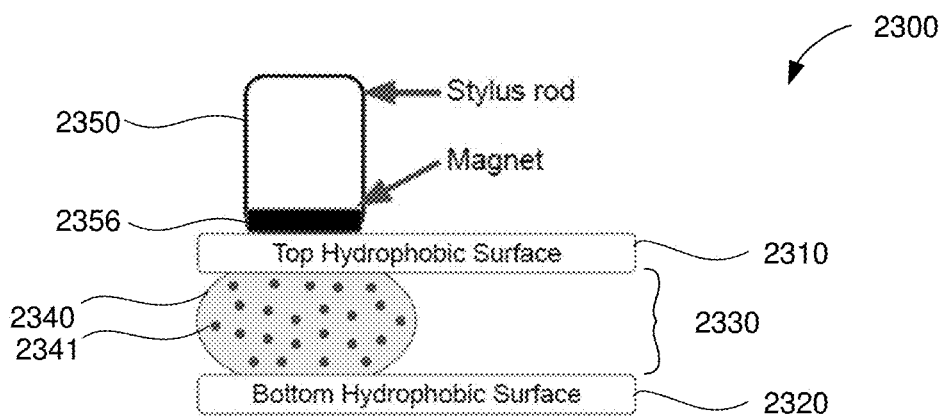
FIGS. 23A-23C show a portion of another microfluidic apparatus.

FIG. 23A shows a portion of another microfluidic device 2300. The microfluidic device 2300 may include a first sheet 2310, a second sheet 2320, a gap 2330, and a stylus 2350 which may be examples of the first sheet 1910, the second sheet 1920, the gap 1930, and the stylus 1950 of FIG. 19A. In addition, the stylus 2350 may include a magnet 2356. The magnet 2356 may be controllable. For example, the magnet 2356 may be an electromagnet that may be enabled and disabled through a control voltage. In another example, the magnet 2356 may be movable. Thus, the magnet 2356 may be moved toward a tip of the stylus 2350 (as shown) or away from the tip of the stylus 2350 (not shown). In this manner, magnetic field strength at or near the tip of the stylus 2350 may be controlled and/or variable. A plurality of ferrous particles 2341 may be distributed (suspended) throughout a droplet 2340.

Figure 23B:
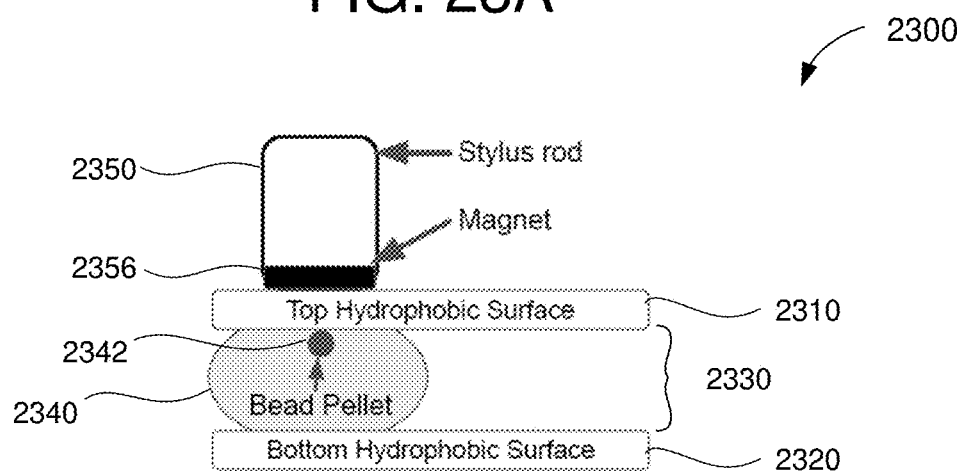

FIG. 23B shows another view of the microfluidic device 2300. In this view, the magnet 2356 is activated or enabled. For example, the magnet 2356 may be an electromagnet that may be enabled through the application of power. In another example, the magnet 2356 may be a permanent magnet that may be moved toward the droplet 2340. The magnet 2356 may attract or cause the ferrous particles 2341 to collect into one or more ferrous beads 2342. Thus, the ferrous particles 2341 may come out of suspension from the droplet 2340.

Figure 23C:
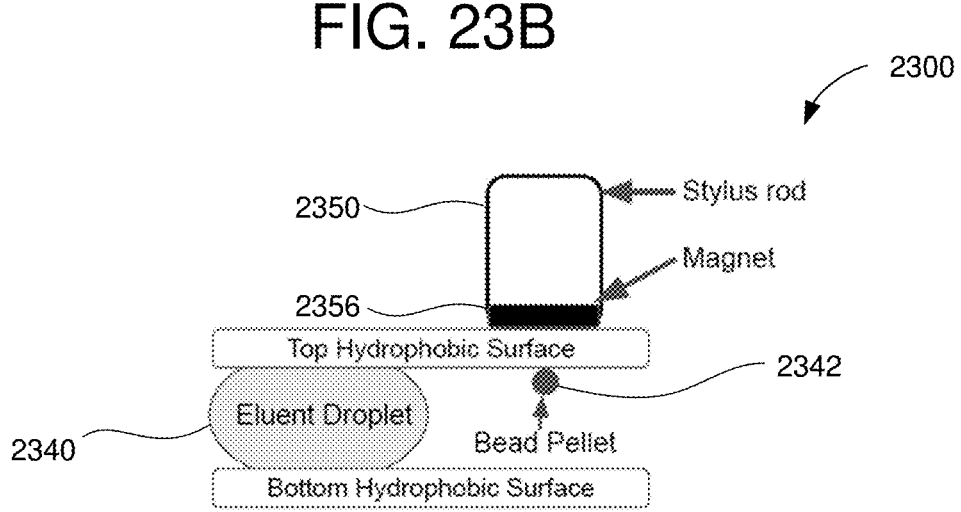

FIG. 23C shows another view of the microfluidic device 2300. While the magnet 2356 is activated or enabled, the stylus 2350 is moved. The movement of the stylus 2350 may filter or remove the ferrous beads 2342 from the droplet 2340.

Figure 24:
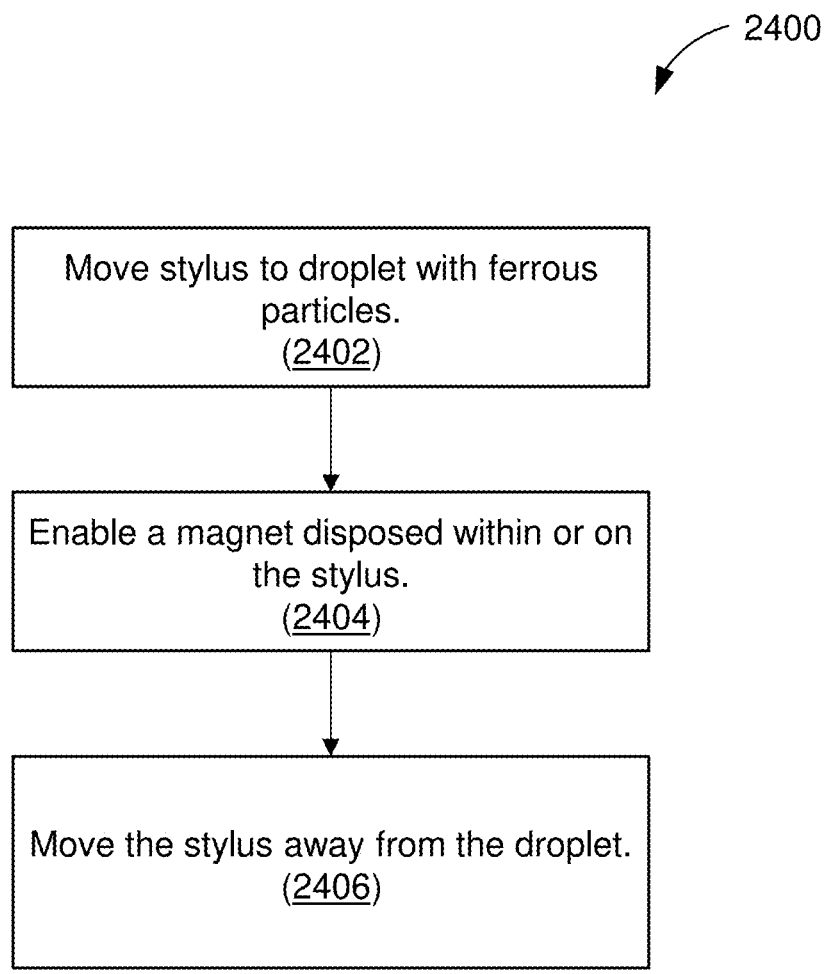
FIG. 24 is a flowchart showing an example operation for removing suspended ferrous particles from a microfluidic droplet.

FIG. 24 is a flowchart showing an example operation 2400 for removing suspended ferrous particles from a microfluidic droplet. The operation 2400 is described with respect to the microfluidic device 2300 of FIGS. 23A-23C, however the operation 2400 may be performed by any other suitable system or device.

The operation 2400 begins in block 2402 as a stylus with a magnet is moved to a region proximate to a droplet with suspended ferrous particles. For example, a stylus 2350 with a magnet 2356 may be moved near a droplet 2340 that includes suspended ferrous particles 2341.

Next, in block 2404 a magnet within or on the stylus is enabled. For example, the magnet 2356 may be an electromagnet that may be enabled through the application of power. In another example, the magnet 2356 may be moved toward the tip of the stylus 2350. In this manner, the magnet 2356 may cause the ferrous particles 2341 to fall out of suspension and collect toward the magnet 2356. In some cases, the collected ferrous particles 2341 may form a ferrous bead 2342.

Next, in block 2406, the stylus may be moved away from the droplet. For example, moving the stylus 2350 may move the ferrous bead 2342 out of the droplet 2340 thereby filtering the ferrous particles 2341 out of the droplet 2340.

In some examples, ferrous material may be placed back into suspension within a droplet through mechanical actuation. Another such example is described below in conjunction with FIGS. 25-26.

Figure 25A:
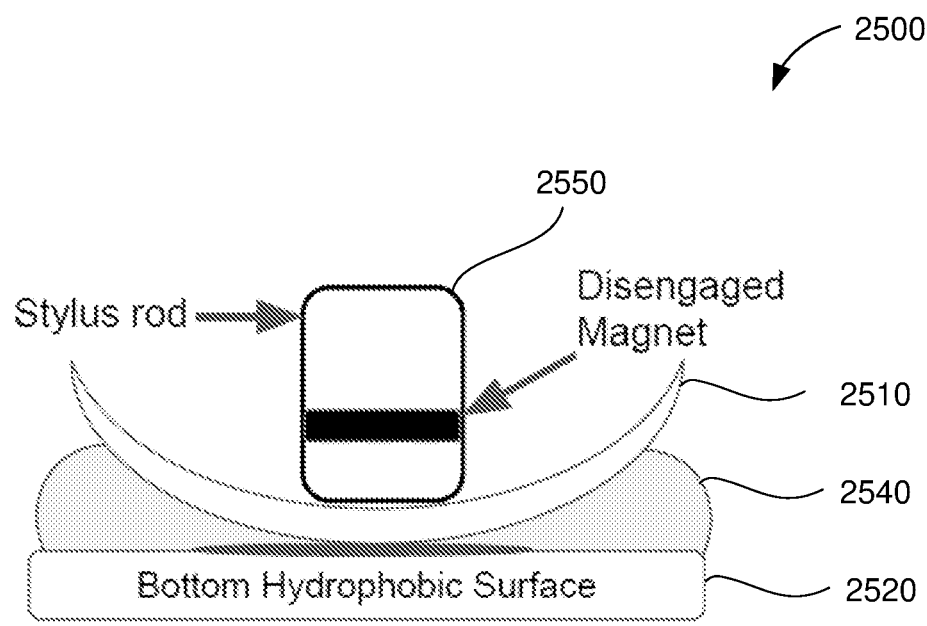
FIGS. 25A and 25B show a portion of another microfluidic apparatus.

FIG. 25A shows a portion of another microfluidic device 2500. The microfluidic device 2500 may include a first sheet 2510, a second sheet 2520, a stylus 2550, and a magnet 2556. The first sheet 2510, the second sheet 2520, the stylus 2550, and the magnet 2556 may be examples of the first sheet 2310, the second sheet 2320, the gap 2330, the stylus 2350 and the magnet 2356 of FIG. 23A. In some examples, the magnet 2556 may be disengaged by either moving the magnet 2556 away from the tip of the stylus 2550 or by removing power if the magnet 2556 is an electromagnet.

A droplet 2540 may include non-dispersed ferrous or non-ferrous particles. A compression force may be applied to the first sheet 2510 and/or the second sheet 2520 (not shown) that can compress or deform the droplet 2540. In some cases, a compression force may be applied to a center or middle of the droplet 2540 by the stylus 2550.

Figure 25B:
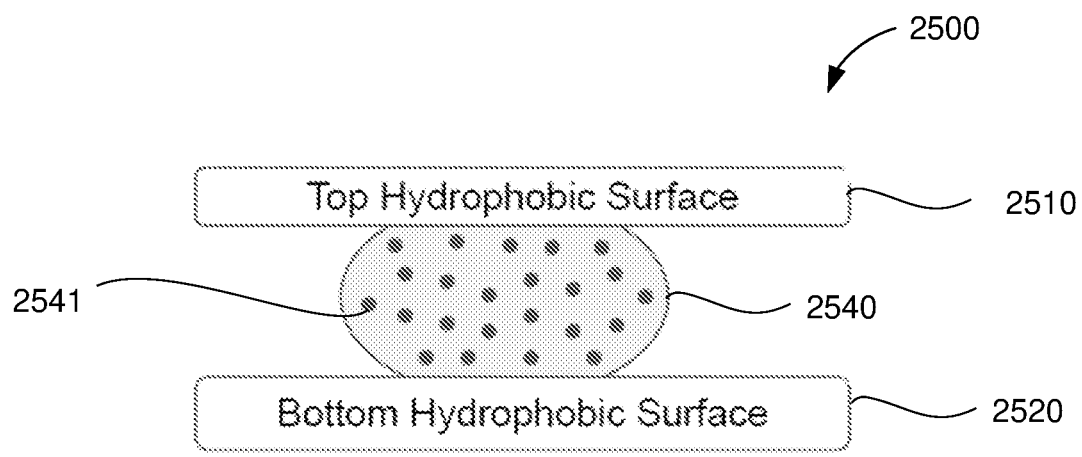

FIG. 25B shows another view of the microfluidic device 2500. The compression force may be removed or reduced from the first sheet 2510 and/or the second sheet 2520. Removal or release of the compression force may allow the droplet 2540 to return to a non-compressed or non-deformed state. Transitioning from a compressed to a non-compressed state (or vice-versa) may cause one or more ferrous or non-ferrous particles 2541 within the droplet 2540 to become suspended. In some cases, the compression force may be applied and/or removed quickly or abruptly. Sudden application and/or removal of compression forces may assist in dispersing ferrous and non-ferrous particles 2541 throughout the droplet 2540. In some cases, the compression force may be repeatedly applied and removed to disperse particles more evenly.

Figure 26:
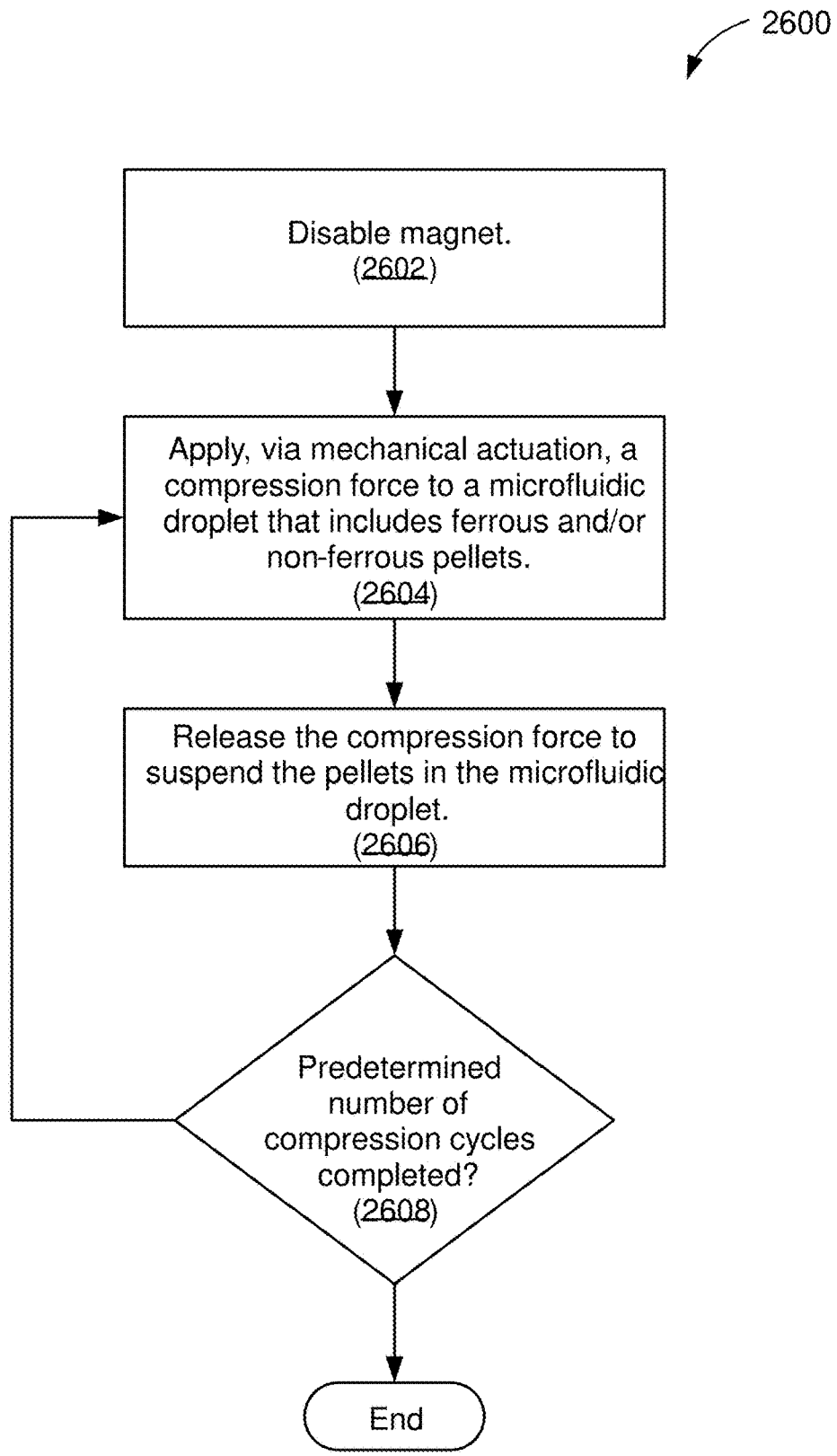
FIG. 26 is a flowchart showing an example operation for dispersing particles in a microfluidic droplet.

FIG. 26 is a flowchart showing an example operation 2600 for dispersing particles in a microfluidic droplet. The operation 2600 is described below with respect to the microfluidic device 2500 of FIGS. 25A and 25B, however the operation 2600 may be performed by any other suitable system or device.

The operation 2600 begins in block 2602 where a magnet is disabled. For example, the magnet 2556 may be disabled either by moving the magnet 2556 away from the tip of the stylus 2550 or by removing power from an electromagnet comprising magnet 2556.

Next, in block 2604 a compression force is applied via mechanical actuation, to a microfluidic droplet that includes ferrous and/or non-ferrous particles that are to be suspended. For example, a compression force may be provided by a mechanical actuation force that may be applied by the stylus 2550 to the first sheet 2510 and/or the second sheet 2520 and also to the droplet 2540. The compression force may cause the droplet 2540 to deform or spread.

Next, in block 2606 the compression force may be released or reduced to suspend the ferrous and/or non-ferrous particles in the droplet. For example, the removal or reduction of the compression force may cause the microfluidic droplet 2540 to return to a spherical or quasi-spherical shape that causes ferrous or non-ferrous particles to become at least partially become suspended within the droplet 2540.

In some cases, additional agitation of the microfluidic droplet may be desired to enhance the distribution of the particles in the microfluidic droplet 2540. To provide the additional agitation, a compression force may be repeatedly applied and removed (or reduced) for a predetermined number of cycles. Therefore, in block 2608, the number of completed compression cycles is determined. A completed compression cycle may include the application and removal or reduction of a compression force. If the number of compression cycles is less than a predetermined number, then the operation 2600 may return to block 2604. On the other hand, if the number of compression cycles is greater than or equal to the predetermined number, then the operation 2600 may end.

Next, in block 2604 a compression force is applied via mechanical actuation, to a microfluidic droplet that includes ferrous and/or non-ferrous particles 2541 that are to be suspended. The compression force may be provided by a mechanical actuation force that may be applied to the first sheet 2510 and/or the second sheet 2520 through the stylus 2550. The compression force may cause the droplet 2540 to deform or spread.

Next, in block 2604 the compression force may be released or reduced to suspend the ferrous and/or non-ferrous particles 2541 in the droplet 2540. The removal or reduction of the compression force may cause the droplet 2540 to return to a spherical or quasi-spherical shape that causes ferrous or non-ferrous particles to become at least partially become suspended within the droplet 2540.

In some examples, a stylus may include or be coupled to a reservoir or other liquid container that may be used to hold liquids aspirated from a gap of a microfluidic device. Example devices are described below in conjunction with FIGS. 27-38.

Figure 27A:
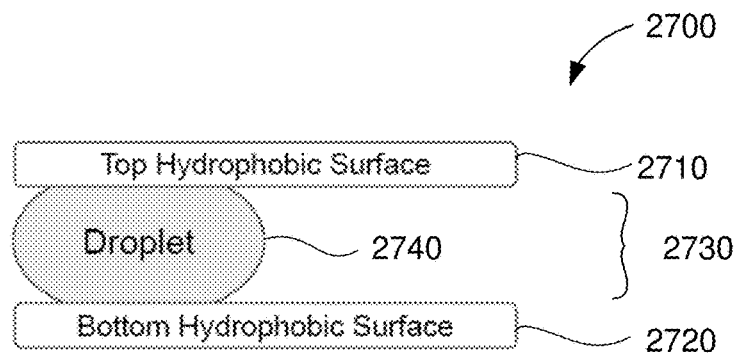
FIGS. 27A-27C show a portion of another microfluidic apparatus.

FIG. 27A shows a portion of another microfluidic device 2700. The microfluidic device 2700 may include a first sheet 2710, a second sheet 2720, and a gap 2730. The first sheet 2710, the second sheet 2720, and the gap 2730 may be examples of the first sheet 1910, the second sheet 1920, and the gap 1930 of FIG. 19A. The first sheet 2710 may include a pre-slit septa or other configurable opening (not shown) that may enable a droplet 2740 to be aspirated (removed) from the gap 2730.

Figure 27B:
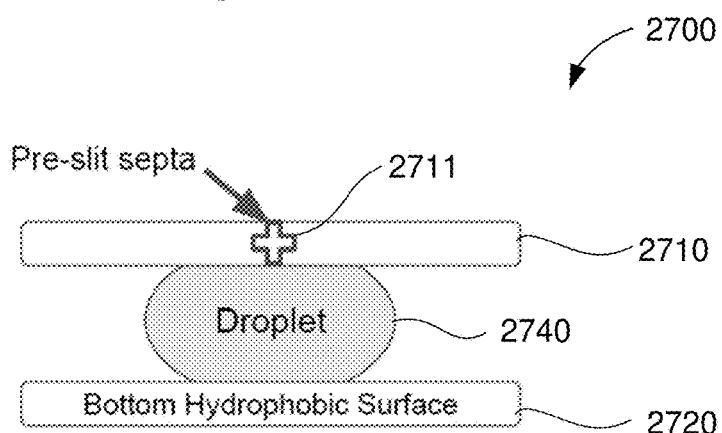

FIG. 27B shows another view of the microfluidic device 2700. A septa 2711 may be included on one of the sheets of the microfluidic device 2700. As shown, the septa 2711 is located on (included with) the first sheet 2710. In some examples, the septa 2711 may remain closed under most operating conditions. For example, a compressive force may be applied to the first sheet 2710 near the septa 2711. However, the septa 2711 may remain substantially closed under the application of the compressive force. In other words, the septa 2711 may have a closing force to prevent liquid from "leaking" from the first sheet 2710. The droplet 2740 may be moved under the septa 2711.

Figure 27C:
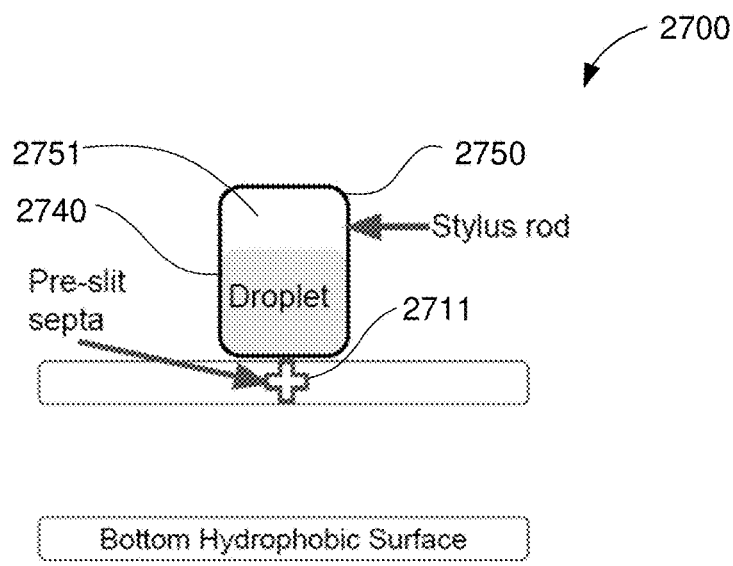

FIG. 27C shows another view of the microfluidic device 2700. A stylus 2750 may be positioned substantially over the septa 2711. The stylus 2750 may include a lumen 2751 that may be coupled to the septa 2711 and configured to receive the droplet 2740. In some examples, a negative pressure may be provided to and/or through the stylus 2750 to aspirate the droplet 2740 through the septa 2711 and into the stylus 2750. The stylus 2750 may now move the droplet 2740 to other locations within the microfluidic device 2700.

Figure 28:
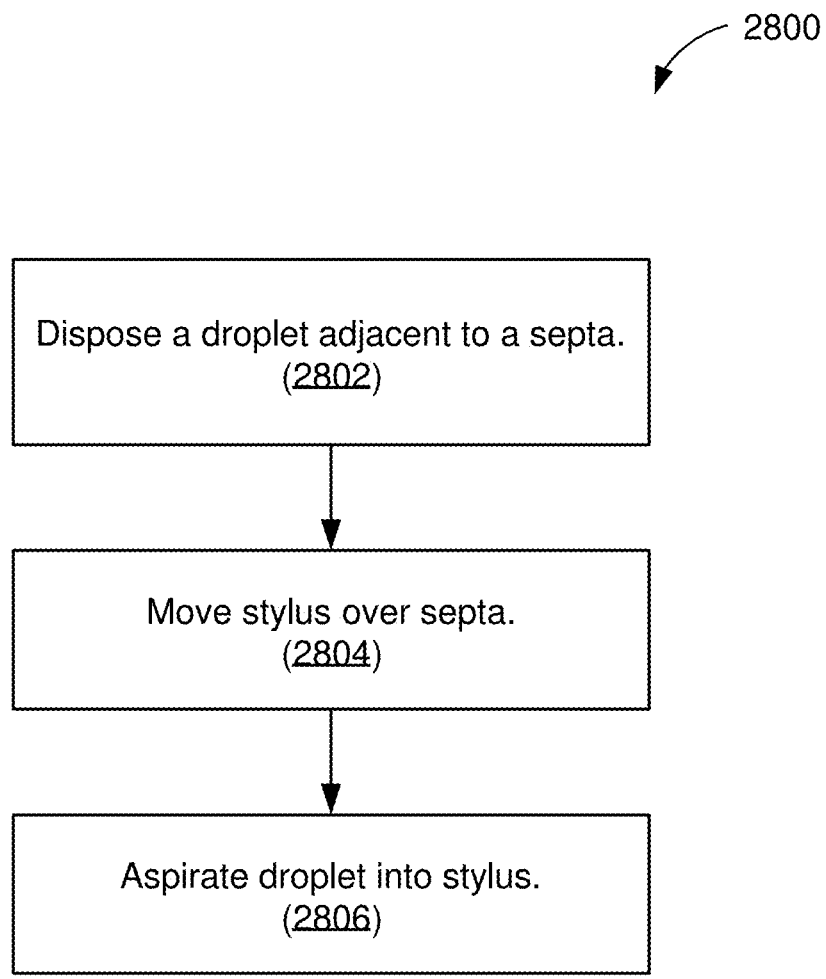
FIG. 28 is a flowchart showing an example operation for aspirating liquids in a microfluidic apparatus.

FIG. 28 is a flowchart showing an example operation 2800 for aspirating liquids in a microfluidic device. The operation 2800 is described below with respect to the microfluidic device 2700 of FIGS. 27A-27C, however the operation 2800 may be performed by any other suitable system or device.

The operation 2800 begins in block 2802 where a droplet is disposed adjacent to a septa. For example, the droplet 2740 may be moved to be substantially under the septa 2711 though any feasible operation disposed herein.

Next, in block 2804 a stylus is moved over the septa. For example, the stylus 2750 may be moved to be over the septa 2711. The stylus 2750 may include a lumen 2751 that may couple to the septa 2711.

Next, in block 2806, a droplet is aspirated into the stylus. For example, a negative pressure may be applied by or through the stylus 2750. The negative pressure may draw the droplet 2740 into the lumen 2751.

In some examples, liquid may be provided or returned to a microfluidic device through a septa. Some examples are described below in conjunction with FIGS. 29 and 30.

Figure 29A:
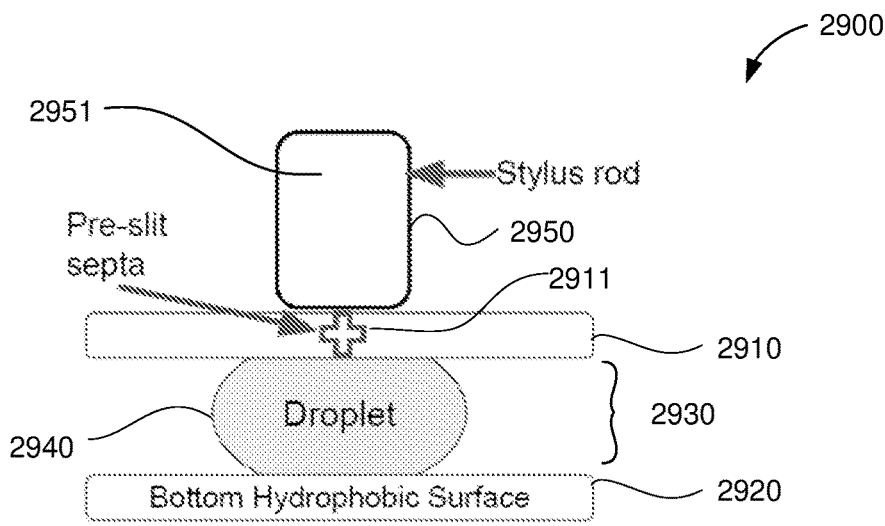
FIGS. 29A-29C shows a portion of another microfluidic apparatus.

FIG. 29A shows a portion of another microfluidic device 2900. The microfluidic device 2900 may include a first sheet 2910, a second sheet 2920, a gap 2930, and a stylus 2950. The first sheet 2910, the second sheet 2920, the gap 2930, and the stylus 2950 may be examples of the first sheet 2710, the second sheet 2720, the gap 2730, and the stylus 2750 of FIG. 27A. Thus, first sheet 2910 may include a septa 2911.

In some examples, liquid that may be included within the stylus 2950 may be injected through the septa 2911 and into the gap 2930. Prior to injecting the liquid, the stylus 2950 may be positioned over the septa 2911. In some examples, a lumen 2951 of the stylus 2950 may be coupled to the septa 2911. A positive pressure may be applied to the lumen 2951 to push the liquid out of the stylus 2950 and form a droplet 2940 within the gap 2930. Thus, the applied pressure may overcome a closing force of the septa 2911.

Figure 29B:
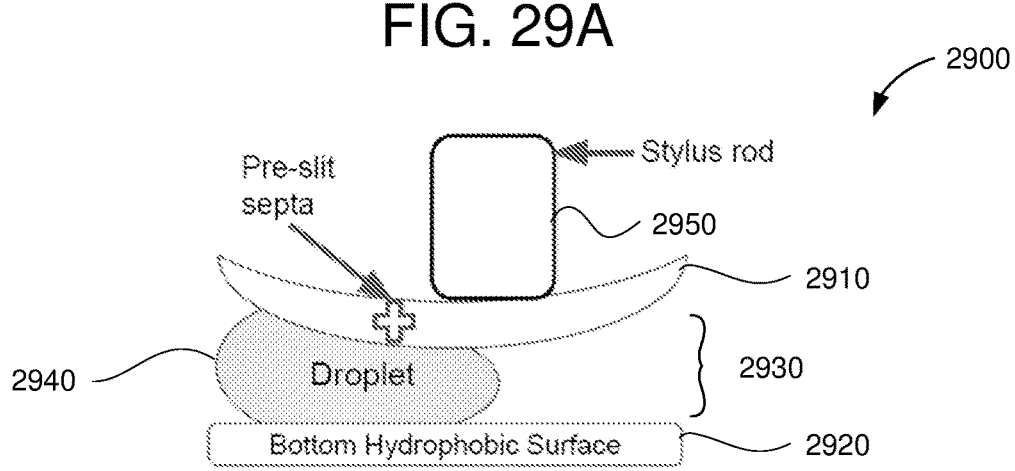

FIG. 29B shows another view of the microfluidic device 2900. The stylus 2950 may be moved away from the droplet 2940. Furthermore, a compressive force may be provided by the stylus 2950 to the first sheet 2910 (and/or the second sheet 2920) to reduce the gap 2930. The reduced gap 2930 may cause the droplet 2940 to move relative to the first sheet 2910 and the second sheet 2920.

Figure 29C:
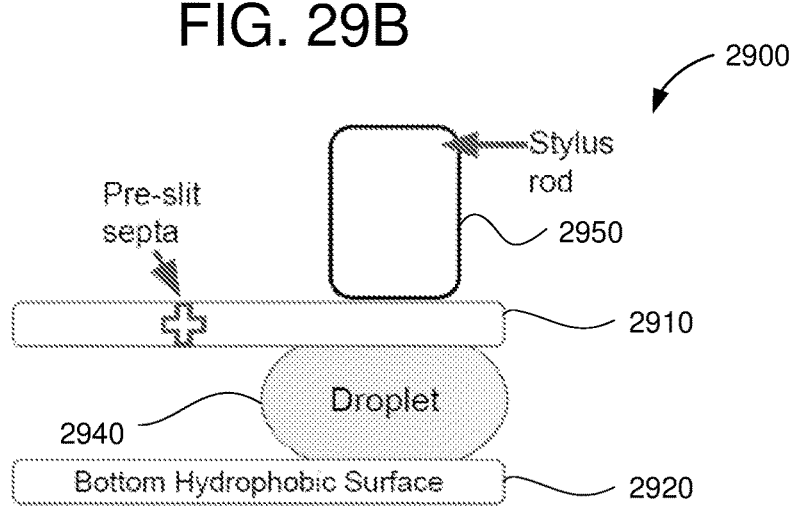

FIG. 29C shows another view of the microfluidic device 2900. The stylus 2950 may move to move the droplet 2940. After the motion of the droplet 2940 is complete, then the stylus 2950 may be positioned to remove the compression source to the first sheet 2910 and/or the second sheet 2920. Thus, the stylus 2950 may operate as a pipette to move liquids (e.g., the droplet 2940) within the microfluidic device 2900.

Figure 30:
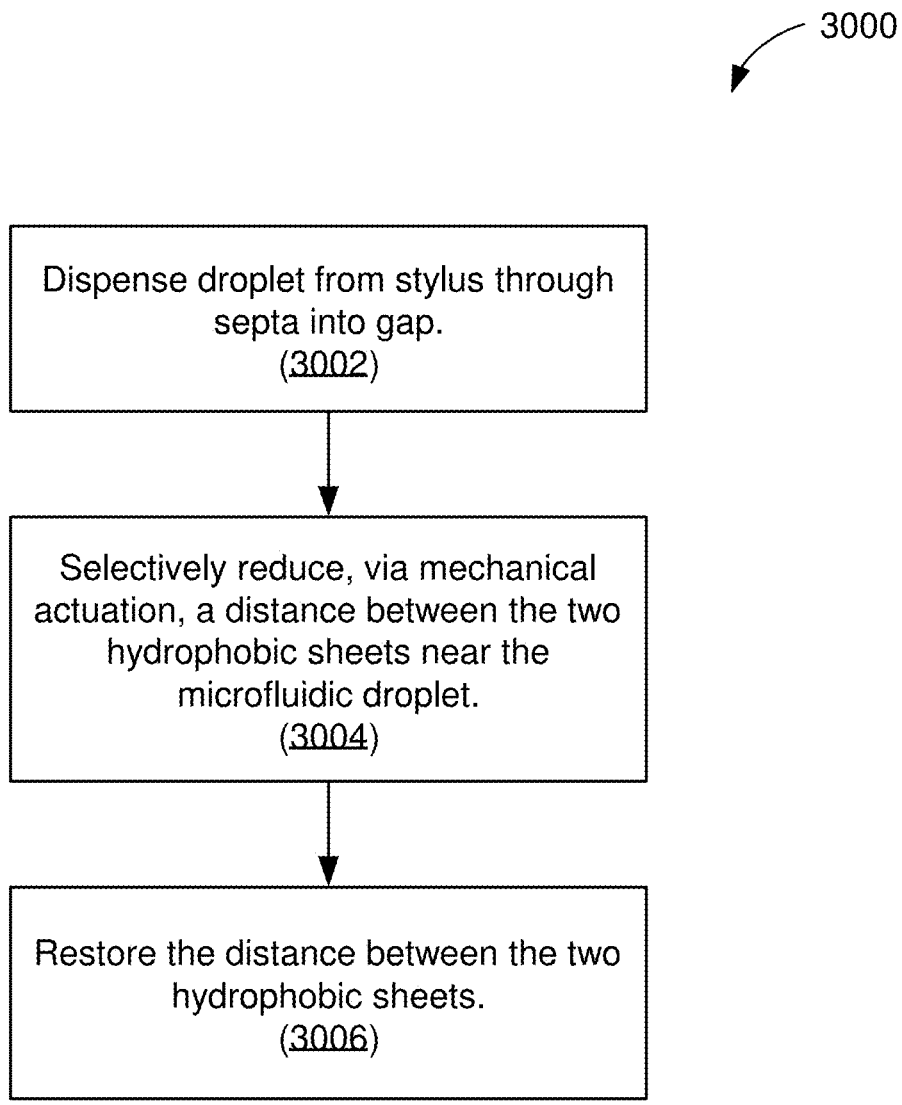
FIG. 30 is a flowchart showing an example operation for manipulating liquids in a microfluidic apparatus.

FIG. 30 is a flowchart showing an example operation 3000 for manipulating liquids in a microfluidic device. The operation 3000 is described below with respect to the microfluidic device 2900 of FIGS. 29A-29C, however the operation 3000 may be performed by any other suitable system or device.

The operation 3000 begins in block 3002 where a droplet is dispensed from a stylus through a septa and into a gap of a microfluidic device. For example, the stylus 2950 may be positioned over the septa 2911. A positive pressure may be applied to the stylus 2950 and/or lumen 2951 to inject a liquid through the septa 2911 into the gap 2930.

Next, in block 3004 the distance between the two sheets is selectively reduced, via mechanical actuation, near the microfluidic droplet. For example, the reduced distance may result in a reduced gap 2930 between the first sheet 2910 and the second sheet 2920. In some examples, a compression force may be provided by the stylus 2950 adjacent to (e.g., next to) one side of the droplet 2940. The compression force may reduce the gap 2930 causing the droplet 2940 to move toward the compression force. In some variations, the compression force may deform one end of the droplet 2940.

Next, in block 3006 the distance between the two sheets is restored. For example, the compression force applied in block 3004 may be removed allowing the first sheet 2910 and/or the second sheet 2920 to return to its initial separation distance. In some examples, the distance between first sheet 2910 and second sheet 2920 is returned to a distance similar to the initial separation distance associated with block 3602.

In some examples, a stylus may include additional devices or systems that may be used to process a droplet within the stylus. Some examples are described below in conjunction with FIGS. 31-38.

Figure 31A:
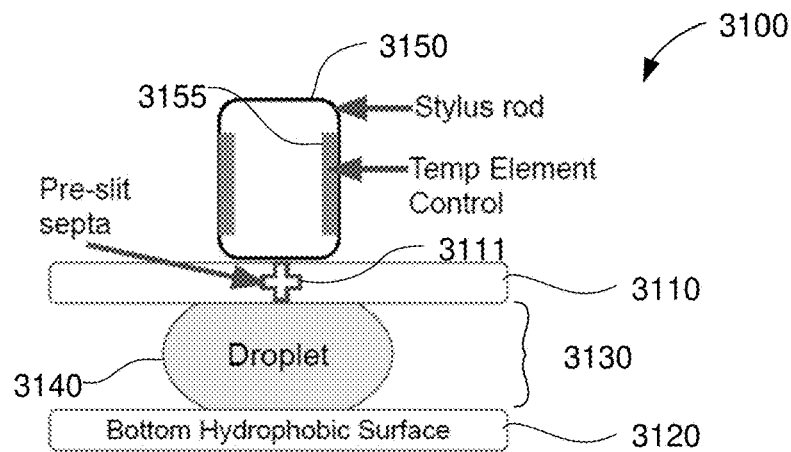
FIGS. 31A-31C shows a portion of another microfluidic apparatus.

FIG. 31A shows a portion of another microfluidic device 3100. The microfluidic device 3100 may include a first sheet 3110, a second sheet 3120, a gap 3130, and a stylus 3150. The first sheet 3110, the second sheet 3120, and the gap 3130 may be examples of the first sheet 1810, the second sheet 1820, and the gap 1830 of FIG. 18A. The stylus 3150 may include a temperature control element 3155. Through the temperature control element 3155, any liquid that is aspirated from the gap 3130 may be heated within the stylus 3150 as part of a chemical assay or other protocol or process. For example, a droplet 3140 may be disposed beneath a septa 3111 that is included in the first sheet 3110. The stylus 3150 may be disposed over the septa 3111. In some examples, the temperature control element 3155 may provide heating or cooling to surrounding area based on a control voltage, signal, or the like.

Figure 31B:
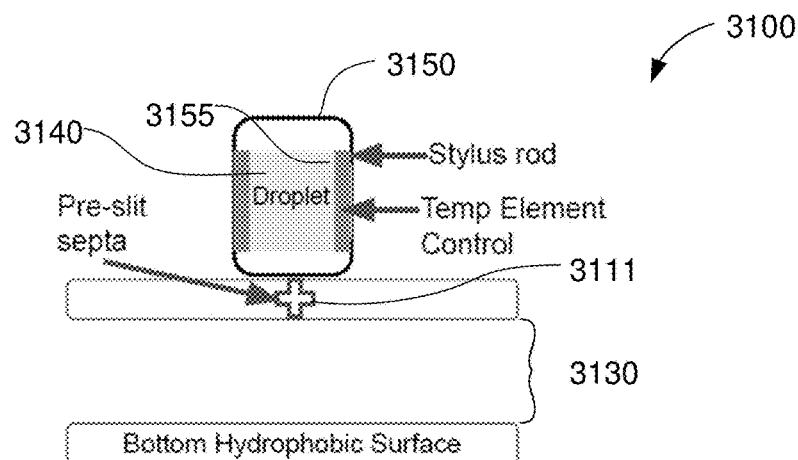

FIG. 31B shows another view of the microfluidic device 3100. The droplet 3140 may be aspirated from the gap 3130, through the septa 3111, and into the stylus 3150. In this manner, while the droplet 3140 is within the stylus 3150, the droplet 3140 may undergo temperature processing as provided by the temperature control element 3155. In some examples, a temperature sensor (not shown) may be included with the stylus 3150 and/or the temperature control element 3155. A controller (not shown) may monitor and control the temperature of the droplet 3140 as part of the temperature processing. For example, the controller may monitor the temperature of the droplet 3140 and control the temperature provided by the temperature control element 3155.

Figure 31C:
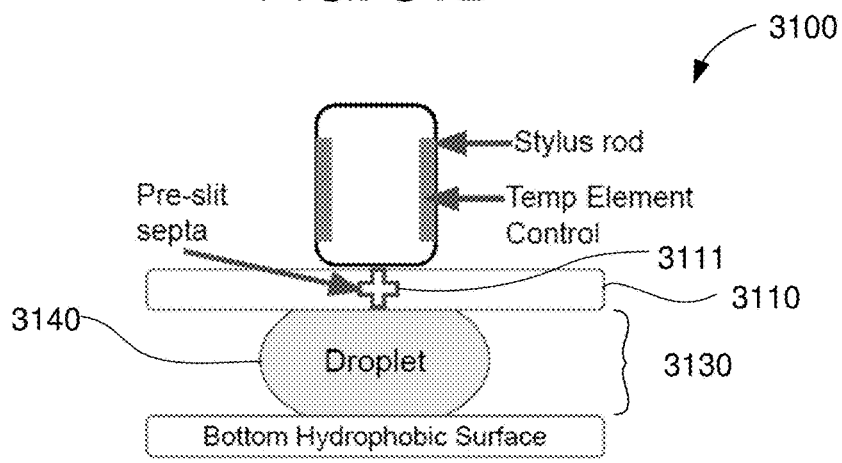

FIG. 31C shows another view of the microfluidic device 3100. After temperature processing, the droplet 3140 may be injected into the gap 3130 through the septa 3111 in the first sheet 3110.

Figure 32:
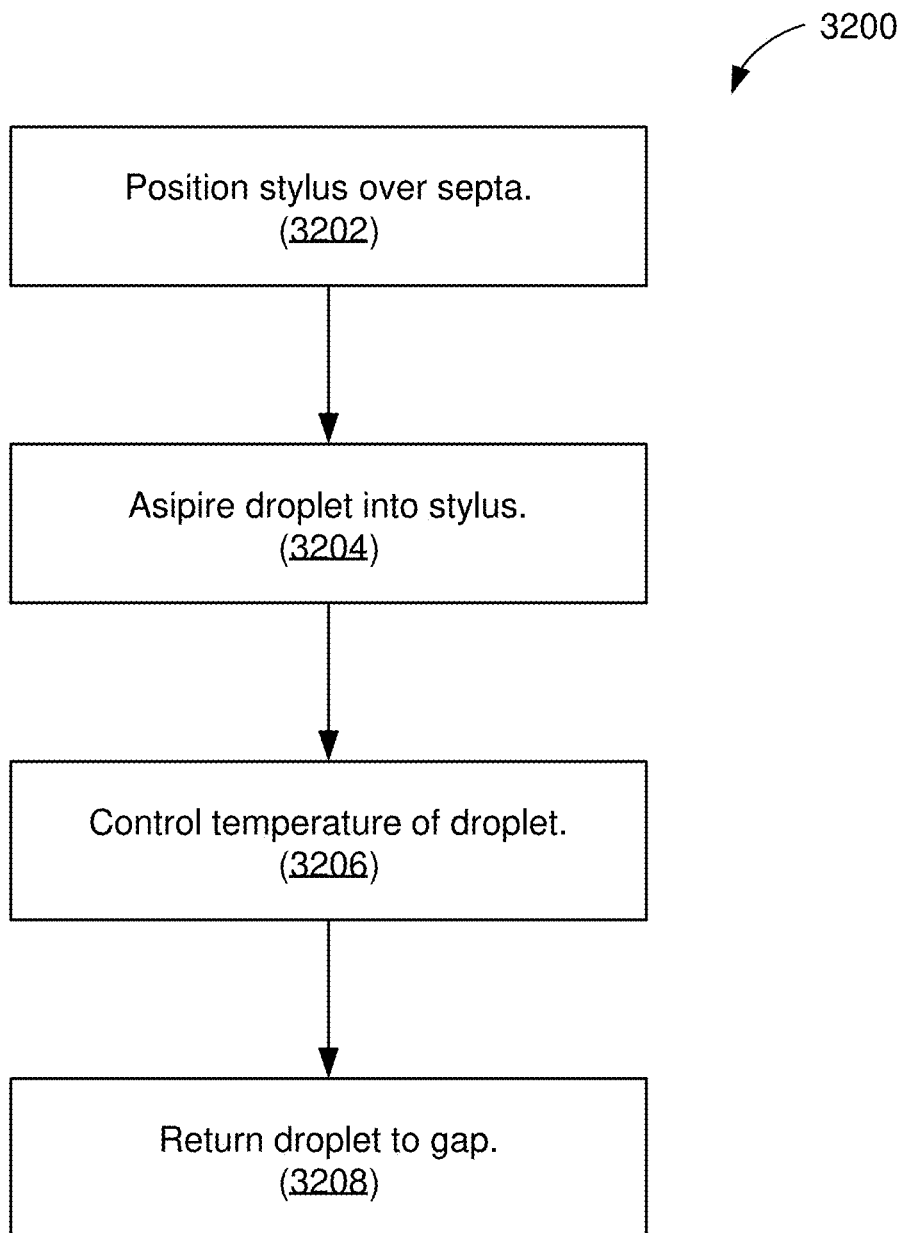
FIG. 32 is a flowchart showing an example operation for thermally treating liquids in a microfluidic apparatus.

FIG. 32 is a flowchart showing an example operation 3200 for thermally treating liquids in a microfluidic device. The operation 3200 is described below with respect to the microfluidic device 3100 of FIGS. 31A-31C, however the operation 3200 may be performed by any other suitable system or device.

The operation begins in block 3202 where a stylus is positioned over a septa and a droplet. For example, the stylus 3150 may be positioned over the septa 3111 which is over a droplet 3140.

Next, in block 3204, the droplet is aspirated into the stylus through the septa. For example, a negative pressure may be provided to the stylus 3150. In response, the droplet 3140 may be drawn through the septa 3111 and into the stylus 3150.

Next, in block 3206, the temperature of the droplet is controlled. For example, a temperature control element 3155 may be used to monitor and control the temperature of the droplet 3140 which is contained within the stylus 3150.

Next, in block 3208, the droplet is injected into the gap through the septa. For example, temperature processing may be complete. A positive pressure may be provided to the stylus 3150 causing the droplet 3140 to be injected though the septa 3111 and into the gap 3130. In some examples, the stylus 3150 may be repositioned with respect to the first sheet 3110 and/or the second sheet 3120 prior to returning the droplet 3140 to the gap 3130.

Figure 33:
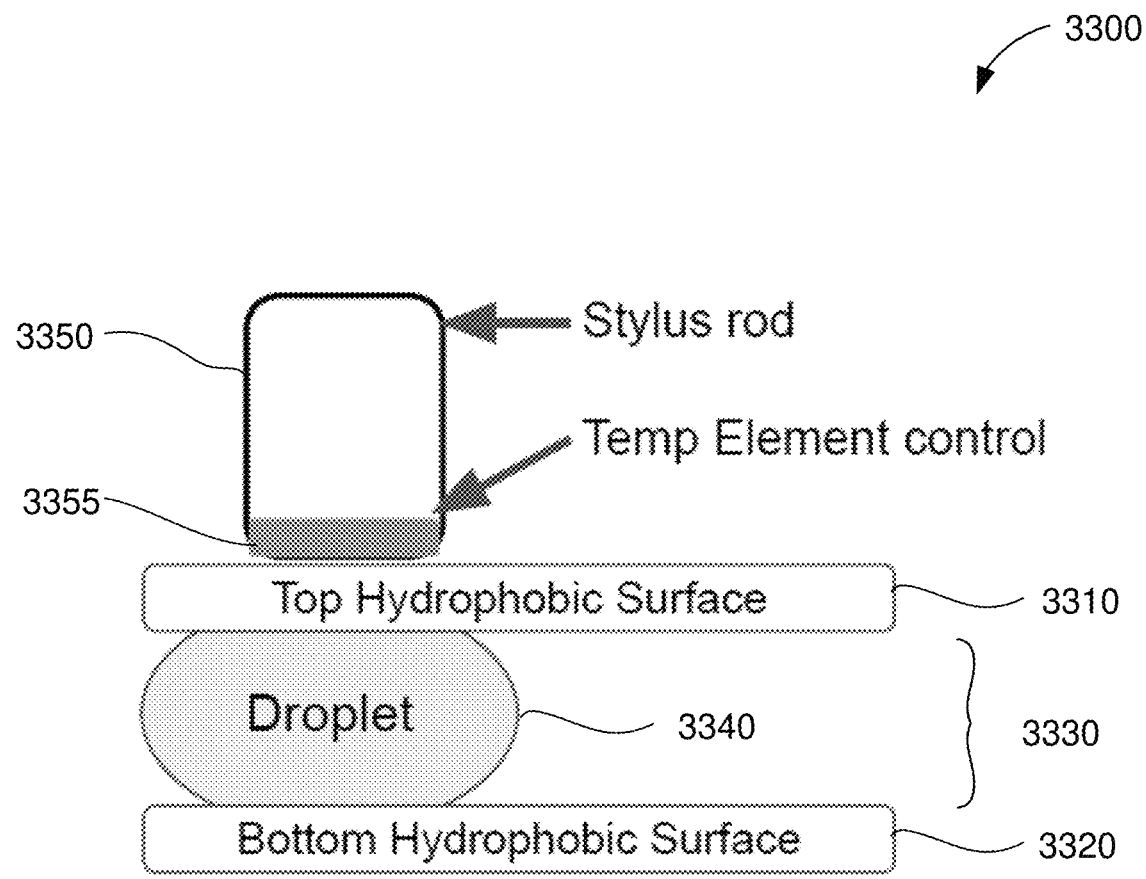
FIG. 33 shows a portion of another microfluidic apparatus.

FIG. 33 shows a portion of another microfluidic device 3300. The microfluidic device 3300 may include a first sheet 3310, a second sheet 3320, a gap 3330, and a stylus 3350. The first sheet 3310, the second sheet 3320, and the gap 3330 may be examples of the first sheet 1810, the second sheet 1820, and the gap 1830 of FIG. 18A. The stylus 3350 may include a temperature control element 3355. The temperature control element 3355 may be disposed toward a portion of the stylus 3350 that may contact the first sheet 3310. The stylus 3350 and the temperature control element 3355 are positioned on the first sheet 3310 over a droplet 3340. In this manner, the temperature control element 3355, may provide heat for any temperature controlled processing to the droplet 3340 through the first sheet 3310.

In some examples, the temperature control element 3355 may include a temperature sensor (not shown). In this manner a controller (also not shown) may control the temperature of the droplet 3340 to be within a desired temperature.

Figure 34A:
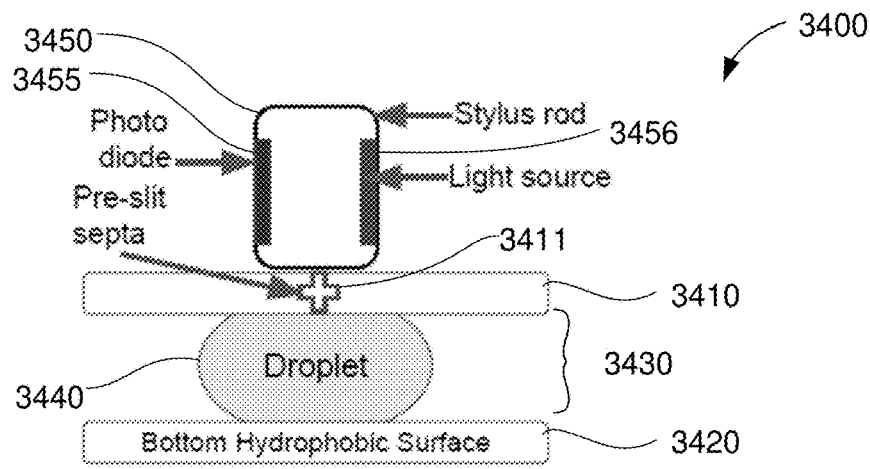
FIGS. 34A-34C show a portion of another microfluidic apparatus.

FIG. 34A shows a portion of another microfluidic device 3400. The microfluidic device 3400 may include a first sheet 3410, a second sheet 3420, a gap 3430, and a stylus 3450. The first sheet 3310, the second sheet 3320, and the gap 3330 may be examples of the first sheet 1810, the second sheet 1820, and the gap 1830 of FIG. 18A. The stylus 3450 may include a light sensor 3455 and a light source 3456. In some examples, a reaction that may have occurred or be occurring within a droplet 3440 may be monitored by sensing light that may be transmitted or reflected through the droplet 3440. Thus, the droplet 3440 may be drawn into the stylus 3450 where transmitted and/or reflected light can be detected and/or measured. The amount of detected light may be associated with the progress or completion of a reaction.

In some examples, to measure a reaction, the stylus 3450 may be positioned over a septa 3411 that is included in the first sheet 3410. Additionally, the droplet 3440 may be located under the septa 3411.

Figure 34B:
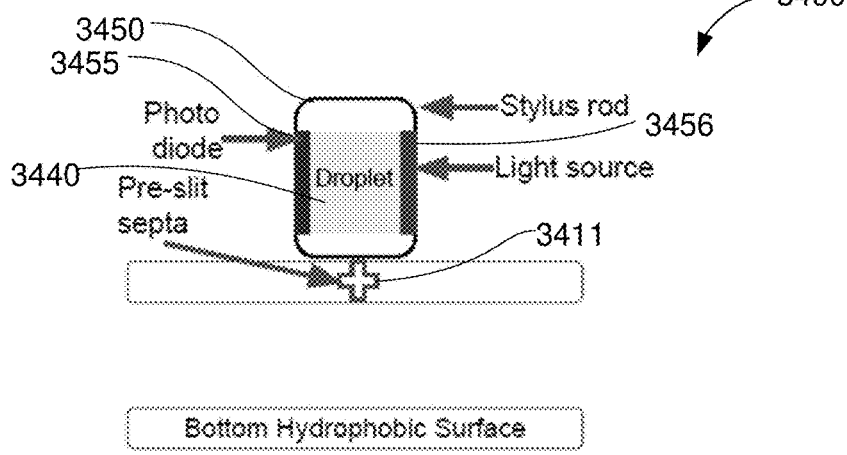

FIG. 34B shows another view of the microfluidic device 3400. As shown, the droplet 3440 may be aspirated through the septa 3411 and into the stylus 3450. The light source 3456 may emit light into the droplet 3440. The light source 3456 may be any feasible solid state and/or incandescent light source. The light may be reflected and/or transmitted through the droplet 3440. This light may be detected by the light sensor 3455. The light sensor 3455 may be any feasible light sensor or detector such as a photo diode or the like. The amount of detected light may be associated with the progress or completion of a reaction. In this manner, the detected light may indicate the progress or completion of a reaction.

Figure 34C:
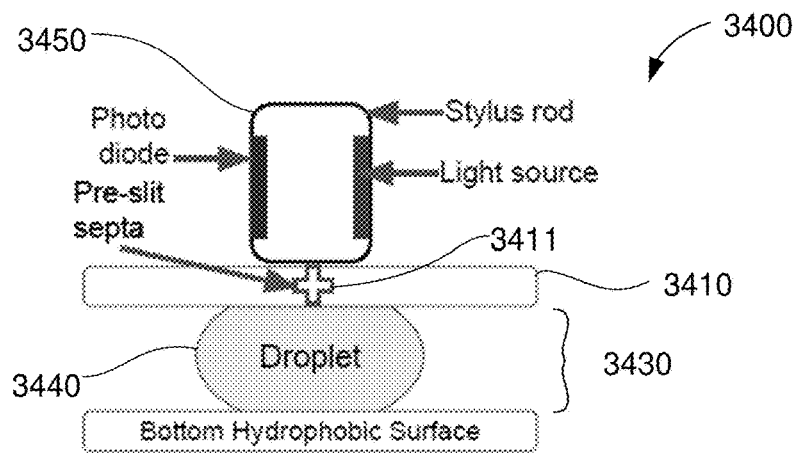

FIG. 34C shows another view of the microfluidic device 3400. As shown, the droplet 3440 may be returned to the gap 3430. In some examples, the stylus 3450 may inject the droplet 3440 through the septa 3411 in the first sheet 3410. In this manner, after determining the light transmission or refraction of the droplet 3440, the droplet 3440 may be returned to the gap 3430 for other processing.

Figure 35:
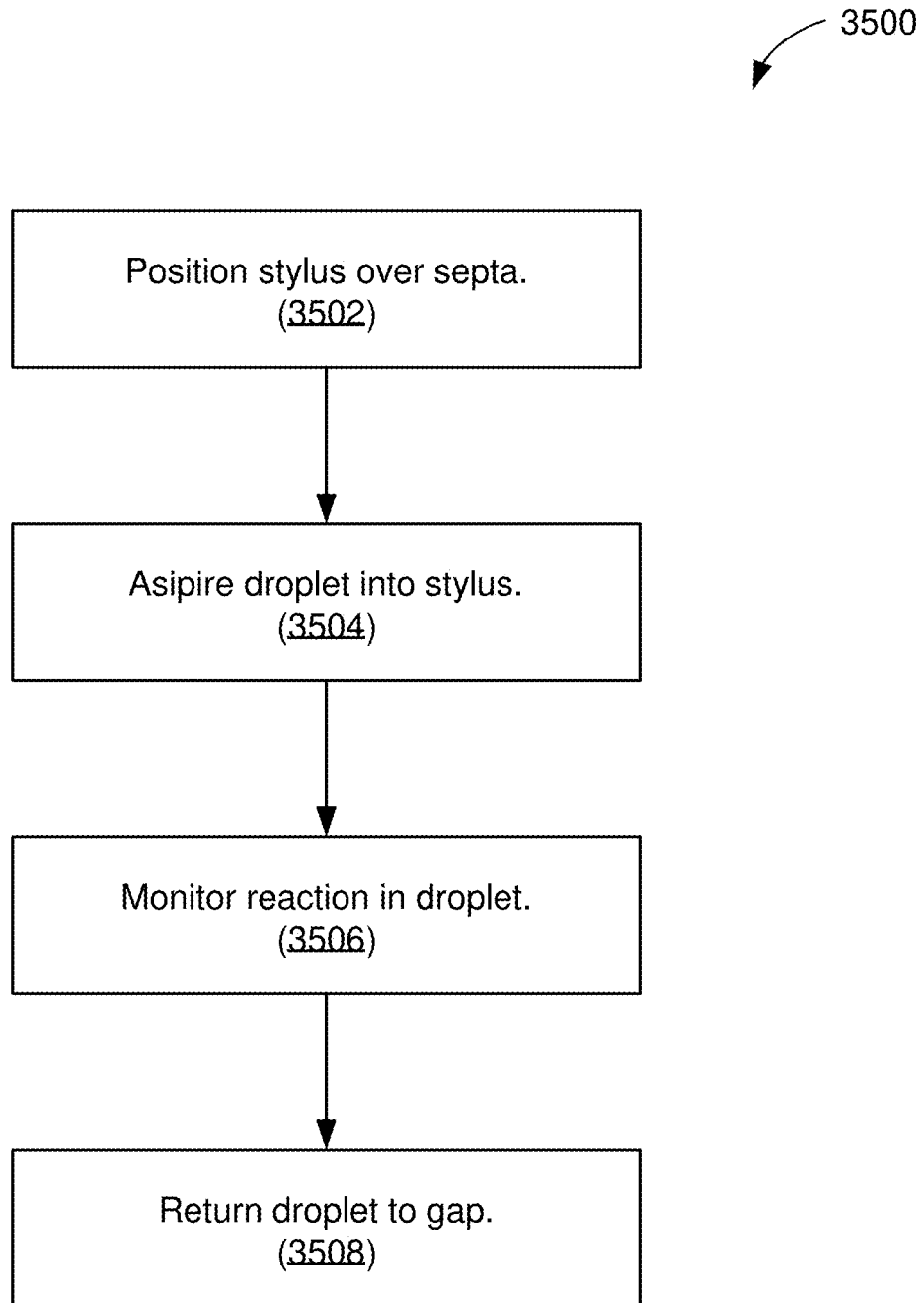
FIG. 35 is a flowchart showing an example operation for performing a reaction measurement.

FIG. 35 is a flowchart showing an example operation 3500 for performing a reaction measurement. The operation 3500 is described below with respect to the microfluidic device 3400 of FIGS. 34A-34C, however the operation 3500 may be performed by any other suitable system or device.

The operation begins in block 3502 where a stylus is positioned over a septa and a droplet. For example, the stylus 3450 may be positioned over the septa 3411 which is over a droplet 3440.

Next, in block 3504, the droplet is aspirated into the stylus through the septa. For example, a negative pressure may be provided to the stylus 3450. In response, the droplet 3440 may be drawn through the septa 3411 and into the stylus 3450.

Next, in block 3506, the reaction of the droplet is monitored. For example, a light source 3456 may be used to emit light in the stylus 3450 and into the droplet 3440. A light sensor 3455 may detect transmitted and/or reflected light from the droplet 3440. In some cases, the transmitted and/or reflected light may be associated with an amount of progress of a reaction occurring within the droplet 3440.

Next, in block 3508, the droplet is injected into the gap through the septa. For example, reaction monitoring may be complete. A positive pressure may be provided to the stylus 3450 causing the droplet 3440 to be injected though the septa 3411 and into the gap 3430. In some examples, the stylus 3450 may be repositioned with respect to the first sheet 3410 and/or the second sheet 3420 prior to returning the droplet 3440 to the gap 3430.

Figure 36:
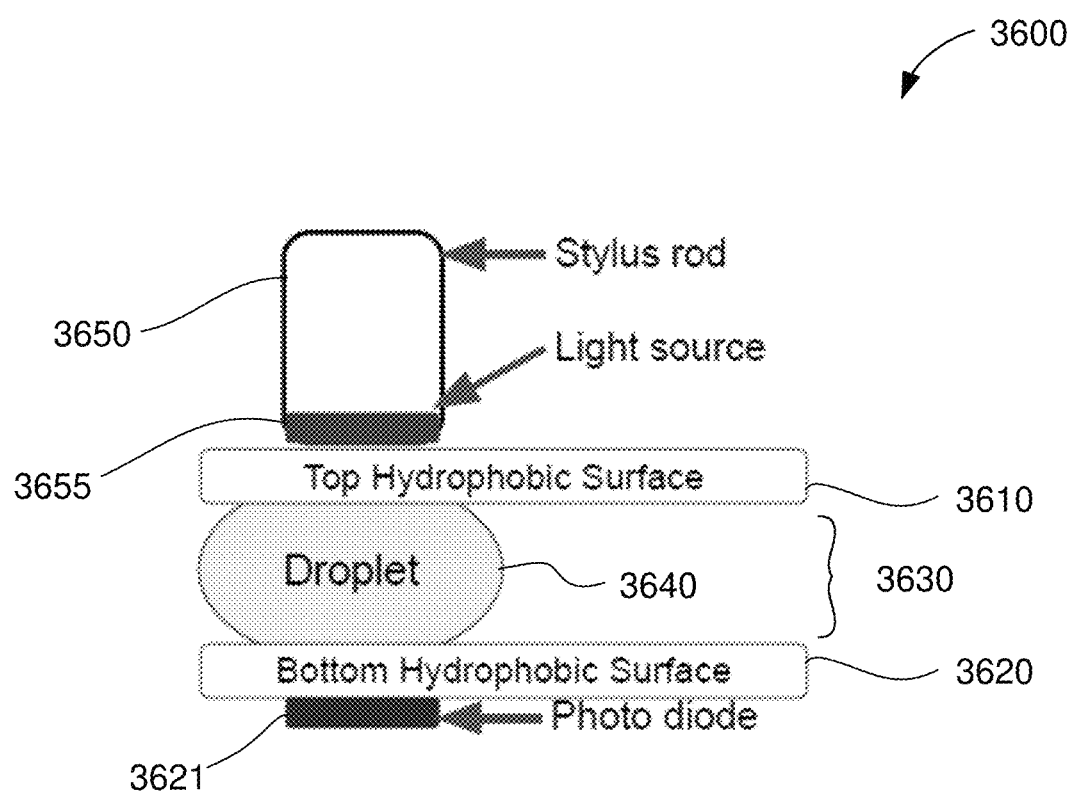
FIG. 36 shows a portion of another microfluidic apparatus.

FIG. 36 shows a portion of another microfluidic device 3600. The microfluidic device 3600 may include a first sheet 3610, a second sheet 3620, a gap 3630, and a stylus 3650. The first sheet 3610, the second sheet 3620, and the gap 3630 may be examples of the first sheet 1810, the second sheet 1820, and the gap 1830 of FIG. 18A. The stylus 3650 may include a light source 3655. The light source 3655 may be disposed toward a portion of the stylus 3650 that may contact the first sheet 3610.

Opposite the light source 3655 may be a light detector 3621. As shown, the light detector 3621 may be disposed on the second sheet 3620. When a droplet 3640 is disposed between the light source 3655 and the light detector 3621, the light detector 3621 may detect transmitted and/or reflected light. Thus, the light source 3655 and the light detector 3621 may monitor progress of a reaction, similar to as described with respect to FIGS. 34 and 35. In some examples the position of the light source 3655 and the light detector 3621 may be reversed. In other words, the light sensor 3621 may be included with the stylus 3650 and the light source 3655 may be disposed on the second sheet 3620.

Figure 37A:
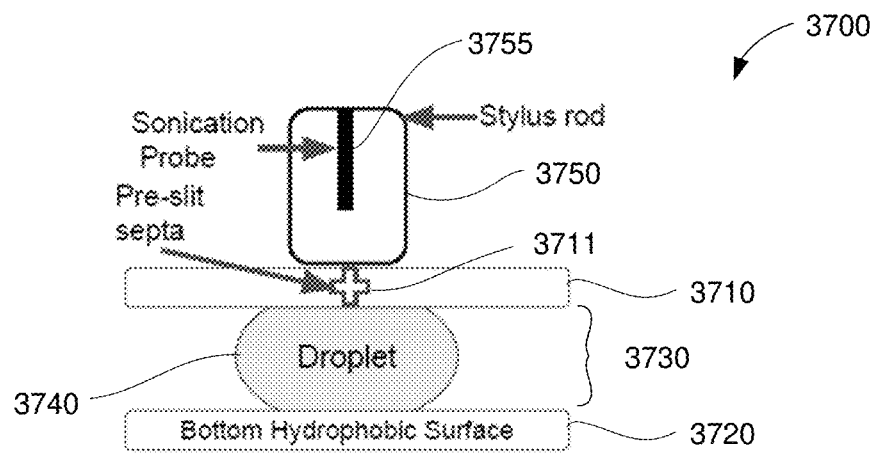
FIGS. 37A-37C show a portion of another microfluidic apparatus.

FIG. 37A shows a portion of another microfluidic device 3700. The microfluidic device 3700 may include a first sheet 3710, a second sheet 3720, a gap 3730, and a stylus 3750. The first sheet 3710, the second sheet 3720, and the gap 3730 may be examples of the first sheet 1810, the second sheet 1820, and the gap 1830 of FIG. 18A. The stylus 3750 may include a sonication probe 3755. In some examples, the sonication probe 3755 may deliver sonic and/or ultrasonic stimulation to a droplet 3740. The sonication probe 3755 may be any feasible piezo-electric device.

In some examples, to deliver sonic or ultrasonic stimulation, the stylus 3750 may be positioned over a septa 3711 that is included in the first sheet 3710. Additionally, the droplet 3740 may be located under the septa 3711.

Figure 37B:
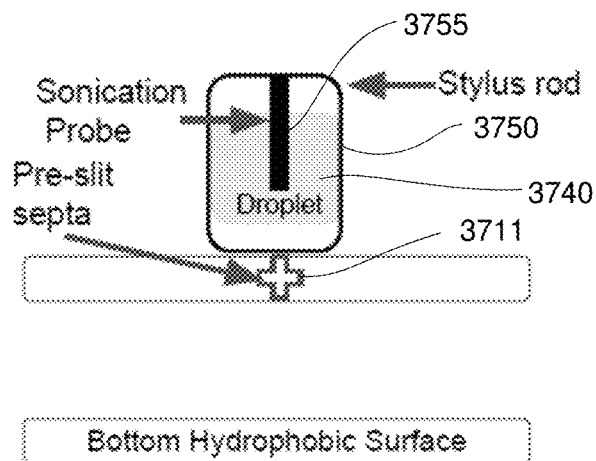

FIG. 37B shows another view of the microfluidic device 3700. As shown, the droplet 3740 may be aspirated through the septa 3711 and into the stylus 3750. Once the droplet 3740 is in the stylus 3750, the sonication probe 3755 may be activated or enabled allowing sonic and/or ultrasonic waves to be provided to the droplet 3740. The delivery sonic stimulation may be controlled by a controller (not shown).

Figure 37C:
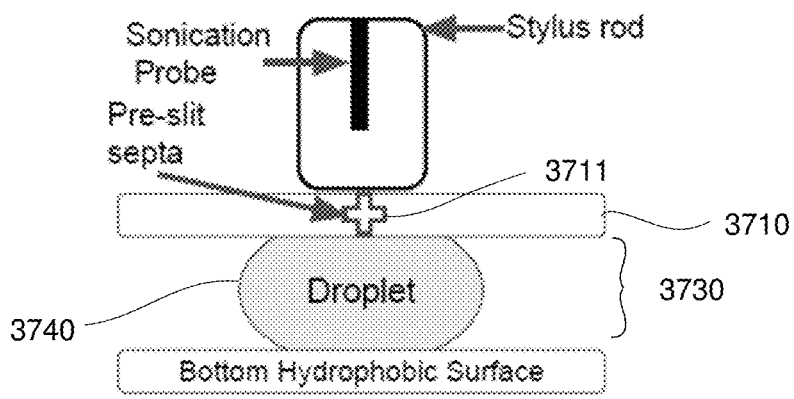

FIG. 37C shows another view of the microfluidic device 3700. As shown, the droplet 3740 may be returned to the gap 3730. In some examples, the stylus 3750 may inject the droplet 3740 through the septa 3711 in the first sheet 3710. In this manner, after delivering sonic stimulation to the droplet 3740, the droplet 3740 may be returned to the gap 3730 for other processing.

Figure 38:
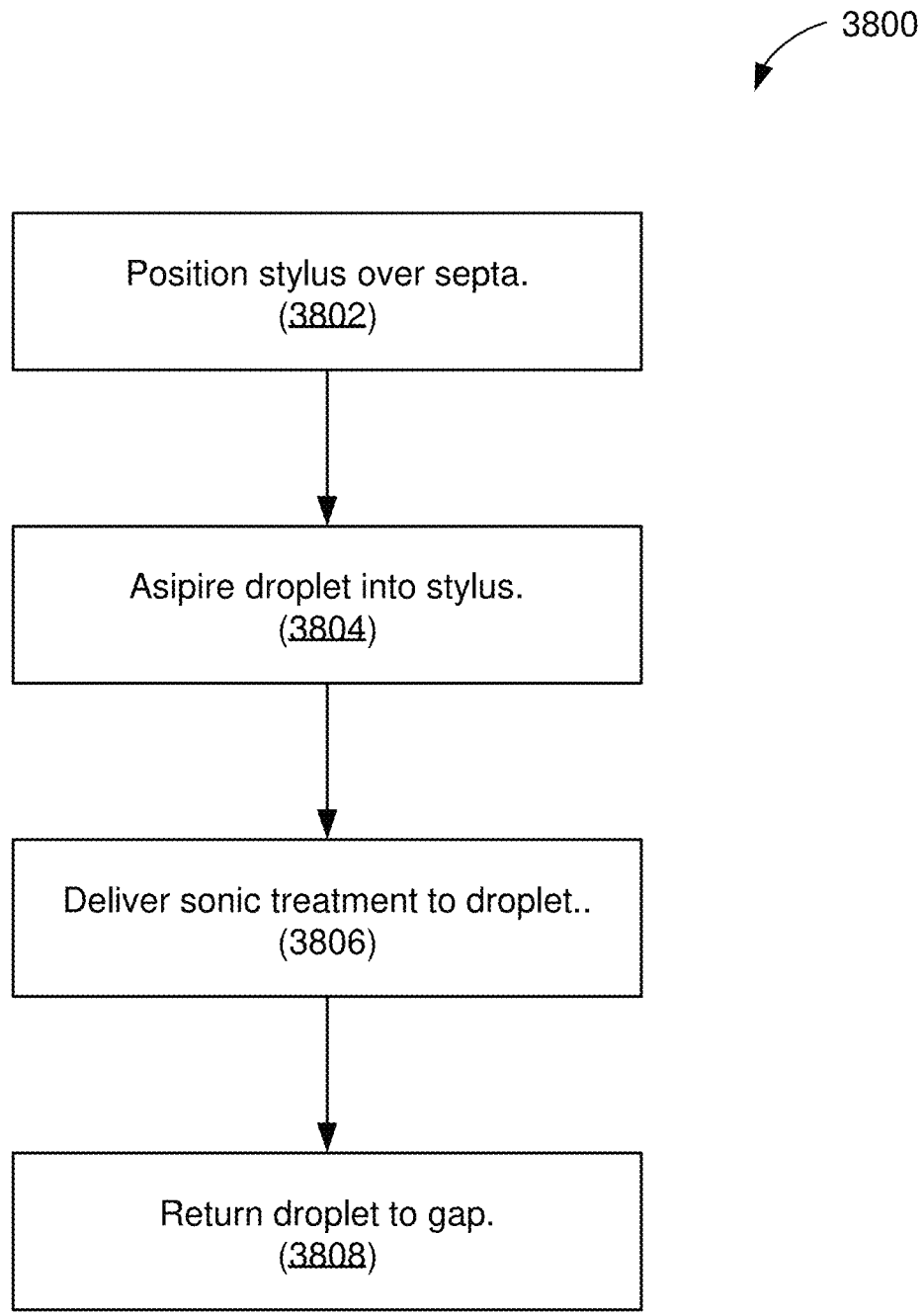
FIG. 38 is a flowchart showing an example operation for performing a sonic treatment.

FIG. 38 is a flowchart showing an example operation 3800 for performing a sonic treatment. The operation 3800 is described below with respect to the microfluidic device 3700 of FIGS. 37A-37C, however the operation 3800 may be performed by any other suitable system or device.

The operation begins in block 3802 where a stylus is positioned over a septa and a droplet. For example, the stylus 3750 may be positioned over the septa 3711 which is over a droplet 3740.

Next, in block 3804, the droplet is aspirated into the stylus through the septa. For example, a negative pressure may be provided to the stylus 3750. In response, the droplet 3740 may be drawn through the septa 3711 and into the stylus 3750.

Next, in block 3806, the sonic treatment may be delivered to the droplet. For example, the sonication probe 3755 may deliver sonic and/or ultrasonic treatment to the droplet 3740.

Next, in block 3808, the droplet is injected into the gap through the septa. For example, sonic treatment may be complete. A positive pressure may be provided to the stylus 3750 causing the droplet 3740 to be injected though the septa 3711 and into the gap 3730. In some examples, the stylus 3750 may be repositioned with respect to the first sheet 3710 and/or the second sheet 3720 prior to returning the droplet 3740 to the gap 3730.

Figure 39:
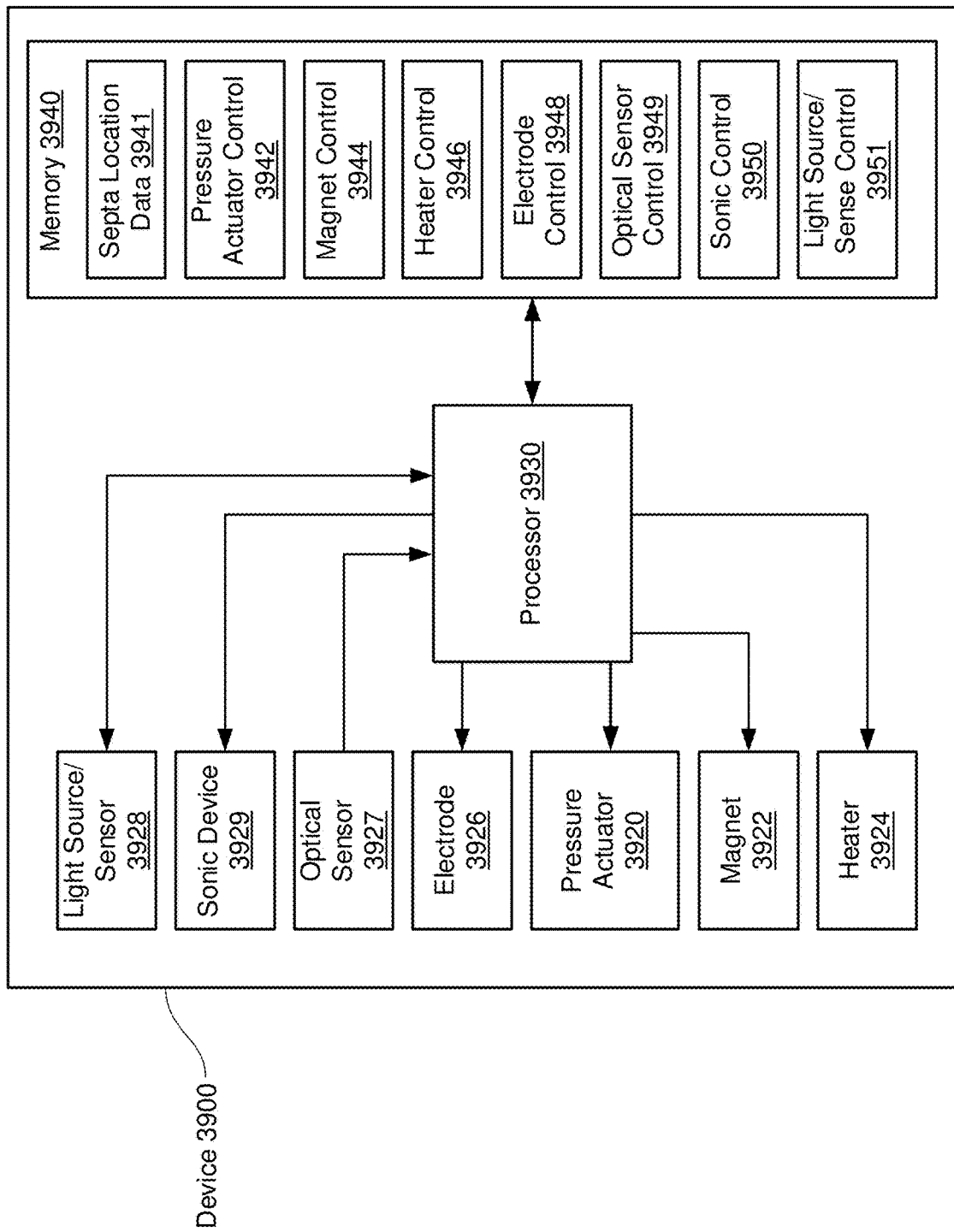
FIG. 39 shows a block diagram of a device that may be one example of a microfluidic apparatus (e.g., mechanical microfluidics actuator) as described herein.

FIG. 39 shows a block diagram of a device 3900 that may be one example of the any microfluidic device or system described herein. The device 3900 may include a pressure actuator 3920, one or more magnets 3922, one or more heaters 3924, one or more electrodes 3926, an optical sensor 3927, a light source and sensor 3928, a sonic device 3929, a processor 3930, and a memory 3940.

In some examples, the pressure actuator 3920, which is coupled to the processor 3930, may be used to provide forces, including compression and actuation forces to one or more sheets of a microfluidic cartridge. In some examples, the pressure actuator 3920 may use mechanical, pneumatic, and/or electrical actuators to provide the compression and/or actuation forces. The compression and/or actuation forces may be provided through a controllable stylus. In some other examples, the pressure actuator 3920 may provide positive and/or negative pressure to a lumen of a stylus. In this manner a droplet may be aspirated from a gap of a microfluidic device and drawn into the stylus.

The one or more magnets 3922, which are also coupled to the processor 3930, may be used to selectively provide magnetic fields that may be used for and during microfluidic droplet manipulation. In some examples the magnet may be disposed adjacent to a side of a hydrophobic and oleophobic sheet. In some other examples, the magnet may be disposed within a stylus.

The one or more heaters 3924, which are also coupled to the processor 3930, may be used to provide heat to one or more microfluidic droplets. The heat may be used during analysis or assay of the microfluidic droplets. In some examples the heater (e.g., heating element) may be disposed adjacent to a side of a hydrophobic and oleophobic sheet. In some other examples, the heater may be disposed within a stylus.

The one or more electrodes 3926, which are also coupled to the processor 3930, may be used to provide electric fields used for electroporation. In some examples, the processor 3930 may include one or more electrical circuits or devices to generate large magnitude electric fields for the one or more electrodes 3926.

The optical sensor 3927, which is also coupled to the processor 3930, may detect the presence and/or position of any droplet, such as any microfluidic droplet disposed between two or more hydrophobic and oleophobic sheets.

The light source and sensor 3928, which are also coupled to the processor 3930, may provide light and detect a transmitted or reflected light associated with a microfluidic droplet. In some examples, the light source and sensor 3928 may be included with a stylus. In some other examples, the light source and sensor 3928 may be disposed on a side of a hydrophobic and oleophobic sheet and the stylus.

The sonic device 3929, which is also coupled to the processor 3930, may provide sonic or ultrasonic treatment to a microfluidic droplet. In some examples, the sonic device 3929 may be included with the stylus. In some examples, the sone device 3929 may be a piezo electric device.

The processor 3930, which is also coupled to the memory 3940, may be any one or more suitable processors capable of executing scripts or instructions of one or more software programs stored in the device 3900 (such as within the memory 3940).

The memory 3940 may include septa location data 3941. In some examples, the septa location data 3941 may be a database of the locations of one or more septa openings that may be disposed on a hydrophobic and oleophobic sheet. Thus, the processor 3930 may use the septa location data 3941 to position the stylus over any particular septa.

The memory 3940 may also include a non-transitory computer-readable storage medium (e.g., one or more non-volatile memory elements, such as EPROM, EEPROM, Flash memory, a hard drive, etc.) that may store the following software modules: a pressure actuator control module 3942 to control the pressure actuator 3920; a magnet control module 3944 to control the one or more magnets 3922; a heater control module 3946 to control the one or more heaters 3924; an electrode control module 3948 to control the one or more electrodes 3926; an optical sensor control module 3949 to control the optical sensor 3927; a sonic control module 3950 to control sonic device 3929; and a light source and sense control module 3951.

Each software module includes program instructions that, when executed by the processor 3930, may cause the device 3900 to perform the corresponding function(s). Thus, the non-transitory computer-readable storage medium of memory 3940 may include instructions for performing all or a portion of the operations described herein.

The processor 3930 may execute the pressure actuator control module 3942 to manipulate one or more microfluidic droplets disposed between at least two hydrophobic and oleophobic sheets by applying forces through the pressure actuator 3920. For example, execution of the pressure actuator control module 3942 may cause compressive, pinning, and/or actuation forces to be applied to at least one of the hydrophobic and oleophobic sheets. The forces may be selectively applied to move, separate, combine, and/or mix one or more microfluidic droplets. In some examples, execution of the pressure control module 3942 may cause a stylus to move across at least one of the hydrophobic and oleophobic sheets, apply a compression force, and cause a droplet to move.

The processor 3930 may execute the magnet control module 3944 to selectively control, enable, and/or disable one or more magnets 3922. In some examples, execution of the magnet control module 3944 may cause power to be applied to electromagnets included in the magnets 3922. In some examples, execution of the magnet control module 3944 may cause one or more magnets 3922 to be moved closer to, or away from, one or more microfluidic droplets.

The processor 3930 may execute the electrode control module 3948 to selectively provide electric fields to the one or more electrodes. For example, execution of the electrode control module 3948 may provide one or more large magnitude electric fields to the electrodes 3926 and cause electroporation to occur on cell membranes within the microfluidic droplet.

The processor 3930 may execute the optical sensor control module 3949 to control and processes data from the optical sensor 3927. For example, execution of the optical sensor control module 3949 may cause the optical sensor 3927 to receive or capture image data as well as causing the processor 3930 to process the image data and determine the presence and/or location of any droplets.

In some examples, the processor 3930 may use image data from the optical sensor 3927 to control actions of the pressure actuator 3920. For example, the processor 3930 may process the image data with the pressure actuator control module 3942 and thereby guide the application of compressive forces on one or more hydrophobic and oleophobic sheets.

The processor 3930 may execute the sonic control module 3950 to control the sonic device 3929. For example, execution of the sonic control module 3950 may activate or enable the sonic device 3929 thereby allowing or enabling the sonic device 3929 to provide sonic and/or ultrasonic stimulation or treatment to a droplet.

The processor 3930 may execute the light source and sense control module 3951 to control the light source and sensor 3928. For example, execution of the light source and sense control module 3951 may cause light to be emitted by a light source and transmitted or reflected light to be sensed by a light detector. In this manner, a reaction or process may be detected in accordance with the detected light.

Cartridges

As mentioned above, the cartridges described herein may generally include a first (e.g., upper) sheet that is elastically deformable, a second (e.g., lower) sheet, and a frame separating the two to form an air gap. The first sheet may be an elastomeric material, such as a polyester (e.g., TPE) natural rubber, synthetic rubber, nitrile rubber, silicone rubber, urethane rubbers, chloroprene rubber, Ethylene Vinyl Acetate (EVA), etc. The second sheet may be the same of a different material. The sheets of the cartridge are generally planar structures and may be a membrane, a layer, etc. The first and second sheets may be held in tension over or against the frame. In some examples, multiple frames may be used. The frame may be formed of any appropriate material, such as a rigid semi-rigid polyester.

Figure 40C:
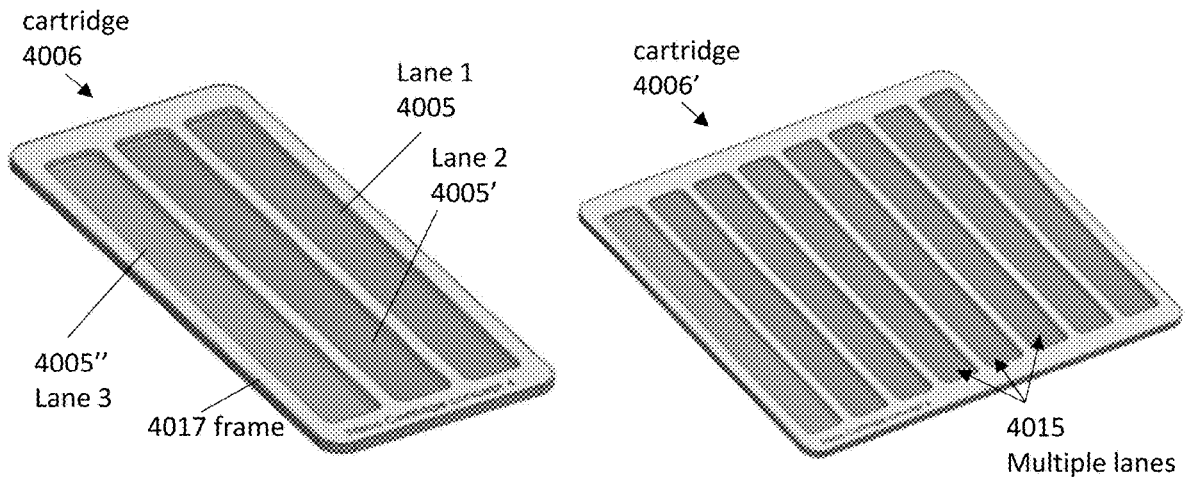
Figure 40C:
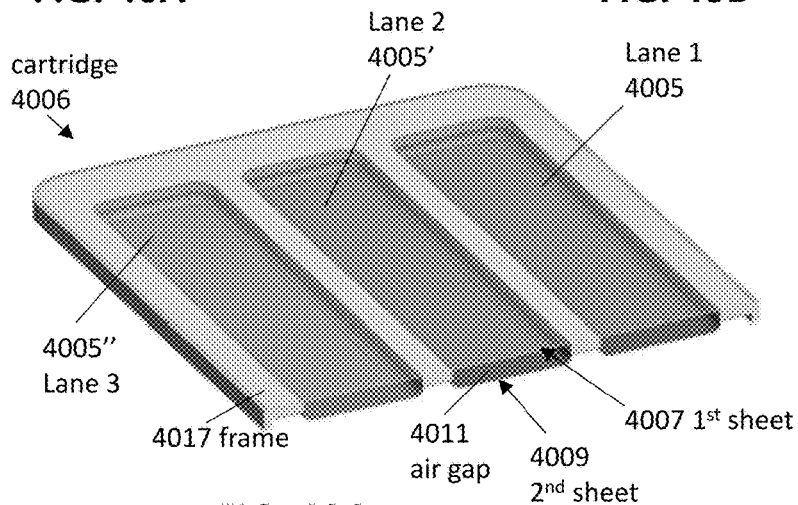
Figure 40D:
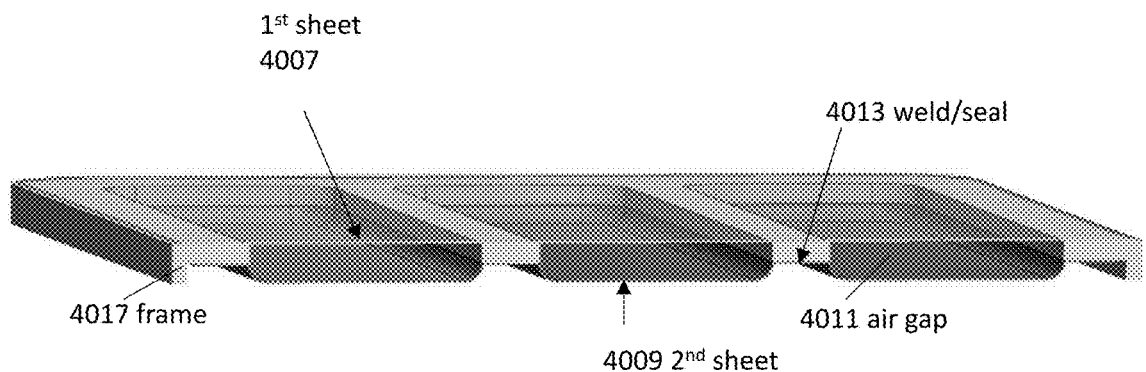

FIGS. 40A-40D illustrate examples of a cartridge 4006, 4006' as described herein. The cartridge includes a frame 4017, a first sheet 4007 and a second sheet 4009. In the example shown in FIGS. 40A, 40C and 40D, the cartridge is divided into three lanes 4005, 4005', 4005". In this example the frame is configured as a divider with the three separate lanes. The example cartridge shown in FIG. 40B has eight lanes 4015. Any appropriate number of lanes may be used (e.g., 1 lane, 2 lanes, 3 lanes, 4 lanes, 5 lanes, 6 lanes, 7 lanes, 8 lanes, 9 lanes, 10 lanes, 12 lanes, 15 lanes, 16 lanes, or more). The sectional view of a cartridge shown in FIGS. 40C-40D illustrates an example with three lanes formed by the frame/divider 4017. The first sheet 4007 is held in tension to the top of the frame, e.g., by welding and/or an adhesive 4013. The second sheet 4009 in this example is also held in tension on the frame and is welded and/or adhesively attached thereto. An air gap 4011 is formed between the first sheet and the second sheet. In FIGS. 40C and 40D, the portion of the cartridge is shown attached to a seating portion of a mechanical microfluidics actuator having a recessed region and a plurality of vacuum ports for sealing the second (bottom) sheet into the seating region to make a tight thermal connection between the second sheet and the seating region. Sealing the second sheet 4009 to the seat also expands the air gap 4011 to a larger height as compared to the unattached configuration of the cartridge, as shown in FIG. 40D.

In the example shown in FIGS. 40A-40E, the initial height of the air gap may be between about 0.5 mm and about 5 mm. In general, the height may be between 0.1 mm and about 7 mm, and may be adjusted down or, as in FIGS. 40C and 40D, up. For example, compressing the first and/or second sheet to form a 0.5 mm air gap height from a neutral height of about 3 mm has been found to be very effective for mobility of droplets. In some examples the neutral height of the air gap may be about 3 mm in height (spacing between the first and second sheets) which has been found to be effective to move droplets without significant damage to the films tested, as compared to larger gap spacing. At a height of about 3 mm, a larger droplet (e.g., 140 uL aqueous+80 uL drop gloss) can touch the top film with a small amount of compression. However, the height of the gap may be adjusted based on the volume of the droplet, and the materials forming the first and second sheets.

Figure 41:
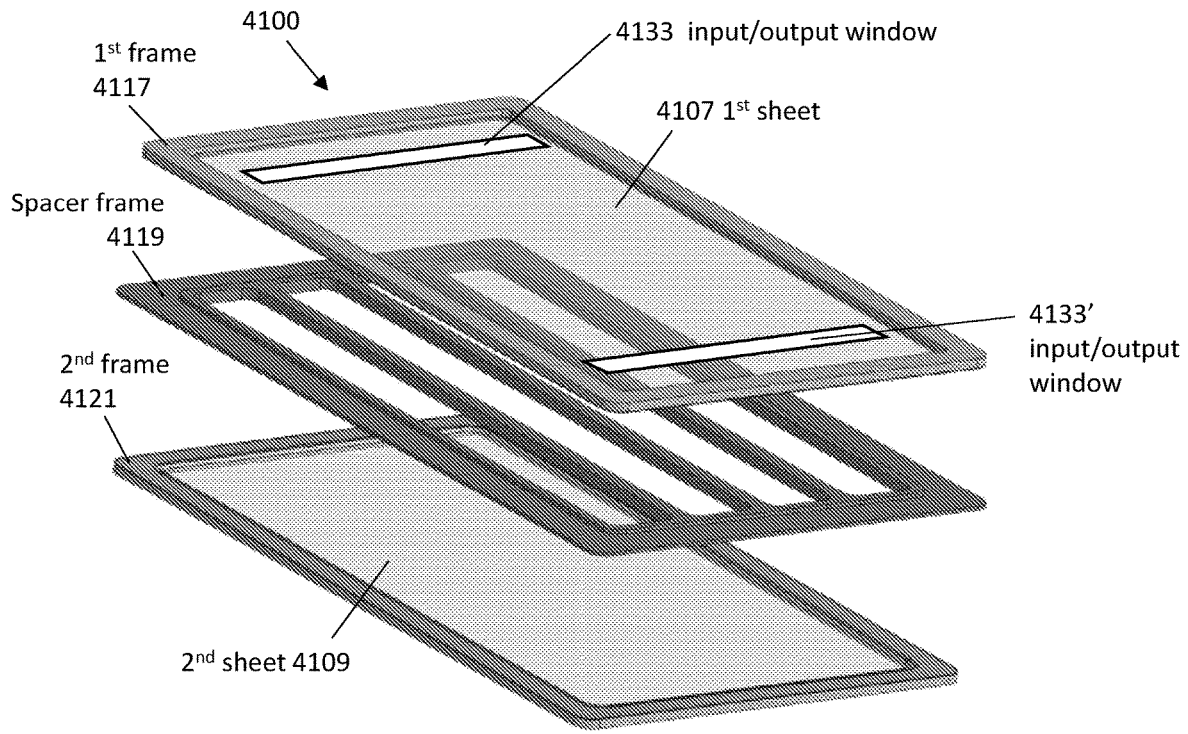
FIG. 41 is an exploded view of an example of another example of a cartridge.

FIG. 41 shows an exploded view of one examples of cartridge 4100. In this example, the cartridge includes a first (e.g., upper) frame 4117 onto which the first sheet 4107 is attached in tension, so that it is pulled flat. All four sides of the sheet may be held in tension. The sheet may be pinned, clamped, welded, adhesively attached, tacked, or otherwise secured to the frame. In this example, the first sheet 4107 also includes a pair of openings 4133, 4133', configured as input/output windows ("windows") into which a fluid material (droplet, drop gloss, etc.) can be applied by manual or automatic means (e.g., pipetting, etc.). Fluid material may be added to the air gap through the window adjacent to the sides of the window so that the mechanical microfluidics actuator may use the force applicator adjacent to the window to pull the droplet further into the air gap and manipulate the droplet (or droplets) within the cartridge. The window 4133, 4133' may be any appropriate size. In some example the entire distal and/or proximal end of the cartridge may be open as a window (e.g., the first sheet may extend just between two opposite sides of the frame (e.g., the first frame). The edges of the window may be reinforced and/or smoothed. In some examples the edges may be thickened (e.g., doubled over itself). The window may be any size, or ratio of the size of the surface of the first sheet. For example, the window may be between 50% and 100% of the width of the surface of the first sheet, and between about 0.1% to 10% of the length of the surface of the first sheet. In some examples the window is between 1 mm and 10 cm long and between 1 mm and 5 cm wide. Larger windows may be used. As mentioned above, in some examples the cartridge may also or alternatively include one or more smaller openings for applying/removing fluid (e.g., by pipetting).

The cartridge shown in FIG. 41 also includes a second frame 4121 to which a second sheet 4109 is attached. The second sheet may be under tension or, as it may be configured to be secured to the base of the mechanical microfluidics actuator, may be more loosely attached. The second sheet 4109 may be attached to the second frame 4121 in any appropriate manner. In this example, the first and second frames may be disposable and the first and second sheets may be, e.g., TPE film, FEP film, etc. The first sheet may be adhesively attached to the first frame by, e.g., an adhesive such as a double-sided adhesive film (e.g., 3M 300 L SE, 2 mil thick double adhesive).

In FIG. 41, the cartridge also includes a spacer frame 4119 that is sandwiched between the first and second frames and the first and second sheets. The first and second sheets may be attached or unattached to the spacer frame. The first frame and the second frame may be secured to the spacer frame. IN some examples the spacer frame is formed of a hydrophobic and oleophobic material, e.g., PTFE.

Alternatively, in some examples only a single frame, which may or may not include spacers, may be used, and the first sheet may be attached to the first side of the frame while the second sheet is attached to the second side of the frame. The frame of the cartridge shown in this example may be rigid; in some examples the frame may be flexible and/or hinged.

Figure 42A:
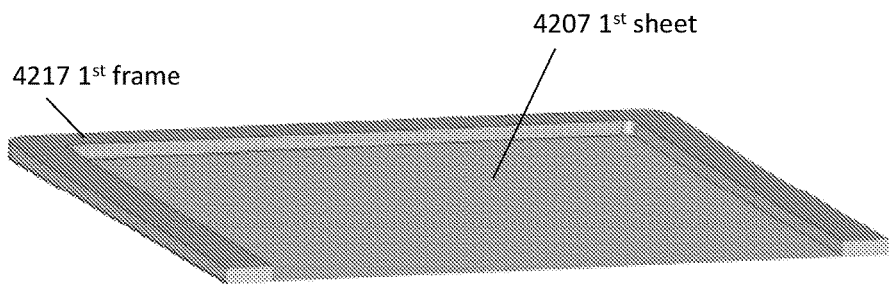
FIGS. 42A and 42B show partial sectional views of a portion of cartridge.
Figure 42B:
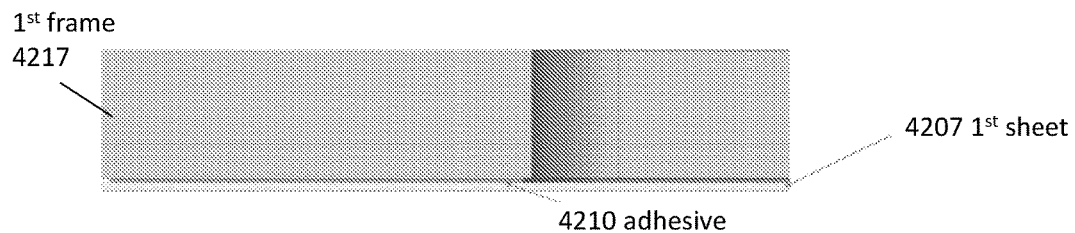

FIGS. 42A-42B illustrate another example of a portion of a cartridge. In this example, the cartridge is shown having a first frame 4217 to which the first sheet 4207 is attached. The first sheet may be attached to the top or bottom of the first frame. In FIGS. 41 and 42A the sheet is shown attached to the bottom of the first frame. Frames may be formed in any appropriate matter, including laser cutting, injection molding, etc., and may be any appropriate material (e.g., polymeric material, such as polyester, ABS or POM (glass filled)). FIG. 42B shows an enlarged side sectional view of the first frame 4217 and first sheet 4207. In this example, the first sheet is a TPE film and is adhesively held to the first frame under tension using an adhesive 4210 (e.g., 3 m 300LSE, 2 mil thick, double-sided adhesive). In FIGS. 40 and 41A-41B, the first and second sheets are between about 20-60 µm thick (e.g., between 25-50 µm thick, etc.) and may be formed of an elastomeric material.

Any of these cassettes may include a frame (backbone) that is hydrophobic, e.g., polypropylene, and may include one or more internal structures including, but not limited to spacer frames. For example, the apparatus may include posts (pinning posts), and/or an absorber (absorber material). The absorber may be used to remove waste (e.g., from rinsing/washing, drop gloss, etc.). In some cases an edge of the frame may include an absorber. The frames may include markings, including computer readable markings (e.g., QR codes, bar codes, etc.) that may uniquely identify the cassette. The cassettes may be oriented, e.g., to allow positioning in the mechanical microfluidics actuator seat in a preferred or exclusive orientation, or they may be non-oriented (allowing application in any orientation). In some cases the cartridge may include a specific "top" and "bottom" and may be marked or coded (including color coded) and or keyed to fit into the mechanical microfluidics actuator seat with the upper surface "up".

Figure 43A:
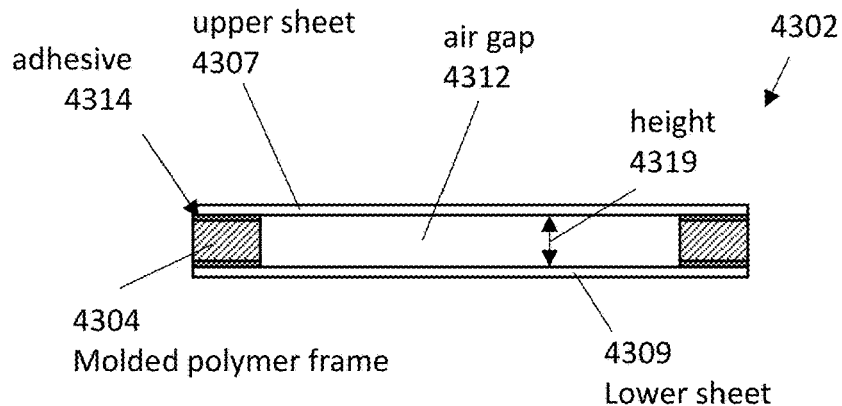
FIG. 43A shows a section view through another example of a cartridge.
Figure 43B:
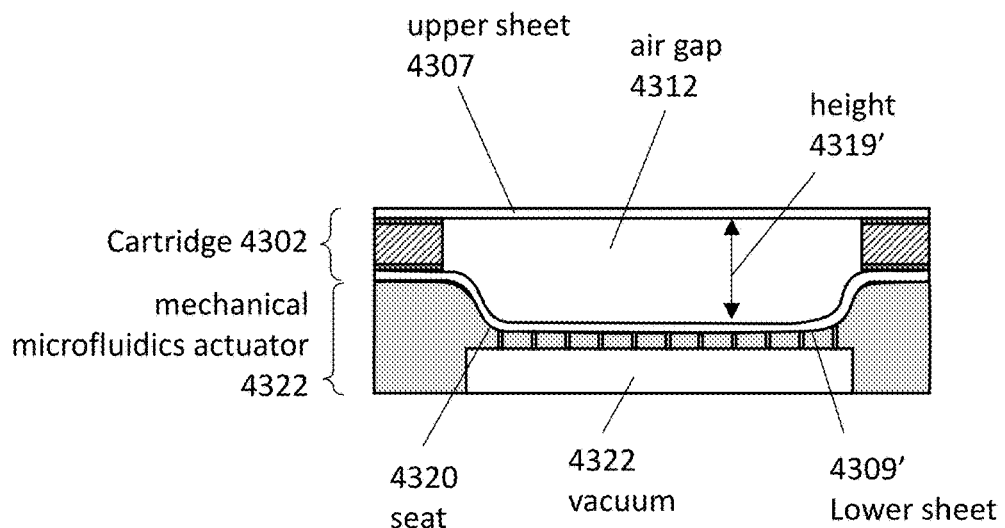
FIGS. 43B and 43C illustrate the cartridge of FIG. 43A seated in a mechanical microfluidics actuator.
Figure 43C:
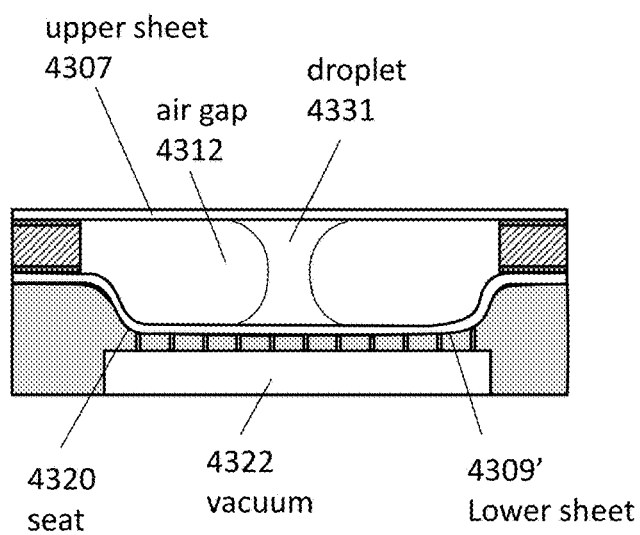
Figure 43D:
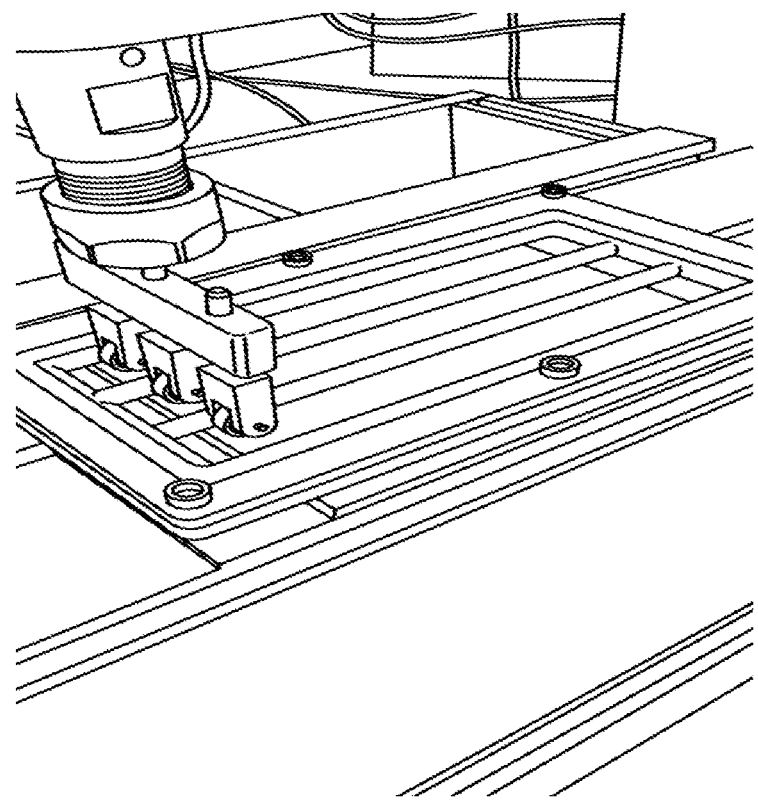
FIG. 43D shows an example of a cartridge seated in an actuator assembly with three parallel lane being concurrently actuated by a roller stylus.
Figure 43E:
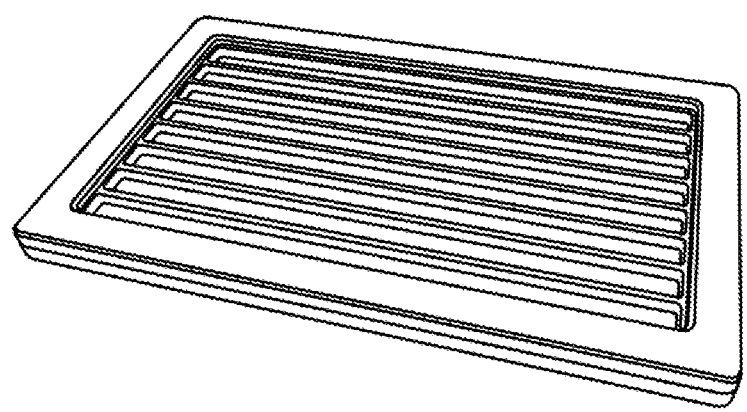
FIG. 43E shows an example of an eight-lane cartridge as described herein.

FIGS. 43A-43C illustrate the insertion of an example of a cartridge 4302 (see FIG. 43A) into a mechanical microfluidics actuator seat (as shown in FIGS. 43B-43C). In this example the cartridge includes an elastically deformable upper sheet 4307 and an elastically deformable lower sheet 4309, 4309' that are both attached to a frame 4304 (e.g., molded polymer frame) to form an air gap 4312 having an initial air gap height 4319. The upper sheet and lower sheet in this example are attached to the same frame 4304 and are shown to be adhesively attached 4314.

In FIG. 43B the cartridge is shown seated on the seat of the mechanical microfluidics actuator 4322. The mechanical microfluidics actuator in this example includes a recessed seating region 4320 that include multiple vacuum ports coupled to a vacuum manifold 4322 coupled to a source of negative pressure and controlled by the controller of the mechanical microfluidics actuator. In FIG. 43B the suction is shown applied, pulling the lower sheet 4309 of the cartridge into continuous contact with the seating region, and increasing the height of the air gap 4312 to a larger height 4319' (as compared to the neutral height 4319).

FIG. 43C illustrates the cartridge within the mechanical microfluidics actuator shown in FIG. 43B with a droplet 4331 shown in the air gap 4312. In this example, the upper and lower sheets 4307, 4309 may be, e.g., an elastomeric polyester and the cartridge frame 4304 may be a molded polyester.

Figure 44A:
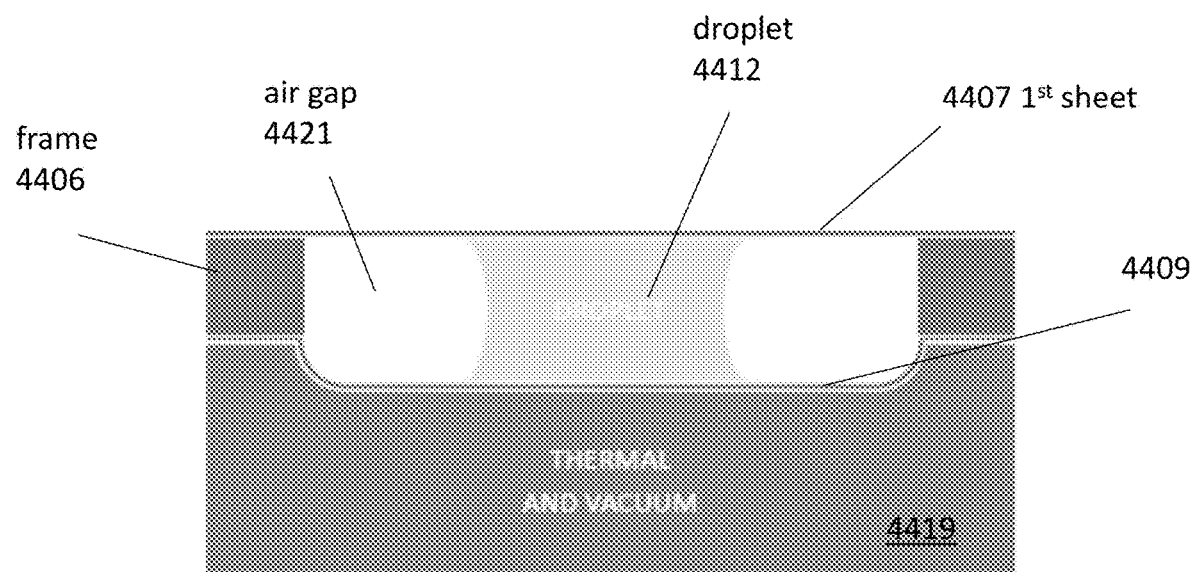
FIGS. 44A-44E illustrate examples of different seating regions of a mechanical microfluidics actuator coupled with a cartridge as described herein.
Figure 44B:
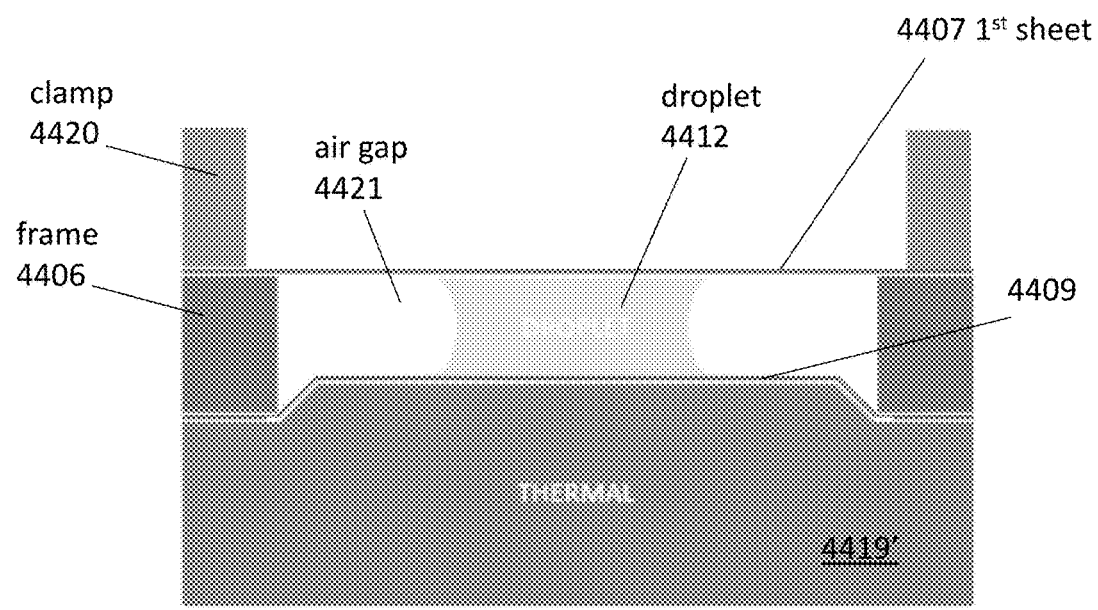

FIGS. 44A-44B schematically show two alternative examples of cartridges seated and secured to mechanical microfluidics actuator seating regions. In FIG. 44A the cartridge includes a frame 4406 to which a first sheet 4407 and a second sheet 4409 are attached, separated from each other to form an air gap 4421. In FIG. 44A, similar to FIGS. 43B-43C, the mechanical microfluidics actuator seating region 4419 includes vacuum ports securing the lower (second) sheet 4409 against the surface of the seating region so that there is no gap between the seating region and the second sheet, which is held immobilized against the seating region, as shown. In FIG. 44A the droplet 4412 may be heated/cooled or otherwise manipulated through the bottom (second) sheet by applying thermal energy through the particular sub-region of the seating region of the mechanical microfluidics actuator. In this example the entire seating region is shown as recessed; in other examples only a portion of the seating region is recessed, forming a well (described below) into which the droplet may be held.

FIG. 44B shows another example of a cartridge held in a seating region of a mechanical microfluidics actuator. In this example the cartridge includes a frame 4406 and an upper sheet 4407 and a lower sheet 4409; this cartridge is secured to the seating region by a securement such as a clamp 4420 applying a securing force against the frame to hold the cartridge immobile in place. In this example the mechanical microfluidics actuator does not need to include a vacuum (e.g., vacuum ports) to secure contact between the second sheet 4409 and the outer seating surface of the mechanical microfluidics actuator; in FIG. 44B the outer seating surface may be raised along the length of the air gap 4421. Thus, any of the mechanical microfluidics actuators described herein may not include a vacuum. Any of the mechanical microfluidics actuator described herein may include a securement (e.g., clamp, lock, etc.) holding the cartridge against the mechanical microfluidics actuator seating region.

As described in greater detail below, any of these mechanical microfluidics actuators may include a controller, and one or more thermal regions that may locally heat/cool the seating region and therefore a droplet within the air gap of the cartridge over this portion of the seating region.

Figure 44C:
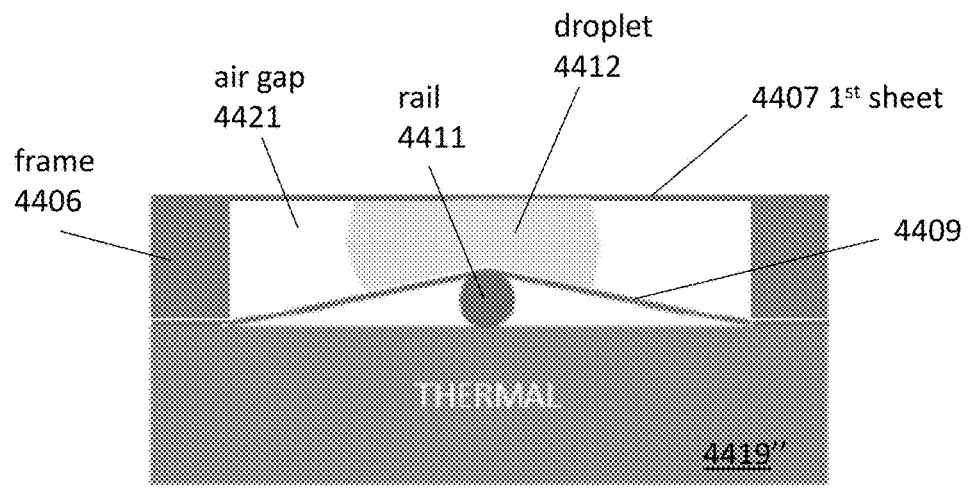
Figure 44D:
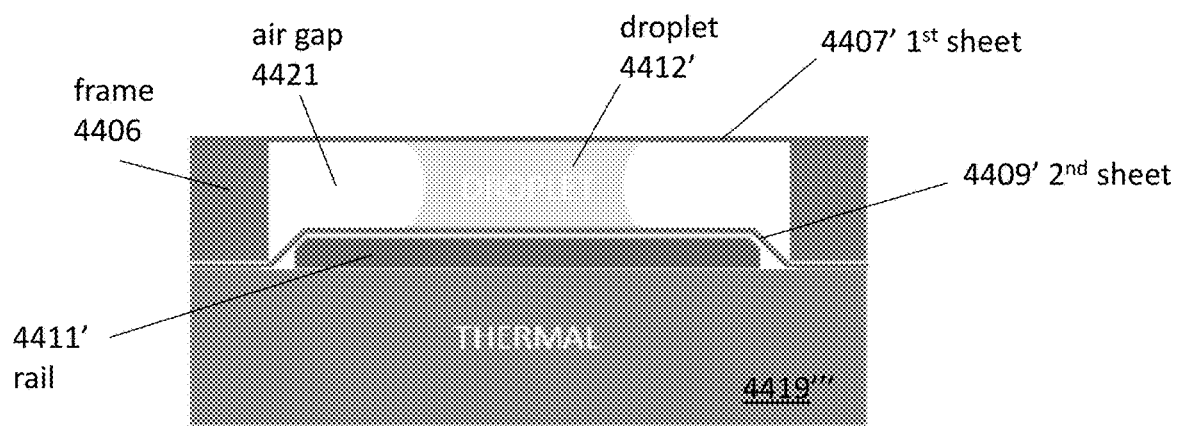
Figure 44E:
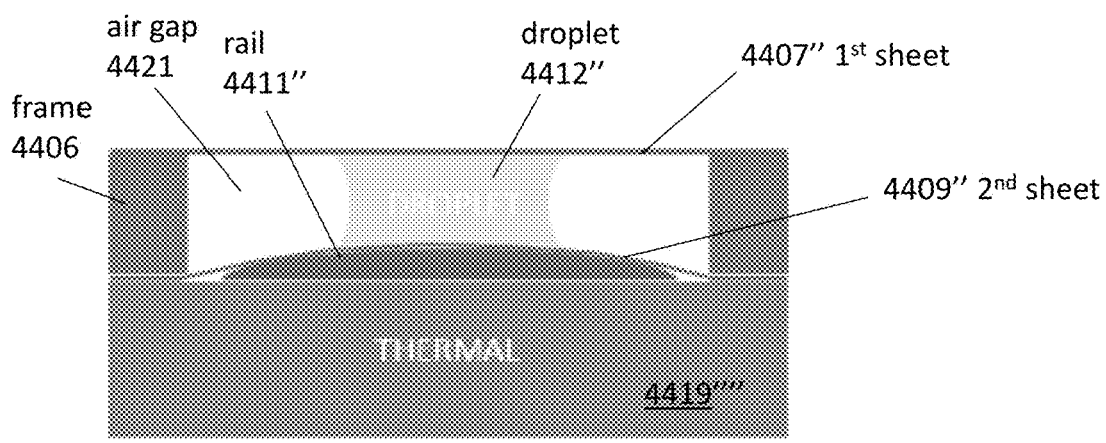

In general, any of the seating regions of the mechanical microfluidics actuators may include a shape to which the lower sheet of the cartridge may conform, which may have numerous benefits, such as securing the droplet (e.g., pinning the droplet) to a particular region and/or enhancing the thermal energy transfer. FIGS. 44C-44E schematically illustrate examples in which the mechanical microfluidics actuator seating region include a projection. In FIG. 44C the cartridge is shown seated on a mechanical microfluidics actuator 4419" seating region including a rail 4411 (e.g., rail region). The cartridge may be held down by a securement (not shown, such as a clamp, magnet, etc.). The droplet 4412 between the first sheet 4407 and the second sheet 4409 is therefore held (e.g., by capillary force) within the center of the air gap 4421 region, and may be moved within the channel (e.g., in/out of the plane of the section shown) by a force applicator applying force to reduce the height of the air gap. FIG. 44D shows an example in which the mechanical microfluidics actuator 4419'" includes a step-up raid 4411' that deforms the lower sheet 4409' slightly into the air gap 4421 but has a wider base than the rail of FIG. 44C. In FIG. 44E the mechanical microfluidics actuator 4419"" is similar to that shown in FIG. 44D but includes a dome-shaped rail 4411". Any of these examples may, but does not need to, including a vacuum manifold with vacuum ports to secure the second sheet 4409, 4409', 4409" to the outer surface of the seating region. Alternatively or additionally these apparatuses may include a securement (such as a clamp, lock, magnetic securement, etc.) to hold the cartridge in position.

In general, the methods and apparatuses described herein may include the use of a rail region within the air gap. The rail region may generally have a gap width that is less than the gap width of a region of the air gap surrounding the rail region, e.g., around the periphery of the air gap, on either side of the rail region. The rail region may form an elevated bed. As mentioned above, the rail region may be formed by deflecting the second (e.g., lower) sheet of the air gap; in some examples the second sheet is more rigid than the first sheet (e.g., is formed of a relatively stiff material) and the rail region may be formed of the more rigid second sheet. Surprisingly, the droplet may avoid the regions in the periphery (adjacent to the rail region) having a greater gap width, which may prevent loss of the droplet volume, particularly with smaller volume droplets (e.g., less than 15 µL, 10 µL or less, 5 µL or less, 1 µL or less, 1 µL or less, etc.).

Mechanical Microfluidics Actuator

Figure 45A:
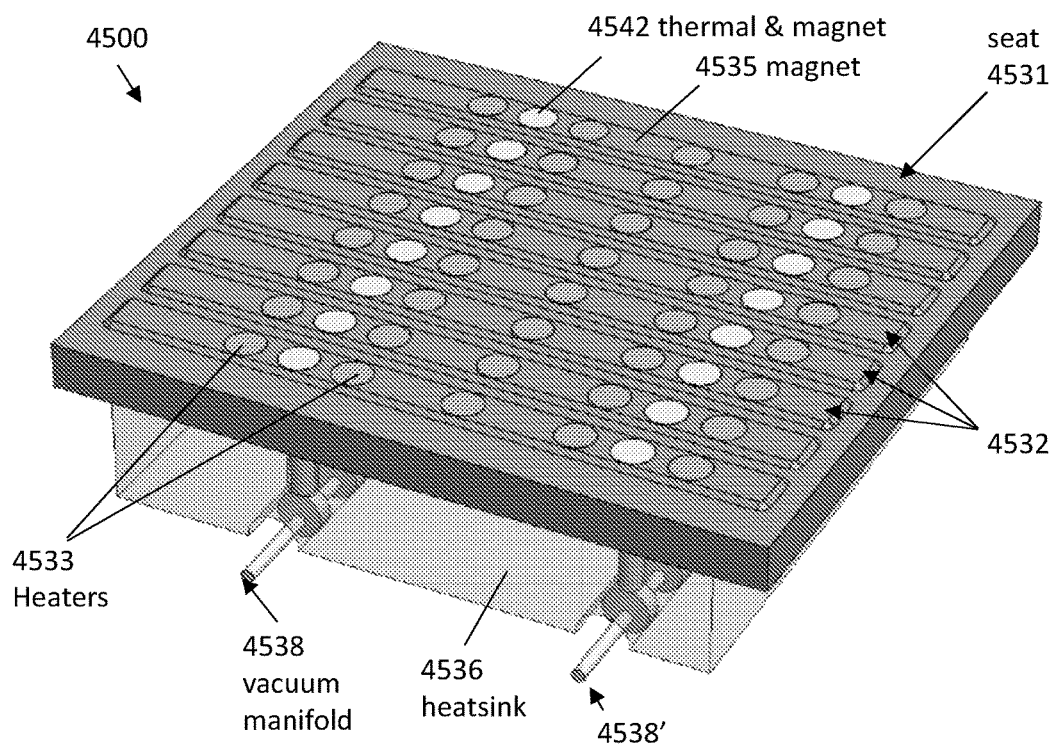
FIGS. 45A-45C illustrate an example of a seating region of a mechanical microfluidics actuator.
Figure 45B:
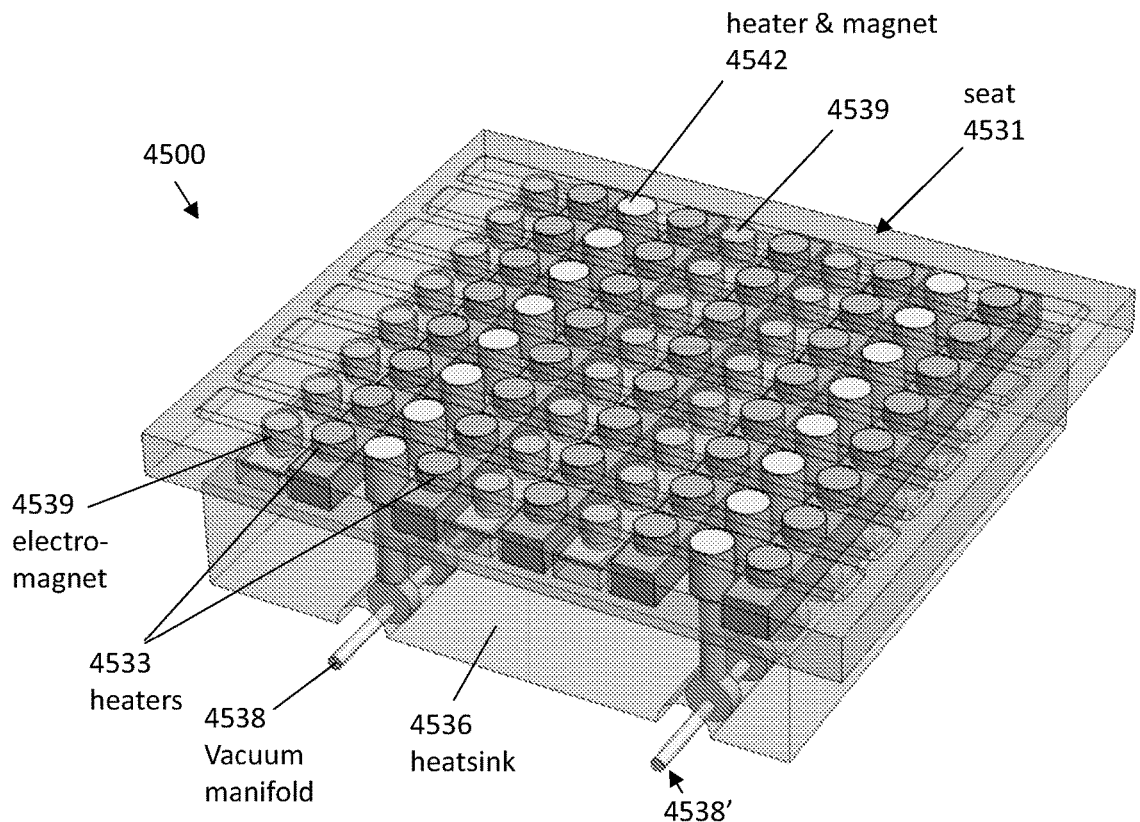
Figure 45C:
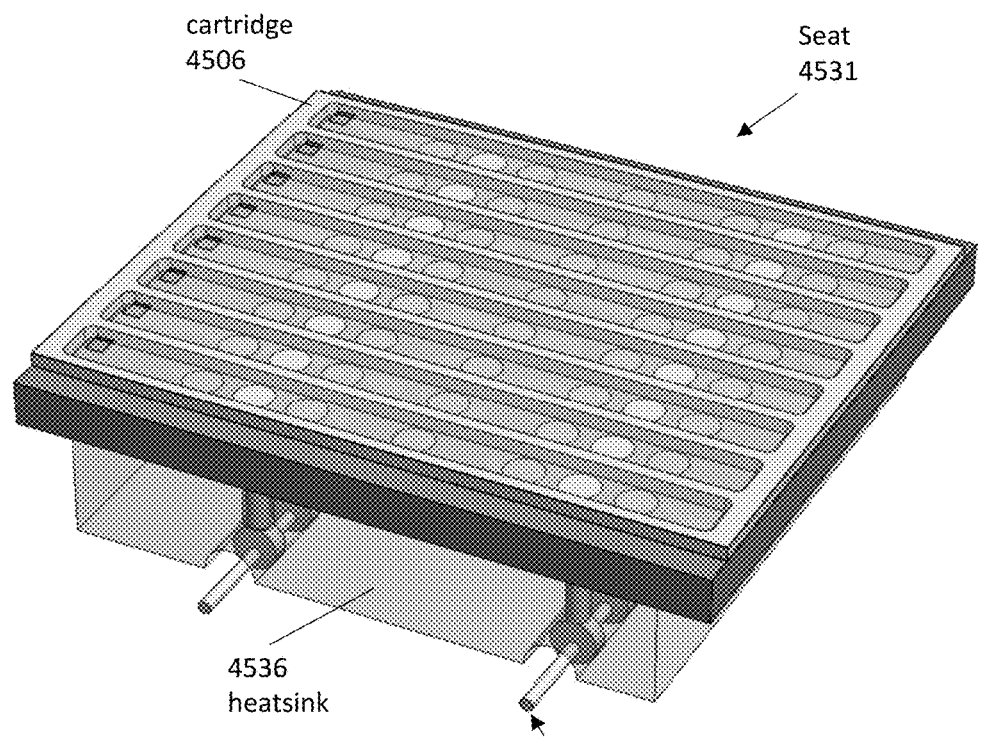

As mentioned, any of these apparatuses may include a mechanical microfluidics actuator. FIGS. 45A-45E illustrate one example of a portion of a mechanical microfluidics actuator. In FIG. 45A the mechanical microfluidics actuator 4500 includes a seating region (seat) 4531 onto which a cartridge may be secured. In the example shown, the seating region includes a plurality of parallel lanes 4532 (eight are shown) running the length of the seating region. The seat in this example includes a plurality of vacuum ports coupled to a vacuum manifold 4538 to apply a suction to conformably secure the lower (second) sheet of a cartridge to the seating region. In addition, each of the lanes of the seating region includes a plurality of different zones for thermal control 4533, magnetic field application 4435, or both magnetic field and thermal control 4542. The thermal control regions may be in thermal communication with a heater/cooler (e.g., Peltier device), and the magnetic control regions may each include a local electromagnet. This is illustrated in FIG. 45B, in which the seating region 4531 has been made transparent to show the thermal control zones 4533, electromagnet zones 4539 and combined thermal control/magnetic zones 4542. In this example the base of the mechanical microfluidics actuator may be a heat sink 4536 to allow local application of heating/cooling. FIG. 45C shows an examples of a seating region of a mechanical microfluidics actuator with a cartridge 4506 attached to the seating region 4531.

Figure 45D:
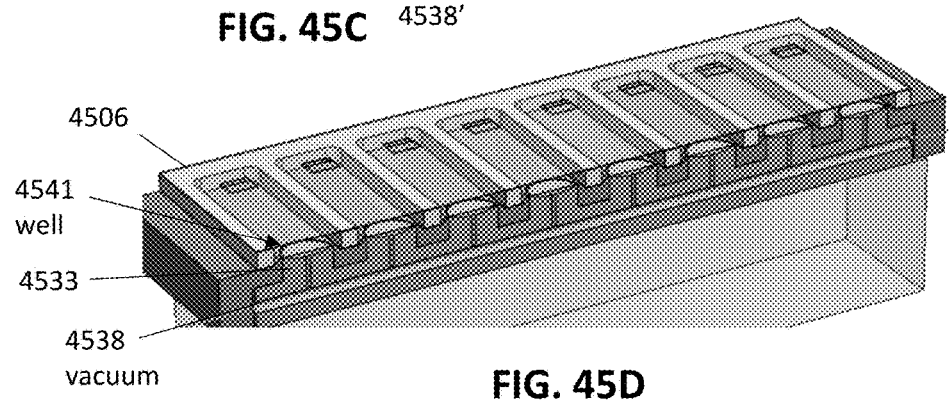
FIGS. 45D and 45E illustrate enlarged sections through the seating region example of FIGS. 45A-45C.
Figure 45E:
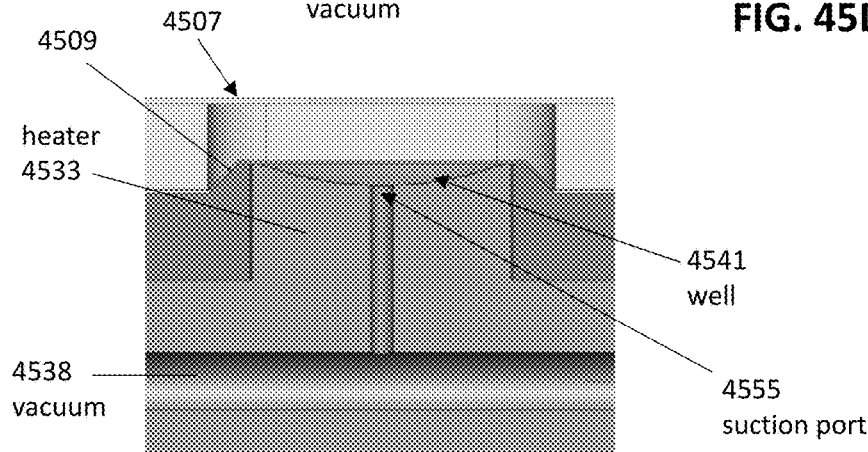

Although this example includes three kinds of zones arranged in an alternating pattern along the length of each lane of the seating region (which may correspond to lanes in the cartridge 4506, as shown in FIG. 45C, other patterns of zones and/or other types of zones (e.g., heating/cooling, magnetic, electrical energy, sensing/imaging, UV applying, sonication application, etc.) may be included. FIGS. 45D and 45E show examples of the seating region topology in slightly greater detail. For example, in FIGS. 45D and 45E the seating regions may include a plurality of wells 4541 formed therein which may underlie a thermal control region. For example, in FIG. 54D the mechanical microfluidics actuator seating region including a plurality of thermal control regions configured as wells 4541 having a shallow, bowl-shaped depression which is formed of a thermally conductive material 4533. The bowl also includes a suction port 4555 in communication with a suction manifold 4538 to hold down the second sheet 4509. The method of driving the droplet (e.g., with the force applicator) into the well may pin droplet in the well and may greatly reduce or limit evaporation, particularly when heating the droplet (e.g., for thermocycling the droplet).

Figure 46:
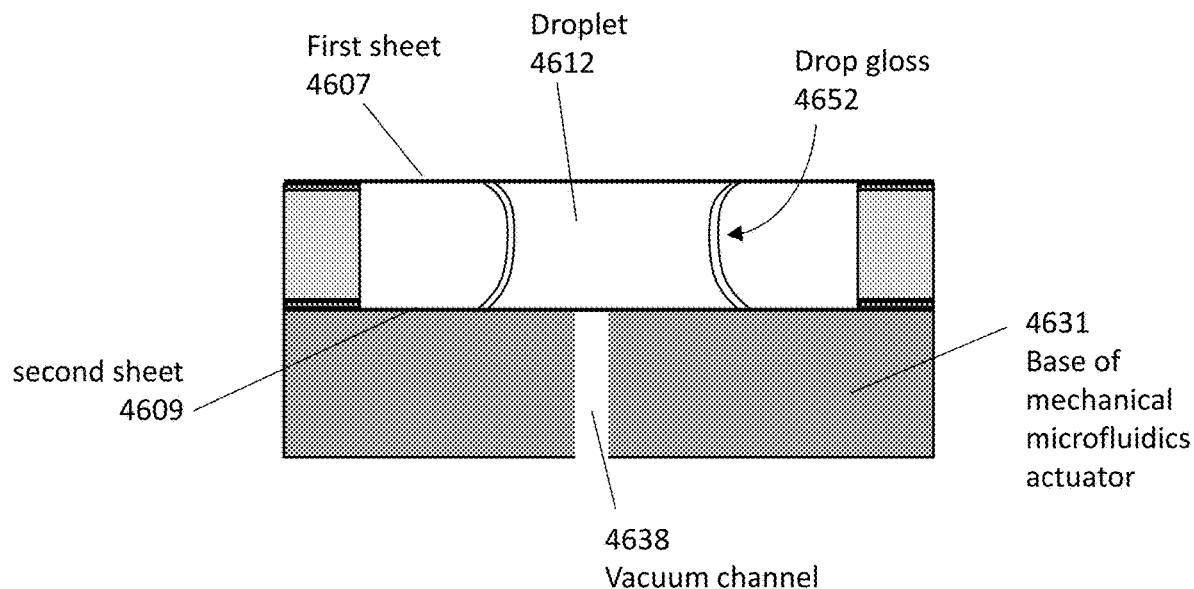
FIG. 46 schematically illustrates one example of a seating portion of a cartridge coupled to a seating region.

FIG. 46 schematically illustrates an example of a portion of an apparatus (such as the cartridge and mechanical microfluidics actuator) similar to that shown in FIG. 45A-45E, including a vacuum port 4638 securing the second sheet 4609 of the cartridge to the seating region of the mechanical microfluidics actuator 4631. In FIG. 46 a droplet 4612 is shown in the air gap region and is coated with a drop gloss 4652 material. The drop gloss coating may be formed of a material that limits evaporation and is immiscible with the droplet.

Figure 47:
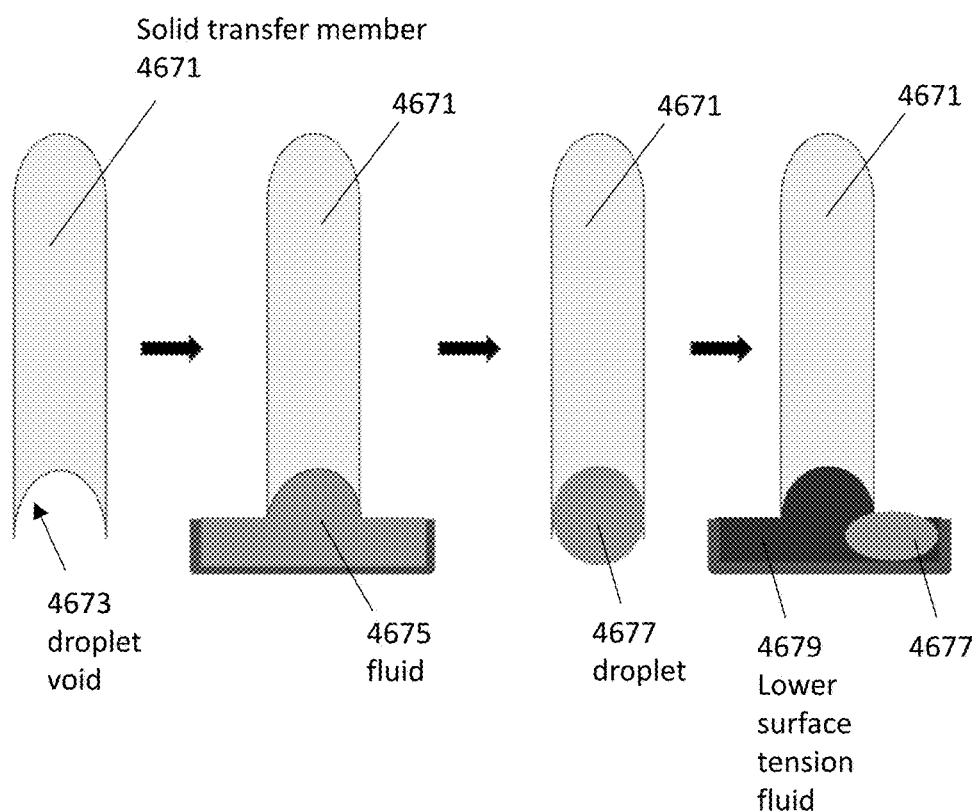
FIG. 47 illustrates a method of transferring a small volume of fluid using a solid (e.g., non-vacuum/non-pipette) technique.

In general, any appropriately sized droplet may be used, including microliter and sub-microliter droplets. However, in some cases it may be difficult for smaller (e.g., less than 2 μL) to be transferred reliably. It may also be beneficial to use fluid transfer of droplets of any size without requiring negative pressure (e.g., suction), e.g., without pipetting. FIG. 47 illustrates one example of a method for reliably transferring a very small droplet, including (but not limited to) transferring into a cartridge as described herein. In this example a solid transfer member 4671 having a concave end region 4673 ("droplet void") may be included at the distal end of the device. This concave region/void may be configured to hold a specific droplet volume, e.g., less than a few microliters in volume (e.g., 0.1 μL, 0.2 μL, 0.3 μL, 0.4 μL, 0.5 μL, 0.6 μL, 0.7 μL, 0.8 μL, 0.9 μL, 1 μL, 1.1 μL, 1.2 μL, 1.3 μL, 1.4 μL, 1.5 μL, 1.6 μL, 1.7 μL, 1.8 μL, 1.9 μL, 2 μL, etc.). Larger volumes may be used as well (e.g., between 1-50 μL, between 0.1-50 μL, etc.). The droplet void region 4673 may be inserted into a solution of the fluid to be transferred 4675 and removed, leaving a droplet of the expected size and volume 4677 captured within the end of the solid transfer member 4671, as shown. This droplet may be released, e.g., within the air gap, by immersing into a solution (e.g., another droplet) having a lower surface tension 4679 (e.g., drop gloss) causing displacement and release of the droplet 4677, as shown.

In general, these apparatuses may handle smaller volume droplets by increasing the volume/amount of the immiscible fluid (drop gloss), so that the final volume is sufficiently large for displacement within the air gap using the mechanical actuator as described herein.

Figure 48:
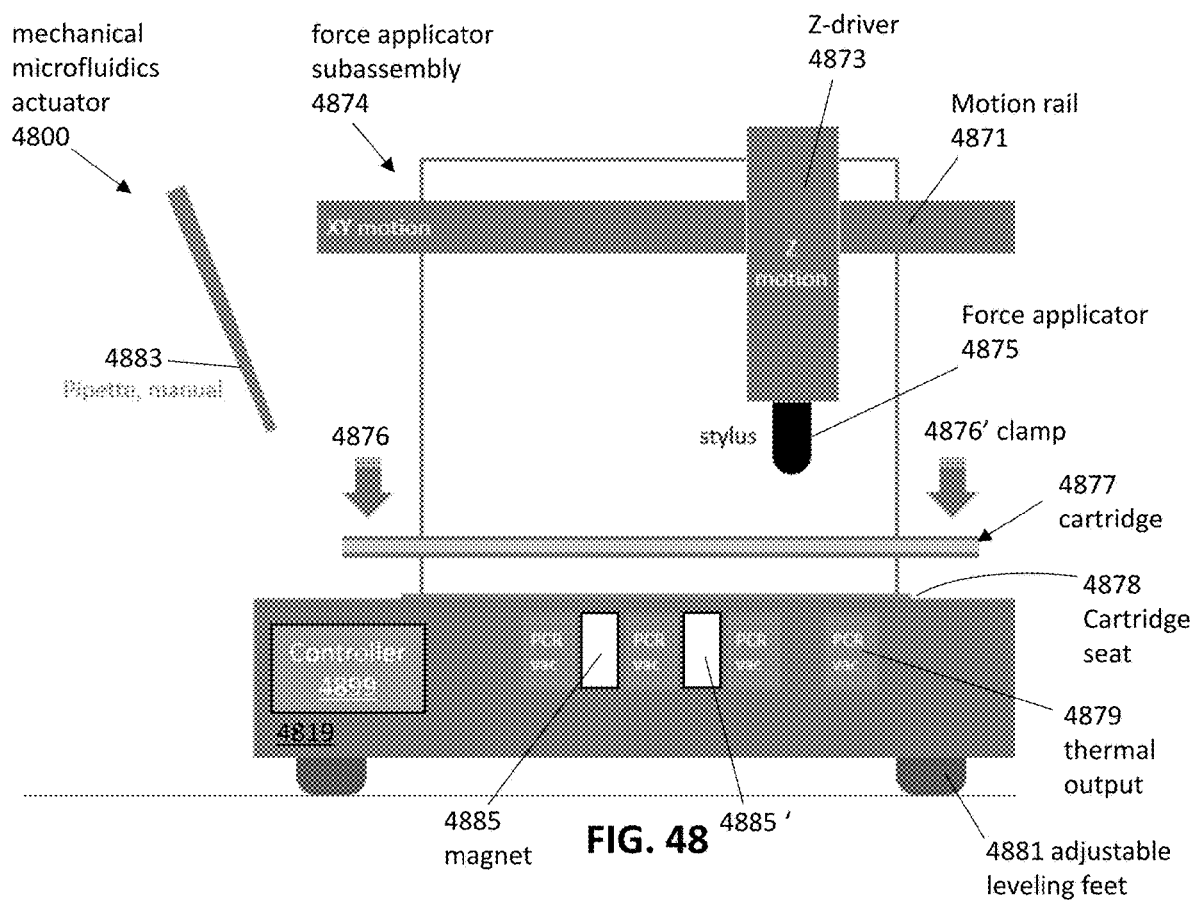
FIG. 48 schematically illustrates an example of a mechanical microfluidics actuator as described herein.

FIG. 48 shows another schematic illustration of a mechanical microfluidics actuator 4800. In this example the mechanical microfluidics actuator includes a force applicator 4878 (e.g., stylus, bearing, roller, etc.), and a force applicator driver subassembly 4874 (e.g., a force applicator subassembly). The force applicator sub-assembly may include one or more drivers (e.g., an x and/or y motion driver, a z-motion driver 4873, etc.), and/or a frame or gantry onto which the force applicator may be driven to change position and/or to apply force to the cartridge 4877 when one is seated in the cartridge seat 4878 of the device. The force applicator sub-assembly may include one or more stepper motors, motion rails (e.g., gantry/frame), and/or home switches.

Figure 49:
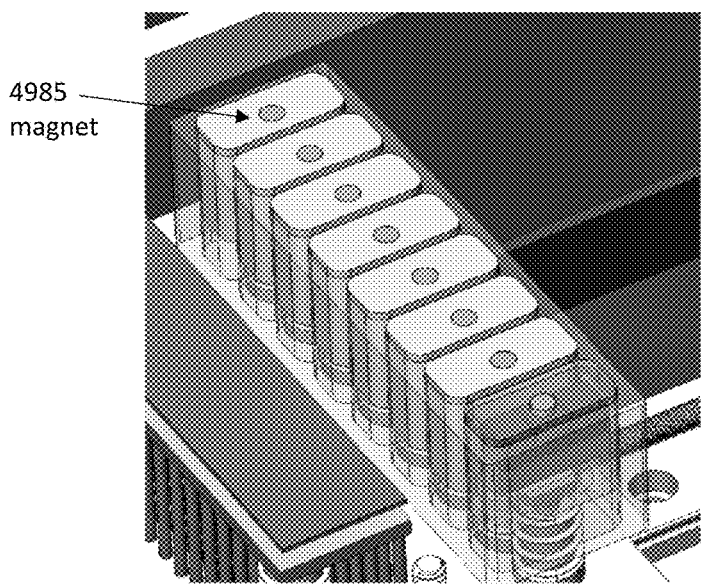
FIG. 49 illustrates an example of an internal region (showing a row of magnetic elements) of a mechanical microfluidics actuator.

The mechanical microfluidics actuator of FIG. 48 also includes a thermal sub-assembly 4879 for controlling the temperature of one or more regions of the air gap. In this example the thermal subassembly may include thermally conductive zones or regions of the seating region that may be in thermal communication with a heating and/or cooling element (e.g., Peltier device) multiple heating/cooling elements may be included. Any of these mechanical microfluidics actuator apparatuses 4800 may also include a magnetic control sub-assembly 4885, 4885' for controllably applying a magnetic field within the air gap. FIG. 49 illustrates an example of a row of magnetic elements (electromagnets) 4985 within the base 4819 of a mechanical microfluidics actuator.

In some examples, the mechanical microfluidics actuator apparatus may include a cartridge securement 4876, 4876' (e.g., a holder, clamp, lock, etc.) for securing a cartridge to a cartridge seat or seating region 4878 of the mechanical microfluidics actuator. In FIG. 48, the apparatus includes a vacuum/suction sub-assembly (not shown) for applying suction to secure the cartridge into the seating region. In some examples the mechanical microfluidics actuator apparatus may include a fluid handling (e.g., pipetting) sub-assembly 4883 for adding and/or removing fluid from the air gap. Other sub-assemblies forming a part of the mechanical microfluidics actuator apparatus may include imaging sub-assemblies (e.g., for imaging droplets within the air gap) and/or for sensing sub-assemblies (e.g., for sensing droplets or other inputs from the air gap and mechanical microfluidics actuator). The mechanical microfluidics actuator apparatuses described herein may also include one or more control inputs (e.g., keyboards, touchscreens, buttons, switches, etc.) and/or one or more outputs (e.g., displays, LEDs, wireless communications outputs/inputs, etc.) and hardware, software and/or firmware for controlling these. In some cases the same features may be used for control inputs and outputs. In general, the mechanical microfluidics actuators described herein may include one or more controllers 4899 for controlling and coordinating operation of the various sub-assemblies.

Any of these apparatuses may include leveling. For example in FIG. 48 the apparatus includes adjustable leveling feet 4881.

Figure 50:
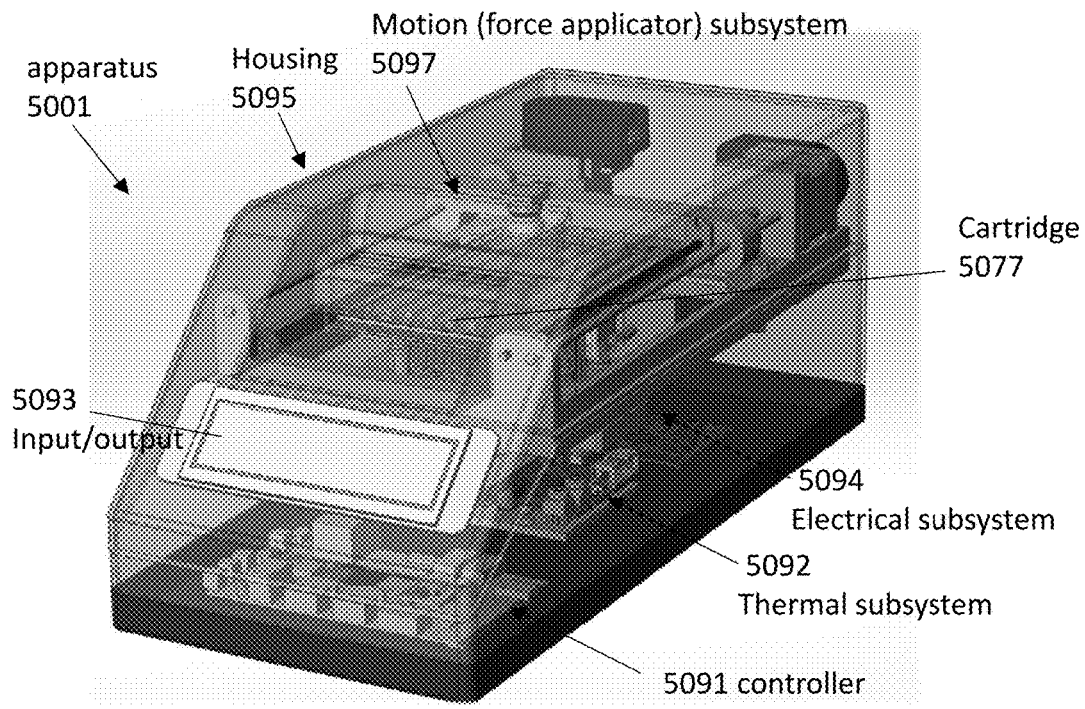
FIG. 50 shows one example of a mechanical microfluidics actuator.
Figure 51:
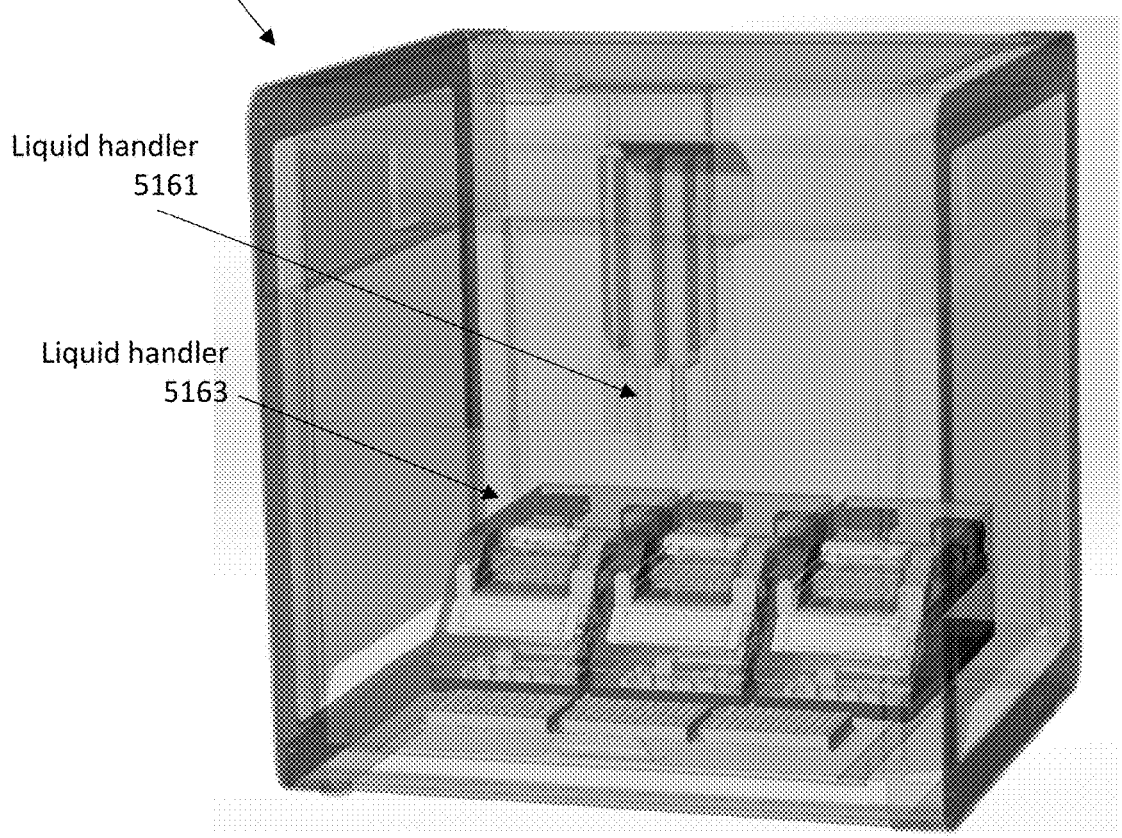
FIG. 51 illustrates an example of a multiplexed apparatus including multiple mechanical microfluidics actuators.

In general, the mechanical microfluidics actuators described herein may be single cartridge use (e.g., for use with a single cartridge at a time) or may be configured to multiple-cartridge use. FIG. 50 illustrate an examples of a mechanical microfluidics actuator apparatus 5001 that is at least partially enclosed within a housing 5095 and is configured for use with a single cartridge 5077. The apparatus includes a force applicator sub-system 5097 (e.g., 3 axis motor, encoders, home and limit sensors, solenoids, raise, shafts, couplings, bearings gears, belt, etc.) and an electrical subsystem 5094 for controlling the power requirements of the apparatus, e.g., controller, power distribution, user-interface boards, touchscreen, etc. (and in some examples, for applying power to one or more electrodes, e.g., for electroporation and/or electrochemical procedures on the cartridge). The apparatus also includes a thermal sub-system 5092 (e.g., Peltier, high-power TEC driver, heat spreader, heat sink, etc.), a controller 5091 and an input/output 5093 (e.g., display/touch screen). FIG. 51 illustrates an example of an apparatus that is multiplexed 5101 to allow parallel handling of multiple cartridges. Either the single-cartridge or a multi-configuration may also include or be configured for use with a fluid handling system (e.g., liquid handler 5163) as shown in FIG. 51.

Figure 52A:
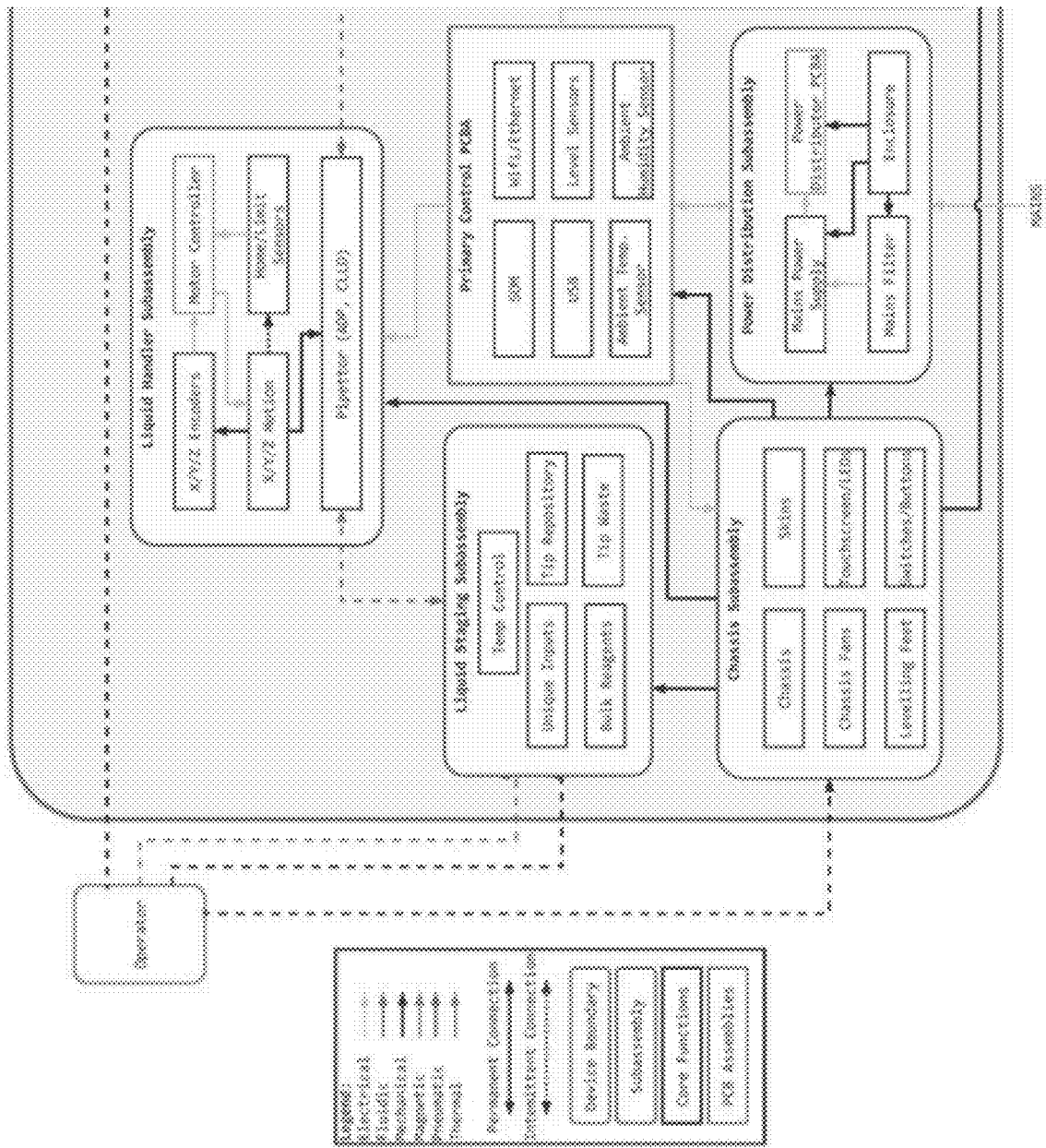
FIGS. 52A-52B show a schematic illustration of one example of an assembly forming a mechanical microfluidics actuator.
Figure 52B:
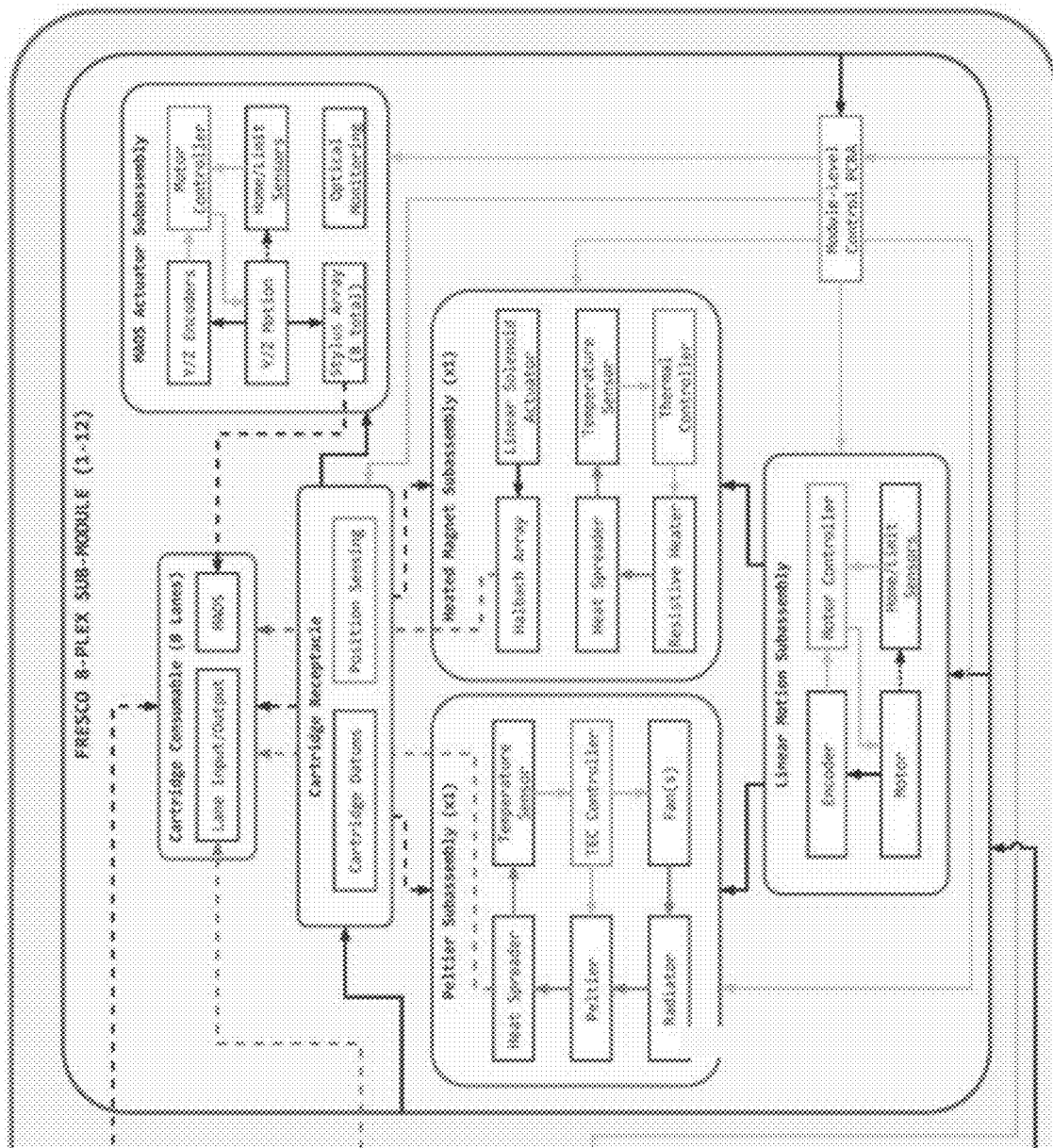

FIGS. 52A-52B schematically illustrates one example of a mechanical microfluidics actuator as described herein, showing one possible arrangement of the subassemblies described here. For example, in FIG. 52A the apparatus includes a liquid staging sub-assembly (e.g., temperature control, inputs, tip repository, tip waste, etc.) for adding/removing liquid from the cartridge, as well as a chassis sub-assembly (e.g., chassis, fans, leveling feet, switches/buttons, touchscreen, etc.) and a power distribution sub-assembly (mains power supply, power distribution circuitry, etc.). The controller (primary control PCBA) may also include sensors (e.g., ambient temperature sensor, ambient humidity sensors, level sensors) and Wi-Fi or other inputs/outputs. The controller may receive input from the chassis subassembly and may output/control all of these sub-assemblies. In particular, the controller may control the liquid handler sub-assembly, which includes motion controllers (drivers, position sensors, etc.), and may control the sub-module with the temperature sub-assembly (Peltier sub-assembly), magnetic sub-assembly, linear motion sub-assembly and cartridge receptacle (e.g., cartridge datum) each of which may provide input to the controller.

Examples

FIGS. 5A-53C illustrate one example of a method of moving an aqueous droplet as described herein. In this example one or more microfluidic droplets is manipulated so that it may be moved virtually anywhere in the air gap 5321 formed between the first elastic sheet 5307 and a second sheet 5309. The second sheet may also be an elastic sheet as described above. Both the first 5391 and second 5392 surfaces of the first and second sheets (which may be referred to as the inner surfaces facing the air gap) may be hydrophobic and oleophobic. The sheets may be formed of a hydrophobic and oleophobic material, or they may be coated with a hydrophobic and oleophobic material.

Figure 53A:
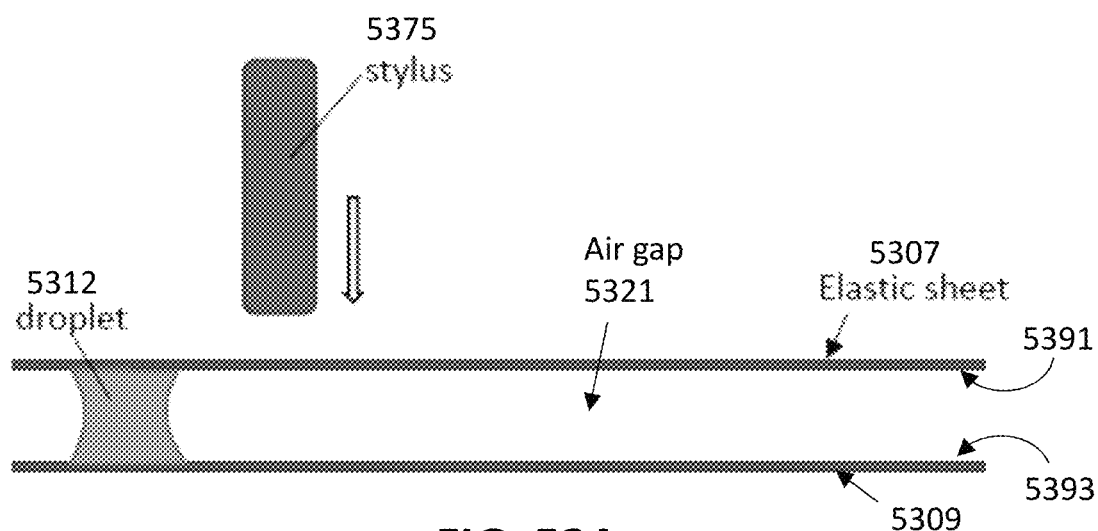
FIGS. 53A-53C illustrate a method of operating an apparatus as described herein.
Figure 53B:
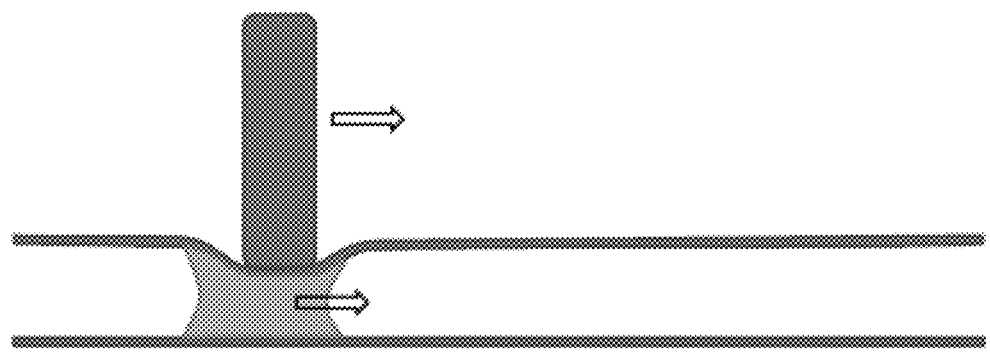
Figure 53C:
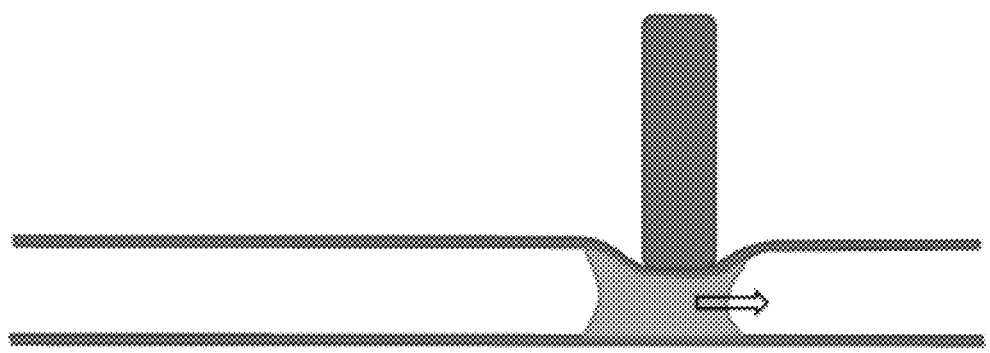

An aqueous fluidic droplet 5312 may be introduced into the air gap formed between the first sheet 5307 having a first surface that is hydrophobic and oleophobic and the second sheet 5309 having a second surface that is hydrophobic and oleophobic. As described above, the first sheet and the second sheet may be secured opposite and approximately parallel at a predetermined distance relative to each other with an air gap therebetween. The first sheet and/or the second sheet may be held in tension. At least the first sheet is formed of an elastomeric material so that it may deform when a force (e.g., a mechanical stylus, as shown in FIGS. 53B and 53C) is driven against it, will return to the approximately parallel configuration when the force is released. For example, in FIG. 53A the mechanical force applicator (stylus 5375) is positioned above the top of the first (e.g., upper) elastomeric sheet 5307. As described above, one or more movement drives (e.g., x, y stage/z-motion, robotic stage or control) may be used to drive the movement of the mechanical force applicator relative to the upper sheet. The first and second sheets may be part of a cartridge that may include one or more tensioners (e.g., tensioning frames, etc.) holding the first and/or second sheets in tension.

As shown in FIG. 53B, the mechanical force actuator 5375 may be driven down against the first sheet to a region that is adjacent to the droplet. Locally reducing the height of the air gap (in a continuous gradient, as shown) may cause the droplet to be driven by the resulting increased capillary force into the lower-height region. Thus, as the mechanical force actuator is driven across the top of the sheet (and against the top sheet), as shown by FIGS. 53B and 53C causes the droplet to move within the air gap.

In any of these examples the height of the air gap may be reduced in a gradient and the distance between the upper and lower (first and second) sheets is reduced but do not contact each other. For example the height is reduced by between about 5% and 90% (e.g., between about 10% and 80%, between about 20% and 60%, between about 10% and 50%, etc.). In some cases it may be advantageous to reduce the height by between about 5% and 60%, but not more than 60% (e.g., not more than 55%, not more than 50%, not more than 45%, not more than 40%, not more than 35%, not more than 30%, not more than 25%, etc.). This may allow the gradient to drive movement but may limit the region to a region that is local to the droplet. This may allow the first (upper) elastic sheet to be restored to a parallel configuration (as shown in FIG. 53C, in the regions where the stylet has moved away from the sheet). As shown in FIGS. 53B-53C, applying force (by the mechanical force applicator/stylet) to elastically deform the first sheet reduces the distance of the air gap between the first sheet and the second sheet in a local region within the air gap that is adjacent to the fluidic droplet, and causes the droplet to move within the air gap, following the reduced height region formed by the stylet.

In any of the methods and apparatuses described herein the sheets forming the air gap are made of a hydrophobic and oleophobic material; non-hydrophobic and oleophobic materials did not work in many of the examples shown. In addition, the materials forming the inner surface of the air gap may be substantially non-porous.

As mentioned, any of the droplets may be coated with a layer of drop gloss, e.g., a gloss coat that may be a low surface-tension material (e.g., oil), and may be immiscible with the droplet, which may also prevent or limit evaporation.

In general, the methods and apparatuses described herein may include the use of at least 0.01% of a surfactant in or surrounding the droplet being moved. Surprisingly, the inventors have found that the use of surfactant in the droplet (e.g., 0.01% or more, 0.02% or more 0.025% or more, between 0.01% and 1%, between 0.01% and 0.7%, between 0.01% and 0.5%, between 0.01% and 0.25%, between 0.01% and 0.1%, etc.) or in a gloss layer surrounding the droplet may allow the droplet to move more predictably within the air gap when pulled by the reduced gap width as described herein. Without being bound by theory, this may be due to the effective surface tension of the droplet; the use of a surfactant in either or both the drop gloss and/or the droplet may therefore allow the droplet to move predictably and robustly. Without the use of a surfactant, the droplet movement may be less predictable and may sometime fail to follow the mechanical actuator as it moved across the surface. Any appropriate surfactant may be used. For example, the drop gloss used may include a nonionic surfactant (e.g., Brij-35) or other hydrophobic polymer. In some examples the droplet may include a surfactant such as pluronics, Tween-20, Tetronic, etc.). Thus, in any of these methods an apparatuses, either or both the drop gloss and/or the droplet may include a surfactant (e.g., 0.01% or more surfactant). In some cases the surfactant may be added before beginning any of the step involving moving the droplet by locally reducing the gap width in the region adjacent to the droplet.

In examples in which a mechanical force applicator (e.g., stylus) is used, the contact surface of the stylus may be sized proportional to the air gap and/or the droplet size/volume. In particular, the aspect ratio of the stylus, e.g., the size of the stylus tip relative to the size of the droplet, and/or the size of the stylus tip relative to the height of the air gap, may be selected to be between 1:0.5 and 1:20 (tip:droplet).

DNA Sequencing and DNA Synthesis

The methods and apparatuses described herein may be used specifically for performing enzymatic process on polynucleotides, including (but not limited to) sequencing and/or synthesis.

For example, these methods and apparatuses may be used to perform DNA Sequencing-By-Synthesis (SBS). SBS provides many significant benefits to the scientific research community and has enabled many new diagnostic application, including an increase in the output by sequencing instrumentation, faster turnaround time for results and the reduction of costs by orders of magnitude versus the prior dominant sequencing methodology, Sanger Sequencing. Sanger Sequencing relies on electrophoretic separation of DNA fragments created by specially modified terminating nucleotides. SBS eliminates the requirement for the separation and allows the implementation of massively parallel sequencing approaches. Several important clinical applications have been developed as a result of these cost and throughput improvements including, Non-Invasive Pre-Natal Testing (NIPT) to detect aneuploidies such as Down's Syndrome in pregnant women's blood, genetic carrier testing to provide information to parents regarding potential genetic risks, oncology patient stratification, tumor profiling and early detection of cancer through the sequencing of nucleic acids in blood (known as cell-free sequencing).

SBS is a flow-based sequencing technique in which a series of liquid formulations are introduced to a flow cell populated with DNA templates isolated, purified and processed to create a sequencing "library" and flowed into the sequencing flow cell. The flow cell is loaded with template DNA onto either random or structured arrays which create a distinct "cluster" for each DNA library fragment. Reagents are delivered in a sequential process which enzymatically adds a single fluorescently labeled nucleotide per cycle. After each fluorescent nucleotide addition, the flow cell is imaged, with each unique fluorescent labels representing a specific base (A, C, G, T) and processed through software which assigns the next base in the sequence. After imaging, the fluorescent dye and the nucleotide blocking group are chemically cleaved and washed away to prepare for the next cycle. Typically, this process is repeated for 75-600 cycles adding another base each cycle which is captured through the imaging process and software analysis. Many protocols have a process (mid-run in most cases) to create a complementary strand of DNA which is also sequenced to improve coverage and accuracy. The method for creating this complementary strand uses similar reagents to create newly synthesized DNA to be sequenced by SBS.

Figure 54:
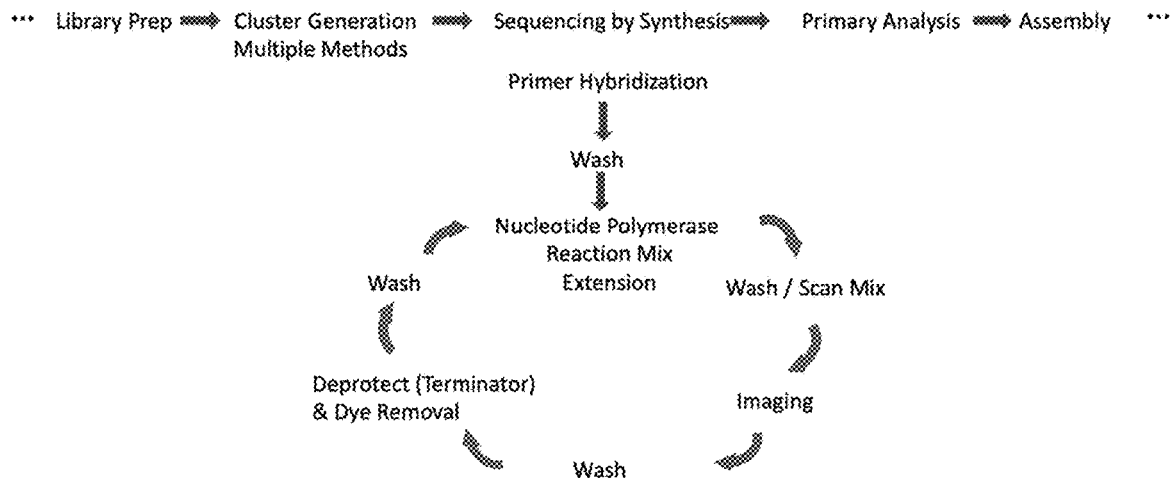
FIG. 54 schematically illustrates a sequencing by synthesis (SBS) method that may be implemented by the techniques described herein.

Current systems typically use a delivery method to provide the continuous flow of each reagent sequentially. These are delivered by a pumping or pressure mechanism which floods the flow cell with each reagent completely filling the flow cell then flushed and replaced with the next reagents required to drive the cycle. While these volumes are fairly small, they do require excess volumes to ensure no carryover from step to step or cycle to cycle which could compromise the resulting sequencing. FIG. 54 schematically illustrates a sequencing cycle and overall process map for SBS. The microfluidic methods and apparatuses described herein may be used to flow the various components within the 'flow cell' configured as described herein, including the wash steps.

Although traditional digital microfluidics (e.g., using electrowetting, etc.) has been proposed for use in sample preparation of nucleic acids as a front end to the sequencing process and as an alternative to manual benchtop library creation or conventional robotic pipetting systems, there are a number of drawbacks. Electro-wetting on Dielectric (EWOD) has been successfully applied to the front-end processes such as the isolation of DNA from patient samples and the creation of a sequencing libraries to be subsequently loaded on a sequencing instrument. While electrowetting has a reasonable fit for the automation of up-front processes, the complexities of the sequencing process itself present several technical and practical economic challenges. Of particular note are the requirements for imaging the flow cell after each nucleotide addition cycle. In an ideal implementation, a completely integrated sequencing processes would allow a sample to be introduced to a system and would provide DNA sequencing results as the output. EWOD is unlikely to be successful as a fluidic solution for such a fully integrated process.

The methods and apparatuses described herein, which may be referred to as mechanical actuation on the surface, in which a mechanical force (e.g., compressive force) is applied to drive one or more droplets may provide significant advantages as compared to other microfluidic techniques, including electrowetting, and may allow for the possibility of using a single fluidic technology across the entire sequencing process, including SBS. As described above, the use of a mechanical compression to change the capillary force to move droplets in two dimensions may have many advantages, particularly in regards to sample preparation, and may be used for virtually all of the necessary steps, such as nucleic acid isolation, library generation, cluster generation, primer loading and hybridization, and multi-cycle sequencing reactions, including the steps illustrated in FIG. 54.

Figure 55A:
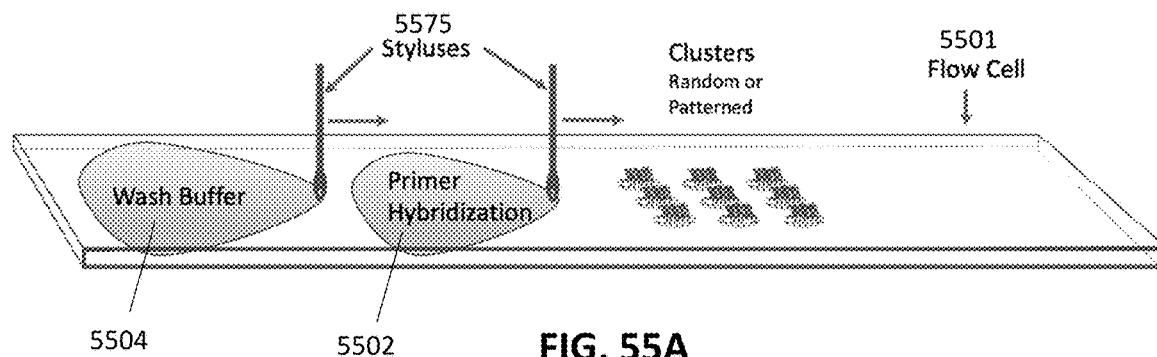
FIGS. 55A-55B illustrate an example of introducing sequencing primers to DNA template in a cartridge (e.g., flow cell) having discrete clusters, which may be part of an SBN method performed using the methods and apparatuses described herein.
Figure 55B:
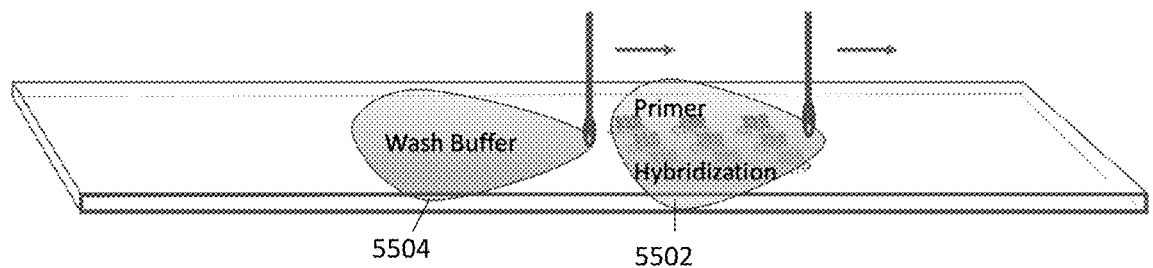

FIGS. 55A-55B illustrate an example of the use of mechanical compression to change the capillary force in order to move droplets within a flow cell 5501 to introduce sequencing primers to clusters of DNA templates (e.g., part of the sequencing by synthesis process described above). FIG. 55A, shows the loading and wash steps associated with primer introduction to the sequencing templates in the flow cell 5501. As in any of the methods described herein, multiple mechanical force applicators (styluses 5575) may be used concurrently on the same flow cell (e.g., cartridge). These mechanical force applicators may be independently or collectively controlled/actuated. In FIG. 55A, the cartridge/flow cell includes a region in which primers to which clusters have been formed are arranged, either in an un-patterned or patterned (e.g., in nanowells) arrangement. The steps for generating the clusters may also be performed using the mechanical force applicator as described herein, or they may be performed by pipetting and washing.

The first droplet 5502 is drawn onto the clusters first using the first stylet and may be allowed to incubate over the clusters (allowing hybridization), as shown in FIG. 55B, and may then be drawn off, and in some cases out of the flow cell (e.g., to a waste depot). The second droplet 5504 (wash buffer) may then be drawn over the clusters to wash the clusters.

FIGS. 56A-56E illustrate the steps associated with each cycle of SBS, as performed in a cartridge (e.g., flow cell) 5501. As described above, either multiple mechanical force applicators (styluses 5575), or the same stylus may be used sequentially. In this examples, the figures show one direction of movement of droplets, e.g., from left to right. However, the methods and apparatuses described herein may allow movement in two dimensions (e.g., in the entire plane of the air gap, and may allow movement in any arbitrary direction in this plane). Thus, in some examples the reagent droplets may be moved to the side and reintroduced and or reused (and even recharged with depleted components, e.g., nucleotides, enzymes, other chemicals).

Figure 56A:
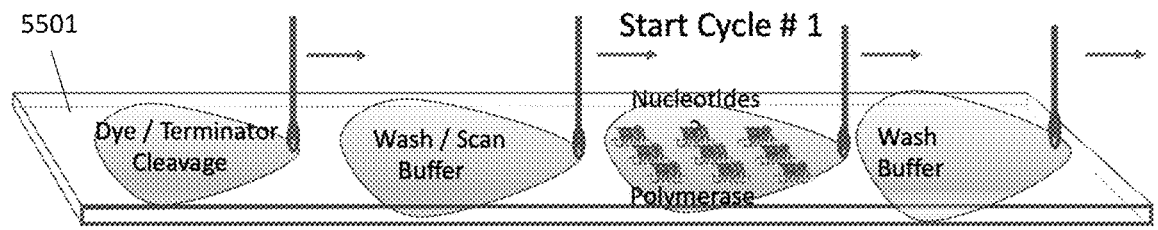
FIGS. 56A-56E schematically illustrate the delivery of SBS reagents using the methods and apparatuses described herein.
Figure 56B:
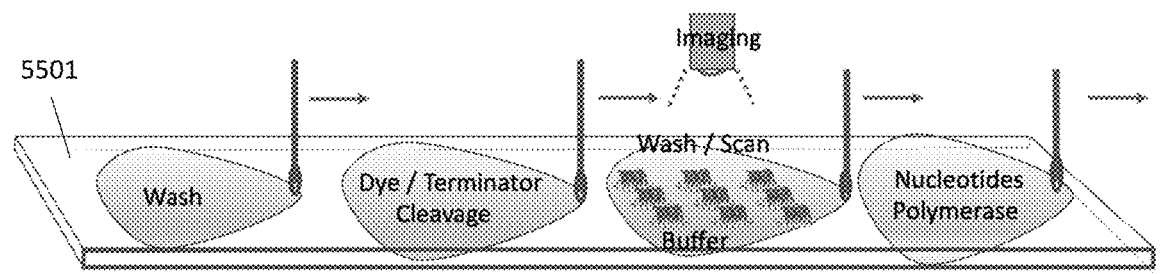
Figure 56C:
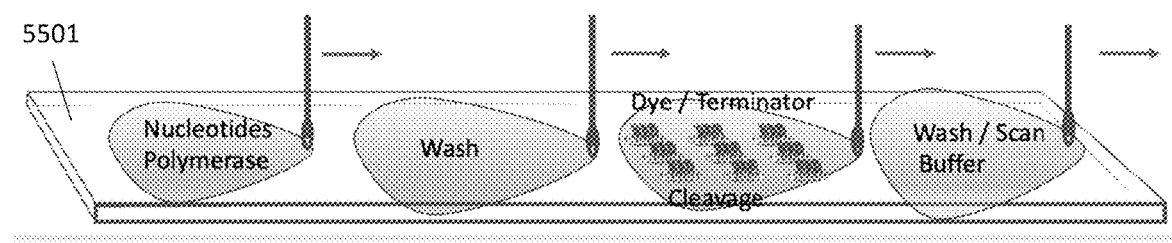
Figure 56D:
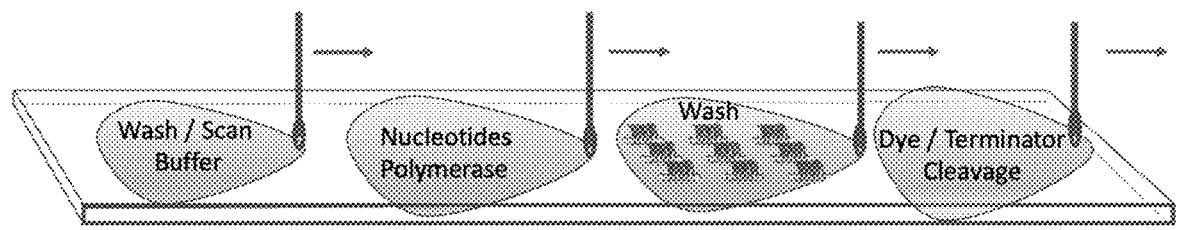
Figure 56E:
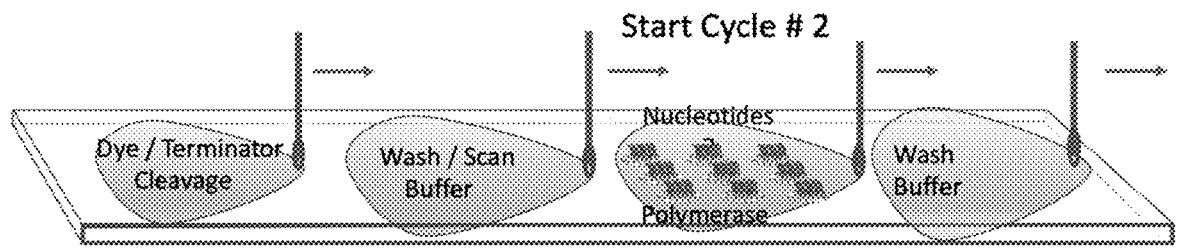

In FIG. 56A, following primer hybridization and washing (see FIGS. 55A-55B), may be followed by the SBS cycles of applying nucleotide, polymerase, reaction mix, washing, and extension with imaging for multiplexed sequencing. FIG. 56A shows the start of the first cycle, in which nucleotides and polymerase are added to the clusters in the air gap of the cartridge/flow cell 5501 by pulling the droplet including the nucleotide and polymerase using a mechanical force actuator. After an appropriate time, the droplet may be pulled off of the clusters and one or more wash droplets may be moved onto the clusters (FIG. 56B) while imaging (to identify the additional nucleotide). The wash droplet may again be moved off of the clusters and a droplet including dye/terminator cleavage components may be pulled onto the clusters (FIG. 56C); this droplet may then be moved off using the mechanical force actuator and the same or a different mechanical force actuator may be used to move another droplet of nucleotides and polymerase for the start of the second cycle (FIG. 56E).

The microfluidic methods and apparatuses described herein may also be used for other applications, in addition to SBS Sequencing. For example, these methods and apparatuses may be used for enzymatic synthesis of DNA oligos (which is very similar to the SBS process), such as cyclical enzymatic addition of nucleotides with reversible terminators. Other non-limiting examples may include DNA oligo synthesis.

Figure 57:
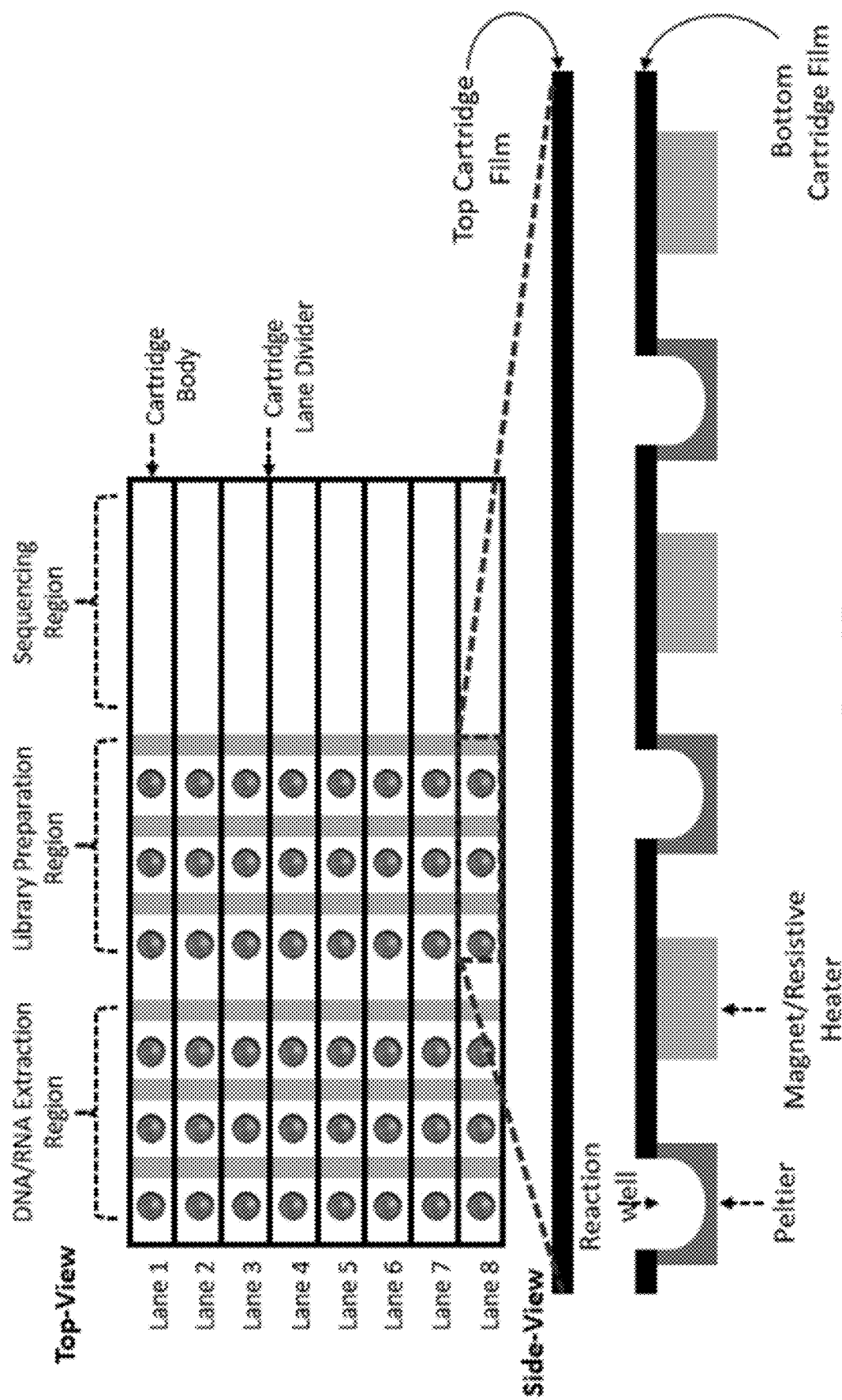
FIG. 57 illustrate a cartridge as described herein.
Figure 58:
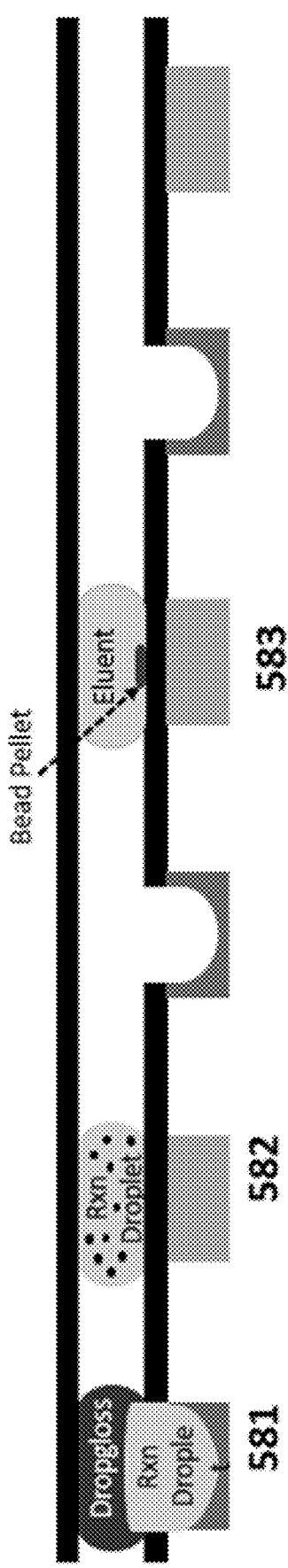
FIG. 58 schematically illustrates a method for polynucleotide extraction from a tissue sample (e.g., blood) that may be performed using the methods and apparatuses described herein.
Figure 59:
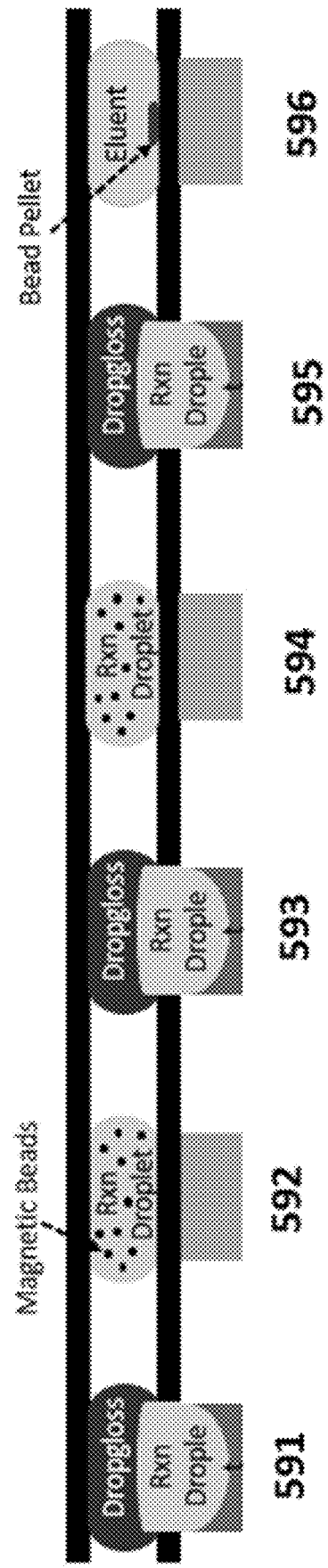
FIG. 59 schematically illustrates a method of performing an RNAseq workflow using the methods and apparatuses described herein.
Figure 60:
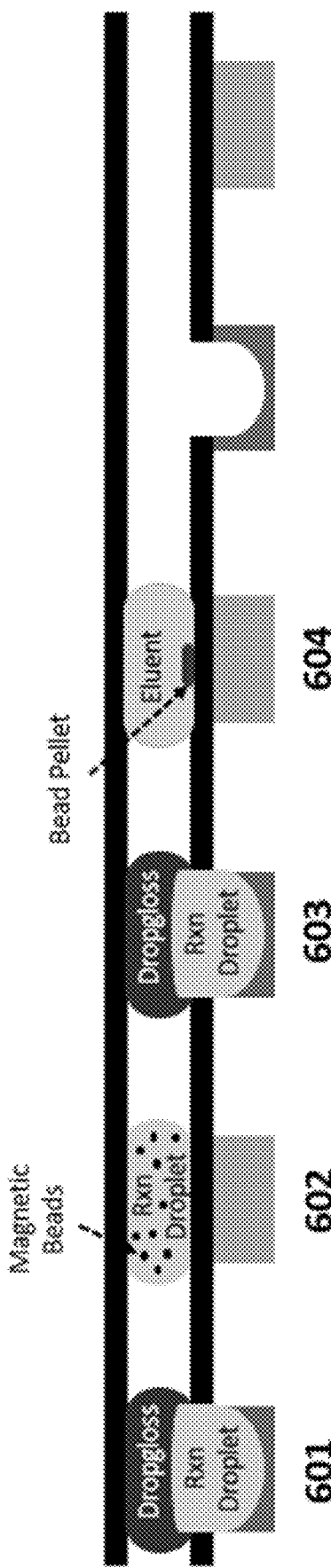
FIG. 60 schematically illustrates a method for Twist exome target enrichment fast hybridization that may be performed using the methods and apparatuses described herein.
Figure 61:
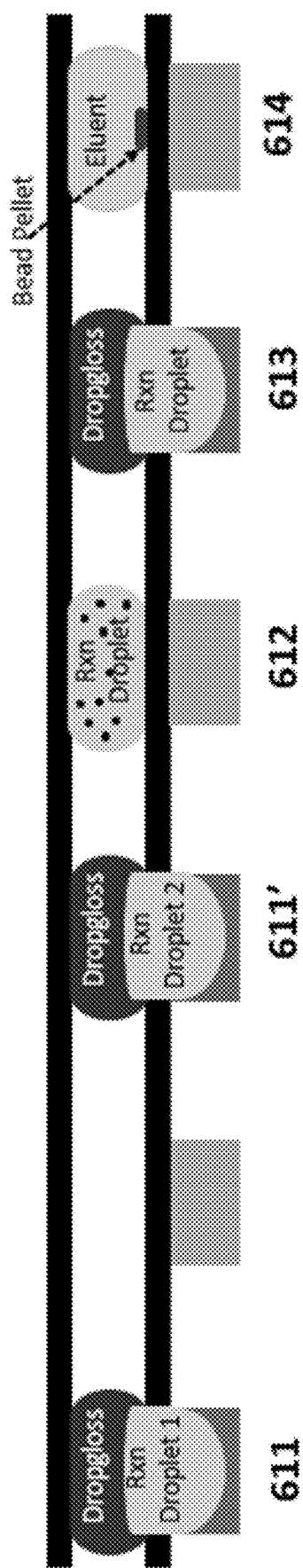
FIG. 61 schematically illustrates a workflow for performing Amplisequ (2 primer pools) using the methods and apparatuses described herein.

For example, the methods and apparatuses described herein may be used for nucleic acid extraction (illustrated in FIGS. 57 and 58A-58B) and library preparation (FIG. 59, FIG. 60, and FIG. 61). FIG. 57 schematically illustrates an overall workflow from nucleic acid extraction to sequencing using a system for mechanical actuation on the surface (e.g., mechanical compression to change the capillary force).

In FIG. 57, a tope and side view of an 8-lane cartridge similar to those described above may be integrated to a system containing an array of cooling regions (e.g., Peltier) and magnetic and/or resistive heating zones that may allow the cartridge and system to perform DNA/RNA extraction, library preparation, and sequencing at specified regions. In FIG. 57 the cartridge includes an air gap with a plurality of different reaction wells (including thermal control/cooling). The cartridge is divided into lanes (8 lanes are shown) and includes regions for DNA/RNA sequencing, Library preparation and sequencing (e.g., SBS). Lane dividers may divide the lanes.

FIG. 58 illustrates the operation of the cartridge and system shown in FIG. 57 for polynucleotide (e.g., DNA, RNA, etc.) extraction from a clinical sample. FIG. 58A shows a side-view schematic of DNA/RNA extraction from a clinical samples on the cartridge. In this example a droplet of a 250 µl clinical sample (e.g., blood, saliva and tissue homogenate, etc.) containing 45 µl of dropgloss and a 310 µL droplet of lysis buffer are merged and mixed by the methods described herein for 5 min in the PCR reaction well and incubate at 70° C. for 10 minutes. The reaction (Rxn) droplet is then actuated to the Magnet/Resistive Heater zone, merged with 400 µL HDQ Binding Buffer and 20 µL Mag-Bind® Particles HDQ, and mixed for 10 minutes; the magnet is then engaged until pellet formation, supernatant is discarded to waste, and the pellet is washed twice with 600 µL VHB wash Buffer. The pellet may be resuspended in 600 µL SPM wash Buffer and driven by mechanical actuation on the surface to clean the Magnet/Resistive Heater zone, the magnet may be engaged, and the wash buffer may be moved to waste. Finally, the elute nucleic acid is eluted in 30 µl of Eluent.

In FIG. 58, the droplet of clinical sample (e.g., blood, saliva and tissue homogenate) merges with the lysis buffer 581 and gets mixed by the techniques described herein (e.g., mechanical actuation on the surface) for 5 min in the reaction well and then incubates at 70° C. for 10 minutes. The lysate droplet is then actuated to the Magnet/Resistive Heater zone 582, merged with Binding Buffer and Magnetic/Binding bead particles and may be mixed for 10 minutes. The magnet may then be engaged until pellet formation 583, the supernatant discarded to waste, and the pellet may be washed twice with wash Buffer. The pellet is resuspended in wash Buffer and driven by mechanical actuation at the surface to clean the Magnet/Resistive Heater zone, the magnet may be engaged, and the wash buffer may be moved to waste. Finally, the elution buffer gets actuated to the pelleted beads to elute nucleic acid off beads.

FIG. 59 illustrates an RNA sequencing workflow. In FIG. 59, a side-view through the cartridge shows a schematic of RNAseq workflow on the cartridge. At step 591, 2 ul droplet of fragmented RNA and first-stranded synthesis master mix with 45 µL of dropgloss droplet are actuated by mechanical actuation at the surface, as described herein (e.g., using a stylus) to the PCR Reaction Well and incubated (25° C. for 10 min, 42° C. for 15 min, 70° C. for 15 min). Thereafter, 6 µl droplet of second-strand synthesis master mix is added to the reaction (Rxn) droplet and incubated at 16° C. for 60 min. The Rxn droplet is actuated to the Magnet/Resistive Heater zone 592, merged with 11.2 ul bead droplet, mixed and incubated for 5 min at RT, the magnet is engaged until pellet formation, the supernatant is discarded to waste, the pellet is washed twice with 25 ul with 80% EtOH (not shown in schematic), and the cDNA sample is eluted off beads into 6 µl elution buffer. Afterwards, 5 ul droplet of cDNA sample is then actuated as described herein to the PCR Reaction Well, merged with 1 µl of end prep master mix (with 10 µl dropgloss), and incubated at 20° C. for 30 min followed by 65° C. for 30 min. Then, 3.1 µl of adaptor ligation master mix and 0.25 µl of adaptors droplets are actuated as described herein, mixed with Rxn droplet and incubated at 20° C. for 15 min 593. The adapter ligation Rxn droplet is actuated to the Magnet/Resistive Heater zone, merged with 7.28 µl of bead droplet, mixed and incubated for 5 min at RT, and the magnet is engaged until pellet formation, after which supernatant is discarded to waste, the pellet is washed twice with 25 ul with 80% EtOH (not shown in schematic), and the DNA library is eluted in 6 µl in nuclease-free water containing 5 uM TRUESEQ BARCODES 594.

5 ul droplet of purified DNA library sample may then be actuated by mechanical actuation (e.g., using a stylus) to the PCR Reaction Well, merged with 10.9 µl of USER/PCR master mix (with 45 µl dropgloss), and incubated at 37° C.

for 15 min, 98° C. for 30, and then cycled 19× at 98° C. for 10 sec, 65° C. for 75 sec 595. The amplified DNA droplet is actuated to the Magnet/Resistive Heater zone, merged with 12.72 µl of bead droplet, mixed and incubated for 5 min at RT, a magnet is engaged until pellet formation, the supernatant is discarded to waste, the pellet is washed twice with 25 ul with 80% EtOH (not shown in schematic), and the DNA library is eluted in 25 µl of Eluent 596.

In FIG. 59, the droplet of fragmented RNA and first-stranded synthesis master mix with dropgloss are actuated by mechanical actuation (e.g., stylus) to the Reaction Well and incubated (25° C. for 10 min, 42° C. for 15 min, 70° C. for 15 min) 591. Then a droplet of second-strand synthesis master mix is added to the reaction (Rxn) droplet and incubated at 16° C. for 60 min. The Rxn droplet is actuated to the Magnet/Resistive Heater zone, merged with SPRI or Ampure beads droplet, mixed and incubated for 5 min at room temperature (RT), magnet engaged until pellet formation, supernatant discarded to waste, pellet washed twice with 80% EtOH (not shown in schematic), and cDNA sample eluted off beads into elution buffer 592. The droplet of cDNA is then actuated (e.g., using a stylus) to the Reaction Well, merged with end prep master mix and incubated at 20° C. for 30 min followed by 65° C. for 30 min 593. Then adaptor ligation master mix and adaptors droplets are actuated by mechanical actuation (e.g., stylus), mixed with Rxn droplet and incubated at 20° C. for 15 min. The adapter ligation Rxn droplet is actuated to the Magnet/Resistive Heater zone, merged with SPRI or Ampure bead droplet, mixed and incubated for 5 min at RT, magnet engaged until pellet formation, supernatant discarded to waste, the pellet washed twice with 80% EtOH (not shown in schematic), and DNA library eluted in nuclease-free water containing primers 594. The purified DNA library plus primers mix is mechanically actuated as described herein (by stylus) to the PCR Reaction Well, merged with USER/PCR master mix with dropgloss and incubated at 37° C. for 15 min, 98° C. for 30, and then cycled up to 19× at 98° C. for 10 sec, 65° C. for 75 sec 595. The amplified DNA droplet is actuated to the Magnet/Resistive Heater zone, merged with SPRI/Ampure bead droplet, mixed and incubated for 5 min at RT, magnet engaged until pellet formation, supernatant discarded to waste, pellet washed twice with 80% EtOH (not shown in schematic), and RNA-seq library eluted in 25 µl of elution buffer 596.

FIG. 61 is a schematic side-view of a second part of a twist exome target enrichment methods using a cartridge as described herein. In this example, an 8.3 µl droplet of DNA and hybridization mix a with 45 µL of dropgloss droplet are actuated as described herein to the PCR Reaction Well and incubated at 95° C. for 5 min and 60 C for 2 hours 601. The Rxn droplet is actuated to the Magnet/Resistive Heater zone, merged with 33.3 µl Streptavidin beads, mixed for 30 min at RT, magnet engaged until pellet formation, supernatant discarded to waste, pellet is initially washed with a 70° C. pre-heated 50 µl buffer droplet followed by a 48° C. pre-heated 50 µl buffer droplet (not shown in schematic), and purified DNA library sample eluted off beads into 7.5 µl elution buffer 602. Thereafter, 7.5 µl droplet of purified DNA library sample is then actuated as described herein to the PCR Reaction Well, merged with 0.83 µl Primer and 8.3 µl of master mix (with 10 µl dropgloss), and incubated at 97° C. for 45 sec followed by 8 cycles at 97° C. for 15 s, 60 for 30 s, 72 C for 30 s, and finally 72 C for 1 min 603. The amplified DNA droplet is actuated to the Magnet/Resistive Heater zone, merged with 30 ul magnetic bead droplet, mixed and incubated for 5 min at RT, magnet engaged until pellet formation, supernatant discarded to waste, pellet washed twice with 25 µl with 80% EtOH (not shown in schematic), and DNA library eluted in 30 µl of Eluent 604.

Thus, in FIG. 60 the method for twist exome target enrichment is performed on a cartridge as described herein, using mechanical actuation of the surface of the cartridge. In FIG. 60 the droplet of DNA and hybridization mix with dropgloss 601 and are actuated as described herein to the Reaction Well and incubated at 95° C. for 5 min and 60 C for up to 4 hours. The Rxn droplet is actuated to the Magnet/Resistive Heater zone, merged with Streptavidin beads, mixed for 30 min at RT, magnet engaged until pellet formation, supernatant discarded to waste, pellet is initially washed with a 70° C. pre-heated buffer droplet followed by a 48° C. pre-heated 50 µl buffer droplet (not shown in schematic), and purified DNA library sample eluted off beads into elution buffer 602. The droplet of purified DNA library sample is then actuated by the mechanical actuation of the surface as described herein to the PCR Reaction Well, merged with Primers and dropgloss and incubated at 97° C. for 45 sec followed up to 18 cycles at 97° C. for 15 s, 60 for 30 s, 72 C for 30 s, and finally 72 C for 1 min 603. The amplified DNA droplet is actuated to the Magnet/Resistive Heater zone, merged with SPRI/Ampure magnetic bead droplet, mixed and incubated for 5 min at RT, magnet engaged until pellet formation, supernatant discarded to waste, pellet washed twice with 80% EtOH (not shown in schematic), and DNA library eluted in Elution buffer 604.

FIG. 61 illustrates a workflow showing Aplicon-seq. For example, FIG. 61 shows a side-view schematic of an Ampliseq (2 primer pools) workflow on a cartridge as described herein. First, three droplets of 13.5 µl DNA, 9 µl HiFi mix and 22.5 µl water are merged by mechanical actuation of the surface (e.g., using a stylus), mixed for 5 sec at RT, split into two equal droplets using a liquid handler (not shown in schematic) 611. Second, each of the droplets were merged with a 5 µl unique primer droplets with 45 µL of dropgloss droplet, and Rxn droplets (1&2) actuated by mechanical actuation of the surface (e.g., using a stylus) to the PCR Reaction Well zones and incubated (99° C. for 2 min, and then 17 cycle: at 99 C for 15 s, 60 C for 4 min) 611'. Next, Rxn droplets 1 &2 are merged by mechanical actuation of the surface (e.g., using a stylus), actuated to the Magnet/Resistive Heater zone, merged with 4 µl FuPa reagent droplet, mixed and incubated at 50° C. for 10 min, 55 C for 10 min and 60 C for 20 min. Second, 8 µl Switch solution, 4 µl Barcode adaptor mix and DNA Ligase droplets were added to the Rxn droplet by mechanical actuation of the surface (e.g., using a stylus) and incubated at 22° C. for 30 min, 68 C for 5 min, and 72 C for 5 min 612. Afterwards, 90 µl droplet of beads were added to the Rxn droplet, mixed and incubated for 5 min at RT, magnet engaged until pellet formation, supernatant discarded to waste, pellet washed twice with 150 ul of 80% EtOH droplets (not shown in schematic), and library eluted off beads into 50 µL of Platinum™ PCR SuperMix HiFi and 2 µL of Equalizer™ Primers droplets.

In 613, 50 µl droplet of purified library is actuated by mechanical actuation of the surface (e.g., using a stylus) to the PCR Reaction Well, and incubated at 98° C. for 2 min and cycled 9 times at 98 C for 15 s, 64 C for 1 min. Second, 10 µL of Equalizer Capture droplet is added to the Rxn droplet and mixed for 5 min at RT. In 614, the Rxn droplet is actuated to the Magnet/Resistive Heater zone, merged with 6 µL of washed Equalizer™ Beads, mixed and incubated for 5 min at RT, magnet engaged until pellet formation, supernatant discarded to waste, pellet washed twice with 150 µl with 80% EtOH (not shown in schematic), and DNA library eluted in 100 µl of Eluent droplet.

Thus, as shown in FIG. 61, the Ampliseq (2 primer pools) workflow, in 611, three droplets of DNA, PCR mastermix and water are merged by mechanical actuation of the surface (e.g., using a stylus), mixed for 5 sec at RT, split into two equal droplets using a liquid handler (not shown in schematic). Second, 611' each of the droplets were merged with a unique primer droplet with dropgloss, and Rxn droplets (1&2) actuated by mechanical actuation of the surface (e.g., using a stylus) to the PCR Reaction Well zones and incubated (99° C. for 2 min, and then 17 cycle: at 99 C for 15 s, 60 C for 4 min). In step 612, first, Rxn droplets 1 &2 are merged by mechanical actuation of the surface (e.g., using a stylus), actuated to the Magnet/Resistive Heater zone, merged with FuPa reagent droplet, mixed and incubated at 50° C. for 10 min, 55 C for 10 min and 60 C for 20 min. Second, Switch solution, Barcode adaptor mix and DNA Ligase droplets were added to the Rxn droplet by mechanical actuation of the surface (e.g., using a stylus) and incubated at 22° C. for 30 min, 68 C for 5 min, and 72 C for 5 min. Third, droplet of beads were added to the Rxn droplet, mixed and incubated for 5 min at RT, magnet engaged until pellet formation, supernatant discarded to waste, pellet washed twice with 80% EtOH droplets (not shown in schematic), and library eluted off beads into Platinum™ PCR SuperMix HiFi and Equalizer™ Primers droplets. In 613, first, 50 ul droplet of purified library is actuated by mechanical actuation of the surface (e.g., using a stylus) to the PCR Reaction Well, and incubated at 98° C. for 2 min and cycled 9 times at 98 C for 15 s, 64 C for 1 min. Second, Equalizer Capture droplet is added to the Rxn droplet and mixed for 5 min at RT. As 614, The Rxn droplet is actuated to the Magnet/Resistive Heater zone, merged with washed Equalizer™ Beads, mixed and incubated for 5 min at RT, magnet engaged until pellet formation, supernatant discarded to waste, pellet washed twice with 80% EtOH (not shown in schematic), and DNA library eluted in Elution droplet.

Introducing and Removing Liquid

FIGS. 62A-62J illustrate one example of a method of applying liquid (droplets) into a cartridge such as the cartridges described herein. For example, in FIG. 62A, a partial section through the cartridge shows an opening into which a pipette tip may be inserted. A standard pipette tip may be used. As an initial step, a droplet of drop gloss material (as described above) may be pipetted into the air gap of the cartridge. For example, between about 10-45 µL of drop gloss may be pipetted into the air gap, and the pipette tip removed (FIG. 62B). A droplet of the aqueous reaction material may then be inserted into the air gap in the same way, as shown in FIG. 62C. The droplet may be pipetted onto, into or adjacent to the drop gloss (which is added first). In some examples, the drop gloss may be combined with the droplet before they are pipetted together. Alternatively, the drop gloss may be added after the aqueous (reaction) droplet is added. In general, the liquid material may be introduced by pipette tip, using a unique (dedicated single tip/sample) application or universal (shared tip for multi-dispense) application of reagents across one or more lanes of the cartridge. In FIG. 62C any volume of aqueous reaction mixture may be used, such as between about 250 nL to 80 µL.

In FIGS. 62C-62D, pre-dispensed drop gloss encapsulates aqueous reagent and protects from surface fouling and evaporation during workflow steps. Ethanol and wash buffers do not need drop gloss. The volume of drop gloss may be more than, less than or the same as the volume of the aqueous droplet. In some example, as shown in FIGS. 62A-62D, the volume of the drop gloss may exceed the volume of the reaction droplet (e.g., by more than 1.5×, 2×, 2.5×, 3×, 3.5×, 4×, 4.5×, 5×, between 1 and 10 times, between 1 and 8 times, between 1 and 7 times, between 1 and 6 times, between 1 and 5 times, between 1 and 4 times, etc. or more). Thus, very small volumes of reaction droplet (e.g., as small as 250 nL) can be manipulated; the reaction droplet may be combined with an excess of drop gloss which may encapsulate it and allow it to be manipulated as described herein (moved, combined, split, heated, mixed, etc.) even in channels having relatively large channel heights (e.g., 1.5 mm or more). Thus, in some examples the systems described herein can dispense as low as 250 nL and as high as 80 uL of reagents/mastermix/sample volumes. In some examples, for drop gloss the system can dispense 10-45 uL volumes. The lane width illustrated in some of these examples can accommodate up to 150 uL total volume (drop gloss+reagent) or up to 80 uL reagent volume. Larger or smaller lane widths and/or heights may be used.

As shown above, during introduction of liquids into each lane's inlet, the dispensing tip is lowered (straight down) against the bottom film surface in a position to ensure that part of the droplet is inside the channel (due to the innate wetting properties of liquids) when dispensed. Capillary pressure may draw the droplet into the air gap and away from the opening (or to the edge of the opening) so that it can be manipulated, as shown in FIGS. 62E-62G. Thus, for small volumes such as 250 nL, a pre-dispensed carrier dropgloss droplet (e.g., ~5-10 ul) may be used into which the 250 nL droplet is dispensed, and then a compression force is applied to the one-side of the port pulling in the carrier drop gloss droplet containing the small volume. For example, as shown in FIG. 62E-62F, the mechanical manipulator (stylus) may be lowered onto the elastically deformable upper sheet to reduce the height (either on or more preferably adjacent to the droplet) and the mechanical manipulator (stylus) may be drawn across the surface of the upper sheet as shown in FIG. 62G to move the droplet, which is surrounded by the drop gloss. As shown, the reagent is protected inside of the drop of drop gloss. In FIG. 62F, the stylus compresses the film surface adjacent to the inlet hole (at a safe distance that will avoid contamination of the stylus). The droplet of drop gloss/reagent is then drawn into the narrower gap (by the capillary action, including the increase in capillary force) and the droplet is now fully inserted to the lane and sandwiched across its surface between a top and bottom film. The stylus will keep driving 2-phase mix (e.g., drop gloss and aqueous droplet) across the heating/cooling and/or magnet/isothermal heater zones to conduct different protocol steps.

FIGS. 62H to 62J illustrate removal of the droplet from the cartridge. The drop gloss material may be first removed from the droplet, e.g., by contacting an oleophilic material that may wick off the material, by mechanical separation, etc. Alternatively, the droplet may contain the drop gloss with the aqueous material. In FIG. 62H, the stylus drives reaction droplet (e.g., containing a product library, or other reaction product, as illustrated and described above) adjacent to the opening through the upper sheet into the air gap (e.g., an inlet hole, etc.) at a safe distance that will avoid contamination of the stylus. This is illustrated in FIG. 62I. The droplet to be removed is near but not in the opening into the air gap. However, because the upper sheet is formed of an elastic material, it may be deformed by the pipette top for access, as shown in FIG. 62J. In this example, the pipette tip is inserted to the inlet hole (FIG>62I) and reaches a position over the bottom film. It then gets moved towards the droplet (FIG. 62J), temporarily deforming the top sheet (film) until it reaches sample position (the droplet is now only partially sandwiched between a top and bottom sheets) and the droplet is aspirated up into the pipette until fully removed or until a specific volume is removed. The pipette tip may then move back to inlet hole opening and then elevates to travel to product destination (e.g., a tube/plate, etc.) so that the operator may collect the material at end of run.

Evaporation Control

In general, these methods and apparatuses may be configured to prevent or reduce evaporation. In general, drop gloss coatings of the aqueous material, alone or in combination with the application of force (e.g., mechanical force) against the droplet may both enhancing uniformity of heating and/or may prevent evaporation. For example in some variations of the methods and apparatuses described herein, the aqueous droplet may experience less than 10% evaporation (e.g., less than 9%, less than 8%, less than 7%, less than 6%, etc.) evaporation when heated to 95 degrees C. or higher for at least 30 minutes. In one example, a droplet of aqueous reaction mixture heated to 95° C. for 30 min (20 µL in 45 µL drop gloss) experienced approximately 5.8% evaporation in total.

Figure 63:
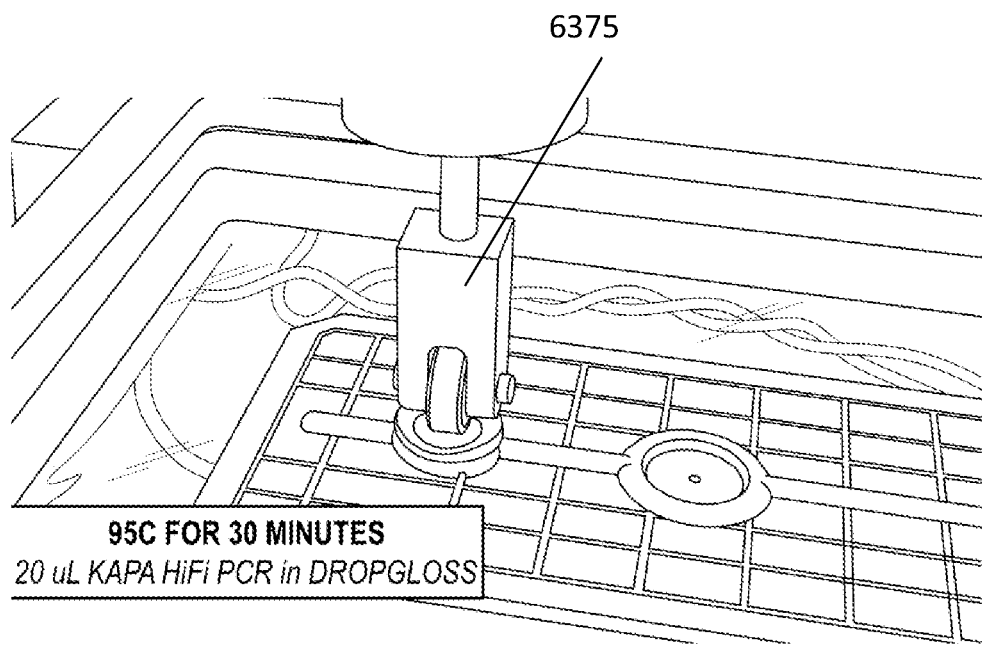
FIG. 63 illustrates evaporation prevention using the methods and apparatuses described herein.

FIG. 63 illustrates an example in which the droplet (e.g., drop gloss plus aqueous droplet) were held in a reaction well formed in the bottom layer by applying suction to conform the bottom layer (which, like the top layer, is elastically deformable) to form a well in the air gap. The base of the drive system holding the cartridge, including the seating region, is therefore shaped to form the well as the bottom layer is attached via suction to the seating region. This well is also a thermal control region including a heater for controlling the temperature of the droplet in the air gap. In FIG. 63 the droplet was heated to 95° C. for 40 min (20 µL in 45 µL drop gloss). The stylet (shown in this example as a roller stylus) may be held over the top of the sheet, over the droplet. This applied mechanical force may hold or pin the droplet in position relative to the heating region. This may also help thermally insulate the droplet. In some examples the portion of the stylet over the droplet may be a thermal insulating material. In some examples the lower layer (sheet) may be more thermally permissive than the upper layer (sheet).

Thus, even as compared to other microfluidic systems, the methods and apparatuses described herein may prevent evaporation in the air gap surprisingly well.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of sequencing by synthesis using mechanical compression, the method comprising:
    sequencing a library of polynucleotide fragments by:
        sequentially moving each droplet of a series of fluidic droplets within a cartridge, wherein the cartridge comprises an air gap formed between a first sheet having a first surface that is hydrophobic and oleophobic and a second sheet having a second surface that is hydrophobic and oleophobic, wherein the first sheet and the second sheet are secured opposite each other with the air gap therebetween, the cartridge further comprising the library of polynucleotide fragments, the library of polynucleotide fragments comprising a plurality of clusters of polynucleotides on the first sheet or the second sheet, wherein moving each droplet comprises moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet;
        imaging the plurality of clusters of polynucleotides to detect addition or hybridization of a nucleotide to clusters of the plurality of clusters of polynucleotides; and
        repeating the steps of sequentially moving each droplet of the series of fluidic droplets and imaging the plurality of clusters to generate sequence data for the plurality of clusters of polynucleotides.

2. The method of claim 1, further comprising introducing the series of fluidic droplets into the air gap.

3. The method of claim 2, wherein sequentially moving each droplet comprises moving each droplet as it is introduced into the air gap.

4. The method of claim 1, wherein imaging comprises imaging the plurality of clusters of polynucleotides after moving the first wash buffer droplet over the plurality of clusters of polynucleotides.

5. The method of claim 1, wherein the plurality of clusters of polynucleotides are arranged in an un-patterned arrangement.

6. The method of claim 1, wherein moving the one or more mechanical force applicators against the first sheet to elastically deform the first sheet comprises moving one or more styluses against the first sheet.

7. The method of claim 1, further comprising repeatedly applying and releasing a compression force to the first sheet over the plurality of clusters of polynucleotides to mix one droplet of the series of fluidic droplets over the plurality of clusters of polynucleotides.

8. The method of claim 1, wherein sequentially moving each droplet of the series of fluidic droplets further comprises removing each droplet of the series of fluidic droplets from the air gap after it been moved over the plurality of clusters of polynucleotides.

9. The method of claim 1, wherein each droplet of the series of fluidic droplets has a volume between $10^{-6}$ and $10^{-15}$ liters.

10. The method of claim 1, wherein the air gap is open to atmospheric pressure and unpressurized.

11. The method of claim 1, further comprising hybridizing a library of polynucleotides to either the first sheet or the second sheet in the air gap to form the clusters of polynucleotides.

12. A method of sequencing by synthesis using mechanical compression, the method comprising:
    sequencing a library of polynucleotide fragments by:
        sequentially moving each droplet of a series of fluidic droplets within a cartridge, wherein the cartridge comprises an air gap formed between a first sheet having a first surface that is hydrophobic and oleophobic and a second sheet having a second surface that is hydrophobic and oleophobic, wherein the first sheet and the second sheet are secured opposite each other at a predetermined spacing relative to each other with the air gap therebetween, the cartridge further comprising the library of polynucleotide fragments, wherein the library of polynucleotide fragments comprises a plurality of clusters of polynucleotides on the second sheet, wherein moving each droplet comprises moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet, and imaging the plurality of clusters of polynucleotides to detect addition or hybridization of a nucleotide to clusters of the plurality of clusters of polynucleotides; and repeating the steps of sequentially moving each droplet of the series of fluidic droplets and imaging the plurality of clusters to generate sequence data for the plurality of clusters of polynucleotides.

13. The method of claim 12, further comprising introducing the series of fluidic droplets into the air gap.

14. The method of claim 12, wherein sequentially moving each droplet comprises moving each droplet as it is introduced into the air gap.

15. The method of claim 12, wherein imaging comprises imaging the plurality of clusters of polynucleotides after moving the first wash buffer droplet over the plurality of clusters of polynucleotides.

16. The method of claim 12, wherein the plurality of clusters of polynucleotides are arranged in a patterned arrangement.

17. The method of claim 12, wherein moving the one or more mechanical force applicators against the first sheet to elastically deform the first sheet comprises moving one or more styluses against the first sheet.

18. The method of claim 12, further comprising repeatedly applying and releasing a compression force to the first sheet over the plurality of clusters of polynucleotides to mix one droplet of the series of fluidic droplets over the plurality of clusters of polynucleotides.

19. The method of claim 12, wherein sequentially moving each droplet of the series of fluidic droplets further comprises removing each droplet of the series of fluidic droplets from the air gap after it been moved over the plurality of clusters of polynucleotides.

20. The method of claim 12, wherein each droplet of the series of fluidic droplets has a volume between $10^{-6}$ and $10^{-15}$ liters.

21. The method of claim 12, wherein the air gap is open to atmospheric pressure and unpressurized.

22. The method of claim 12, further comprising hybridizing a library of polynucleotides to either the first sheet or the second sheet in the air gap to form the clusters of polynucleotides.

23. A method of sequencing by synthesis using mechanical compression, the method comprising:
sequencing a library of polynucleotide fragments by:
sequentially introducing a series of fluidic droplets into an air gap formed between:
a first sheet having a first surface that is hydrophobic and oleophobic; and
a second sheet having a second surface that is hydrophobic and oleophobic, wherein the first sheet and the second sheet are secured opposite at a predetermined spacing relative to each other with the air gap therebetween, the second sheet further comprising the library of polynucleotide fragments, wherein the library of polynucleotide fragments comprises a plurality of clusters of polynucleotides on the second sheet;
sequentially moving each droplet of the series of fluidic droplets over the plurality of clusters of polynucleotides by moving one or more mechanical force applicators against the first sheet to elastically deform the first sheet and create a region of reduced spacing between the first and second sheets so that each droplet follows the region of reduced spacing over the plurality of clusters of polynucleotides, wherein the series of fluidic droplets includes: a nucleotide polymerase reaction mix droplet, a first wash buffer droplet, a dye/terminator cleavage mix droplet, and a second wash buffer droplet;
imaging the plurality of clusters of polynucleotides to detect addition or hybridization of a nucleotide to clusters of the plurality of clusters of polynucleotides; and
repeating the steps of sequentially introducing each droplet of the series of fluidic droplets, moving each droplet and imaging the plurality of clusters to generate sequence data for the plurality of clusters of polynucleotides.

* * * * *